United States Patent
Stein et al.

(10) Patent No.: US 6,297,233 B1
(45) Date of Patent: Oct. 2, 2001

(54) LACTAM INHIBITORS OF FXA AND METHOD

(75) Inventors: Philip D. Stein, Pennington; Gregory S. Bisacchi, Ringoes, both of NJ (US); Yan Shi, Flourtown, PA (US); Stephen P. O'Connor, Lambertville; Chi Li, Randolph, both of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/496,571

(22) Filed: Feb. 2, 2000

Related U.S. Application Data

(60) Provisional application No. 60/167,428, filed on Nov. 24, 1999, and provisional application No. 60/119,372, filed on Feb. 9, 1999.

(51) Int. Cl.[7] ............... C07D 223/12; C07D 223/10; C07D 403/06; A61K 31/55
(52) U.S. Cl. ............... 514/212.03; 514/212.08; 540/524; 540/527
(58) Field of Search ................... 540/524, 527; 514/212.03, 212.08

(56) References Cited

U.S. PATENT DOCUMENTS

| | | | |
|---|---|---|---|
| 5,155,102 | 10/1992 | Giannessi et al. | 514/212 |
| 5,340,798 | 8/1994 | Nutt et al. | 514/18 |
| 5,484,917 | 1/1996 | Lowe | 540/523 |
| 5,502,032 | 3/1996 | Haupt et al. | 514/17 |
| 5,618,811 | 4/1997 | Lowe | 514/218 |
| 5,672,598 | 9/1997 | De et al. | 514/212 |
| 5,703,208 | 12/1997 | Semple et al. | 530/331 |
| 5,932,733 | 8/1999 | Semple et al. | 546/188 |
| 6,066,648 | 5/2000 | Duggan et al. | 514/300 |

FOREIGN PATENT DOCUMENTS

| | | |
|---|---|---|
| 0796855A1 | 9/1997 | (EP). |
| 0761680A2 | 12/1997 | (EP). |
| WO93/14113 | 7/1993 | (WO). |
| WO 94/09029 | 4/1994 | (WO). |
| WO95/35311 | 12/1995 | (WO). |
| WO95/35313 | 12/1995 | (WO). |
| WO 96/11940 | 4/1996 | (WO). |
| WO 96/29313 | 9/1996 | (WO). |
| WO 97/14417 | 4/1997 | (WO). |
| WO 97/16425 | 5/1997 | (WO). |
| WO 97/30073 | 8/1997 | (WO). |
| WO 98/08840 | 3/1998 | (WO). |
| WO 98/12211 | 3/1998 | (WO). |
| WO 98/16523 | 4/1998 | (WO). |
| WO 98/16525 | 4/1998 | (WO). |
| WO 98/35941 | 8/1998 | (WO). |
| WO 98/41510 | 9/1998 | (WO). |
| WO 98/56365 | 12/1998 | (WO). |
| WO 99/07731 | 2/1999 | (WO). |
| WO 99/07732 | 2/1999 | (WO). |
| WO 99/14191 | 3/1999 | (WO). |
| WO 99/30709 | 6/1999 | (WO). |
| WO 99/30713 | 6/1999 | (WO). |
| WO 99/52896 | 10/1999 | (WO). |
| WO 00/05208 | 2/2000 | (WO). |
| WO 00/08015 | 2/2000 | (WO). |
| WO 00/53264 | 9/2000 | (WO). |

OTHER PUBLICATIONS

Lowe et al, "5,7–Diphenyl–3–ureidohexahydrozepin–2–ones as Cholecystokinin–B Receptor Ligands", Bioorganic & Medicinal Chem. Letter, vol. 4, No. 24, pp. 2877–2882, 1994.

Semple et al, "Design, Synthesis, and Evolution of a Novel, Selective, and Orally Bioavailable Class of Thrombin Inhibitors: P1–Argininal Derivatives Incorporating P3–P4 Lactam Sulfonamide Moieties", J. Med. Chem. 1996, 39, 4531–4536.

Angelucci et al, "Synthesis and Amnesia–Reversal Activity of a Series of 7–and 5–Membered 3–Acylamino Lactams", Journal of Medicinal Chemistry, vol. 36, No. 11, May 28, 1993.

Sreenivasan et al, "Synthesis and Dopamine Receptor Modulating Activity of Lactam Conformationally Constrained Analogues of Pro–Leu–Gly–NH2", J. Med. Chem. 1993, 36, 256–263.

Skiles et al, "Elastase Inhibitors Containing Conformationally Restricted Lactams as P3–P2 Dipeptide Replacements", Bioorganic & medicinal Chem. Letters, vol. 3, No. 4, pp. 773–778, 1993.

Adang et al, "Novel Acylguanidine Containing Thrombin Inhibitors With Reduced Basicity at the P1 Moiety", Bioorganic & Medicinal Chem. Letters 8 (1998), 3603–3608.

Freidinger et al, "Protected Lactam–Bridged Dipeptides for Use as Conformational Constraints in Peptides", J. Org. Chem. 1982, 47, 104–109.

*Primary Examiner*—Bruck Kifle
(74) *Attorney, Agent, or Firm*—Burton Rodney

(57) ABSTRACT

Caprolactam inhibitors are provided which have the structure

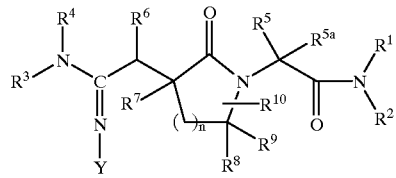

including pharmaceutically acceptable salts thereof and all stereoisomers thereof, and prodrugs thereof, wherein n is 1 to 5; and and Y $R^1$, $R^2$, $R^3$, $R^5$, $R^{5a}$, $R^6$, $R^7$, $R^8$, $R^9$ and $R^{10}$ are as defined herein. These compounds are inhibitors of Factor Xa and thus are useful as anticoagulants. A method for treating cardiovascular diseases associated with thromboses is also provided.

18 Claims, No Drawings

LACTAM INHIBITORS OF FXA AND METHOD

This application claims priority from application Ser. Nos. 60/119,372 filed Feb. 9, 1999 and 60/167,428 filed No. 24, 1999.

FIELD OF THE INVENTION

The present invention relates to lactam inhibitors of the enzyme Factor Xa which are useful as anticoagulants in the treatment of cardiovascular diseases associated with thromboses.

BRIEF DESCRIPTION OF THE INVENTION

In accordance with the present invention, novel lactam derivatives are provided which are inhibitors of the enzyme Factor Xa and have the structure I

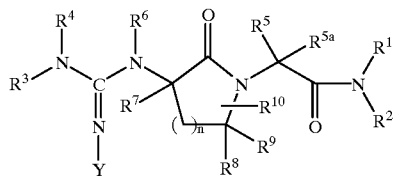

(I)

including pharmaceutically acceptable salts thereof and all stereoisomers thereof, and prodrugs thereof, wherein n is an integer from 1 to 5;

Y is selected from hydrogen, alkyl, substituted alkyl, alkenyl, substituted alkenyl, alkynyl, substituted alkynyl, aryl, cycloalkyl, heteroaryl, cycloheteroalkyl, cyano, nitro, hydroxy, amino, —ORa, —SRa,

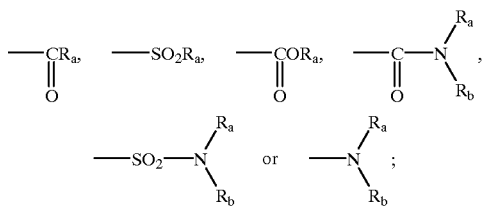

$R^1$, $R^2$, $R^4$, $R^6$, $R^8$, and $R^9$ are the same or different and are independently selected from hydrogen, alkyl, substituted alkyl, alkenyl, substituted alkenyl, alkynyl, substituted alkynyl, aryl, heteroaryl cycloheteroalkyl, cycloalkyl, alkylcarbonyl, arylcarbonyl, cycloalkylcarbonyl, substituted alkylcarbonyl, cycloheteroalkylcarbonyl and heteroarylcarbonyl;

$R^3$ is hydrogen, alkyl, substituted alkyl, alkenyl, substituted alkenyl, alkynyl, substituted alkynyl, aryl, heteroaryl, cycloalkyl, cycloheteroalkyl, cyano, nitro, hydroxy, —ORa, —SRa,

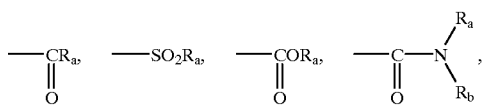

-continued

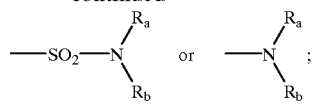

$R^5$, $R^{5a}$, and $R^7$ are the same or different and are independently selected from hydrogen, halogen, alkyl, substituted alkyl, alkenyl, substituted alkenyl, alkynyl, substituted alkynyl, heteroaryl, cycloalkyl, aryl, cycloheteroalkyl,

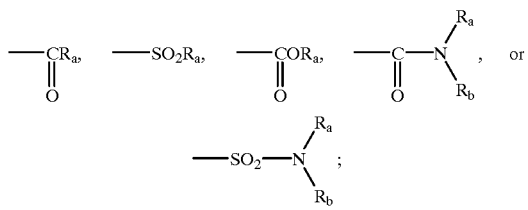

$R^{10}$ is selected from hydrogen, halogen, alkyl, substituted alkyl, alkenyl, substituted alkenyl, alkynyl, substituted alkynyl, aryl, heteroaryl, cycloalkyl, alkylcarbonyl, arylcarbonyl, cycloheteroalkyl, cycloalkylcarbonyl, substituted alkyl-carbonyl, cycloheteroalkylcarbonyl, heteroarylcarbonyl,

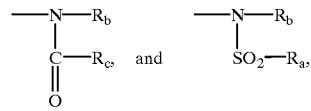

or when $R^9$ is hydrogen and $R^8$ and $R^{10}$ are on adjacent carbons they join to complete a cycloalkyl or phenyl ring;

$R_a$ and $R_b$ are the same or different and are independently selected from hydrogen, alkyl, substituted alkyl, alkenyl, substituted alkenyl, alkynyl, substituted alkynyl, aryl, heteroaryl, cycloheteroalkyl, cycloalkyl, alkylcarbonyl, arylcarbonyl, cycloalkylcarbonyl, substituted alkyl-carbonyl, cycloheteroalkylcarbonyl, heteroarylcarbonyl, aminocarbonyl, alkylaminocarbonyl and dialkylaminocarbonyl;

$R_c$ is hydrogen, halogen, alkyl, substituted alkyl, alkenyl, substituted alkenyl, aryl, heteroaryl, cycloalkyl, cycloheteroaryl,

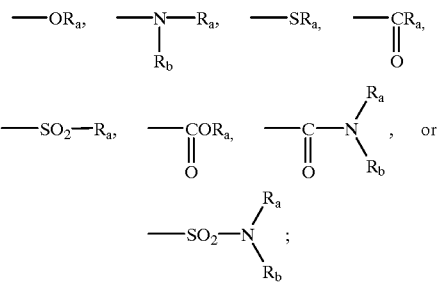

and wherein $R^1$ and $R^2$, and/or $R^3$ and $R^4$ and/or $R_a$ and $R_b$ can be taken together with the nitrogen to which they are attached, i.e.

to form a cycloheteroalkyl ring or a heteroaryl ring;

$R^3$ and Y can be taken together to form a heteroaryl ring;

$R^3$ or $R^4$ or Y can form a ring with $R^6$ which can be a cycloheteroalkyl or a heteroaryl ring;

$R^5$ and $R^{5a}$ can be taken together to the carbon to which they are attached to form a cycloalkyl ring, a heteroaryl ring or a cycloheteroalkyl ring; and where one or more of $R^3$ $R^4$ or $R^6$ are H, then double bond isomers are possible which are included in the present invention.

In addition, in accordance with the present invention, a method for preventing, inhibiting or treating cardiovascular diseases associated with thromboses is provided, wherein a compound of formula I is administered in a therapeutically effective amount which inhibits Factor Xa.

DETAILED DESCRIPTION OF THE INVENTION

The following definitions apply to the terms as used throughout this specification, unless otherwise limited in specific instances.

The term "alkyl" or "alk" as employed herein alone or as part of another group includes both straight and branched chain hydrocarbons containing 1 to 20 carbons, preferably 1 to 12 carbons, more preferably 1 to 8 carbons in the normal chain. Examples include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the various additional branched chain isomers thereof. The term "lower alkyl" includes both straight and branched chain hydrocarbons containing 1 to 4 carbons.

The term "alkenyl" as employed herein alone or as part of another group includes both straight and branched hydrocarbons having one or more double bonds, preferably one or two, and being of 2 to 20 carbons, preferably 2 to 12 carbons, and more preferably 2 to 8 carbons in the normal chain. Examples include

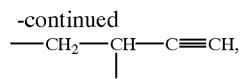

The term "alkynyl" as employed herein alone or as part of another group includes both straight and branched hydrocarbons having one or more triple bonds, preferably one or two, and being of 2 to 20 carbons, preferably 2 to 12 carbons, and more preferably 2 to 8 carbons in the normal chain. Examples include $$—C\equiv CH, \quad —CH_2—C\equiv CH,$$

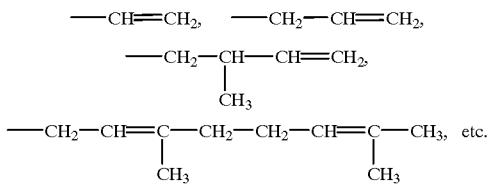

The terms "substituted alkyl", "substituted lower alkyl", "substituted alkenyl" and "substituted alkynyl" refer to such groups as defined above having one, two, or three substituents selected from halo, alkoxy, haloalkoxy, cycloalkyl, cycloheteroalkyl, aryl, heteroaryl, arylcycloalkyl, aryloxy, arylalkoxy, heteroaryloxo, hydroxy, —$N_3$, nitro, cyano, $(R_{20})(R_{21})N$—, carboxy, thio, alkylthio, arylthio, arylalkylthio, heteroarylthio, alkyl-C(O)—, alkoxycarbonyl, $(R_{20})(R_{21})N$—C(O)—, arylcarbonyloxy, alkyl-C(O)—NH—, alkyl-C(O)—N(alkyl)—, aryl-C(O)—NH—, aryl-C(O)—N(alkyl)—, aryl-C(O)—, arylalkoxycarbonyl, alkoxycarbonyl-NH—, alkoxycarbonyl-N(alkyl)—, cycloalkyl-C(O)—, cycloheteroalkyl-C(O)—, heteroaryl-C(O)—, cycloalkyl-C(O)—NH—, cycloalkyl-C(O)—N(alkyl), cycloheteroalkyl-C(O)—NH—, cycloheteroalkyl-C(O)—N(alkyl)—, heteroaryl-C(O)—NH—, heteroaryl-C(O)—N(alkyl)—, arylsulfinyl, alkylsulfinyl, cycloalkylsulfinyl, cycloheteroalkylsulfinyl, heteroarylsulfinyl, arylsulfonyl, alkylsulfonyl, cycloalkylsulfinyl, cycloheteroalkylsulfinyl, heteroarylsulfinyl, $(R_{20})(R_{21})$N-sulfinyl, $(R_{20})$ $(R_{21})$N-sulfonyl, alkyl-$SO_2$—NH—, alkyl-$SO_2$-N(alkyl)—, aryl-$SO_2$—NH—, aryl-$SO_2$—N(alkyl)—, cycloalkyl-$SO_2$—NH—, cycloalkyl-$SO_2$-N(alkyl)—, cycloheteroalkyl-$SO_2$—NH—, cycloheteroalkyl-$SO_2$—N(alkyl)—, heteroaryl-$SO_2$—NH—, heteroaryl-$SO_2$—N(alkyl)—, $(R_{20})$ $(R_{21})$N—C(O)—NH—, $(R_{20})$ $(R_{21})$N—C(O)—N(alkyl)—, hydroxy-NH—C(O)—, hydroxy-N(alkyl)—C(O)—,

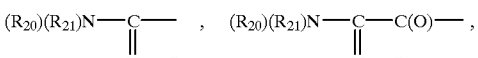

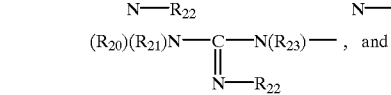

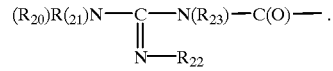

The term "halo" refers to chloro, bromo, fluoro and iodo.

The term "cycloalkyl" as employed herein alone or as part of another group includes saturated or partially unsaturated (containing 1 or 2 double bonds and/or 1 or 2 triple bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons forming the rings. Also included within the definition of "cycloalkyl" are such rings fused to an aryl, cycloheteroalkyl, or heteroaryl ring and bridged multicyclic rings containing 5 to 20 carbons, preferably 6 to 12 carbons, and 1 or 2 bridges. Examples include cyclopropyl, cyclobutyl, cyclopentyl, cyclohexyl, cycloheptyl, cyclooctyl, cyclodecyl and cyclododecyl, cyclohexenyl,

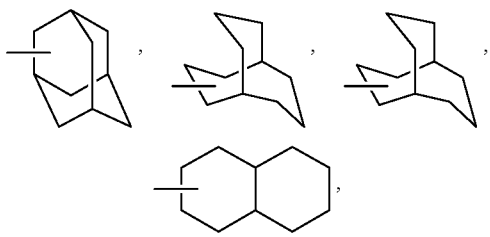

cyclopentenyl, cyclohexenyl, cycloheptenyl, cyclooctenyl, cyclohexadienyl, cycloheptadienyl, cyclopentynyl, cyclohexynyl, cycloheptynyl, cyclooctynyl, etc. Also included within the definition of "cycloalkyl" are such groups having one, two or three substituents selected from alkyl, substituted alkyl, halo, hydroxy, $(R_{20})(R_{21})N-$, alkoxycarbonyl, alkoxy, aryl, aryloxy, arylthio, heteroaryl and cycloheteroalkyl.

The term "aryl" as employed herein alone or as part of another group refers to phenyl, 1-naphthyl, and 2-naphthyl as well as such rings fused to a cycloalkyl, aryl, cycloheteroalkyl, or heteroaryl ring. Examples include

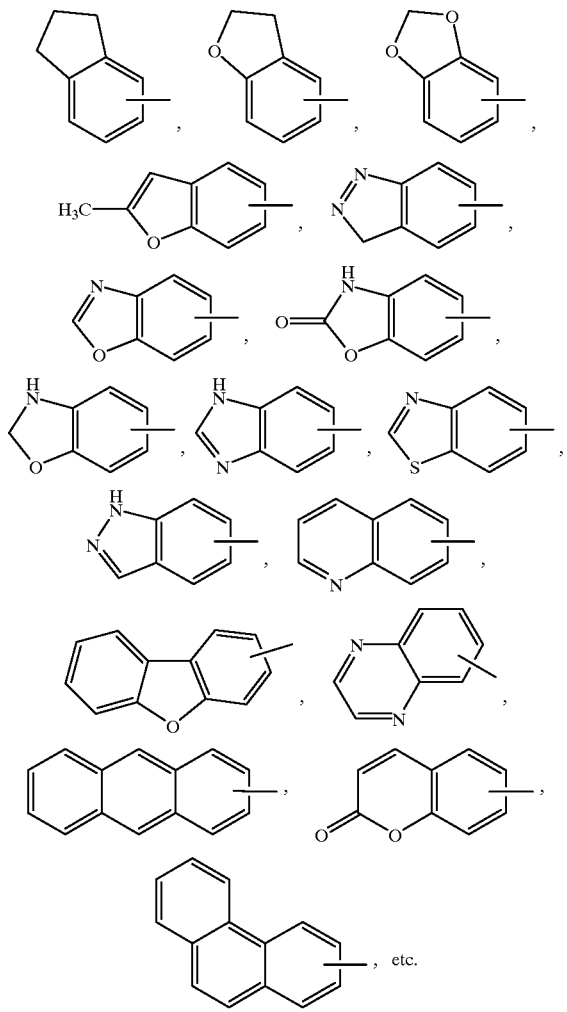

The term "aryl" also includes such ring systems wherein the phenyl, 1-naphthyl, or 2-naphthyl has one two, or three substitutents selected from halo, hydroxy, alkyl, alkenyl, alkoxy, haloalkoxy, carboxy, cyano, nitro, substituted alkyl, substituted alkenyl, alkylcarbonyl, (substituted alkyl)—C(O)—, aryloxy, arylalkoxy, arylthio, arylalkylthio, cycloheteroalkyl, heteroaryl, $-N(R_{20})(R_{21})$, alkyl-$SO_2$—, (substituted alkyl)-$SO_2$—, aryl-$SO_2$—, cycloalkyl-$SO_2$—, cycloheteroalkyl-$So_2$—, heteroaryl-$SO_2$—, alkyl-$SO_2$—NH—, aryl-$SO_2$—NH—, cycloheteroalkyl-$SO_2$—NH—, heteroaryl-$SO_2$—NH—, alkyl-$SO_2$—N(alkyl)—, (substituted alkyl)-$SO_2$—N(alkyl)—, cycloalkyl-$SO_2$—N(alkyl)—, aryl-$SO_2$—N(alkyl)—, cycloheteroalkyl-$SO_2$—N(alkyl)—, heteroaryl-$SO_2$—N(alkyl)—, $(R_{20})(R_{21})N-$C(O)—, $(R_{20})(R_{21})N-$C(O)—NH—, aryl-C(O)—, cycloalkyl-C(O)—, cycloheteroalkyl-C(O)—, heteroaryl-C(O)—, $(R_{20})(R_{21})N-$C(O)—N(alkyl)—,

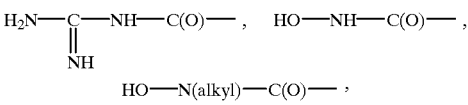

formyl, HC(O)—NH—, arylalkoxycarbonyl-NH—C(O)—, arylalkoxycarbonyl-N(alkyl)—C(O)—, $(R_{20})(R_{21})N-$C(O)-alkyl-NH—C(O)—, $(R_{20})(R_{21})N-$C(O)—alkyl-N(alkyl)—C(O)—, aryl-C(O)—NH—$SO_2$—, aryl-C(O)—N(alkyl)—$SO_2$—, cycloalkyl-C(O)—NH—$SO_2$—, cycloalkyl-C(O)—N(alkyl)—$SO_2$—, heteroaryl-C(O)—NH—$SO_2$—, cycloheteroalkyl-C(O)—NH—$SO_2$—, heteroaryl-C(O)—N(alkyl)—$SO_2$—, cycloheteroalkyl-C(O)—N(alkyl)—$SO_2$—, alkyl-C(O)—NH—$SO_2$—, alkyl-C(O)—N(alkyl)—$SO_2$—, substituted alkyl-C(O)—NH—$SO_2$—, substituted alkyl-C(O)—N(alkyl)—$SO_2$—, $(R_{20})(R_{21})N-$C(O)—alkyl-NH—C(O)-alkyl—NH—C(O)—, $(R_{20})(R_{21})N-$C(O)-alkyl-N(alkyl)—C(O)-alkyl—NH—C(O)—, and $(R_{20})(R_{21})N-$C(O)-alkyl-NH—C(O)-alkyl-N(alkyl)—C(O)—, as well as pentafluorophenyl. Phenyl and substituted phenyl are the preferred aryl groups.

The term "cycloheteroalkyl" as used herein alone or as part of another group refers to 3-, 4-, 5-, 6- or 7- membered saturated or partially unsaturated rings which includes 1 to 2 hetero atoms such as nitrogen, oxygen and/or sulfur, linked through a carbon atom or an available nitrogen atom. Also included within the definition of cycloheteroalkyl are such rings fused to a cycloalkyl or aryl ring and spiro cycloheteroalkyl rings. One, two, or three available carbon or nitrogen atoms in the cycloheteroalkyl ring can be substituted with an alkyl, substituted alkyl, $(R_{20})(R_{21})N-$, aryl, cycloalkyl, keto, alkoxycarbonyl, arylalkoxycarbonyl, alkoxycarbonyl-NH—, alkoxycarbonyl-N(alkyl)—, arylalkoxycarbonyl-NH—arylalkoxycarbonyl-N(alkyl)—, alkylcarbonyl—NH—, alkylcarbonyl-N(alkyl)—, arylcarbonyl, alkylsulfonyl, arylsulfonyl, substituted alkylsulfonyl, HO—N═, alkoxy-N═, (O)CH—, or $(R_{20})(R_{21})N-$C(O)—. Also, an available nitrogen or sulfur atom in the cycloheteroalkyl ring can be oxidized. Examples of cycloheteroalkyl rings include

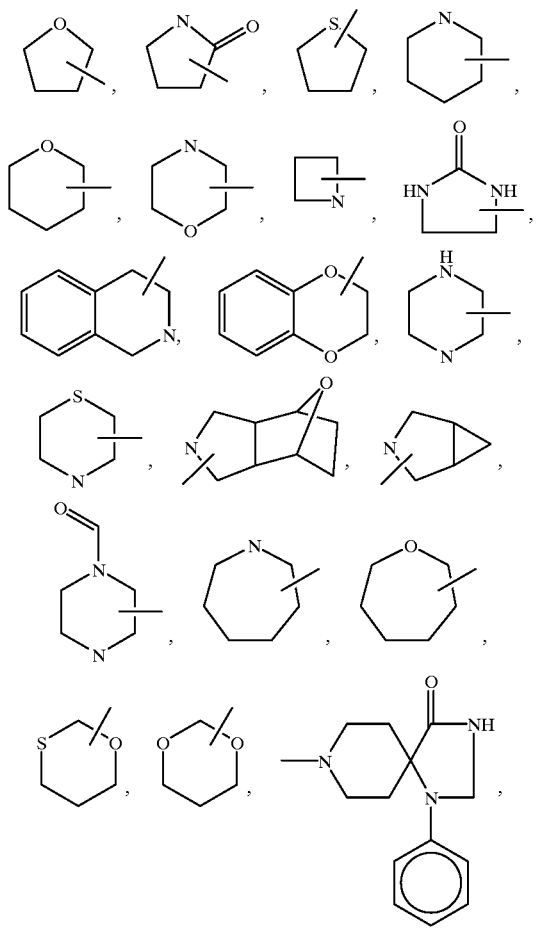

etc. Depending on the point of attachment, a hydrogen may be missing from the nitrogen atom in the above rings.

The term "heteroaryl" as used herein alone or as part of another group refers to a 5- 6- or 7-membered aromatic rings containing from 1 to 4 nitrotgen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be substituted with an alkyl, substituted alkyl, alkoxy, alkylthio, keto, halo, hydroxy, cycloalkyl, aryl, cycloheteroalkyl, heteroaryl, $(R_{20})(R_{21})N$—, nitro, carboxy, cyano, alkoxycarbonyl, aryloxycarbonyl, alkylcarbonyl, substituted alkyl-C(O)—, arylcarbonyl, cycloalkylcarbonyl, $(R_{20})(R_{21})N$—C(O)—, guanidinylcarbonyl, $(R_{20})(R_{21})N$—C(O)-alkyl-NH—C(O)—, $(R_{20})(R_{21})N$—C(O)-alkyl-N(alkyl)—C(O)—, alkyl-C(O)—NH—, alkyl-C(O)—N(alkyl)—, substituted alkyl-C(O)—NH—, substituted alkyl-C(O)—N(alkyl)—, cycloalkyl-C(O)—NH—, cycloalkyl-C(O)—N(alkyl)—, aryl-C(O)—NH—, aryl-C(O)—N(alkyl)—, heteroaryl-C(O)—NH—, heteroaryl-C(O)—N(alkyl)—, cycloheteroalkyl-C(O)—NH—, cycloheteroalkyl-C(O)—N(alkyl)—, alkyl-SO$_2$—, substituted alkyl-S$_{20}$—, aryl-SO$_2$—, cycloalkyl-SO$_2$—, cycloheteroalkyl-SO$_2$—, or heteroaryl-S$_2$. Also an available nitrogen or sulfur atom in the heteroaryl ring can be oxidized. Examples of heteroaryl rings include

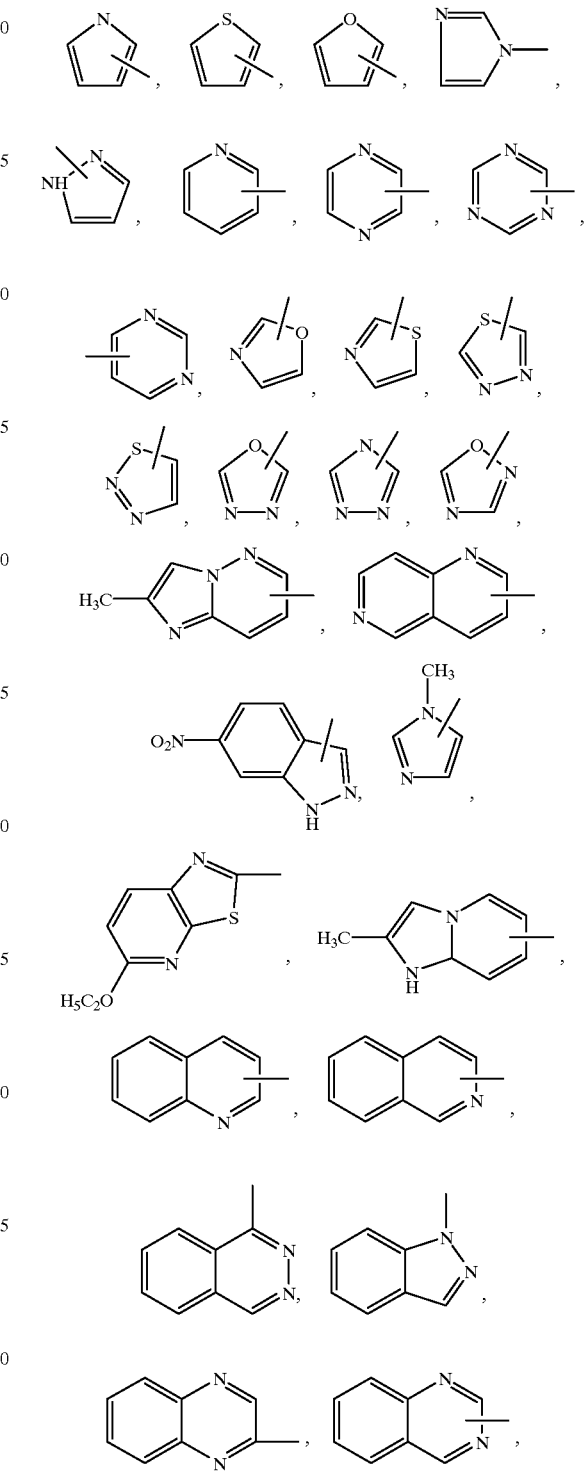

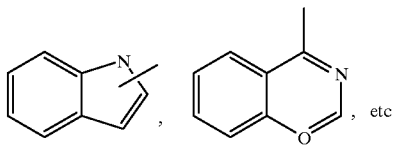

Again, depending on the point of attachment, a hydrogen may be missing from the nitrogen atom in the above rings.

The term "alkoxy" as employed herein alone or as part of another group includes "alkyl" groups as defined above bonded to an oxygen. Similarly, the term "alkylthio" as employed herein above or as part of another group includes "alkyl" groups as defined above bonded to a sulfur.

$R_{20}$, $R_{21}$, $R_{22}$ and $R_{23}$ are the same or different and are independently selected from hydrogen, alkyl, substituted alkyl, cycloalkyl, aryl, cycloheteroalkyl and heteroaryl.

The compounds of formula I can be prepared as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, with saturated or unsaturated dicarboxylic acids, for example oxalic, malonic, succinic, maleic, fumaric, phthalic or terephthalic acid, with hydroxycarboxylic acids, for example ascorbic, glycolic, lactic, malic, tartaric or citric acid, with amino acids, (for example aspartic or glutamic acid or lysine or arginine), or benzoic acid, or with organic sulfonic acids, such as ($C_1$–$C_4$)-alkyl- or arylsulfonic acids which are unsubstituted or substituted, for example by halogen, for example methane- or p-toluene sulfonic acid. Corresponding acid addition salts can also be formed if the compounds of formula I have an additional basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When enantiomeric or diastereomeric products are prepared, they can be separated by conventional methods for example, chromatographic or fractional crystallization.

It should be understood that the present invention includes prodrug forms of the compounds of formula I such as alkylesters of acids or any known prodrugs for lactam derivatives.

The compounds of the instant invention may, for example, be in the free or hydrate form, and may be obtained by methods exemplified by the following descriptions.

The compounds of formula I may be prepared by the exemplary processes described in the following reaction schemes. Exemplary reagents and procedures for these reactions appear hereinafter and in the working Examples.

In one method, lactam, II, is converted to IV by protection followed by substitution (via IIa) or by substitution followed by protection (via III). The CBZ protecting group or trifluoroacetyl group may be used in place of the BOC-group, for example.

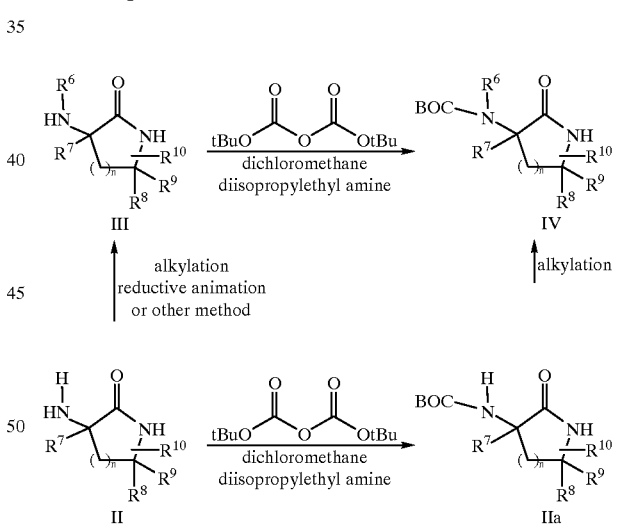

Compound IV is then converted to compound V by alkylation with haloamide VI. Haloamide VI is obtained from bromoacetyl chloride (or other halo acid chloride) by acylation under standard conditions. The protecting group is then removed from V by treatment with TFA to provide VII.

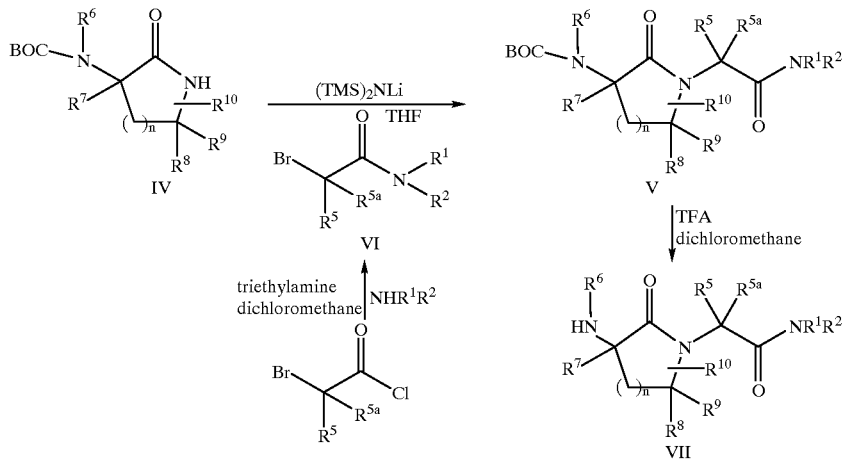

Compounds of type VII can then be converted to the target compounds as shown in the schemes below. In one method, an isothiocyanate VIII is converted to compound IX using sodium cyanamide. The salt IX is then coupled to compound VII by using 1-[3-(dimethylamino)propyl]-3-ethyl-carbodiimide (WSC or EDCI) in DMF to yield the targets.

contains the MeS group, a mercury salt (such as mercuric acetate) can be used to speed the reaction.

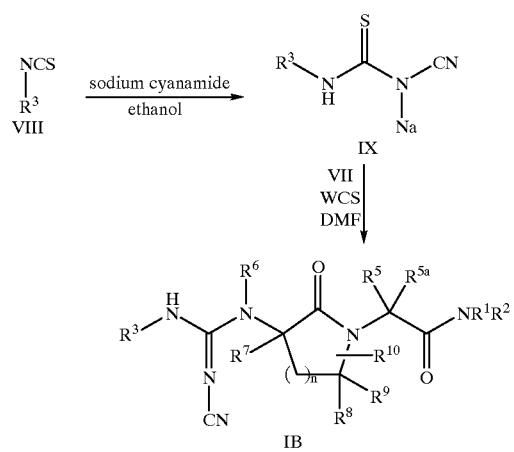

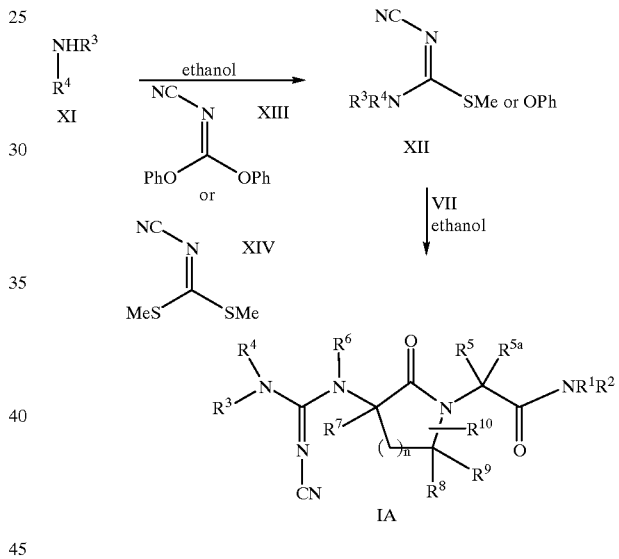

In another method, amine XI is converted to intermediate XII by reaction with XIII or XIV. Intermediate XII is then converted to target compounds IA by reaction in ethanol, ethyl acetate, DMF and the like. In the case where XII In another route, compound VII can be reacted with XIII or XIV to prepare XV. Compound XV is then converted to IA by reaction with an amine in a solvent like acetonitrile or ethanol or DMF.

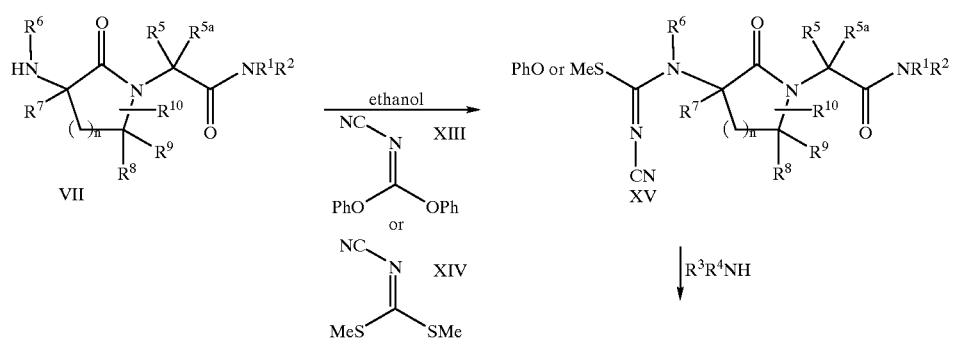

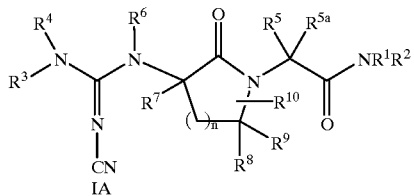

Other compounds of type IA can be obtained by acylation with an acid chloride or acid anhydride in the presence of sodium hydride.

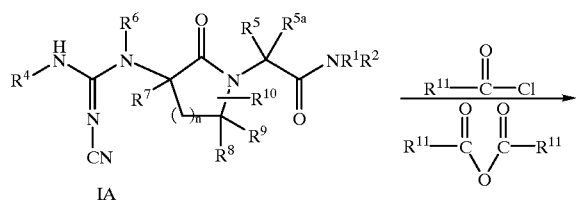

(where $R^{11}$ is alkyl, arylalkyl, aryl or heteroaryl).

The target compounds can also be prepared by converting compounds of type IV to esters of type XVI as described above. These esters can be elaborated in similar manner to provide XVII. Conversion of the ester XVII to the acid XVIII can be accomplished, for example, by hydrogenation if $R^{11}$ is benzyl or by hydrolysis if $R^{11}$ is methyl, ethyl, or benzyl.

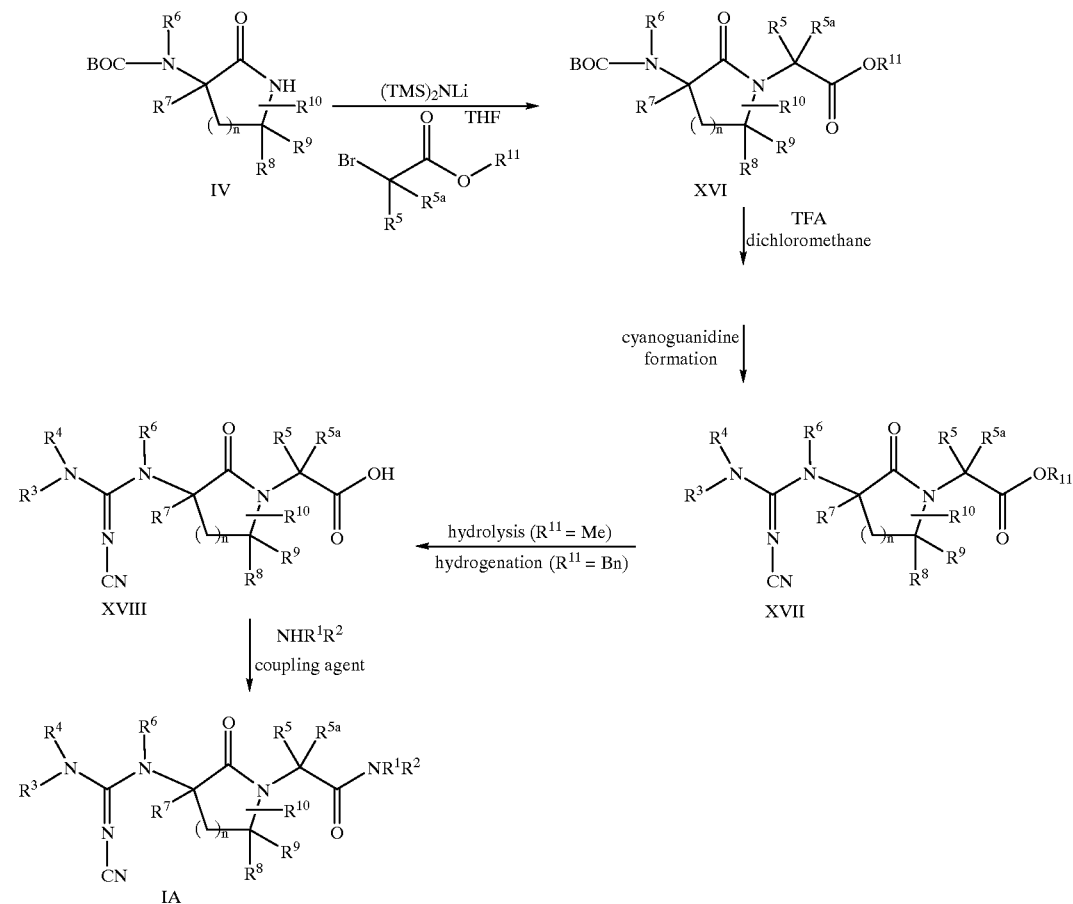

Compounds of the invention of type IB can be prepared by hydrolysis of compounds IA using aqueous HCl, or sodium hydroxide or other acids or bases or other methods for the conversion of nitrites to amides known in the literature.

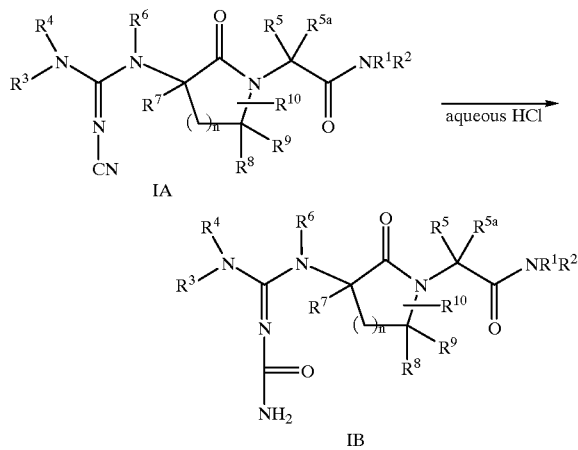

Compounds of the invention of type IC or ID can be prepared from thioureas of type XXI. The reaction is carried out in the presence of a coupling agent such as ethyl 3-(dimethylamino)propylcarbodiimide hydrochloride (WSC, EDCI) or the like. Alternatively, the reaction can be carried out in the presence of a mercury salt (such as mercuric chloride, mercuric acetate, mercuric trifluoroacetate, mercuric oxide and the like) or salts of other metals such as silver, cadmium and the like.

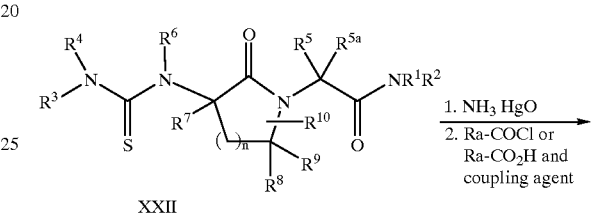

Alternatively, compounds such as IC or ID can be obtained from thioureas of type XXII in a similar manner.

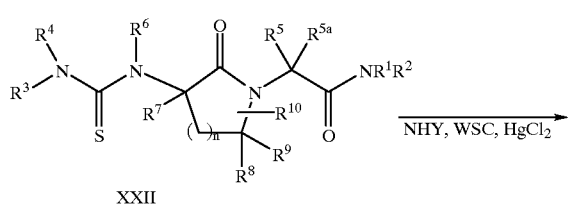

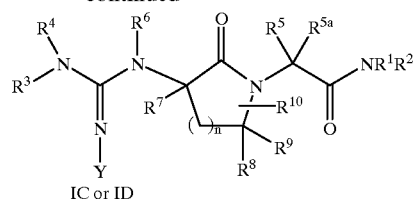

Thioureas of type XXI and type XXII can be prepared by methods known in the literature. For example, an isothiocyanate can be reacted with a nitrogen-containing compound in an inert solvent (DMF, acetonitrile, THF, or the like) optionally in the presence of a base such as triethylamine, sodium hydride, tert-butylimino-tris(pyrrolidino) phosphorane, Hunig's base, and the like.

Alternatively, a multi-step procedure may be used to prepare compounds of type IE (where Y=Ra—C(O)).

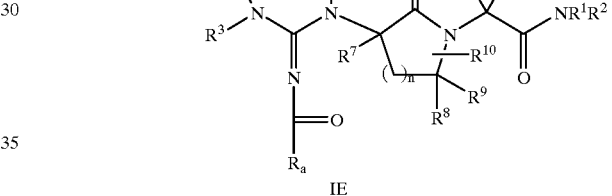

In addition, reagents such as XXIII may be used as described above for the synthesis of compounds of type IC and ID

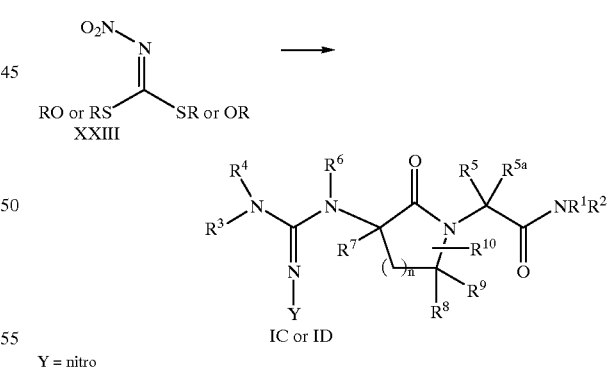

Preferred compounds of this invention are those of formula I including a pharmaceutically acceptable salt thereof wherein:

n is an integer from 1 to 4;

$R^1$ and $R^2$ are the same or different and are selected from alkyl, substituted alkyl, alkenyl, substituted alkenyl, cycloalkyl, and cycloheteroalkyl or $R^1$ and $R^2$ taken together with the nitrogen to which they are attached form a cycloheteroalkyl ring;

$R^3$ is hydrogen, alkyl, substituted alkyl, alkenyl, substituted alkenyl, aryl, heteroaryl or cycloheteroalkyl;

Y is cyano, nitro, aryl, heteroaryl, cycloheteroalkyl,

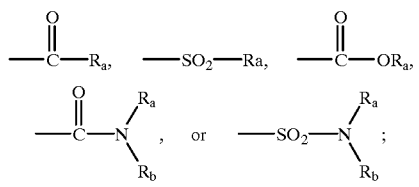

$R_a$ and $R_b$ are the same or different and are hydrogen, alkyl, substituted alkyl, alkenyl, substituted alkenyl, aryl, heteroaryl or cycloheteroalkyl;

$R^4$, $R^5$, $R^{5a}$, $R^6$, $R^7$, $R^8$, $R_9$ and $R^{10}$ are each hydrogen; and the configuration at the chiral center is S— (as judged where $R^7$ is hydrogen)

The following compounds of formula I including a pharmaceutically acceptable salt thereof are more preferred:

n is 3 or 4, especially 3;

$R^1$ and $R^2$ taken together with nitrogen to which they are attached complete a pyrrolidyl, substituted pyrrolidyl, or pyrrolidyl having a fused cycloalkyl ring;

$R^3$ is aryl; especially a substituted benzofuranyl ring;

Y is cyano, heteroaryl,

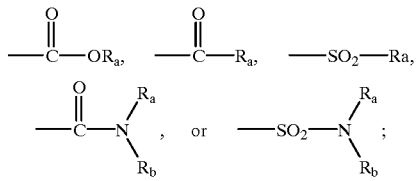

$R_a$ and $R_b$ are the same or different and are hydrogen, alkyl, aminocarbonyl, heteroaryl, aryl, or cycloheteroalkyl;

$R^4$, $R^5$, $R^{5a}$, $R^6$, $R^7$, $R^8$, $R^9$ and $R^{10}$ are each hydrogen; and the configuration at the chiral center is S— (as judged where $R_7$ is hydrogen).

The following compounds of formula I including a pharmaceutically acceptable salt thereof are most preferred:

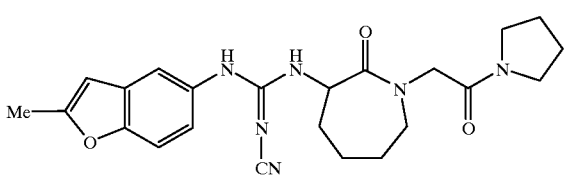

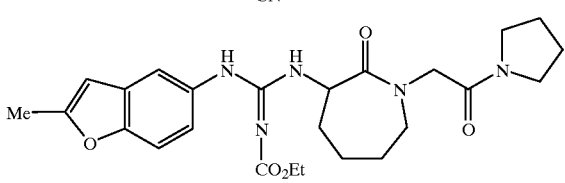

-continued

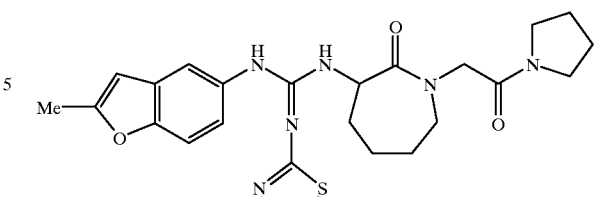

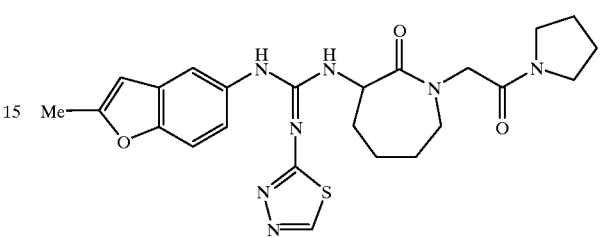

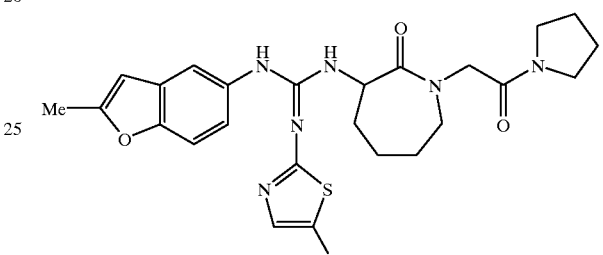

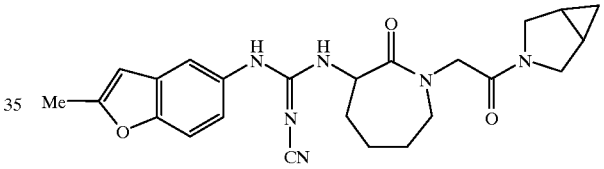

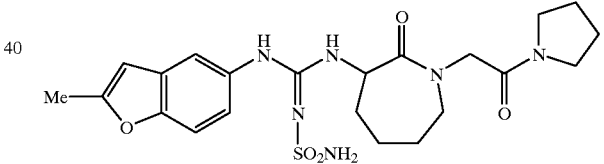


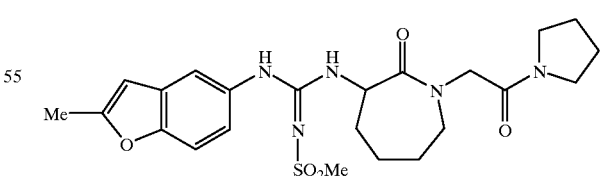

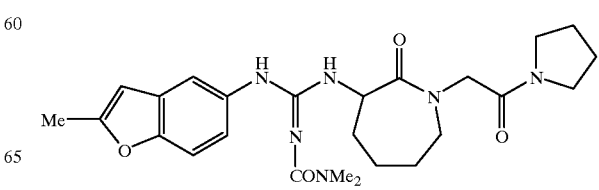

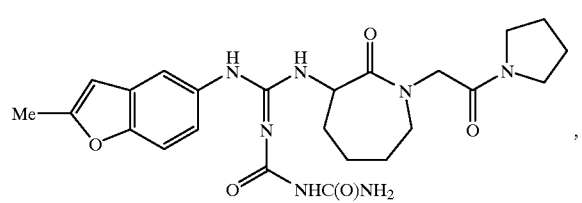
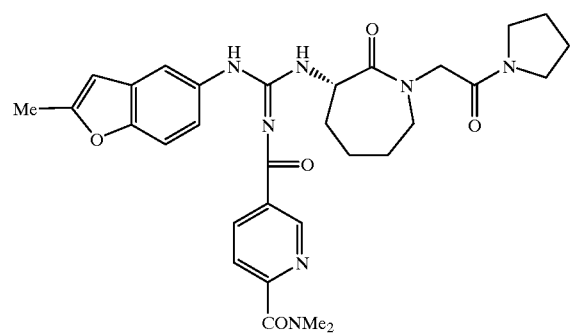
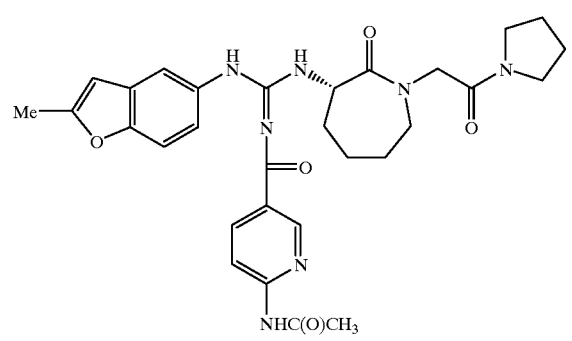
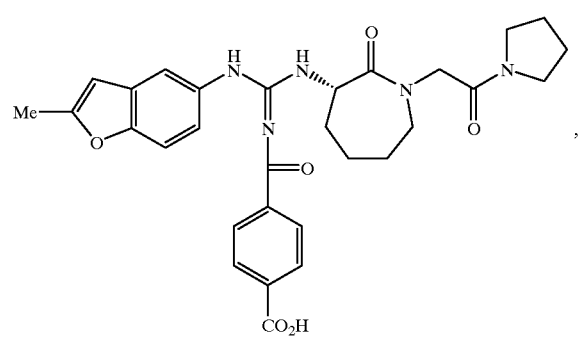
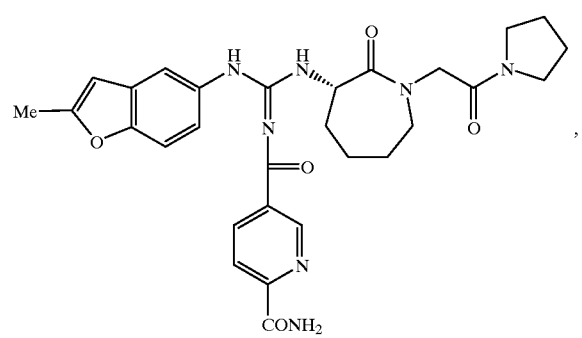

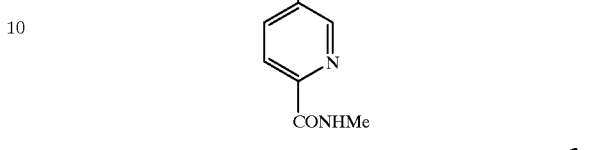
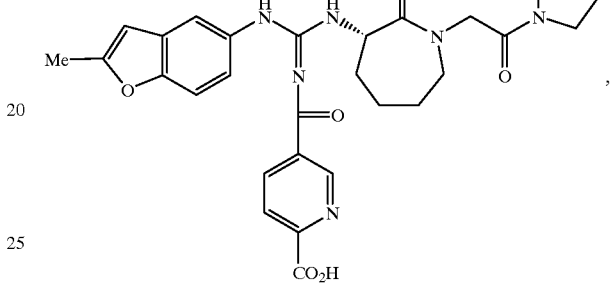
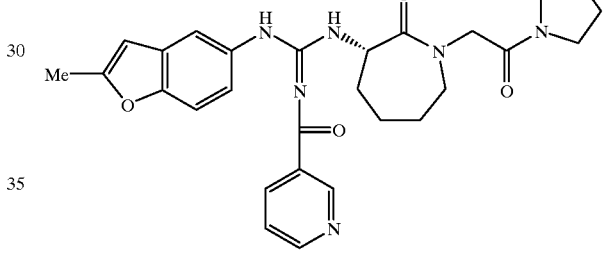
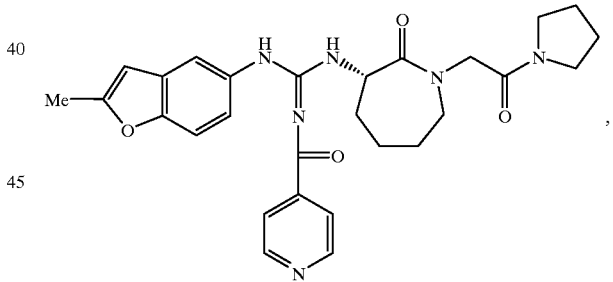
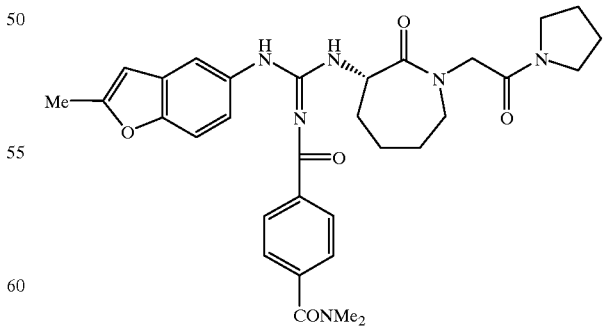

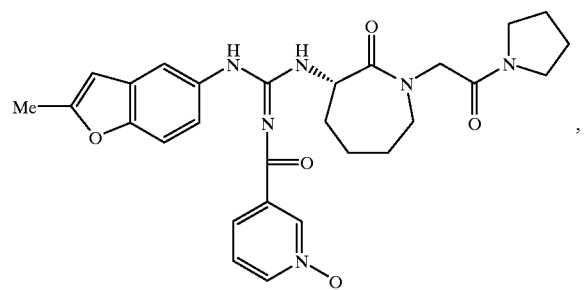
,
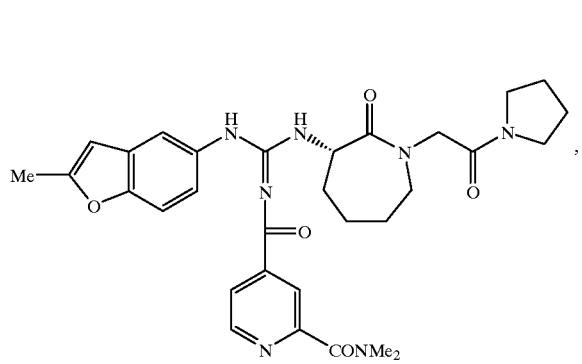
,
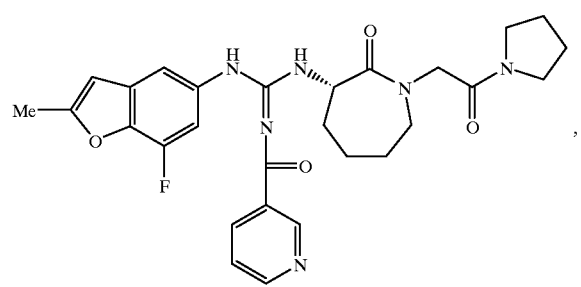
,
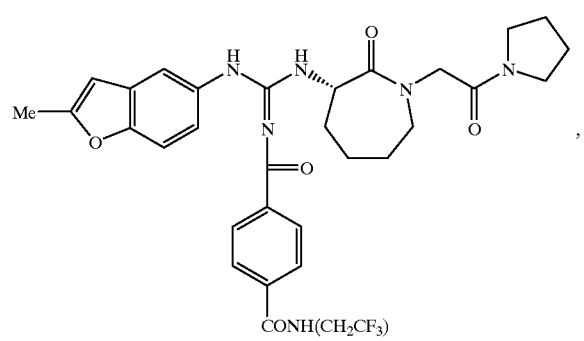
,
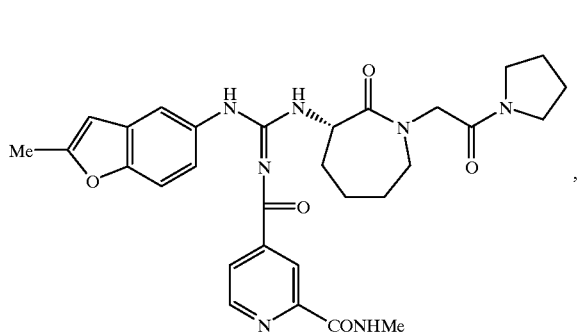
,
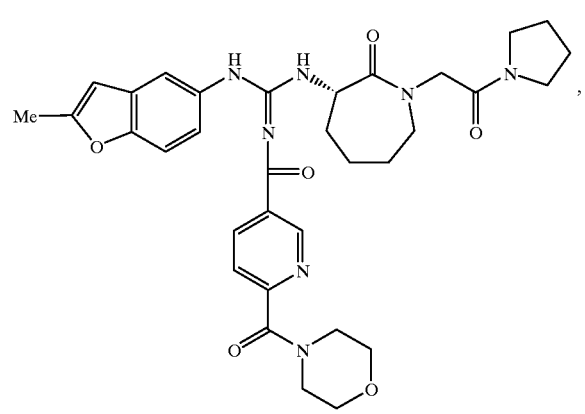
,
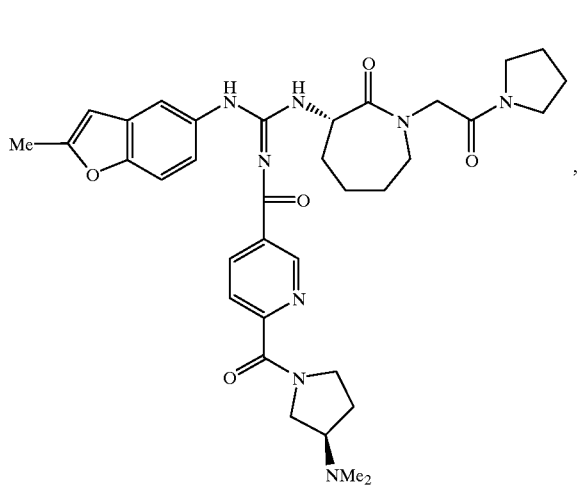
,
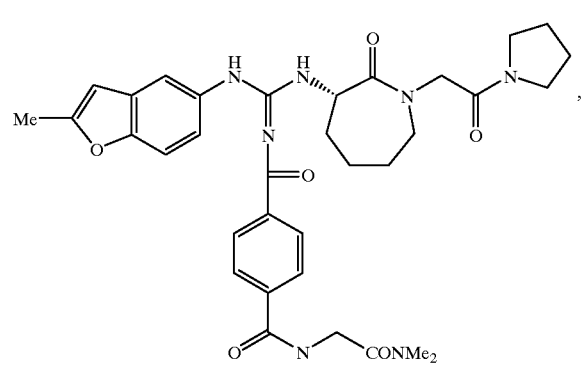
,
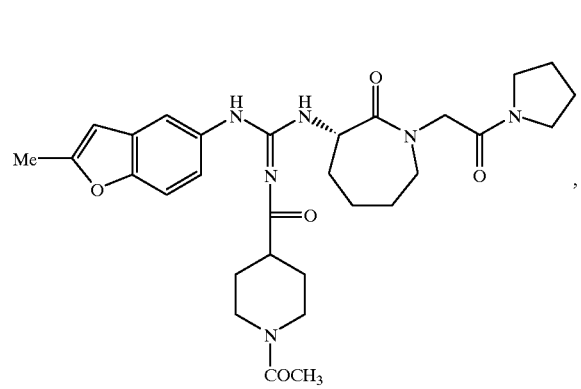
, 23
-continued
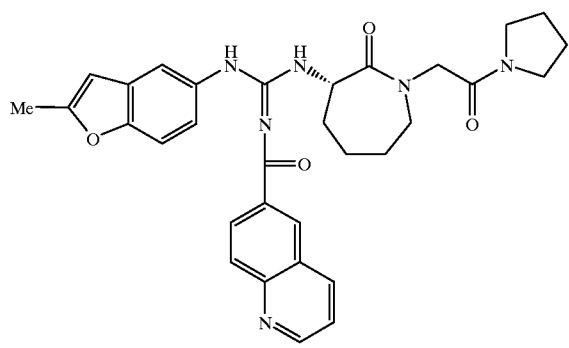
,
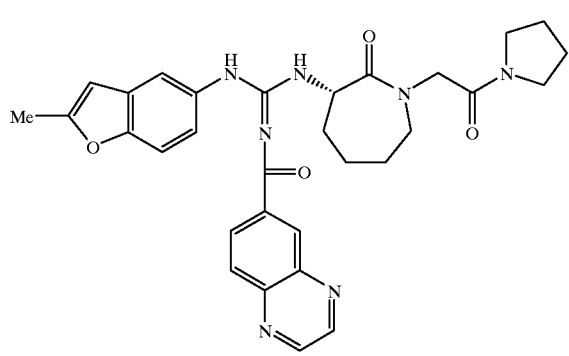
,
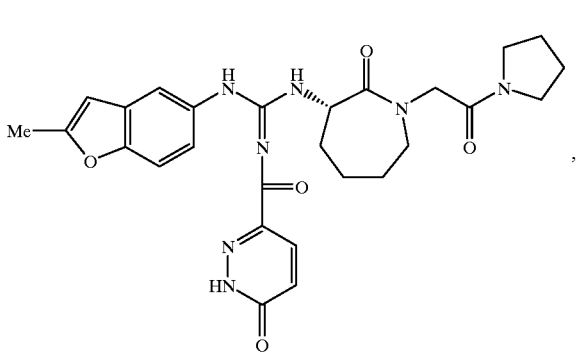
,
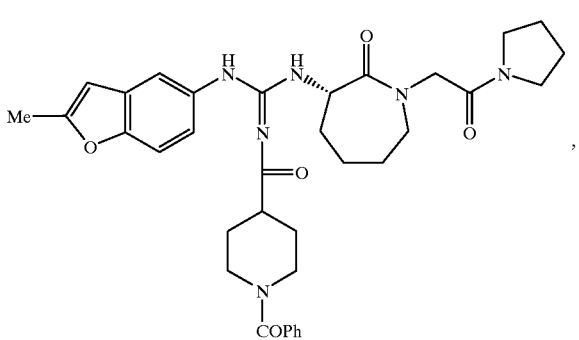
,
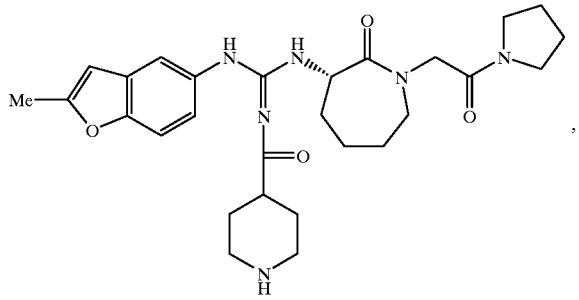
,
24
-continued
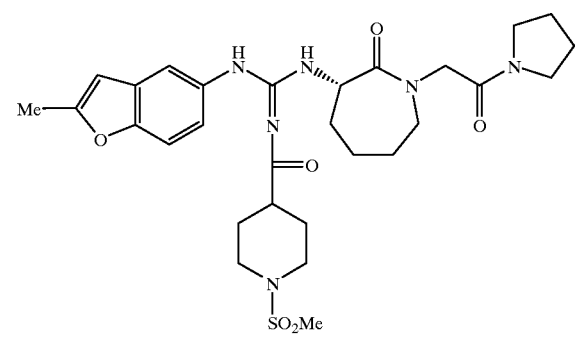
,
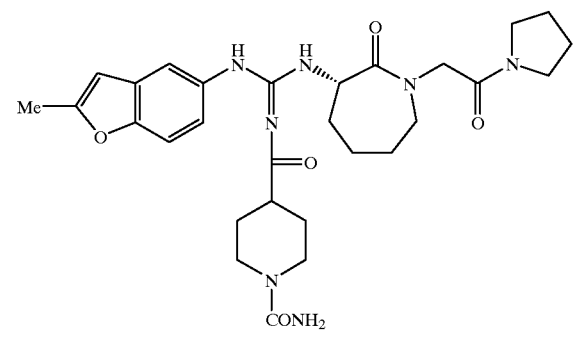
,
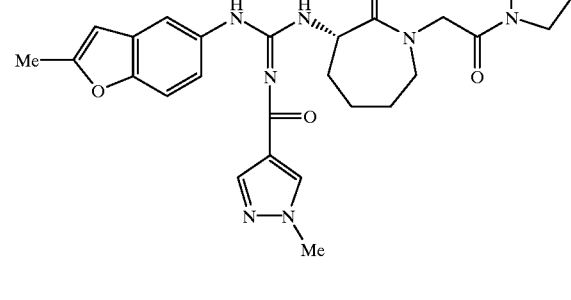
,
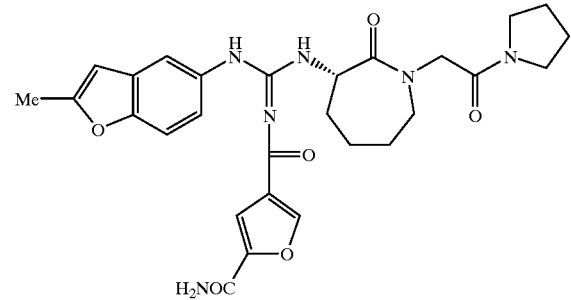
,
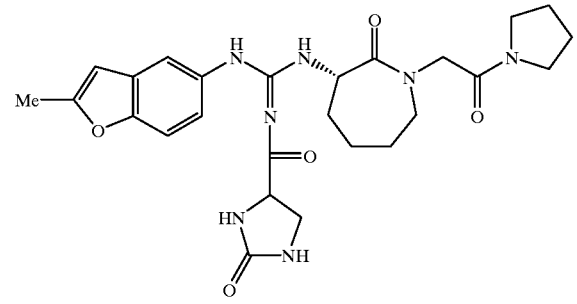
, -continued

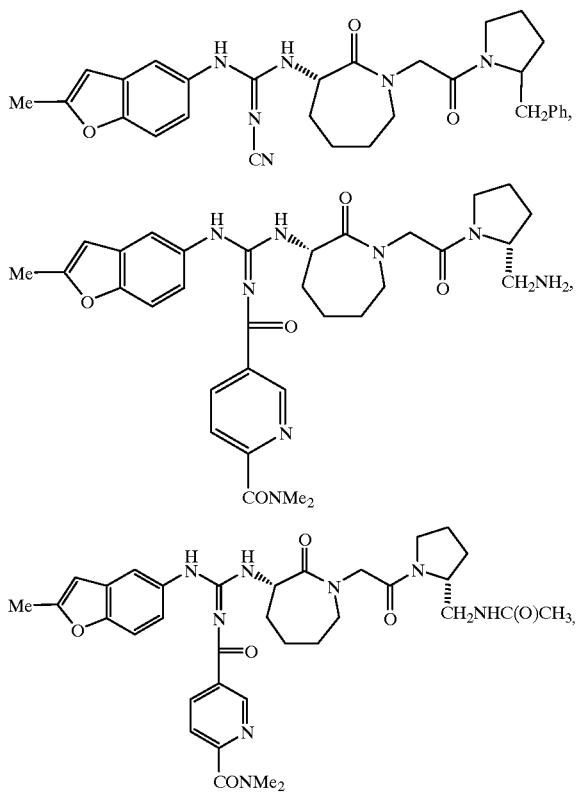

and

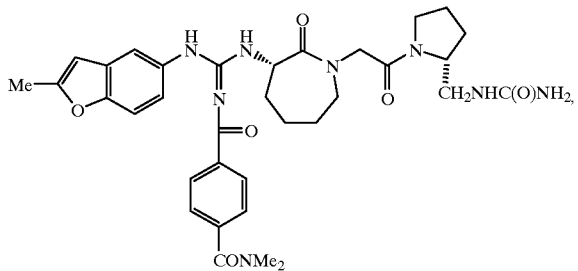

especially

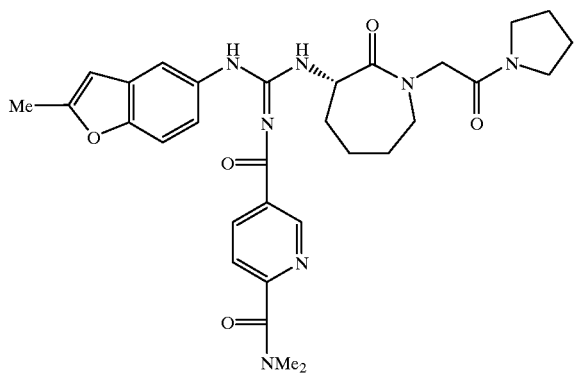

In the above formulas Me represents methyl and Et represents ethyl, and Ph represents phenyl.

The compounds of the present invention are inhibitors of the activated coagulation serine protease known as Factor Xa and thus are useful for the treatment or prophylaxis of those processes which involve the production and/or action of Factor Xa. Thus, the compounds of the invention are useful in the treatment or prevention of thrombotic events associated with coronary artery and cerebrovascular disease. This includes a number of thrombotic and prothrombotic states in which the coagulation cascade is activated which include, but are not limited to, formation of atherosclerotic plaques, venous or arterial thrombosis, coagulation syndromes, ischemia and angina (stable and unstable), deep vein thrombosis (DVT), disseminated intravascular coagulopathy, Kasabach-Merritt syndrome, pulmonary embolism, myocardial infarction, cerebral infarction, cerebral thrombosis, atrial fibrillation, cerebral embolism, thromboembolic complications of surgery (such as hip replacement, introduction of artificial heart valves and endarterectomy) and peripheral arterial occlusion. The compounds of the invention are also useful as inhibitors of blood coagulation such as during the preparation, storage and fractionation of whole blood.

The present compounds may also be useful in maintaining whole and fractionated blood in the fluid phase such as required for analytical and biological testing. Examples include, but are not limited to, ex vivo platelet and other cell function studies, bioanalytical procedures and quantitation of blood-containing components.

In addition, the compounds of the present invention may be useful to prevent restenosis following arterial injury induced by endogenous (rupture of an atherosclerotic plaque) or exogenous (invasive cardiological procedure such as vessel wall injury resulting from angioplasty) events.

The compounds of the present invention may also be used as an anticoagulant in extracorpeal blood circuits, such as those necessary in dialysis and surgery (such as coronary artery bypass surgery).

In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation.

The compounds of the present invention may be useful for the treatment of heparin-intolerant patients, including those with congenital and acquired antithrombin III deficiencies, heparin-induced thrombocytopenia, and those with high levels of polymorphonuclear granulocyte elastase.

The compounds of the present invention may also be useful for the treatment of inflammatory diseases and the prevention of septic shock and vascular damage due to bacterial and/or viral infections.

The compounds of the present invention may also be useful in the treatment of malignancies, prevention of metastases, prevention of prothrombotic complications of cancer, and as an adjunct to chemotherapy.

The compounds of the present invention may also be used in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like. The compounds of the present invention may act in a synergistic fashion with one or more of the above agents to prevent reclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention may also inhibit other serine proteases, for example, thrombin, Factor VIIa, urokinase-type plasminogen activator (urokinase), tryptase and/or trypsin. As a result, these compounds may additionally be useful as angiogenesis inhibitors in the treatment of cancer, as antiinflammatory agents particularly in the treatment of chronic asthma and in the treatment or prevention of allergic rhinitis, rheumatoid arthritis, inflammatory bowel disease, psoriasis, and conjunctivitis and in the treatment or prevention of pancreatitis.

The compounds of the present invention may also be used in combination with other antithrombotic or anticoagulant drugs such as thrombin inhibitors, platelet aggregation inhibitors such as clopidogrel, ticlopidine, PAI-1 inhibitors such as XR-330 and T-686, inhibitors of α-2-antiplasmin such as anti-α-2-antiplasmin antibody and thromboxane receptor antagonists (such as ifetroban), prostacyclin mimetics, phosphodiesterase (PDE) inhibitors, such as dipyridamole or cilostazol, PDE inhibitors in combination with thromboxane receptor antagonists/thromboxane A synthetase inhibitors (such as picotamide), serotonin-2-receptor antagonists (such as ketanserin), fibrinogen receptor antagonists, aspirin, hypolipidemic agents, (such as HMG-CoA reductase inhibitors for example pravastatin or simvastatin, or microsomal triglyceride transport protein inhibitors such as disclosed in U.S. Pat. Nos. 5,739,135, 5,712,279 and 5,760,246), antihypertensive agents, (such as angiotensin converting enzyme inhibitors, for example, captopril, lisinopril or fosinopril, angiotensin II receptor antagonists, for example, irbesartan, losartan or valsartan, and ACE/NEP inhibitors, for Example omapatrilat), PDE inhibitors in combination with aspirin, ifetroban, picotamide, ketanserin or clopidogrel and the like.

The compounds of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. The composition or carrier will contain about 5 to about 500 mg per unit of dosage of a compound or mixture of compounds of formulas I, IA., IB, IC and ID. They may be compounded in conventional matter with a physiologically acceptable vehicle or carrier, excipient, binder, preservative, stabilizer, flavor, etc., as called for by accepted pharmaceutical practice.

The following working Examples represent preferred embodiments of the present invention.

General Experimental and Definitions:
TFFH: Tetramethylfluoroformamidinium hexafluorophosphate.
EDCI and WSC: 1-[3-(dimethylamino)propyl]-3-ethylcarbodiimide hydrochloride.
DMF: N,N-dimethylformamide
Unless otherwise noted all mass spectral data are positive ion spectra.

The following conditions were used for HPLC:
Method A:
YMC A-ODS S-5, 4.6 mm×50 mm; 4 mL/min.; detection at 220 nm; solvent A=90:10 water:methanol, solvent B=10:90 water:methanol (both containing 0.2% phosphoric acid); 0% B to 100% B (4 min linear gradient) and then hold
Method C:
YMC A-ODS S-3, 4.6 mm×50 mm; 2.5 mL/min.; detection at 220 nm; solvent A=90:10 water:methanol, solvent B=10:90 water:methanol (both containing 0.2% phosphoric acid; 0% B to 100% B (8 min linear gradient) and then hold
Method B:
Zorbax, 4.5 mm×75 mm; 4.6 mm×15 cm; 2.5 mL/min.; detection at 220 nm; solvent A=90:10 water:methanol, solvent B=10:90 water:methanol (both containing 0.2% phosphoric acid; 0% B to 100% B (8 min linear gradient) and then hold
Method D:
Phenomenox LUNA S-5, 4.6 mm×50 mm; 4 mL/min.; detection at 220 nm; solvent A=90:10 water:methanol, solvent B=10:90 water:methanol (both containing 0.2% phosphoric acid); 0% B to 100% B (4 min linear gradient) and then hold
Method E:
Same as Method A with 0.2% trifluoroacetic acid in place of phosphoric acid
Method F:
YMC A-ODS S-5, 4.6 mm×50 mm; 4 mL/min.; detection at 220 nm; solvent A=90:10 water:methanol, solvent B=10:90 water:methanol (both containing 0.1% trifluoroacetic acid); 0% B to 100% B (4 min linear gradient) and then hold

EXAMPLE 1

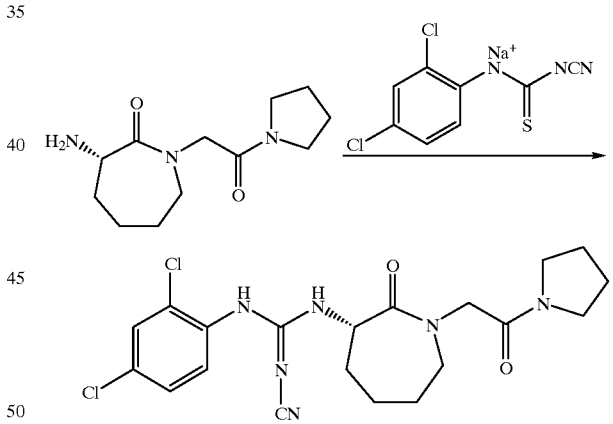

(S)-1-[(3-Amino-hexahydro-2-oxo-1H-azepin-1-yl) acetyl]pyrrolidine (53 mg, 0.22 mmol), N-cyano-N'-(2,4-dichlorophenyl)thiourea sodium salt (54 mg, 0.20 mol) and WSC (40 mg, 0.20 mmol) were stirred in ethanol (0.5 mL) and $CH_3CN$ (0.5 mL). After stirring at ambient temperature overnight, $CH_3CN$ (5 mL) was added. The reaction mixture was added to a SCX column (Varian Mega Bond Elute, 3 g SCX, pretreated 2×10 mL with MeOH and 1×10 mL with $CH_3CN$). The column was then washed with $CH_3CN$ (15 mL) and eluted with 50% MeOH/$CH_3CN$ (2×10 mL) and MeOH (10 mL). Evaporation of the product-containing fractions afforded crude product which was further purified by column chromatography (silica gel, 4% MeOH/$CH_2Cl_2$) to afford title compound (23 mg, 25%): LRMS (ESI) m/z 451; HPLC: (method A) $t_R$=3.64 min.

EXAMPLES 2 to 12

Using the methodology described in Example 1, the following compounds were prepared.

| Example | Structure | characterization |
|---|---|---|
| 2 | 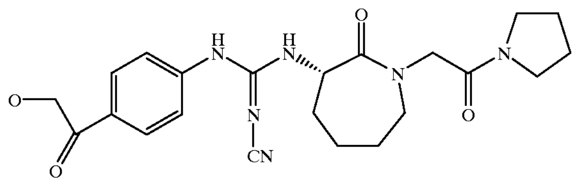 | LRMS (ESI) m/z 441<br>HPLC (method A)<br>$t_R$ = 3.26 min |
| 3 | 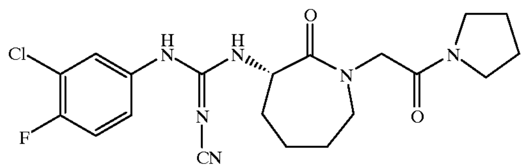 | LRMS (ESI) m/z 435<br>HPLC (method A)<br>$t_R$ = 3.54 min |
| 4 | 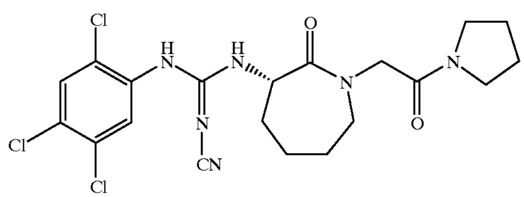 | LRMS (ESI) m/z 435<br>HPLC (method A)<br>$t_R$ = 3.89 min |
| 5 | 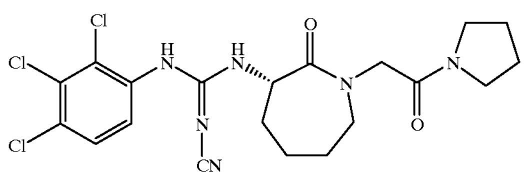 | LRMS (ESI) m/z 435<br>HPLC (method A)<br>$t_R$ = 3.90 min |
| 6 | 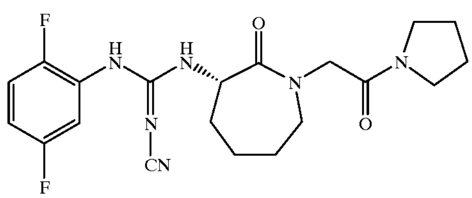 | LRMS (ESI) m/z 419<br>HPLC (method A)<br>$t_R$ = 3.13 min |
| 7 | 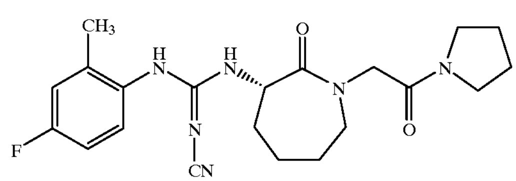 | LRMS (ESI) m/z 415<br>HPLC (method A)<br>$t_R$ = 3.30 min |
| 8 | 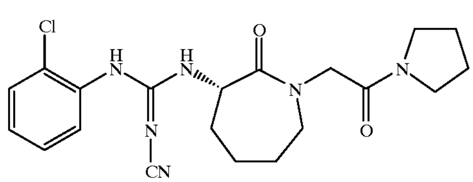 | LRMS (ESI) m/z 417<br>HPLC (method A)<br>$t_R$ = 3.26 min |

| Example | Structure | characterization |
|---|---|---|
| 9 | 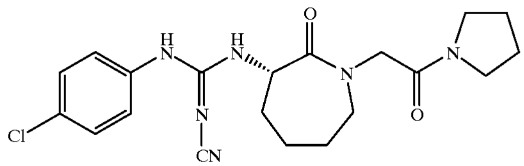 | LRMS (ESI) m/z 417<br>HPLC (method A)<br>$t_R$ = 3.53 min |
| 10 | 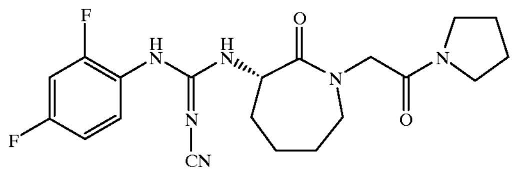 | LRMS (ESI) m/z 419<br>HPLC (method A)<br>$t_R$ = 3.20 min |
| 11 | 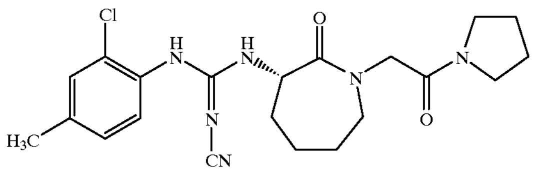 | LRMS (ESI) m/z 431<br>HPLC (method A)<br>$t_R$ = 3.76 min |
| 12 | 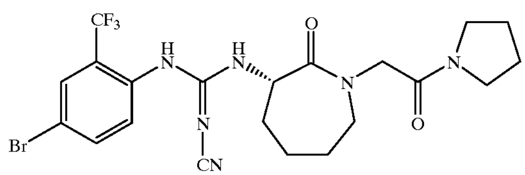 | LRMS (ESI) m/z 529<br>HPLC (method A)<br>$t_R$ = 3.79 min |

EXAMPLE 13

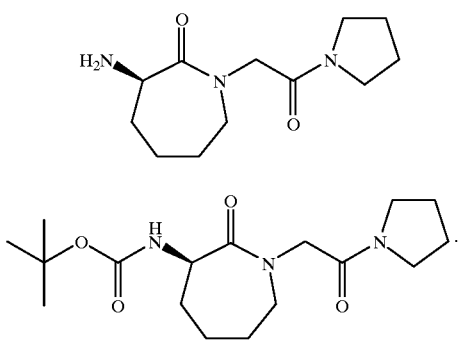

Lithium bis(trimethylsilyl)amnide (1 N in THF, 8.3 mL, 8.3 mmol) in THF (4 mL) was added dropwise over 2 h to a solution of 1,1-dimethylethyl [(3R)—hexahydro-2-oxo-1H-azepin-3-yl]carbamate (0.95 g, 4.1 mmol) in THF (70 mL) stirring at ambient temperature under argon. A solution of 1-(bromoacetyl)pyrrolidine (0.88 g, 4.6 mol) in THF (12 mL) was then added slowly over 15 min. After stirring at ambient temperature overnight, the reaction was quenched with 5% $KHSO_4$ and transferred to a separatory funnel with ethyl acetate. Washing with 5% $KHSO_4$ and brine and drying over $MgSO_4$ afforded 1.7 g of crude title product which was purified by column chromatography (silica gel, 3% MeOH/$CH_2Cl_2$) to afford pure product: (1.11 g, 80%); $^1$H-NMR (CDCl$_3$, δ) 5.94 (m, 1H), 4.44 (m, 1H), 4.22 (d, 1 H, J=16.1 Hz), 4.11 (d, 1 H, J=16.1 Hz), 3.71 (m, 1 H), 3.45 (m, 4 H), 3.28 (m, 1 H), 2.10–1.30 (m, 10 H), 1.44 (s, 9 H).

Part A compound (1.1 g, 3.3 mmol) and trifluoroacetic acid (3.7 g, 33 mmol) in $CH_2Cl_2$ (20 mL) were stirred at ambient temperature overnight. Evaporation and sequential azeotroping with $CH_2Cl_2$ and MeOH afforded the product as the TFA salt (1.6 g). Column chromatography (BIORAD AG-50W, H$^+$ Form, packed in 50% $H_2O$/MeOH) eluting with MeOH and then with 1.5 N $NH_3$ in MeOH afforded title amine (0.54 g, 69%): $^1$H-NMR (CDCl$_3$, δ) 4.33 (d, 1 H, J=16.1 Hz), 4.02 (d, 1 H, J=16.1 Hz), 3.62 (m, 2 H), 3.45 (m, 4 H), 3.28 (m, 1 H), 2.05–1.50 (m, 10 H); [α]$_D$ (CHCl$_3$, 4.9)=+11.4°.

EXAMPLES 14 to 17

Using the methodology described in Example 1 and Example 13, the following compounds were prepared from the Example 13 compound.

| Example | Structure | characterization |
|---|---|---|
| 14 | 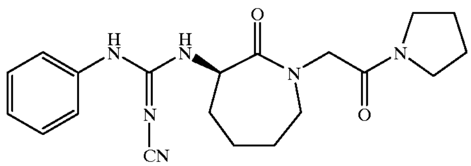 | LRMS (ESI) m/z 383<br>HPLC (method A)<br>$t_R$ = 3.19 min |
| 15 | 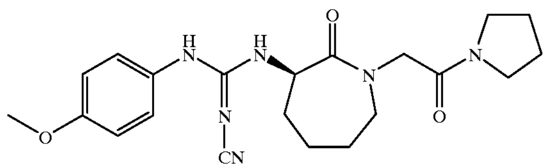 | LRMS (ESI) m/z 413<br>HPLC (method A)<br>$t_R$ = 3.25 min |
| 16 | 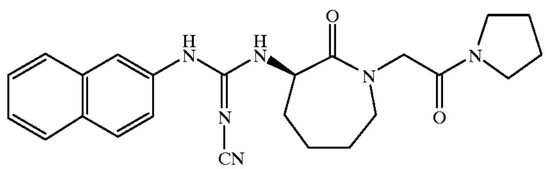 | LRMS (ESI) m/z 433<br>HPLC (method A)<br>$t_R$ = 3.71 min |
| 17 | 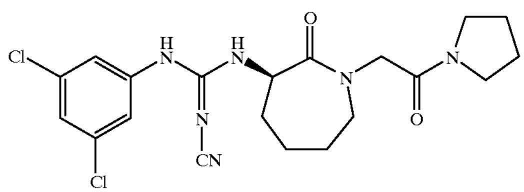 | LRMS (ESI) m/z 451<br>HPLC (method A)<br>$t_R$ = 3.96 min |

EXAMPLES 18–21

Using methodology described in Examples 1 and 13, the following compounds were prepared from 1,1-dimethylethyl ((S)-2-oxo-3-piperidinyl)carbamate.

| Example | Structure | characterization |
|---|---|---|
| 18 | 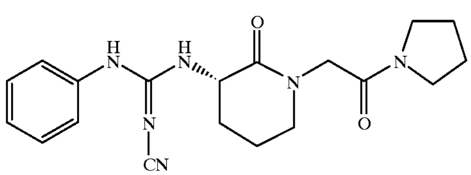 | LRMS (ESI) m/z 369<br>HPLC (method A)<br>$t_R$ = 2.76 min |
| 19 | 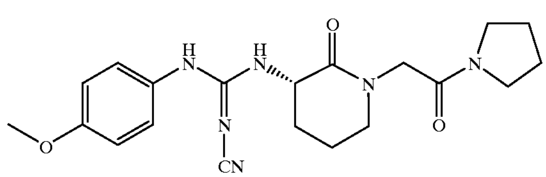 | LRMS (ESI) m/z 399<br>HPLC (method A)<br>$t_R$ = 2.84 min |
| 20 | 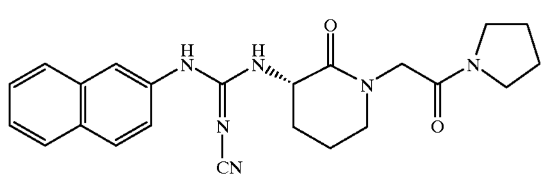 | LRMS (ESI) m/z 419<br>HPLC (method A)<br>$t_R$ = 3.44 min |

| Example | Structure | characterization |
|---|---|---|
| 21 | 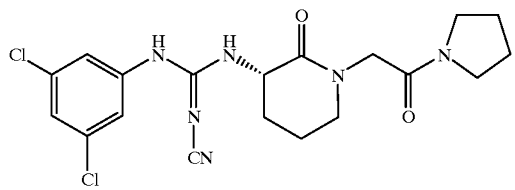 | LRMS (ESI) m/z 437<br>HPLC (method A)<br>$t_R$ = 3.78 min |

EXAMPLES 22 to 25

Using methodology described in Examples 1 and 13, the following compounds were prepared from 1,1-dimethylethyl [(3S)-2-oxo-3-pyrrolidinyl]carbamate.

| Example | Structure | characterization |
|---|---|---|
| 22 | 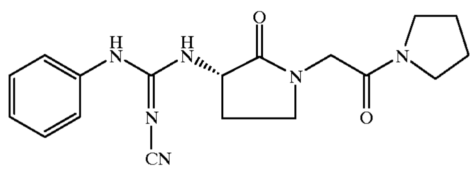 | LRMS (ESI) m/z 355<br>HPLC (method A)<br>$t_R$ = 2.48 min |
| 23 | 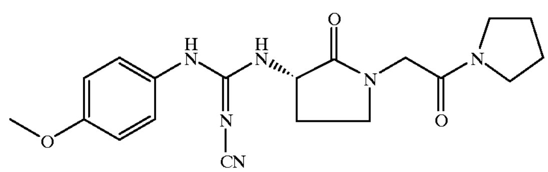 | LRMS (ESI) m/z 385<br>HPLC (method A)<br>$t_R$ = 2.61 min |
| 24 | 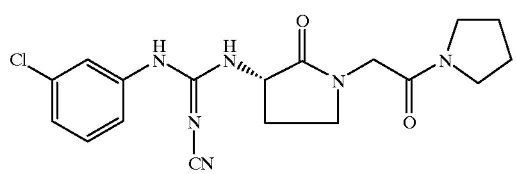 | LRMS (ESI) m/z 389<br>HPLC (method A)<br>$t_R$ = 3.04 min |
| 25 | 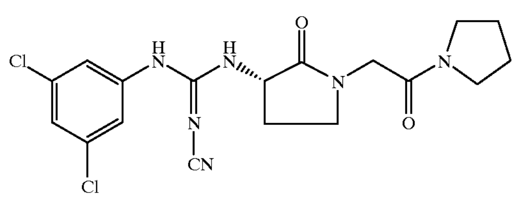 | LRMS (ESI) m/z 423<br>HPLC (method A)<br>$t_R$ = 3.59 min |

EXAMPLE 26

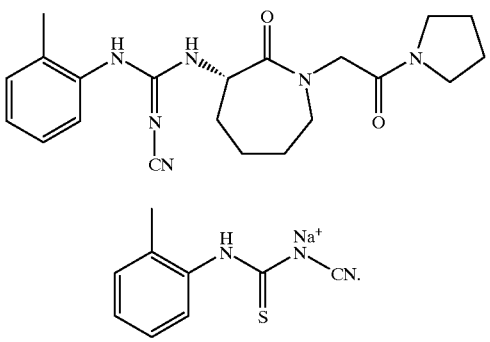

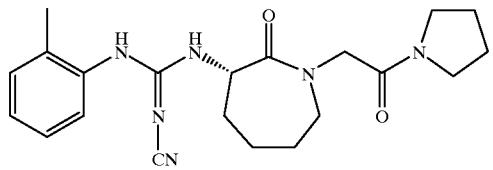

(2-Methyl)phenyl isothiocyanate (2.22 g, 14.8 mmol) and sodium cyanamide (1.06 g, 16.4 mmol) were dissolved in 70 mL of ethanol. The reaction mixture was stirred at 50° C. for 24 h. The ethanol was removed by rotary evaporation, and the resulting crude solid residue was triturated with 50 mL of ether. Title compound (2.80 g 88%) was obtained as a white solid by filtration.

(S)-1-[(3-Amino-hexahydro-2-oxo-1H-azepin-1-yl)acetyl]pyrrolidine (53 mg, 0.22 mmol) and Part A compound (43 mg, 0.20 mmol) were dissolved in 1 mL of DMF, and then WSC (40 mg, 0.20 mmol) was added. The reaction mixture was stirred at room temperature for 20 hours. The solvent was removed by rotary evaporation. The residue was diluted with 2 mL of acetonitrile and loaded onto an SCX cartridge (Varian Mega Bond Elute, 3 g SCX, prewashed with 20 mL of methanol and 20 mL of acetonitrile). The cartridge was eluted with 20 mL of acetonitrile and four 10-mL portions of 1:1 acetonitrile/methanol. Product-containing fractions were concentrated to provide title compound (59 mg, 75%): LRMS (ESI) m/z 397 (M+H); HPLC (method C) $t_R$=6.0 min.

EXAMPLES 27 to 60

Using the same methodology described for Title compound of Example 26, the following compounds were prepared. Some of the compounds required additional purification by preparative gradient HPLC after the SCX cartridge purification (YMC-pack ODS-A, solvent A: 90:10 $H_2O$:MeOH+0.2% TFA and solvent B: 10:90 $H_2O$:MeOH+0.2% TFA).

| Example | Structure | characterization |
|---|---|---|
| 27 | 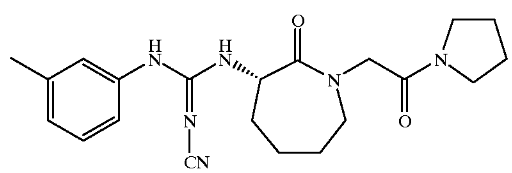 | HPLC (method C) $t_R$ = 6.4 min. LRMS (ESI) m/z 397 |
| 28 | 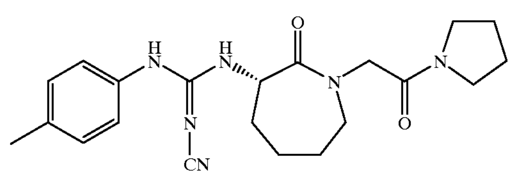 | HPLC (method C) $t_R$ = 6.4 min. LRMS (ESI) m/z 397 |
| 29 | 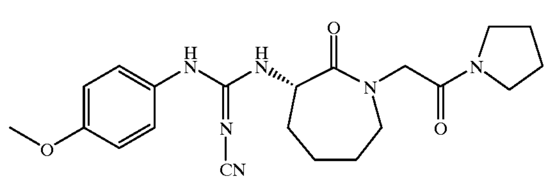 | HPLC (method C) $t_R$ = 5.9 min. LRMS (ESI) m/z 413 |
| 30 | 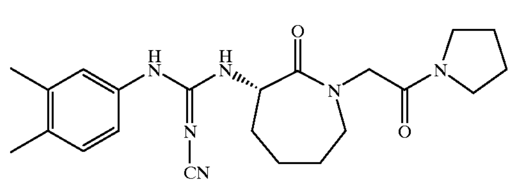 | HPLC (method C) $t_R$ = 6.9 min. LRMS (ESI) m/z 411 |

-continued
| Example | Structure | characterization |
|---|---|---|
| 31 | 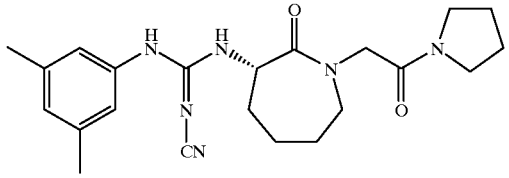 | HPLC (method C) $t_R$ = 7.0 min. LRMS (ESI) m/z 411 |
| 32 | 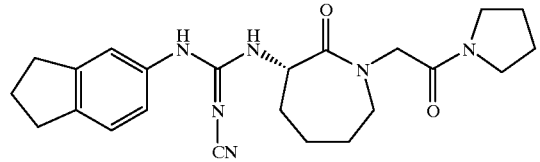 | HPLC (method C) $t_R$ = 7.2 min. LRMS (ESI) m/z 423 |
| 33 | 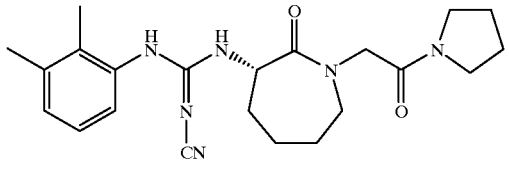 | HPLC (method C) $t_R$ = 6.2 min. LRMS (ESI) m/z 411 |
| 34 | 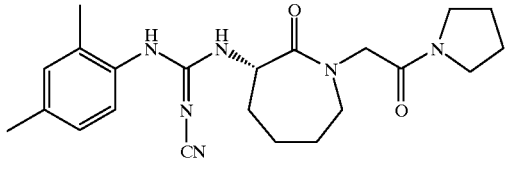 | HPLC (method C) $t_R$ = 6.3 min. LRMS (ESI) m/z 411 |
| 35 | 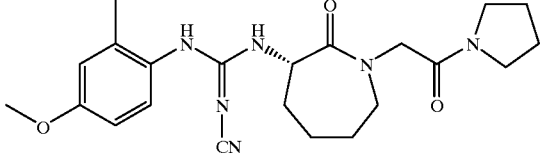 | HPLC (method C) $t_R$ = 5.8 min. LRMS (ESI) m/z 427 |
| 36 | 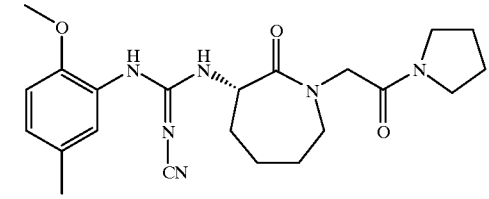 | HPLC (method C) $t_R$ = 6.0 min. LRMS (ESI) m/z 427 |
| 37 | 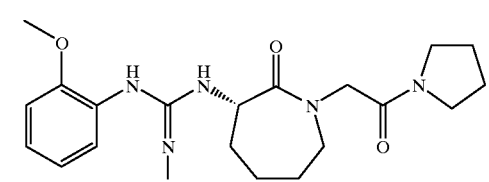 | HPLC (method C) $t_R$ = 5.5 min. LRMS (ESI) m/z 413 |
| 38 | 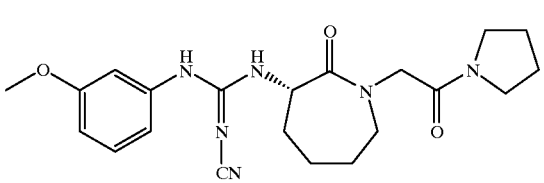 | HPLC (method C) $t_R$ = 5.7 min. LRMS (ESI) m/z 413 |

-continued

| Example | Structure | characterization |
|---|---|---|
| 39 | 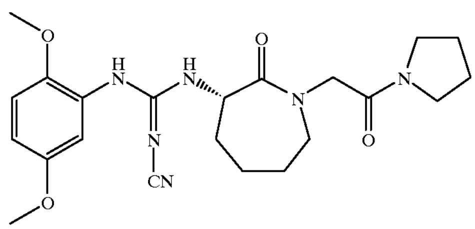 | HPLC (method C) $t_R$ = 5.6 min. LRMS (ESI) m/z 443 |
| 40 | 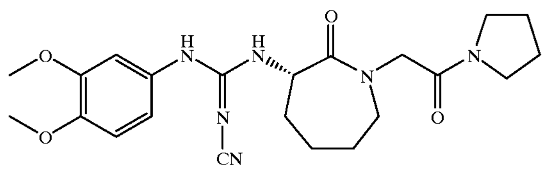 | HPLC (method C) $t_R$ = 5.3 min. LRMS (ESI) m/z 443 |
| 41 | 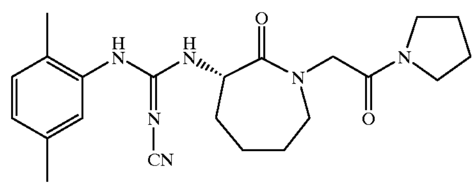 | HPLC (method C) $t_R$ = 6.2 min. LRMS (ESI) m/z 411 |
| 42 | 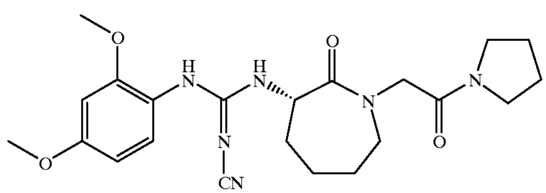 | HPLC (method C) $t_R$ = 5.6 min. LRMS (ESI) m/z 443 |
| 43 | 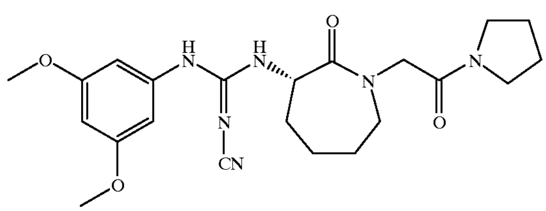 | HPLC (method C) $t_R$ = 6.0 min. LRMS (ESI) m/z 443 |
| 44 | 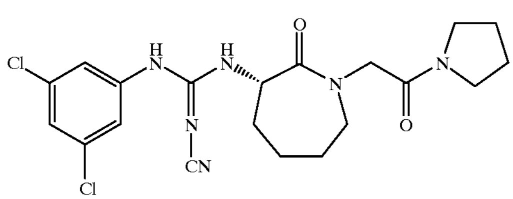 | HPLC (method C) $t_R$ = 6.4 min. LRMS (ESI) m/z 451 |
| 45 | 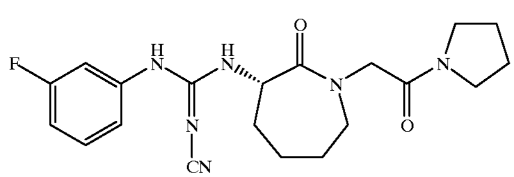 | HPLC (method C) $t_R$ = 6.4 min. LRMS (ESI) m/z 401 |

| Example | Structure | characterization |
|---|---|---|
| 46 | 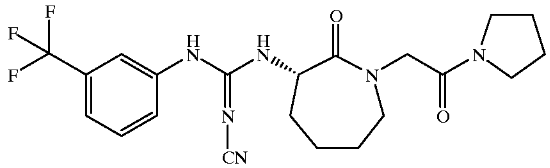 | HPLC (method C) $t_R$ = 7.4 min. LRMS (ESI) m/z 451 |
| 47 | 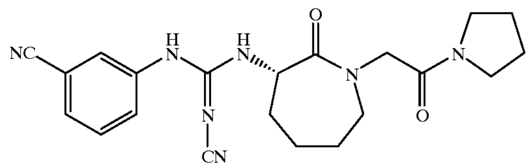 | HPLC (method C) $t_R$ = 5.9 min. LRMS (ESI) m/z 408 |
| 48 | 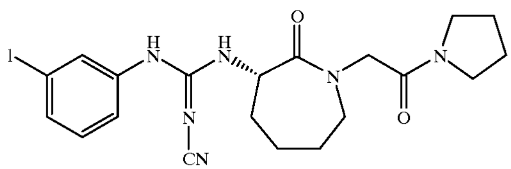 | HPLC (method C) $t_R$ = 7.4 min. LRMS (ESI) m/z 509 |
| 49 | 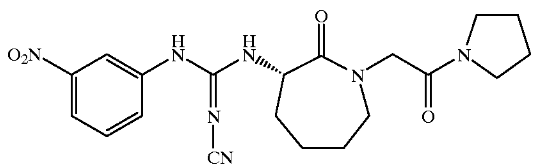 | HPLC (method C) $t_R$ = 6.3 min. LRMS (ESI) m/z 428 |
| 50 | 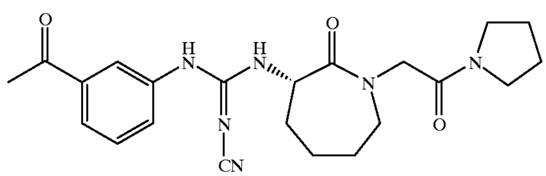 | HPLC (method C) $t_R$ = 6.0 min. LRMS (ESI) m/z 425 |
| 51 | 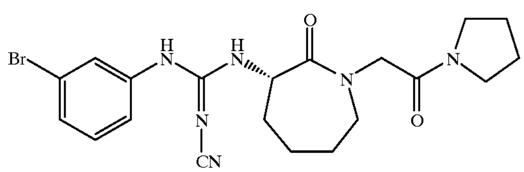 | HPLC (method C) $t_R$ = 7.2 min. LRMS (ESI) m/z 461 |
| 52 | 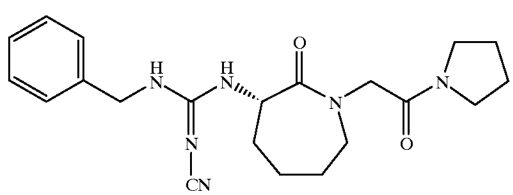 | HPLC (method C) $t_R$ = 5.7 min. LRMS (ESI) m/z 397 |
| 53 | 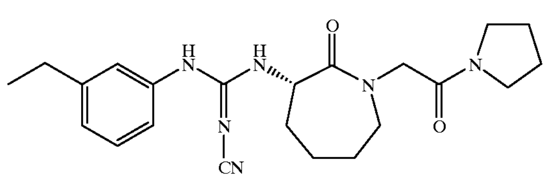 | HPLC (method C) $t_R$ = 6.5 min. LRMS (ESI) m/z 411 |

| Example | Structure | characterization |
|---|---|---|
| 54 | 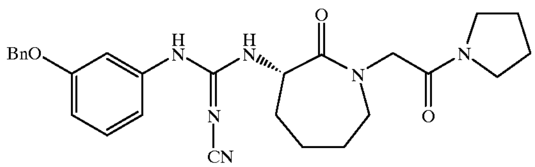 | HPLC (method C)<br>$t_R$ = 7.2 min.<br>LRMS (ESI) m/z<br>489 |
| 55 | 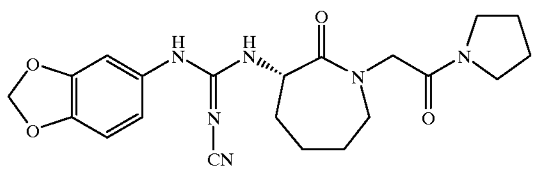 | HPLC (method C)<br>$t_R$ = 5.5 min.<br>LRMS (ESI) m/z<br>427 |
| 56 | 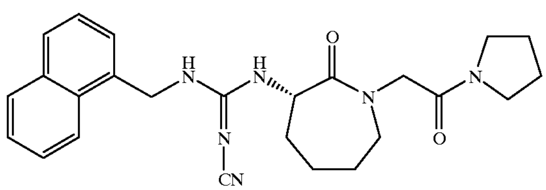 | HPLC (method B)<br>$t_R$ = 7.0 min.<br>LRMS (ESI) m/z<br>447 |
| 57 | 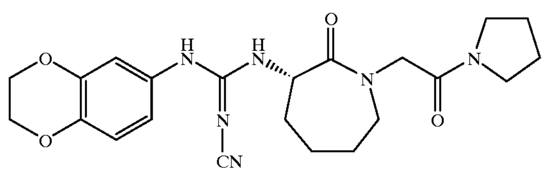 | HPLC (method B)<br>$t_R$ = 6.0 min.<br>LRMS (ESI) m/z<br>441 |
| 58 | 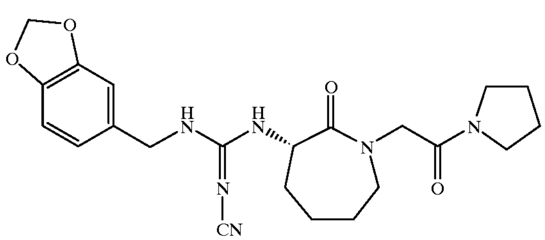 | HPLC (method B)<br>$t_R$ = 6.1 min.<br>LRMS (ESI) m/z<br>441 |
| 59 | 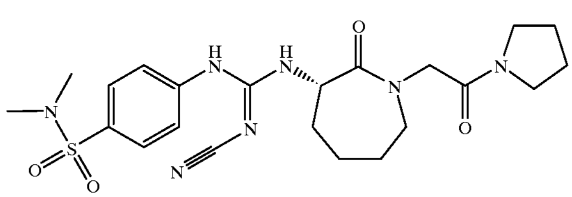 | HPLC (method D)<br>$t_R$ = 2.9 min.<br>LCMS (ESI) m/z<br>490 (M + H) |

| Example | Structure | characterization |
|---|---|---|
| 60 | 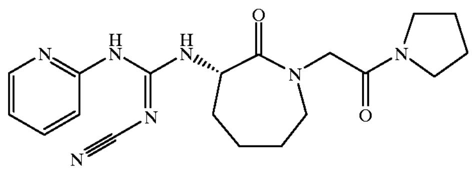 | HPLC (method D) $t_R$ = 2.0 min. LCMS (ESI) m/z 384 (M + H) |

EXAMPLE 61

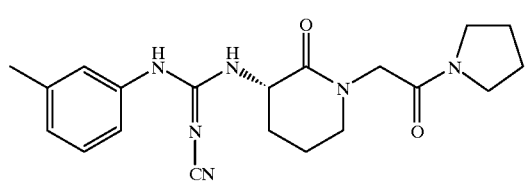

3-Methylaniline (21 mg, 0.20 mmol) and diphenyl cyanocarbonimidate(47 mg, 0.20 mmol) were stirred at 55° C. in ethyl acetate. After 5 hours, (S)-1-[(3-amino-2-oxo-1-piperidinyl)acetyl]pyrrolidine (50 mg, 0.22 mmol) was added and the reaction was stirred at 55° C. After stirring overnight, the reaction mixture was purified by column chromatography (silica gel, 5% MeOH/CH$_2$Cl$_2$) to afford title compound (69 mg, 90%): LRMS (ESI) m/z 383; HPLC (method A) $t_R$=3.14 min

EXAMPLES 62 to 65

Using the methodology described in Example 61, the following compounds were prepared. When amine hydrochloride salts were used, 1 equivalent of triethylamine was added to the reaction. For some reactions acetonitrile or DMF was used as solvent.

| Example | Structure | characterization |
|---|---|---|
| 62 | 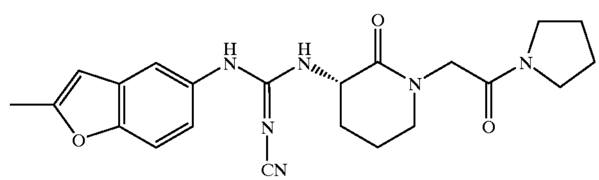 | LRMS (ESI) m/z 423 HPLC (method A) $t_R$ = 3.35 min |
| 63 | 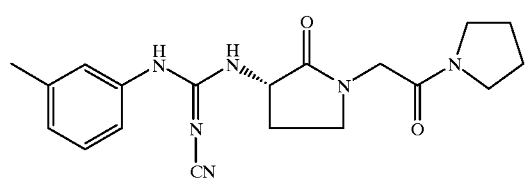 | LRMS (ESI) m/z 369 HPLC (method A) $t_R$ = 2.88 min |
| 64 | 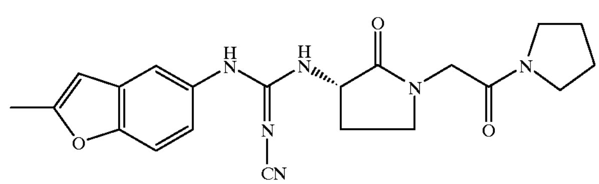 | LRMS (ESI) m/z 409 HPLC (method A) $t_R$ = 3.09 min |
| 65 | 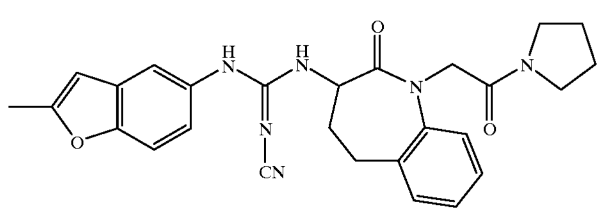 | LRMS (ESI) m/z 485 HPLC (method A) $t_R$ = 3.84 min |

EXAMPLE 66

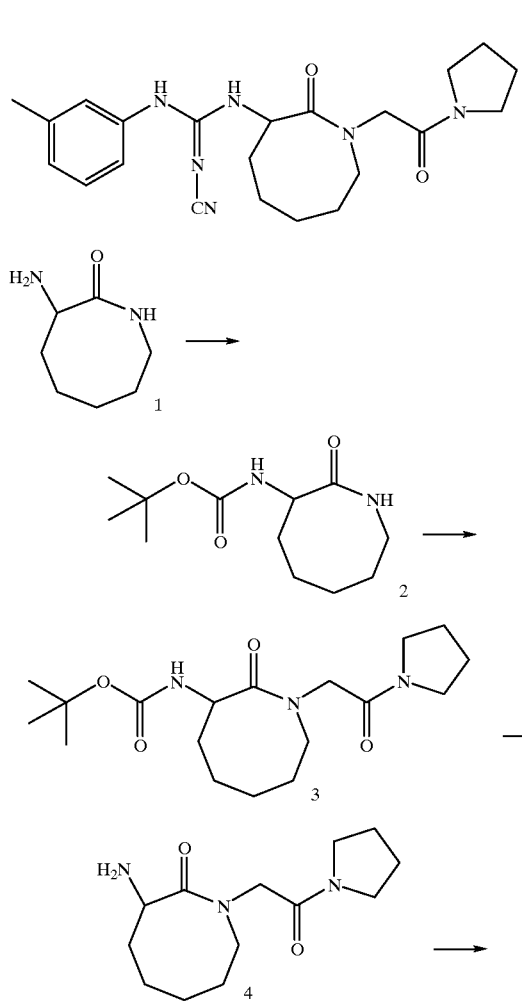

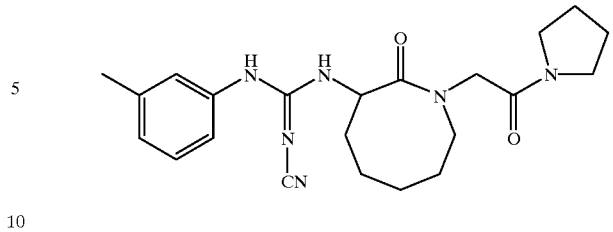

A. Preparation of 2. Boc-anhydride (1.7 g, 7.6 mmol) in CH$_2$Cl$_2$ (9 mL) was added to a solution of amine 1 (1.1 g, 6.4 mmol) and diisopropylethyl amine (1.1 g, 1.5 mL, 8.1 mmol) in CH$_2$Cl$_2$ (25 mL) stirring at 0° C. under argon. The ice bath was removed and the reaction stirred at ambient temperature overnight. Washing the reaction solution with 1 N NaOH, 5% KHSO$_4$, and water, and drying over MgSO$_4$ afforded 2.5 g of crude product after evaporation of the solvent. Column chromatography (silica gel, 4% MeOH/CH$_2$Cl$_2$) afforded part A compound 2 (0.70 g, 45%): $^1$H-NMR (CDCl$_3$, δ) 5.70 (m, 1 H), 5.52 (m, 1H), 4.58 (m, 1 H), 3.55 (m, 1 H), 3.25 (m, 1 H), 2.07 (m, 1 H), 1.62 (m, 7 H), 1.44 (s, 9 H)

B. Preparation of 4. Using methodology described in Example 13 Part A lactam was transformed to compound 4.

C. Preparation of Title Compound. Using the methodology described in Example 26, compound 4 was converted to title compound: LRMS (ESI) m/z 411 (M+H); HPLC (method A) $t_R$=3.52 min.

EXAMPLE 67

Using the methodology described in Examples 61 or 66 the following compound was prepared from 4.

| Example | Structure | characterization |
|---|---|---|
| 67 | 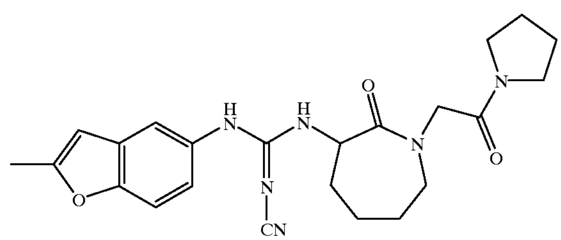 | LRMS (ESI) m/z 451<br>HPLC (method A) $t_R$ = 3.70 min |

EXAMPLE 68

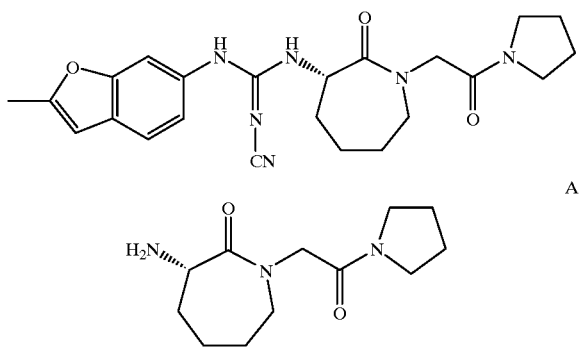

A

To a 0° C. solution of (3S)-aminohexahydro-2H-azapin-2-one (200 g, 1.56 mol) in 2 N NaOH (2 L) was added benzyl chloroformate (272 mL, 1.81 mol) over 2 h. After stirring 1 h at 0° C. and at room temperature for 1 h, the precipitate was collected by filtration, washed with water (4×2 L), heptane (4×5 L) and dried to provide 396 g, 100%) of [(3S)-hexahydro-2-oxo-1H-azapin-3 yl]carbamic acid phenylmethyl ester.

To a −10° C. solution of [(3S)-hexahydro-2-oxo-1H-azapin-3yl]carbamic acid phenylmethyl ester (1 kg, 3.8 mol) in THF (10 L) was added lithium hexamethyldisilamide (1 N in THF, 5 L). After 30 min, methyl bromoacetate (4.3 mol) was added. After 1 h, pyrrolidine (7.3 mol) was added. The reaction was stirred overnight at room temperature. Over 30 min, 2 N HCl (2 L) was added. In vacuo, 7.5 L of solvent was removed. Ethyl acetate (7.5 L) was added. The organic layer was washed with 2 N HCl. The combined aqueous layers were extracted with ethyl acetate (2×1 L). The combined organic layers were washed with saturated sodium bicarbonate (2×1.5 L) and were then concentrated. The residue was crystallized from ethyl acetate/heptane to provide 1.1 kg (75%) of 1-[((3S)-3-[(phenylmethoxy)carbonyl] amino-hexahydro-2-oxo-1H-azepin-1-yl)acetyl]pyrrolidine.

To a 30° C. mixture of 1-[((3S)-3-[(phenylmethoxy) carbonyl]amino-hexahydro-2-oxo-1H-azepin-1-yl)acetyl] pyrrolidine (20 g, 54 mmol), ethanol (100 mL), THF (100 mL) and wet 10% Pd/C (4 g) was added ammonium formate (5.1 g, 81 mmol) over 45 min. After stirring for 3 h, the reaction was cooled to room temperature and filtered. The filtrate was concentrated, taken up in TBME (150 mL) and filtered again. The filtrate was concentrated in vacuo to provide 12.3 g (95%) of (S)-1-[(3-amino-hexahydro-2-oxo-1H-azepin-1-yl)acetyl]pyrrolidine.

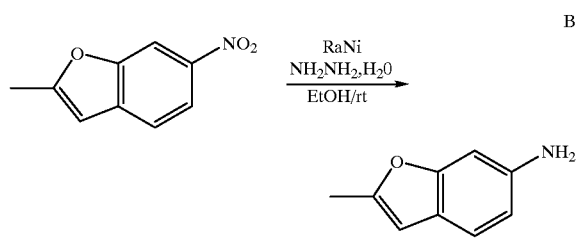

B

To a suspension of excess Raney nickel in ethanol (3 mL) was added 2-methyl-6-nitrobenzofuran (300 mg, 1.69 mmol). Hydrazine hydrate (153 mg, 3.06 mmol) was then added and the flask was capped at room temperature (rt). The flask was periodically vented to avoid over-pressurization as gas evolution occured. After 60 minutes, the reaction mixture was filtered through Celite and the filtrate concentrated in vacuo to provide 200 mg (81%) of a brown oil: LC-MS (method F, ESI) m/z 148 (M+H), $t_R$=1.7 min

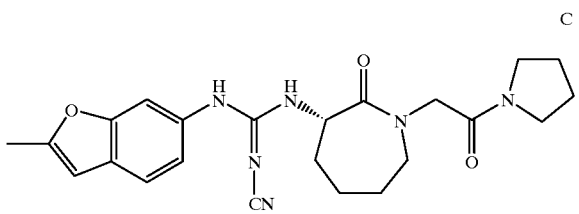

C

To Part B compound (55 mg, 0.37 mmol) in ethyl acetate (1 mL) was added diphenyl cyanocarbonimidate (88 mg, 0.37 mmol) and the mixture was heated at reflux for 30 minutes. After cooling to room temperature, (S)-1-[(3-amino-hexahydro-2-oxo-1H-azepin-1-yl)acetyl]pyrrolidine (88 mg, 0.37 mmol) was added and the resultant mixture heated for an additional 120 minutes. The reaction mixture was placed directly on a silica column and the product eluted with 2% methanol in chloroform. The product-containing fractions were then further purified by elution through a reverse-phase cartridge (Varian C-18 Mega Bond Elut) eluting with a gradient of 100% water to 100% methanol. Concentration of product-containing fractions provided 53 mg (33%) of title compound as a white powder: LC-MS (method F, ESI) m/z 437 (M+H), $t_R$=3.7 min.

EXAMPLE 69

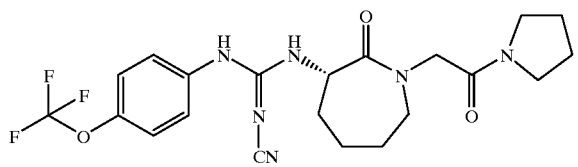

A suspension of 4-(trifluoromethoxy)aniline (26 mg, 0.15 mmol) and diphenyl cyanocarbonimidate (35 mg, 0.15 mmol) in ethanol (0.3 mL) was heated at 70° C. for 10 hours. (S)-1-[(3-amino-hexahydro-2-oxo-1H-azepin-1-yl)acetyl]pyrrolidine (36 mg, 0.15 mmol) was then added, and the reaction mixture was stirred at 80° C. for 10 hours. The resulting solution was concentrated to give a yellow oil which was purified by flash chromatography (silica gel, 2 to 9% methanol in dichloromethane) to provide title compound in the form of a white solid (37 mg, 54%): LRMS (ESI) m/z 467 (M+H); HPLC (method A) $t_R$=3.79 min.

EXAMPLES 70 to 73

Using the methodology described for the title compound of Example 69, the following compounds were prepared.

| Example | Structure | Characterization |
|---|---|---|
| 70 | 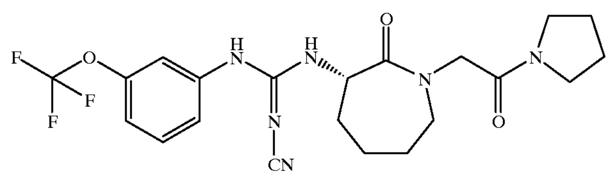 | LRMS (ESI) m/z 467<br>HPLC (method A) $t_R$ = 3.8 min. |
| 71 | 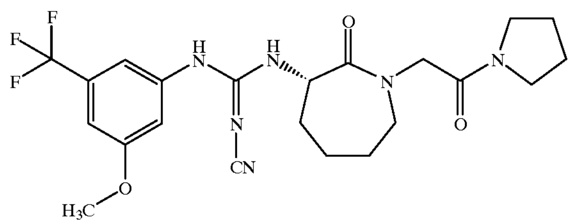 | LRMS (ESI) m/z 481<br>HPLC (method A) $t_R$ = 3.9 min. |
| 72 | 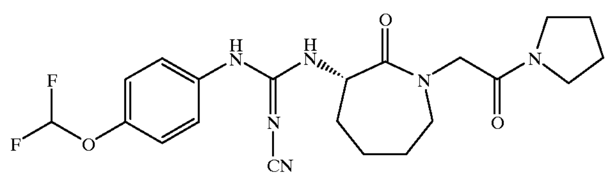 | LRMS (ESI) m/z 449<br>HPLC (method A) $t_R$ = 3.5 min. |
| 73 | 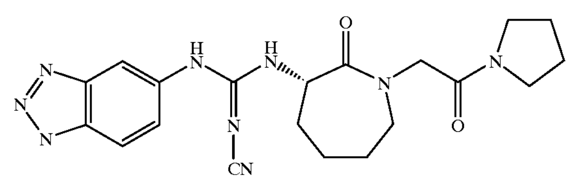 | LRMS (ESI) m/z 424<br>HPLC (method A) $t_R$ = 2.8 min. |

EXAMPLE 74

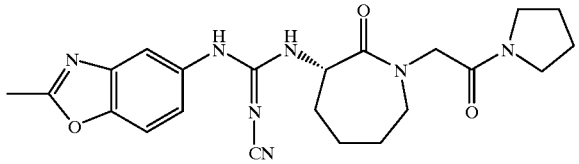

A solution of 2-methyl-5-benzoxazolamine (20 mg, 0.14 mmol) and diphenyl cyanocarbonimidate (32 mg, 0.13 mmol) in DMF (0.3 mL) was heated at 70° C. for 4 hours. (S)-1-[(3-amino-hexahydro-2-oxo-1H-azepin- 1-yl)acetyl] pyrrolidine (36 mg, 0.15 mmol) was then added, and the reaction mixture was stirred at 80° C. for 12 hours. The resulting solution was concentrated to give a yellow oil which was purified by flash chromatography (silica gel, 1 to 4% methanol in dichloromethane) to provide title compound in the form of a white solid (25 mg, 43%): LRMS (ESI) m/z 438; HPLC (method A) $t_R$=3.1 min.

EXAMPLES 75 to 105

Using the methodology described for the title compound in Example 74, the following compounds were prepared. For some compounds acetonitrile was used in place of DMF.

| Example | Structure | Characterization |
|---|---|---|
| 75 | 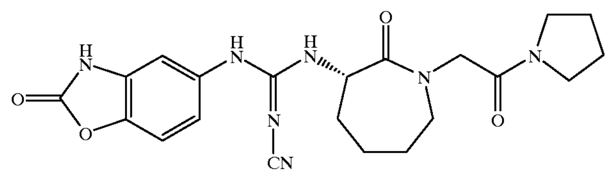 | LRMS (ESI) m/z 440<br>HPLC (method A)<br>$t_R$ = 2.79 min. |
| 76 | 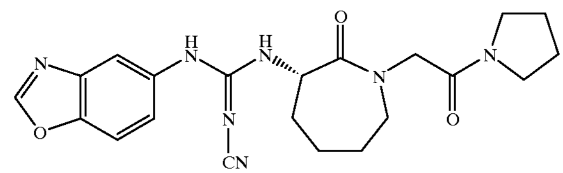 | LRMS (ESI) m/z 424<br>HPLC (method A)<br>$t_R$ = 2.87 min. |
| 77 | 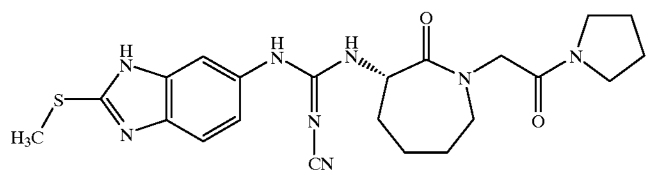 | LRMS (ESI) m/z 469<br>HPLC (method A)<br>$t_R$ = 2.43 min. |
| 78 | 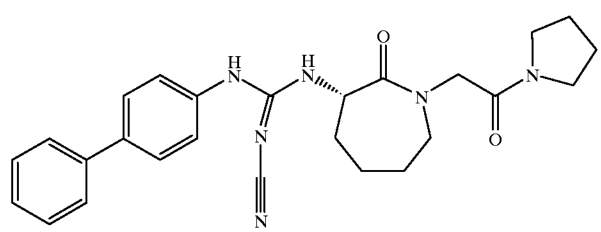 | HPLC (method D)<br>$t_R$ = 3.8 min<br>LCMS (ESI) m/z 459 (M+H) |
| 79 | 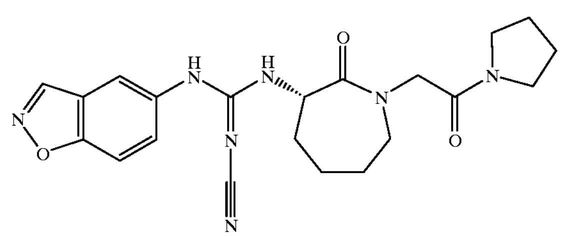 | HPLC (method D)<br>$t_R$ = 2.7 min<br>LCMS (ESI) m/z 424 (M+H) |
| 80 | 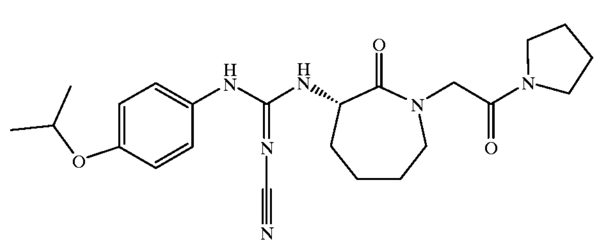 | HPLC (method D)<br>$t_R$ = 3.3 min<br>LCMS (ESI) m/z 441 (M+H) |

-continued
| Example | Structure | Characterization |
|---|---|---|
| 81 | 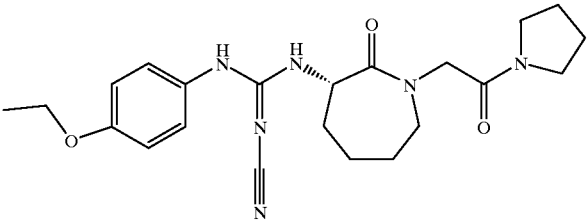 | HPLC (method D)<br>$t_R$ = 3.3 min<br>LCMS (ESI) m/z<br>427 (M+H) |
| 82 | 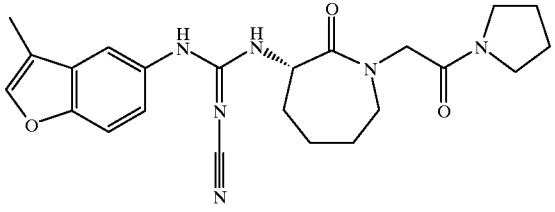 | HPLC (method D)<br>$t_R$ = 3.5 min<br>LCMS (ESI) m/z<br>437 (M+H) |
| 83 | 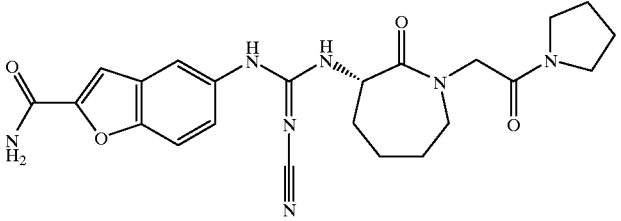 | HPLC (method D)<br>$t_R$ = 2.7 min<br>LCMS (ESI) m/z<br>466 (M+H) |
| 84 | 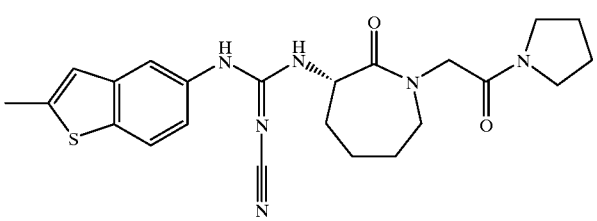 | HPLC (method D)<br>$t_R$ = 3.6 min<br>LCMS (ESI) m/z<br>453 (M+H) |
| 85 | 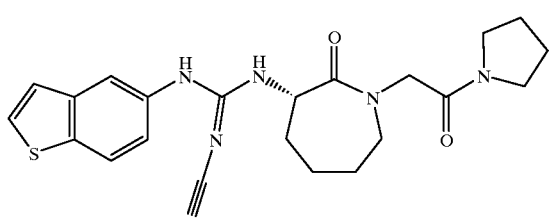 | HPLC (method D)<br>$t_R$ = 3.4 min<br>LCMS (ESI) m/z<br>439 (M+H) |
| 86 | 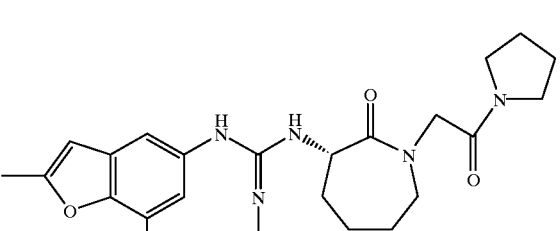 | HPLC (method D)<br>$t_R$ = 3.6 min<br>LCMS (ESI) m/z<br>455 (M+H) |

-continued

| Example | Structure | Characterization |
|---|---|---|
| 87 | 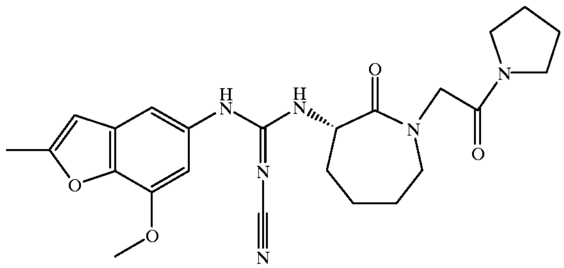 | HPLC (method D) $t_R$ = 3.4 min LCMS (ESI) m/z 467 (M+H) |
| 88 | 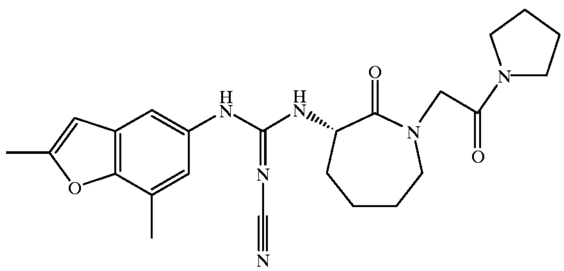 | HPLC (method D) $t_R$ = 3.7 min LCMS (ESI) m/z 451 (M+H) |
| 89 | 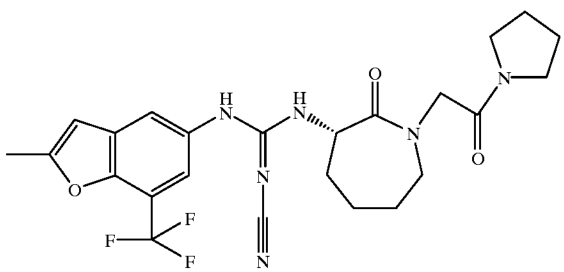 | HPLC (method D) $t_R$ = 3.8 min LCMS (ESI) m/z 505 (M+H) |
| 90 | 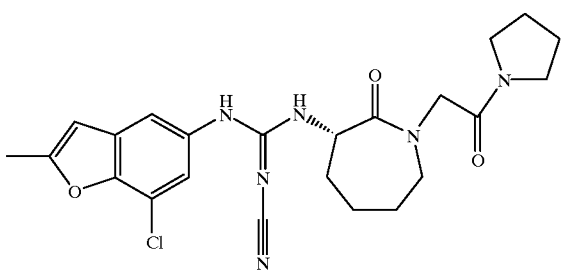 | HPLC (method D) $t_R$ = 3.7 min LCMS (ESI) m/z 471 (M+H) |
| 91 | 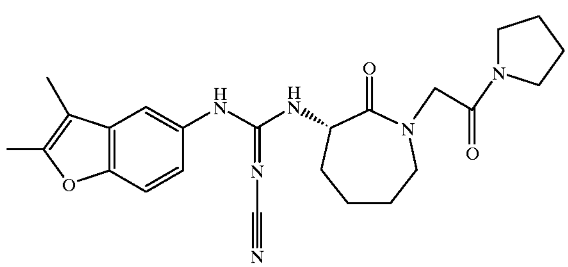 | HPLC (method D) $t_R$ = 3.7 min LCMS (ESI) m/z 451 (M+H) |

-continued

| Example | Structure | Characterization |
|---------|-----------|------------------|
| 92 | 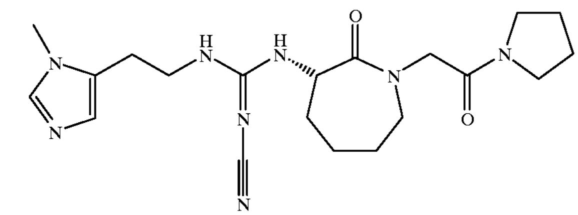 | HPLC (method A)<br>$t_R$ = 1.8 min<br>LRMS (ESI) m/z<br>415 (M+H) |
| 93 | 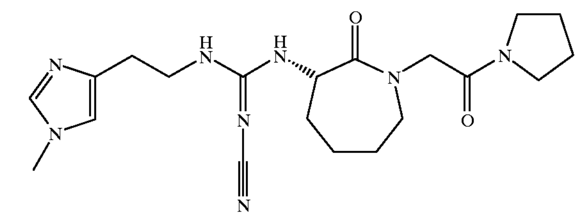 | HPLC (method A)<br>$t_R$ = 1.8 min<br>LRMS (ESI) m/z<br>415 (M+H) |
| 94 | 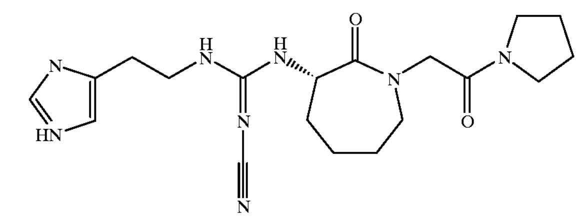 | HPLC (method A)<br>$t_R$ = 1.8 min<br>LRMS (ESI) m/z<br>401 (M+H) |
| 95 | 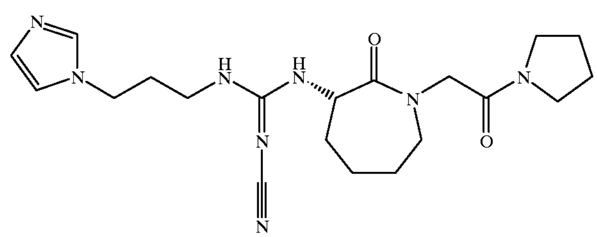 | HPLC (method A)<br>$t_R$ = 1.8 min<br>LRMS (ESI) m/z<br>415 (M+H) |
| 96 | 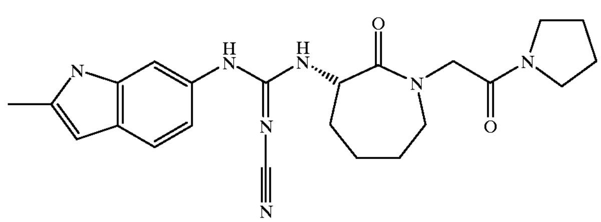 | HPLC (method A)<br>$t_R$ = 3.5 min<br>LRMS (ESI) m/z<br>436 (M+H) |
| 97 | 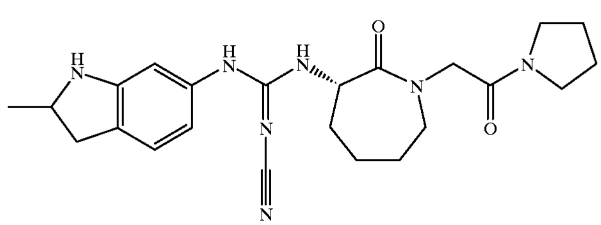 | HPLC (method A)<br>$t_R$ = 2.4 min<br>LRMS (ESI) m/z<br>438 (M+H) |

-continued

| Example | Structure | Characterization |
| --- | --- | --- |
| 98 | 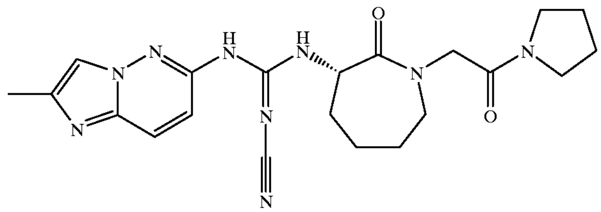 | HPLC (method A)<br>$t_R$ = 2.7 min<br>LRMS (ESI) m/z<br>438 (M+H) |
| 99 | 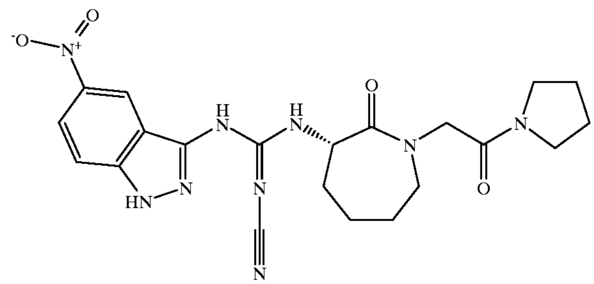 | HPLC (method A)<br>$t_R$ = 3.4 min<br>LRMS (ESI) m/z<br>468 (M+H) |
| 100 | 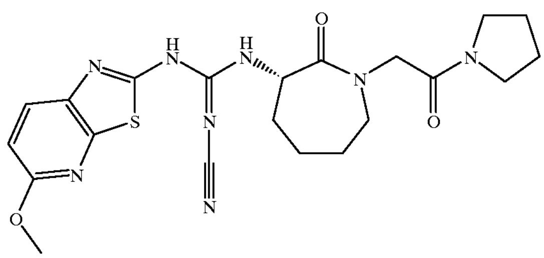 | HPLC (method A)<br>$t_R$ = 2.7 min<br>LRMS (ESI) m/z<br>471 (M+H) |
| 101 | 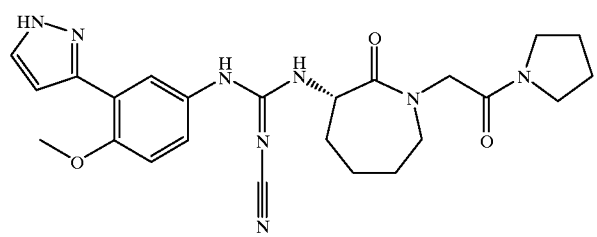 | HPLC (method A)<br>$t_R$ = 3.3 min<br>LRMS (ESI) m/z<br>479 (M+H) |
| 102 | 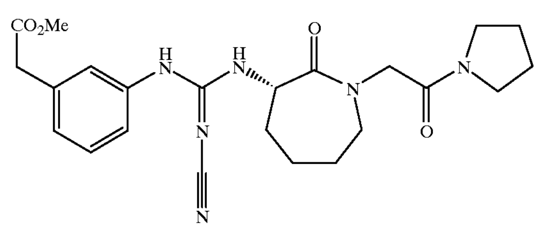 | HPLC (method A)<br>$t_R$ = 3.5 min<br>LRMS (ESI) m/z<br>455 (M+H) |
| 103 | 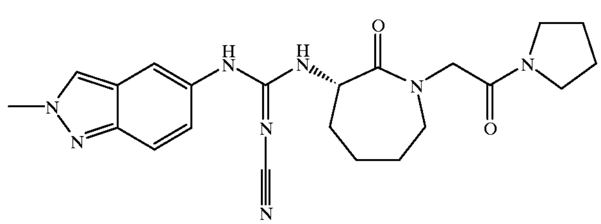 | HPLC (method A)<br>$t_R$ = 3.4 min<br>LRMS (ESI) m/z<br>437 (M+H) |

| Example | Structure | Characterization |
|---|---|---|
| 104 | 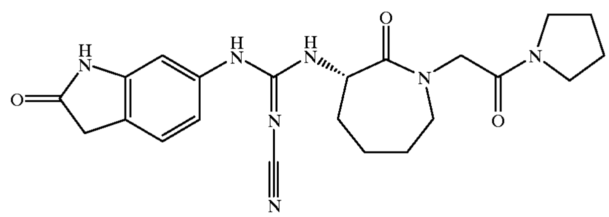 | HPLC (method A)<br>$t_R$ = 3.0 min<br>LRMS (ESI) m/z<br>438 (M+H) |
| 105 | 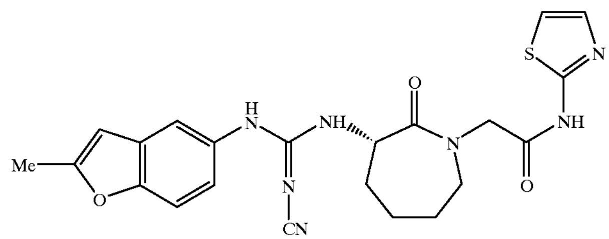 | HPLC (method A)<br>$t_R$ = 3.7 min<br>LRMS (ESI) m/z<br>466 (M+H) |

EXAMPLE 106

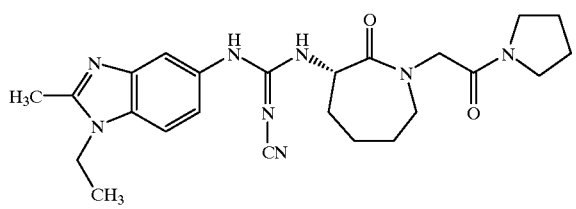

A solution of 1-ethyl-2-methyl-1H-Benzimidazol-5-amine hydrochloride (21 mg, 0.09 mmol), diphenyl cyanocarbonimidate (20 mg, 0.08 mmol) and triethylamine (0.03 mL, 0.18 mmol) in DMF (0.2 mL) was heated at 60° C. for 6 hours. (S)-1-[(3-amino-hexahydro-2-oxo-1H-azepin-1-yl)acetyl]pyrrolidine (20 mg, 0.08 mmol) was then added, and the reaction mixture was stirred at 80° C. for 14 hours. The resulting solution was concentrated, and the residue was purified by preparative HPLC to provide title compound in the form of a white solid (14 mg, 36%): LRMS (ESI) m/z 465; HPLC (method A) $t_R$=2.31 min

EXAMPLE 107

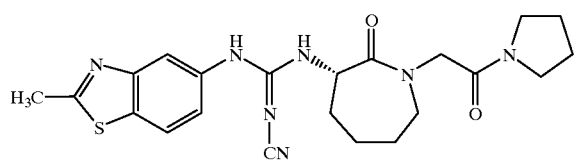

A

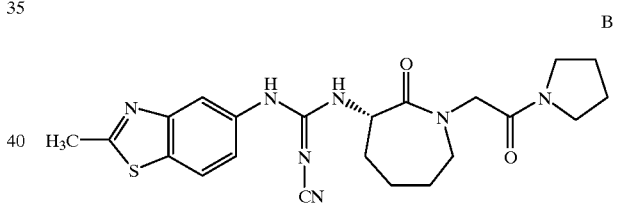

2-Methyl 5-benzothiazolamine (0.32 g, 2.0 mmol) and diphenyl cyanocarbonimidate (0.48 g 2.0 mmol) were dissolved in 5 mL of ethanol. The reaction mixture was stirred at room temperature for 24 hours and then concentrated by rotary evaporation. The residue was dissolved in 50 mL of methylene chloride and the organic solution was washed with 50 mL of 5% $KHSO_4$ and 50 mL of brine. The organic layer was dried over $MgSO_4$ and concentrated to give part A compound (0.62 g, 99%).

B

Part A compound (62 mg 0.2 mmol) and (S)-1-[(3-amino-hexahydro-2-oxo-1H-azepin-1-yl)acetyl]pyrrolidine (48 mg, 0.2 mmol) were dissolved in 1 mL of ethanol. The reaction mixture was stirred at 60° C. for 24 hours and the solvent was removed by rotary evaporation. Title compound (40 mg, 45%) was obtained after purification by preparative HPLC: LRMS (ESI) m/z 454; HPLC (method A) $t_R$=3.2 min.

EXAMPLES 108 to 113

Using the same methodology described for title compound of Example 107, the following compounds were prepared.

| Example | Structure | Characterization |
|---|---|---|
| 108 | 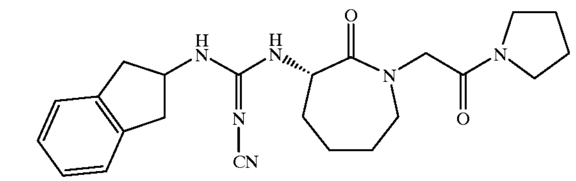 | HPLC (method A) $t_R$ = 3.5 min. LRMS (ESI) m/z 423 |
| 109 | 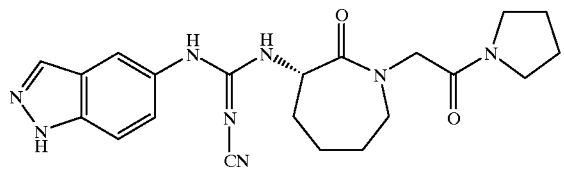 | HPLC (method A) $t_R$ = 2.7 min. LRMS (ESI) m/z 423 |
| 110 | 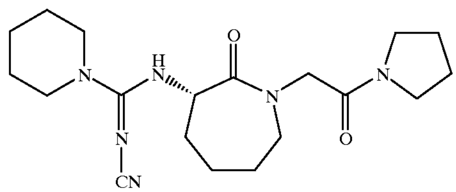 | HPLC (method A) $t_R$ = 2.9 min. LRMS (ESI) m/z 375 |
| 111 | 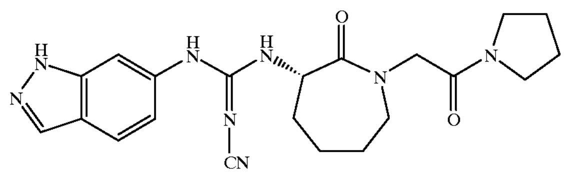 | HPLC (method A) $t_R$ = 2.9 min. LRMS (ESI) m/z 423 |
| 112 | 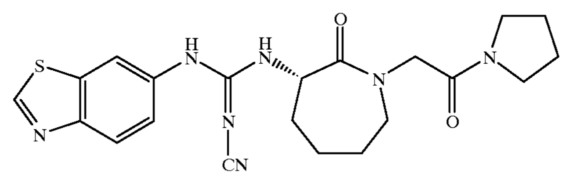 | HPLC (method A) $t_R$ = 2.9 min. LRMS (ESI) m/z 440 |
| 113 | 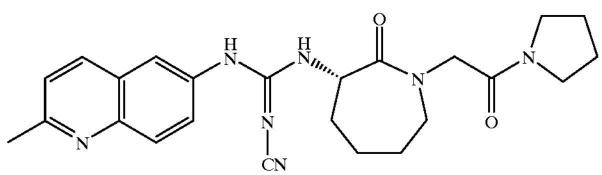 | HPLC (method A) $t_R$ = 2.2 min. LRMS (ESI) m/z 448 |

EXAMPLE 114

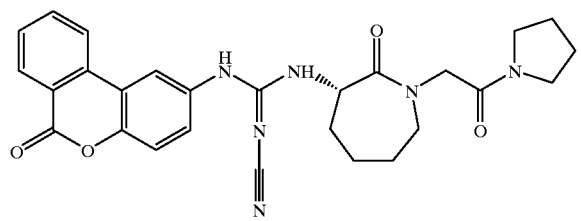

2-amino-6H-Dibenzo[b,d]pyran-6-one (52.8 mg, 0.250 mmol) and diphenyl cyanocarbonimidate (49.8 mg, 0.209 mmol) were dissolved in DMF (0.3 mL). The reaction mixture was heated at 50° C. for 8 h. (S)-1-[(3-amino-hexahydro-2-oxo-1H-azepin-1-yl)acetyl]pyrrolidine (50.0 mg, 0.209 mmol) was added and the reaction mixture was heated at 50° C. for another 40 h. Flash chromatography (silica, ethyl acetate) gave the Title compound as a white solid (51.2 mg, 49%): HPLC (method A) $t_R$=3.60 min; LRMS (ESI) m/z 501 (M+H).

EXAMPLES 115 to 135

Using the procedure described in Example 114 the following compounds were prepared.

| Example | Structure | characterization |
|---|---|---|
| 115 | 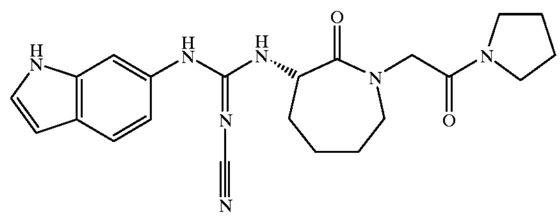 | HPLC (method A) $t_R$ = 3.31 min LRMS (ESI) m/z 422 (M+H) |
| 116 | 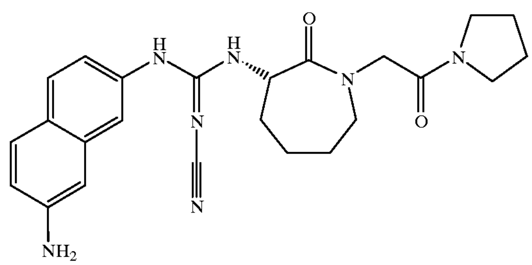 | HPLC (method A) $t_R$ = 2.5 min LRMS (ESI) m/z 448 (M+H) |
| 117 | 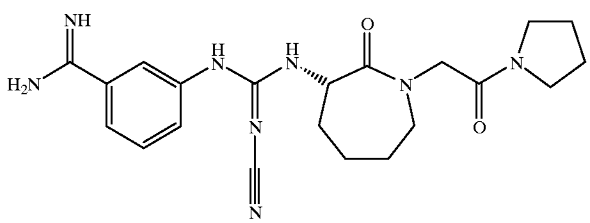 | HPLC (method A) $t_R$ = 2.09 min LRMS (ESI) m/z 425 (M+H) |
| 118 | 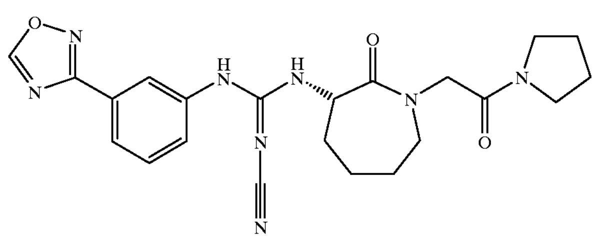 | HPLC (method A) $t_R$ = 3.13 min LRMS (ESI) m/z 451 (M+H) |
| 119 | 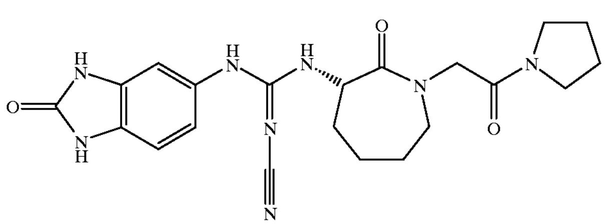 | HPLC (method A) $t_R$ = 2.59 min LRMS (ESI) m/z 439 (M+H) |
| 120 | 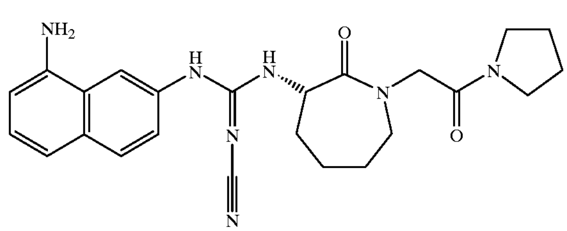 | HPLC (method A) $t_R$ = 2.80 min LRMS (ESI) m/z 448 (M+H) |

-continued

| Example | Structure | characterization |
| --- | --- | --- |
| 121 | 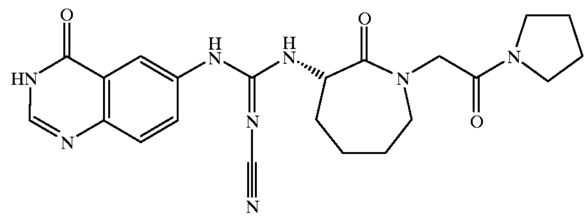 | HPLC (method A) $t_R$ = 2.59 min LRMS (ESI) m/z 451 (M+H) |
| 122 | 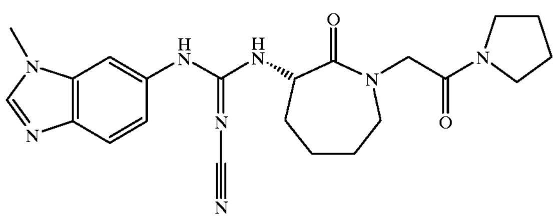 | HPLC (method A) $t_R$ = 2.04 min LRMS (ESI) m/z 437 (M+H) |
| 123 | 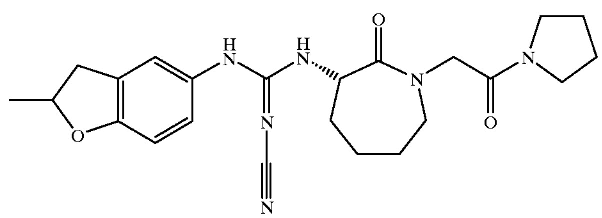 | HPLC (method A) $t_R$ = 3.46 min LRMS (ESI) m/z 439 (M+H) |
| 124 | 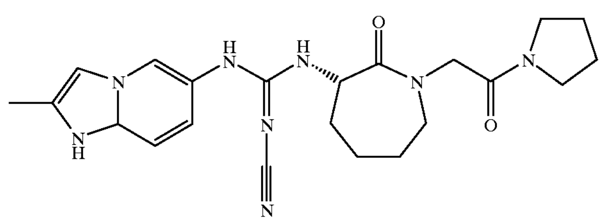 | HPLC (method A) $t_R$ = 2.15 min LRMS (ESI) m/z 437 (M+H) |
| 125 | 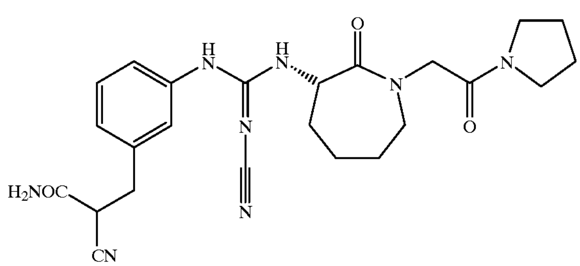 | HPLC (method A) $t_R$ = 3.44 min LRMS (ESI) m/z 479 (M+H) |
| 126 | 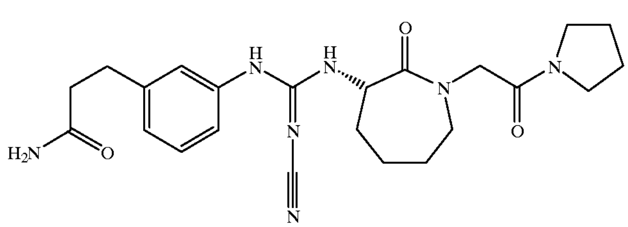 | HPLC (method A) $t_R$ = 2.77 min LRMS (ESI) m/z 454 (M+H) |

| Example | Structure | characterization |
|---|---|---|
| 127 | 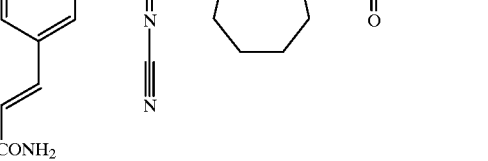 | HPLC (method A)<br>$t_R$ = 3.05 min<br>LRMS (ESI) m/z<br>452 (M+H) |
| 128 | 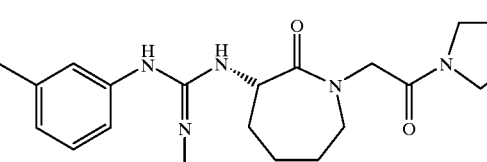 | HPLC (method A)<br>$t_R$ = 3.44 min<br>LRMS (ESI) m/z<br>409 (M+H) |
| 129 | 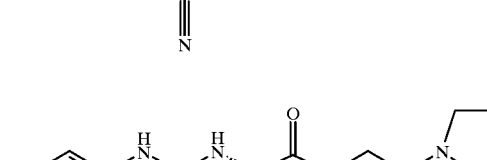 | HPLC (method A)<br>$t_R$ = 2.44 min<br>LRMS (ESI) m/z<br>424 (M+H) |
| 130 | 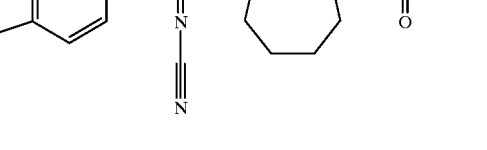 | HPLC (method A)<br>$t_R$ = 2.79 min<br>LRMS (ESI) m/z<br>422 (M+H) |
| 131 | 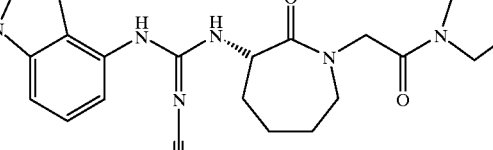 | HPLC (method A)<br>$t_R$ = 3.01 min<br>LRMS (ESI) m/z<br>422 (M+H) |
| 132 | 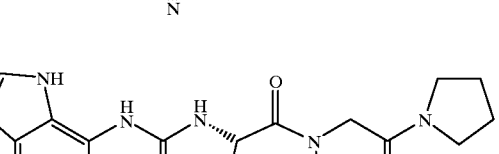 | HPLC (method A)<br>$t_R$ = 2.42 min<br>LRMS (ESI) m/z<br>434 (M+H) |

| Example | Structure | characterization |
|---|---|---|
| 133 | 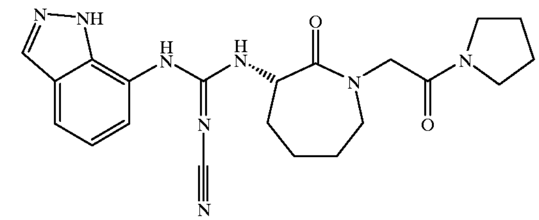 | HPLC (method A) $t_R$ = 2.66 min LRMS (ESI) m/z 423 (M+H) |
| 134 | 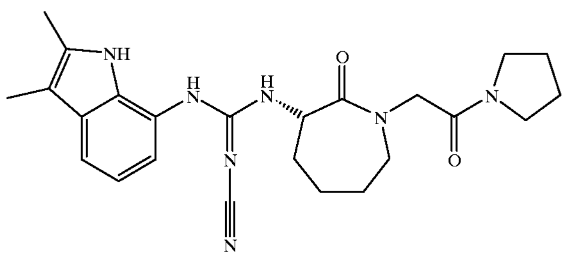 | HPLC (method A) $t_R$ = 3.5 min LRMS (ESI) m/z 450 (M+H) |
| 135 | 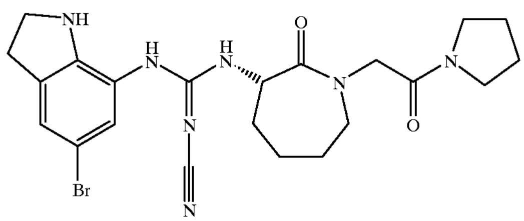 | HPLC (method A) $t_R$ = 3.50 min LRMS (ESI) m/z 503 (M+H) |

EXAMPLE 136

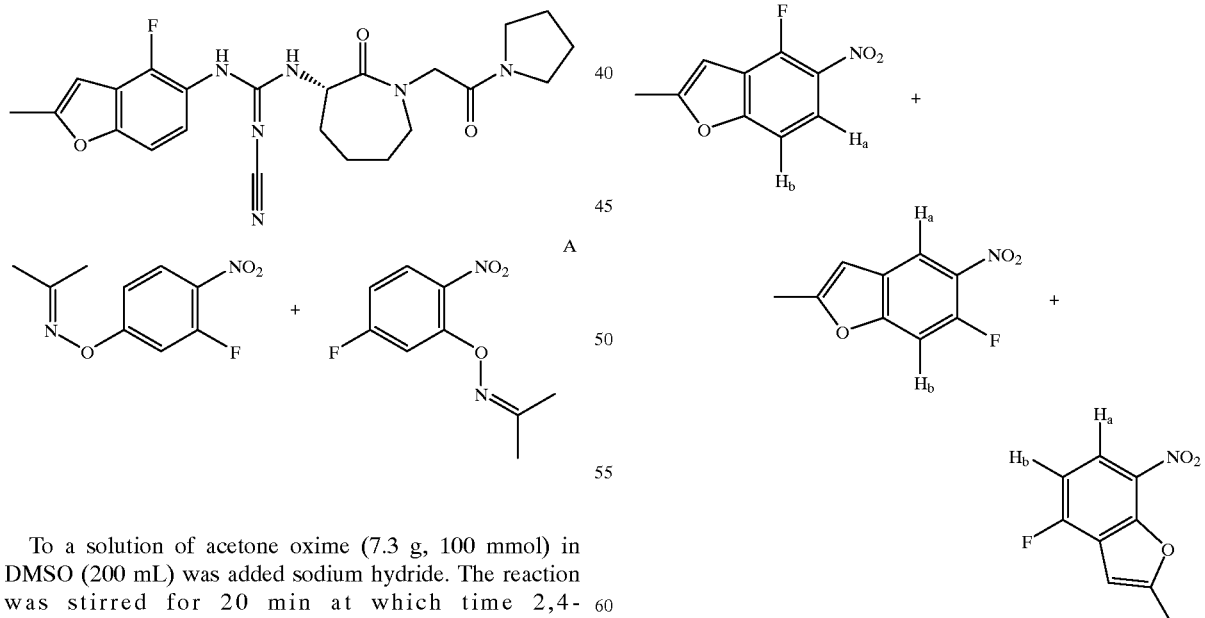

To a solution of acetone oxime (7.3 g, 100 mmol) in DMSO (200 mL) was added sodium hydride. The reaction was stirred for 20 min at which time 2,4-difluoronitrobenzene was added in one portion. The reaction was stirred for 40 min. Water (200 mL) was added and the mixture was extracted with dichloromethane (3×150 mL). After drying over magnesium sulfate and removing the solvent, the residue was chromatographed (silica, 2–5% ethyl acetate in hexanes) to provide a mixture of the part A compounds (10 g).

A solution of part A compound mixture dissolved in saturated ethanolic HCl (200 mL) was refluxed for 2 hours. After cooling, the reaction was filtered. The filtrate was concentrated and the residue was chromatographed (silica, 2–10% ethyl acetate in hexanes) to provide a mixture of the part B compounds. Purification of a portion of this material by preparative TLC (5 % ethyl acetate in hexanes) separated the isomers. The 4-fluoro-2-methyl-5-nitrobenzofuran is the least polar compound and the 6-fluoro-2-methyl-5-nitrobenzofuran is the most polar. For 4-fluoro-2-methyl-5-nitrobenzofuran: $^1$H-NMR (270 MHz, CDCl$_3$) δ 8.06 (dd, Ha, J=8.9, 4.7 Hz), 6.96 (dd, Hb, J=8.9, 8.4 Hz), 6.58 (s, 1H), 2.56 (s, 3H). For 6-fluoro-2-methyl-5-nitrobenzofuran: $^1$H-NMR (270 MHz, CDCl$_3$) δ 8.13 (d, Ha, J=7.2 Hz), 7.22 (d, Hb, J=11.7 Hz), 6.41 (s, 1H), 2.42 (s, 3H). For 4-fluoro-2-methyl-7-nitrobenzofuran: $^1$H-NMR for (270 MHz, CDCl$_3$) δ 7.6 (dd, Ha, J=8.4, 4.6 Hz), 7.1 (dd, Hb, J=11.1, 8.4 Hz), 6.44 (s, 1Hc), 2.50 (s, 3H).

C

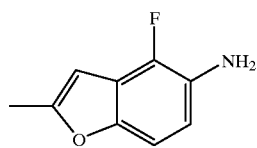

Using the procedure described in Example 68 part B, part C compound was prepared from 4-fluoro-2-methyl-5-nitrobenzofuran.

D

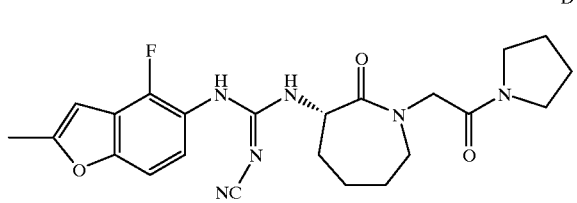

Using the procedure described in Example 68 part C, the Title compound was prepared from part C compound using DMF as solvent: LRMS (ESI) m/z 455 (M+H); HPLC (Method A) $t_R$=3.6 min.

EXAMPLE 137

Using the procedures described in Example 136, the following compound was prepared.

EXAMPLE 138

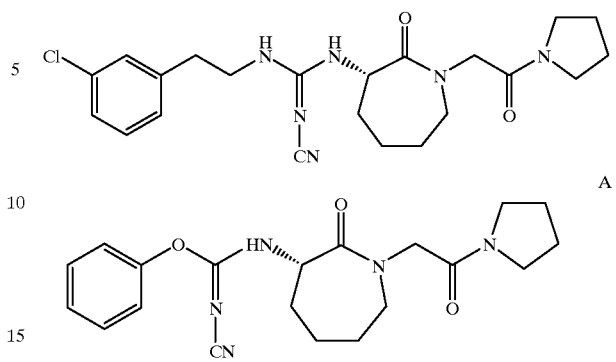

A

B (S)-1-[(3-Amino-hexahydro-2-oxo-1H-azepin-1-yl) acetyl]pyrrolidine (2.20 g, 9.20 mmol) and diphenyl cyanocarbonimidate (2.63 g 11.0 mmol) were dissolved in 25 mL of ethyl acetate. The reaction mixture was stirred at 55° C. for 24 hours and was then concentrated by rotary evaporation. Chromatography (silica, 3% methanol in methylene chloride) provided part A compound as a solid (3.50 g, 99%).

B

Part A compound (77 mg 0.2 mmol) and 3-chlorobenzeneethanamine (64 mg, 0.4 mmol) were dissolved in 1 mL of acetonitrile. The reaction mixture was stirred at 60° C. for 24 hours. The reaction was loaded onto an SCX cartridge (Varian Mega Bond Elute, prewashed with 30 mL of methanol and 30 mL of acetonitrile). The cartridge was eluted with 40 mL of acetonitrile, 20 mL of 1:1 acetonitrile/methanol and then with 20 mL of methanol. Product-containing fractions were concentrated to provide title compound (41 mg, 47%): LRMS (ESI) m/z 445 (M+H); HPLC (method A) $t_R$=3.6 min

| Example | Structure | characterization |
|---|---|---|
| 137 | 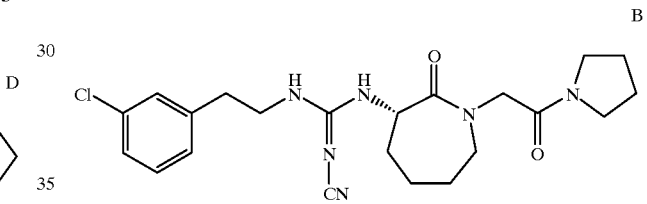 | HPLC (method A) $t_R$ = 3.6 min LRMS (ESI) m/z 566 (M+H) |

EXAMPLES 139 to 226

Using the same methodology described for title compound of Example 138, the following compounds were prepared. Some of the compounds required additional purification by preparative HPLC after the SCX cartridge purification (YMC-pack ODS-A, solvent A: 90:10 $H_2O$:MeOH+ 0.1% TFA and solvent B: 10:90 $H_2O$:MeOH+0.1% TFA).

| Example | Structure | Characterization |
|---|---|---|
| 139 | 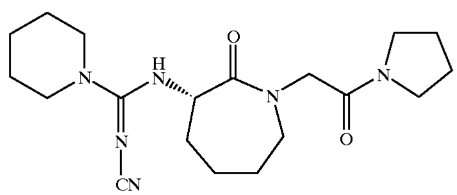 | HPLC (method A) $t_R$ = 2.9 min. LRMS (ESI) m/z 375 |
| 140 | 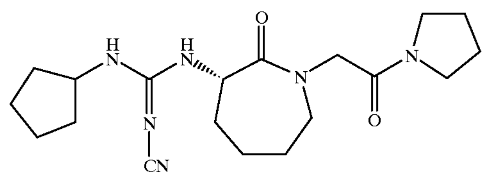 | HPLC (method A) $t_R$ = 3.2 min. LRMS (ESI) m/z 375 |
| 141 | 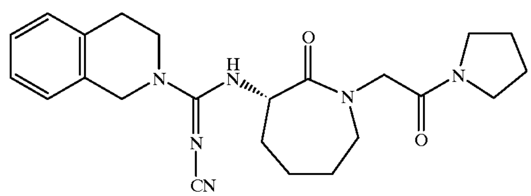 | HPLC (method A) $t_R$ = 3.4 min. LRMS (ESI) m/z 423 |
| 142 | 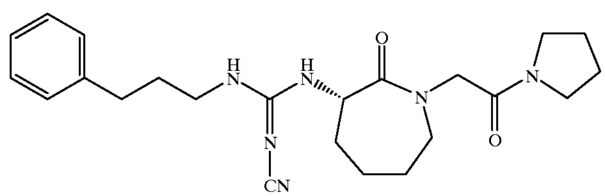 | HPLC (method A) $t_R$ = 3.6 min. LRMS (ESI) m/z 425 |
| 143 | 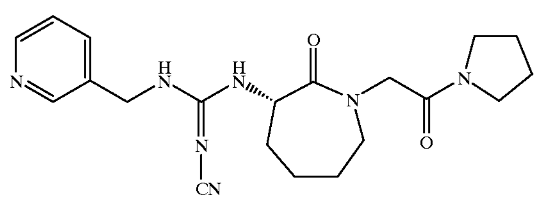 | HPLC (method A) $t_R$ = 1.7 min. LRMS (ESI) m/z 398 |
| 144 | 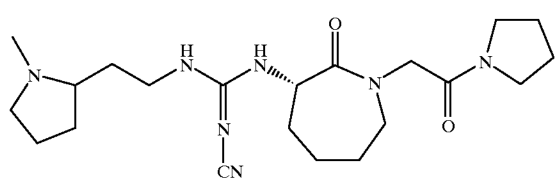 | HPLC (method A) $t_R$ = 1.9 min. LRMS (ESI) m/z 418 |

-continued

| Example | Structure | Characterization |
|---|---|---|
| 145 | 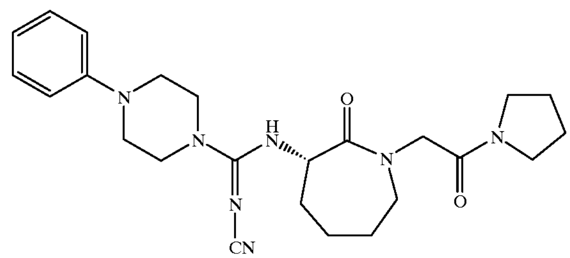 | HPLC (method A)<br>$t_R$ = 3.2 min.<br>LRMS (ESI) m/z<br>452 |
| 146 | 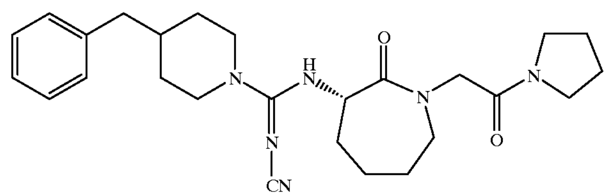 | HPLC (method A)<br>$t_R$ = 3.9 min.<br>LRMS (ESI) m/z<br>465 |
| 147 | 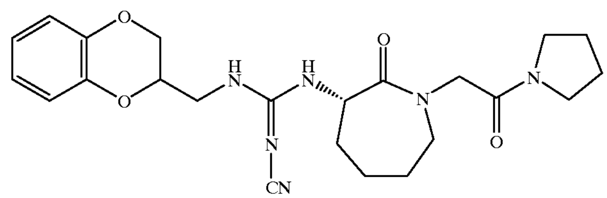 | HPLC (method A)<br>$t_R$ = 3.4 min.<br>LRMS (ESI) m/z<br>455 |
| 148 | 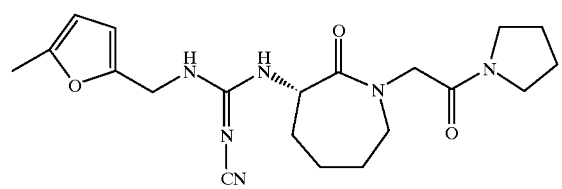 | HPLC (method A)<br>$t_R$ = 3.1 min.<br>LRMS (ESI) m/z<br>401 |
| 149 | 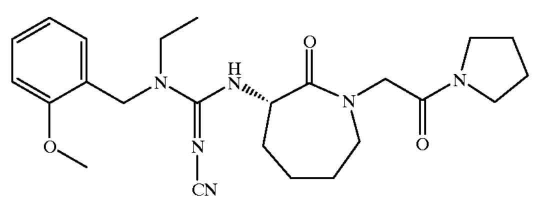 | HPLC (method A)<br>$t_R$ = 3.6 min.<br>LRMS (ESI) m/z<br>455 |
| 150 | 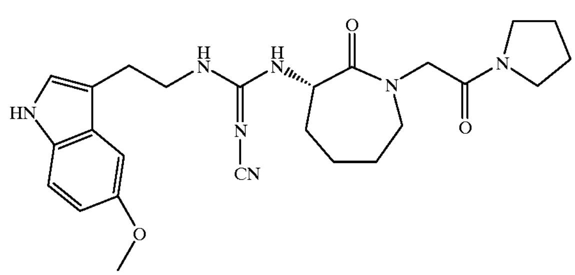 | HPLC (method A)<br>$t_R$ = 3.2 min.<br>LRMS (ESI) m/z<br>480 |

-continued

| Example | Structure | Characterization |
|---------|-----------|------------------|
| 151 | 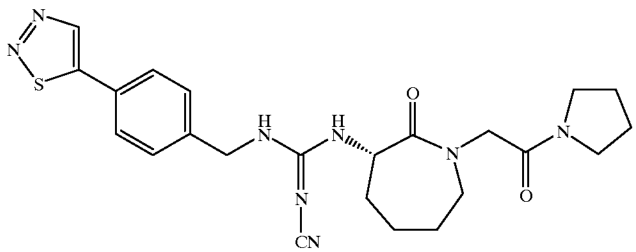 | HPLC (method A) $t_R$ = 3.2 min. LRMS (ESI) m/z 481 |
| 152 | 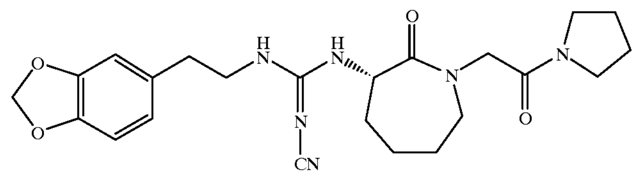 | HPLC (method A) $t_R$ = 3.3 min. LRMS (ESI) m/z 455 |
| 153 | 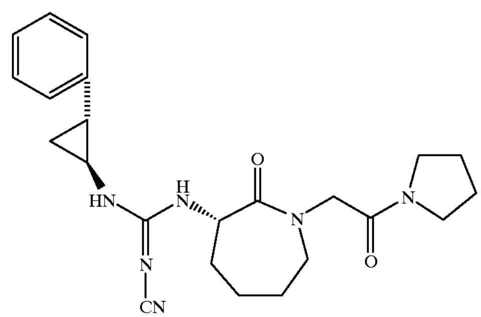 | HPLC (method A) $t_R$ = 3.5 min. LRMS (ESI) m/z 423 |
| 154 | 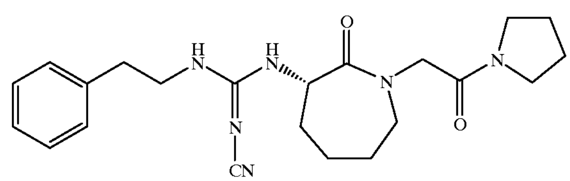 | HPLC (method A) $t_R$ = 3.5 min. LRMS (ESI) m/z 411 |
| 155 | 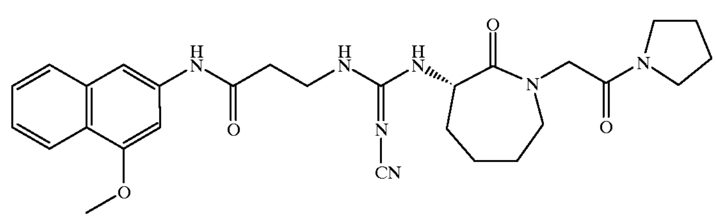 | HPLC (method D) $t_R$ = 3.8 min. LRMS (ESI) m/z 534 |
| 156 | 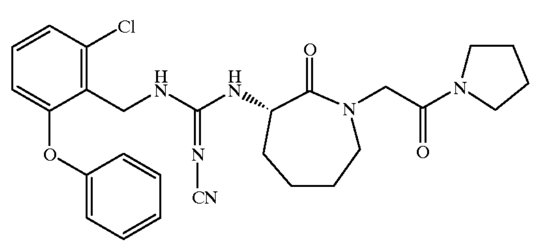 | HPLC (method D) $t_R$ = 4.0 min. LRMS (ESI) m/z 523 |

-continued

| Example | Structure | Characterization |
|---|---|---|
| 157 | 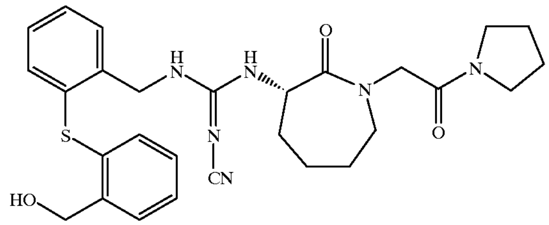 | HPLC (method D) $t_R$ = 3.7 min. LRMS (ESI) m/z 535 |
| 158 | 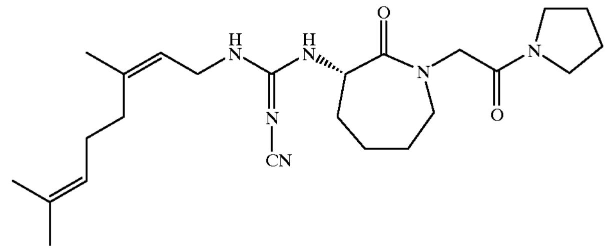 | HPLC (method D) $t_R$ = 4.2 min. LRMS (ESI) m/z 443 |
| 159 | 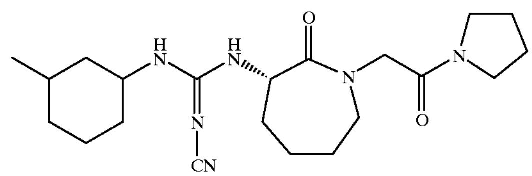 | HPLC (method D) $t_R$ = 3.7 min. LRMS (ESI) m/z 403 |
| 160 | 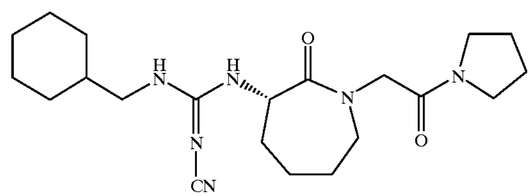 | HPLC (method D) $t_R$ = 3.7 min. LRMS (ESI) m/z 403 |
| 161 | 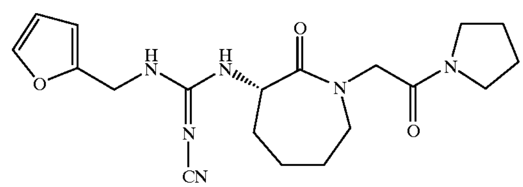 | HPLC (method D) $t_R$ = 2.9 min. LRMS (ESI) m/z 387 |
| 162 | 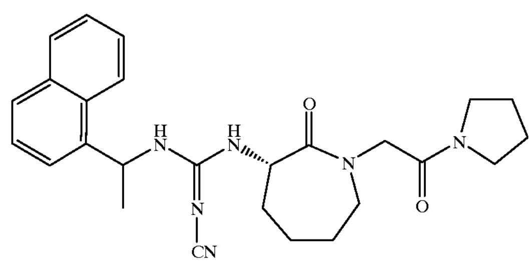 | HPLC (method D) $t_R$ = 3.8 min. LRMS (ESI) m/z 461 |
| 163 | 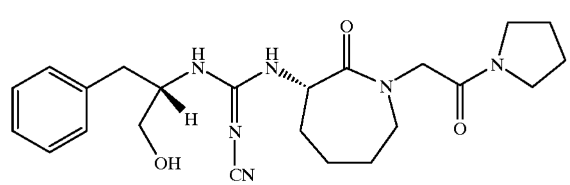 | HPLC (method D) $t_R$ = 3.2 min. LRMS (ESI) m/z 441 |

-continued

| Example | Structure | Characterization |
|---|---|---|
| 164 | 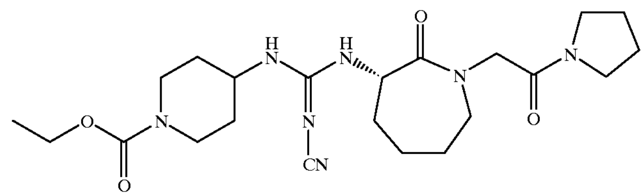 | HPLC (method D) $t_R$ = 3.2 min. LRMS (ESI) m/z 462 |
| 165 | 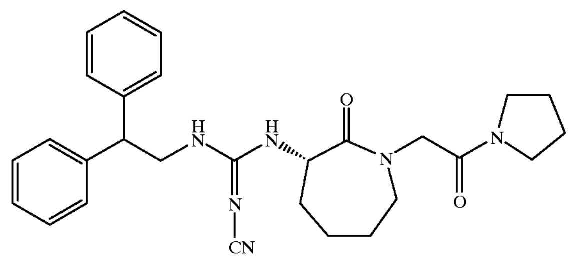 | HPLC (method D) $t_R$ = 3.9 min. LRMS (ESI) m/z 487 |
| 166 | 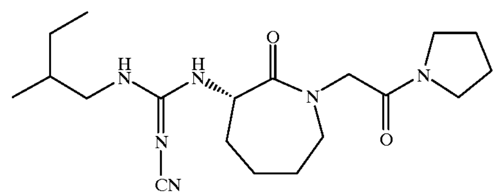 | HPLC (method D) $t_R$ = 3.4 min. LRMS (ESI) m/z 377 |
| 167 | 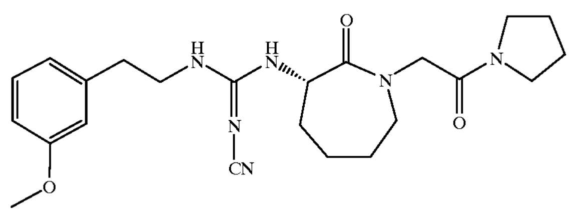 | HPLC (method D) $t_R$ = 3.4 min. LRMS (ESI) m/z 441 |
| 168 | 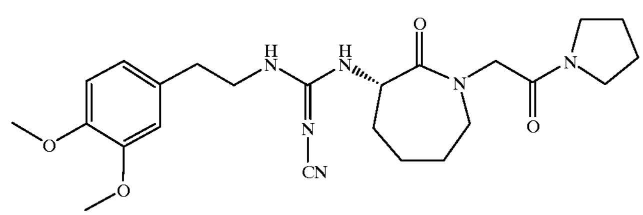 | HPLC (method D) $t_R$ = 3.1 min. LRMS (ESI) m/z 471 |
| 169 | 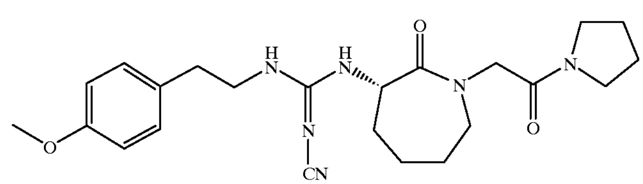 | HPLC (method D) $t_R$ = 3.3 min. LRMS (ESI) m/z 441 |
| 170 | 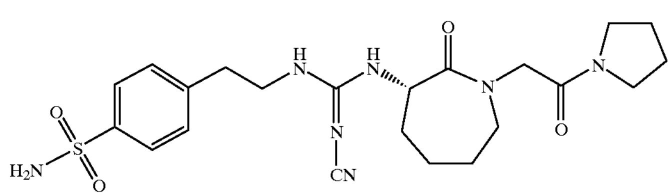 | HPLC (method D) $t_R$ = 2.6 min. LRMS (ESI) m/z 490 |

-continued

| Example | Structure | Characterization |
|---|---|---|
| 171 | 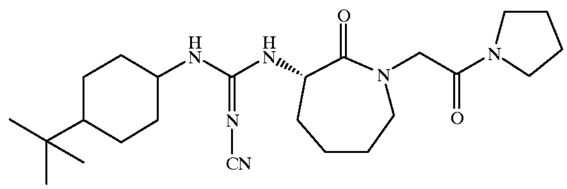 | HPLC (method D)<br>$t_R$ = 4.3 min.<br>LRMS (ESI) m/z<br>445 |
| 172 | 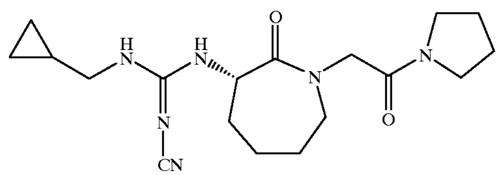 | HPLC (method D)<br>$t_R$ = 2.9 min.<br>LRMS (ESI) m/z<br>361 |
| 173 | 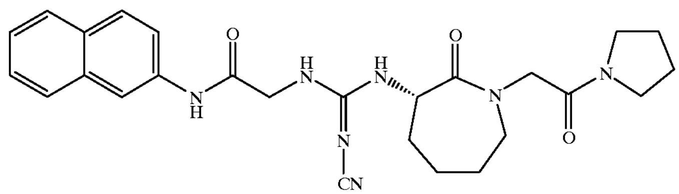 | HPLC (method D)<br>$t_R$ = 3.4 min.<br>LRMS (ESI) m/z<br>490 |
| 174 | 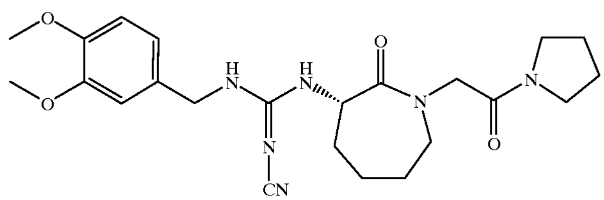 | HPLC (method D)<br>$t_R$ = 3.0 min.<br>LRMS (ESI) m/z<br>457 |
| 175 | 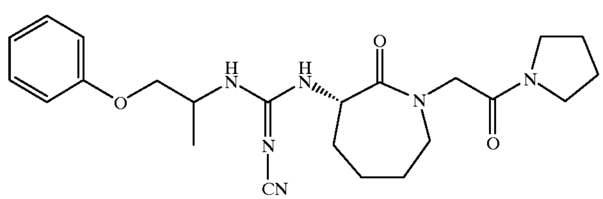 | $T_R$ = 3.5 min.<br>LRMS (ESI) m/z<br>441 |
| 176 | 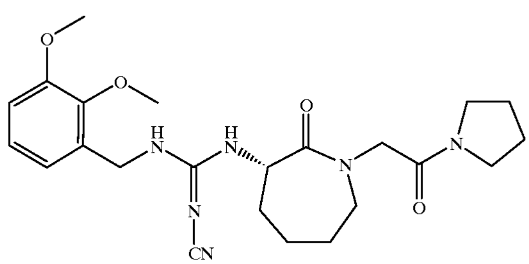 | HPLC (method D)<br>$t_R$ = 3.2 min.<br>LRMS (ESI) m/z<br>457 |
| 177 | 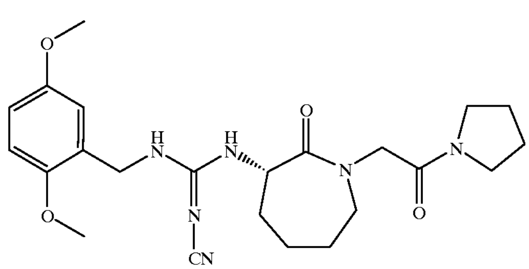 | HPLC (method D)<br>$t_R$ = 3.3 min.<br>LRMS (ESI) m/z<br>457 |

-continued
| Example | Structure | Characterization |
|---|---|---|
| 178 | 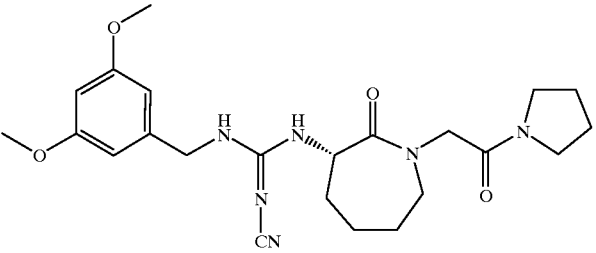 | HPLC (method D)<br>$t_R$ = 3.3 min.<br>LRMS (ESI) m/z 457 |
| 179 | 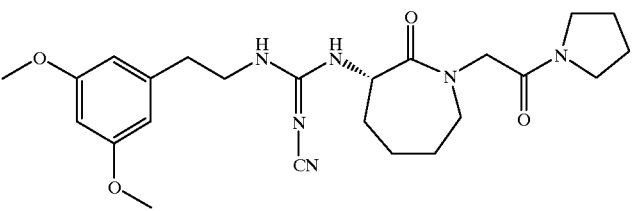 | HPLC (method D)<br>$t_R$ = 3.4 min.<br>LRMS (ESI) m/z 471 |
| 180 | 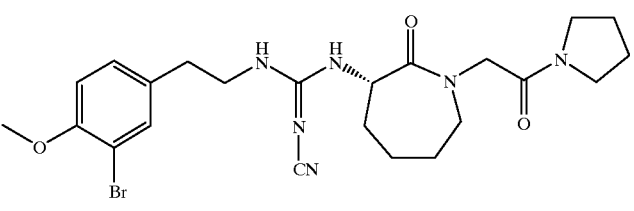 | HPLC (method D)<br>$t_R$ = 3.6 min.<br>LRMS (ESI) m/z 519 |
| 181 | 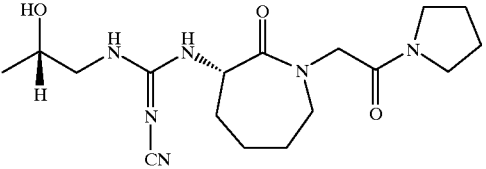 | HPLC (method D)<br>$t_R$ = 2.4 min.<br>LRMS (ESI) m/z 365 |
| 182 | 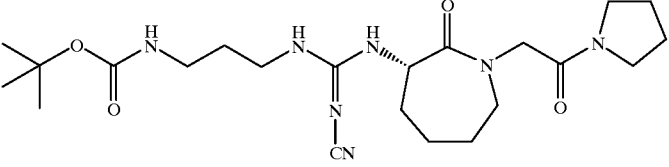 | HPLC (method D)<br>$t_R$ = 3.3 min.<br>LRMS (ESI) m/z 464 |
| 183 | 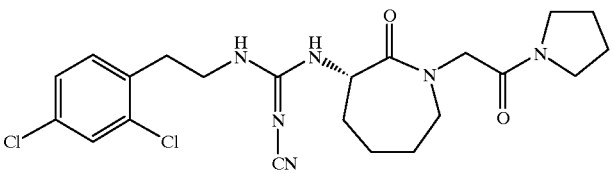 | HPLC (method D)<br>$t_R$ = 4.0 min.<br>LRMS (ESI) m/z 479 |
| 184 | 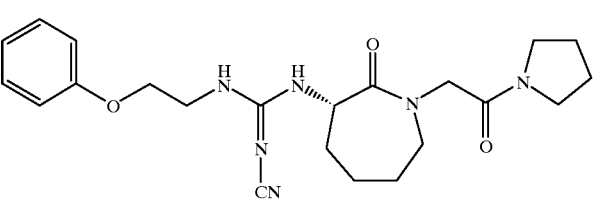 | HPLC (method D)<br>$t_R$ = 3.4 min.<br>LRMS (ESI) m/z 427 |

-continued

| Example | Structure | Characterization |
|---|---|---|
| 185 | 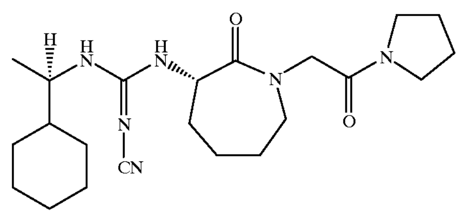 | HPLC (method D) $t_R$ = 3.9 min. LRMS (ESI) m/z 417 |
| 186 | 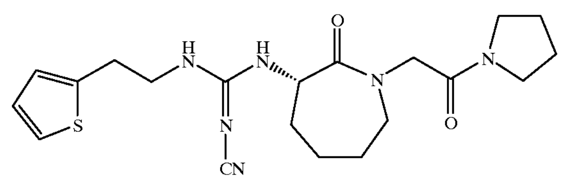 | HPLC (method D) $t_R$ = 3.3 min. LRMS (ESI) m/z 417 |
| 187 | 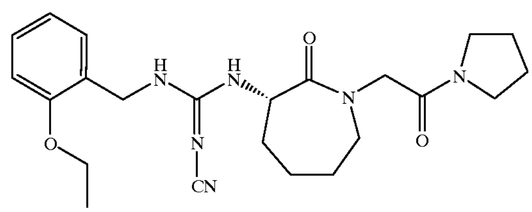 | HPLC (method D) $t_R$ = 3.5 min. LRMS (ESI) m/z 441 |
| 188 | 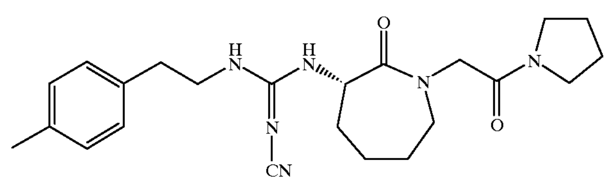 | HPLC (method D) $t_R$ = 3.6 min. LRMS (ESI) m/z 425 |
| 189 | 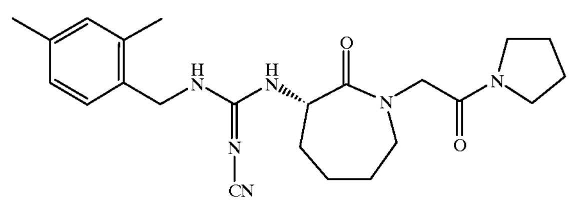 | HPLC (method D) $t_R$ = 3.7 min. LRMS (ESI) m/z 425 |
| 190 | 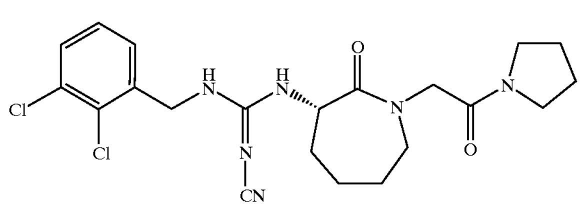 | HPLC (method D) $t_R$ = 3.8 min. LRMS (ESI) m/z 465 |
| 191 | 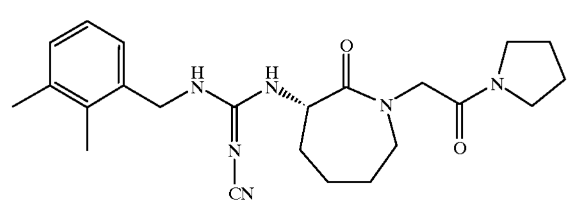 | HPLC (method D) $t_R$ = 3.6 min. LRMS (ESI) m/z 425 |

-continued
| Example | Structure | Characterization |
|---|---|---|
| 192 | 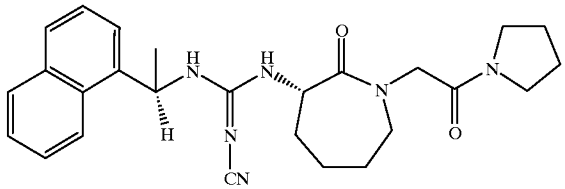 | HPLC (method D) $t_R$ = 3.8 min. LRMS (ESI) m/z 461 |
| 193 | 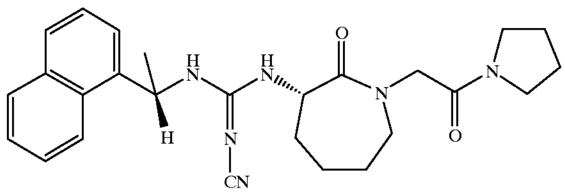 | HPLC (method D) $t_R$ = 3.8 min. LRMS (ESI) m/z 461 |
| 194 | 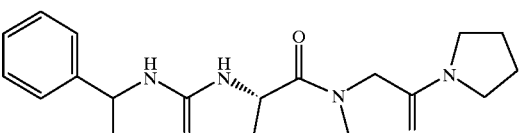 | HPLC (method D) $t_R$ = 3.8 min. LRMS (ESI) m/z 473 |
| 195 | 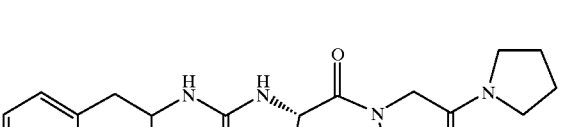 | HPLC (method D) $t_R$ = 3.9 min. LRMS (ESI) m/z 487 |
| 196 | 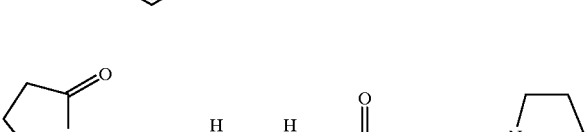 | HPLC (method A) $t_R$ = 2.5 min. LRMS (ESI) m/z 432 |
| 197 | 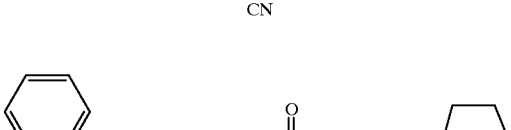 | HPLC (method D) $t_R$ = 3.2 min LC/MS (ESI) m/z 415 (M + H) |

-continued

| Example | Structure | Characterization |
|---|---|---|
| 198 | 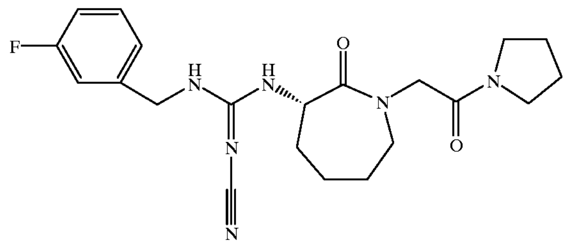 | HPLC (method D) $t_R$ = 3.2 min LC/MS (ESI) m/z 415 (M + H) |
| 199 | 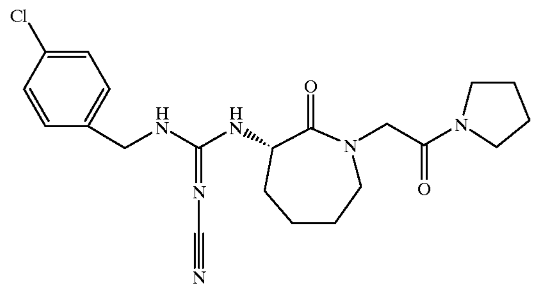 | HPLC (method D) $t_R$ = 3.5 min LC/MS (ESI) m/z 431 (M + H) |
| 200 | 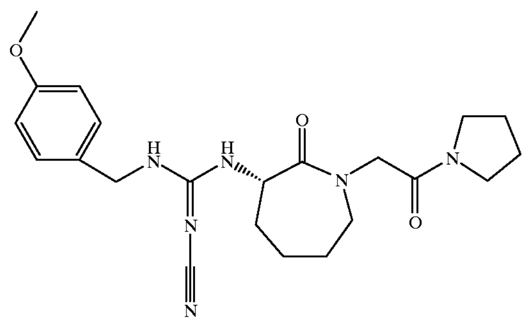 | HPLC (method D) $t_R$ = 3.2 min LC/MS (ESI) m/z 427 (M + H) |
| 201 | 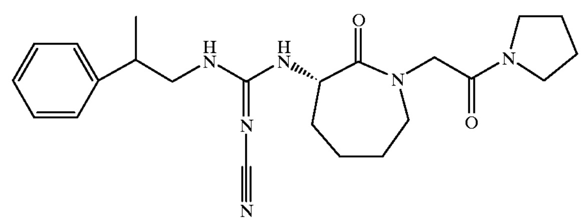 | HPLC (method D) $t_R$ = 3.5 min LC/MS (ESI) m/z 425 (M + H) |
| 202 | 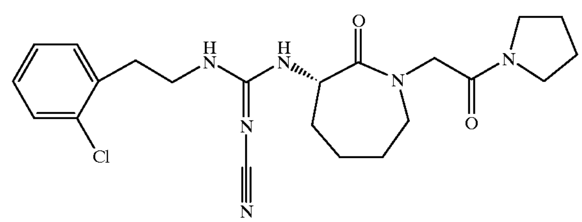 | HPLC (method D) $t_R$ = 3.5 min LC/MS (ESI) m/z 445 (M + H) |
| 203 | 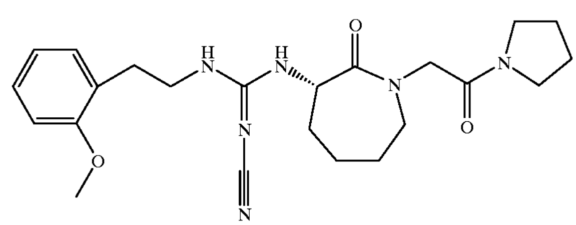 | HPLC (method D) $t_R$ = 3.5 min LC/MS (ESI) m/z 441 (M + H) |

-continued

| Example | Structure | Characterization |
|---|---|---|
| 204 | 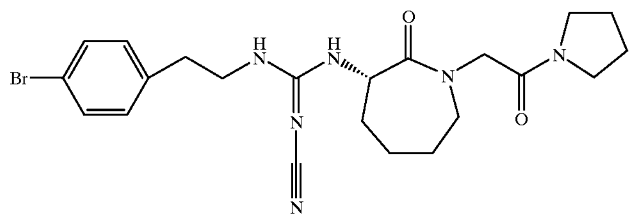 | HPLC (method D)<br>$t_R$ = 3.7 min<br>LC/MS (ESI) m/z<br>489 (M + H) |
| 205 | 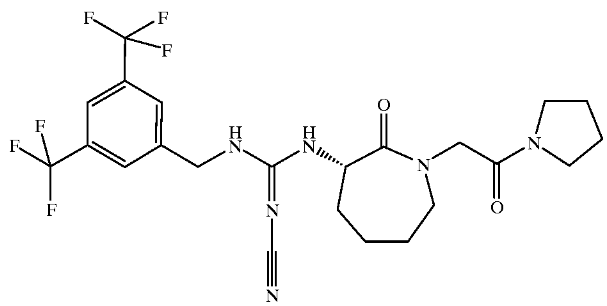 | HPLC (method D)<br>$t_R$ = 4.0 min<br>LC/MS (ESI) m/z<br>533 (M + H) |
| 206 | 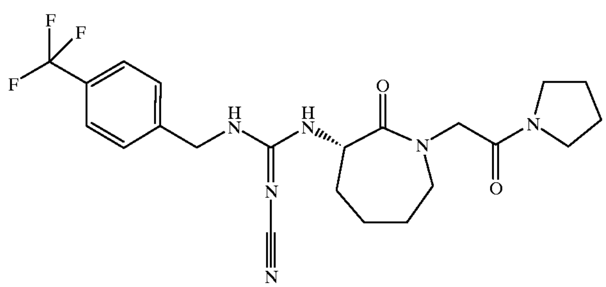 | HPLC (method D)<br>$t_R$ = 3.6 min<br>LC/MS (ESI) m/z<br>465 (M + H) |
| 207 | 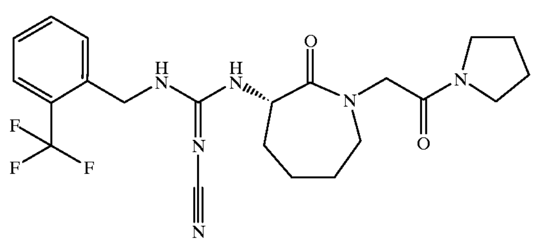 | HPLC (method D)<br>$t_R$ = 3.6 min<br>LC/MS (ESI) m/z<br>465 (M + H) |
| 208 | 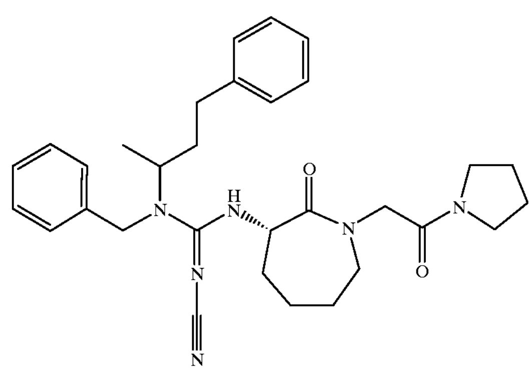 | HPLC (method D)<br>$t_R$ = 4.2 min<br>LC/MS (ESI) m/z<br>529 (M + H) |

-continued

| Example | Structure | Characterization |
|---------|-----------|------------------|
| 209 | 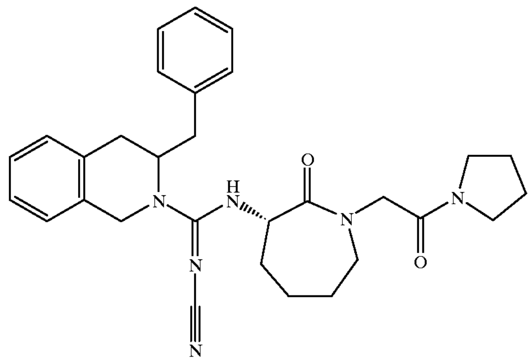 | HPLC (method D)<br>$t_R$ = 4.1 min<br>LC/MS (ESI) m/z<br>513 (M + H) |
| 210 | 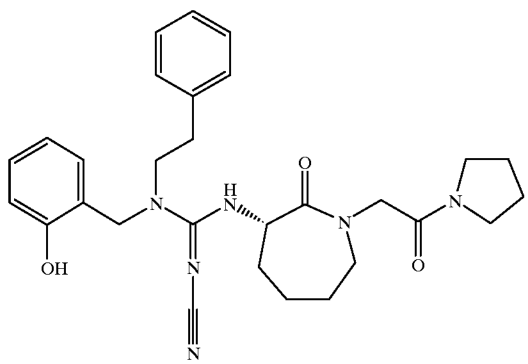 | HPLC (method D)<br>$t_R$ = 4.0 min<br>LC/MS (ESI) m/z<br>517 (M + H) |
| 211 | 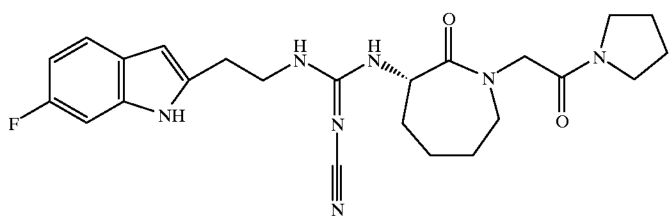 | HPLC (method D)<br>$t_R$ = 3.4 min<br>LC/MS (ESI) m/z<br>468 (M + H) |
| 212 | 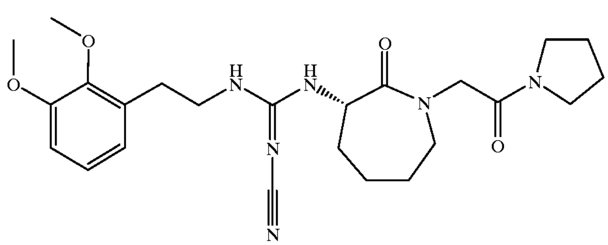 | HPLC (method D)<br>$t_R$ = 3.4 min<br>LC/MS (ESI) m/z<br>471 (M + H) |
| 213 | 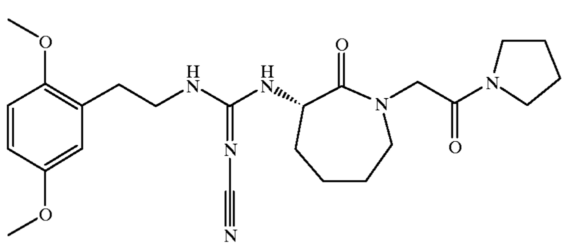 | HPLC (method D)<br>$t_R$ = 3.4 min<br>LC/MS (ESI) m/z<br>471 (M + H) |

| Example | Structure | Characterization |
|---|---|---|
| 214 | 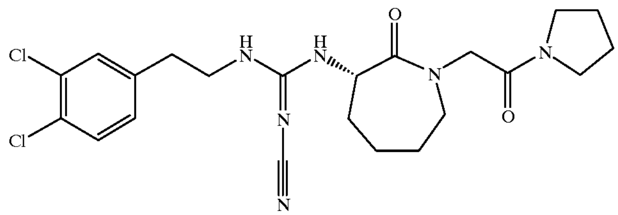 | HPLC (method D)<br>$t_R$ = 3.9 min<br>LC/MS (ESI) m/z<br>479 (M + H) |
| 215 | 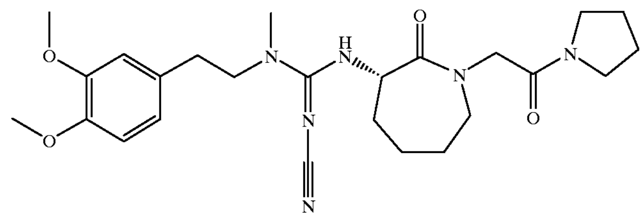 | HPLC (method D)<br>$t_R$ = 3.2 min<br>LC/MS (ESI) m/z<br>485 (M + H) |
| 216 | 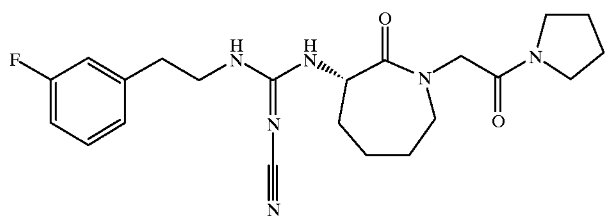 | HPLC (method D)<br>$t_R$ = 3.4 min<br>LC/MS (ESI) m/z<br>429 (M + H) |
| 217 | 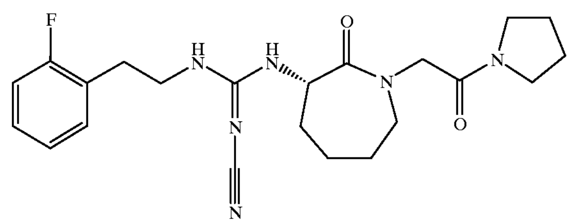 | HPLC (method D)<br>$t_R$ = 3.4 min<br>LC/MS (ESI) m/z<br>429 (M + H) |
| 218 | 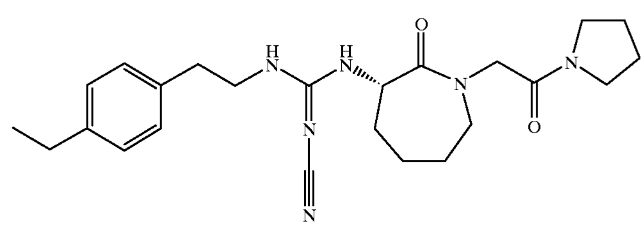 | HPLC (method D)<br>$t_R$ = 3.8 min<br>LC/MS (ESI) m/z<br>439 (M + H) |
| 219 | 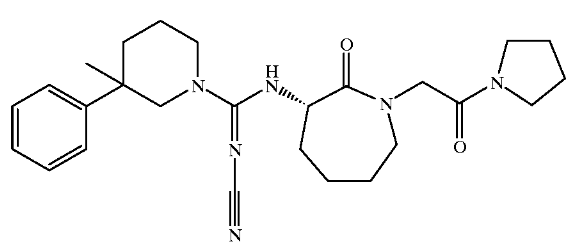 | HPLC (method D)<br>$t_R$ = 3.8 min<br>LC/MS (ESI) m/z<br>465 (M + H) |

-continued

| Example | Structure | Characterization |
|---|---|---|
| 220 | 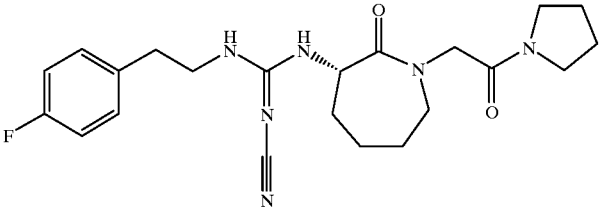 | HPLC (method D)<br>$t_R$ = 3.4 min<br>LC/MS (ESI) m/z<br>429 (M + H) |
| 221 | 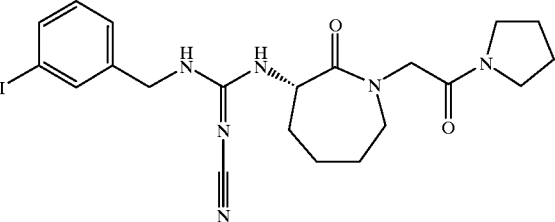 | HPLC (method D)<br>$t_R$ = 3.6 min<br>LC/MS (ESI) m/z<br>523 (M + H) |
| 222 | 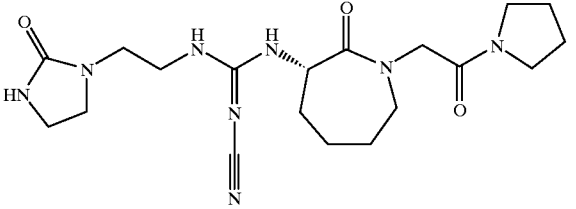 | HPLC (method D)<br>$t_R$ = 2.2 min<br>LC/MS (ESI) m/z<br>419 (M + H) |
| 223 | 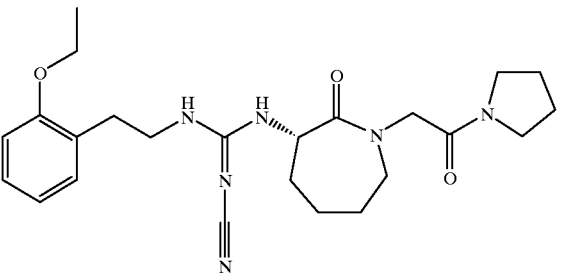 | HPLC (method D)<br>$t_R$ = 3.7 min<br>LC/MS (ESI) m/z<br>455 (M + H) |
| 224 | 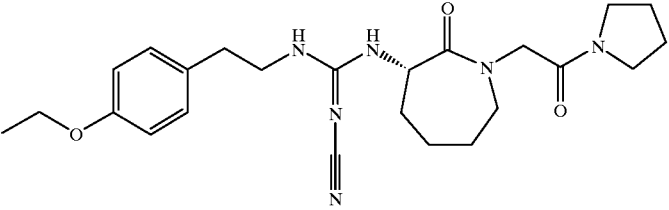 | HPLC (method D)<br>$t_R$ = 3.5 min<br>LC/MS (ESI) m/z<br>455 (M + H) |
| 225 | 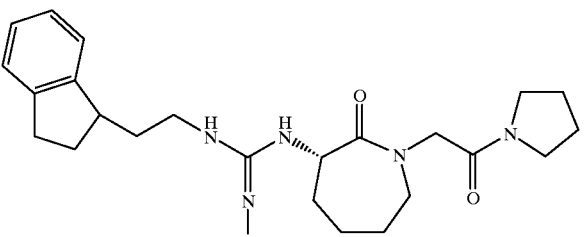<br>isomer 1 | HPLC (method D)<br>$t_R$ = 3.5 min<br>LC/MS (ESI) m/z<br>423 (M + H) |

| Example | Structure | Characterization |
|---|---|---|
| 226 | 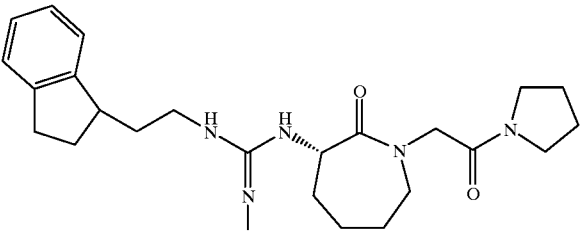<br>isomer 2 | HPLC (method D)<br>$t_R$ = 3.6 min<br>LC/MS (ESI) m/z<br>423 (M + H) |

EXAMPLE 227

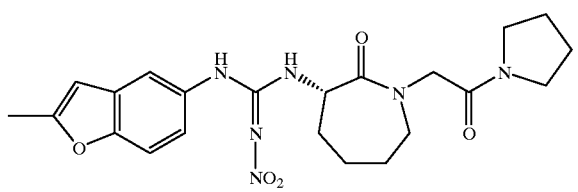

To a solution of 1,1-bis(methylthio)ethene (26.5 mg, 0.16 mmol) in dry ethanol (0.5 ml) was added 2-methyl-5-benzofuranamine (25.8 mg, 0.18 mmol). The reaction was stirred at room temperature for 20 min. (S)-1-[(3-Amino-hexahydro-2-oxo-1H-azepin-1-yl)acetyl]pyrrolidine (59 mg, 0.25 mmol) was then added. The reaction was stirred at 60° C. for 2.5 hr. After removing the solvent, the residue was purified by silica chromatography eluting with 2% methanol in ethyl acetate. The Title compound (47.7 mg, 64% yield) was isolated as a pale yellow solid: LRMS (ESI) m/z 457 (M+H); HPLC (Method A) $t_R$=3.6 min.

EXAMPLE 228

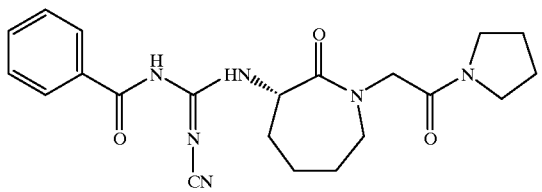

A

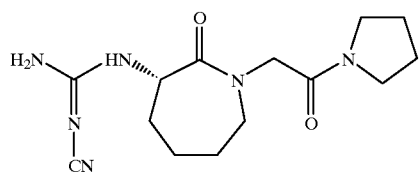

Example 138 part A compound (0.92 g, 2.4 mmol) was dissolved in 10 mL of 7 N ammonia in methanol. The reaction mixture was stirred at 50° C. for 20 hours and then concentrated by rotary evaporation. The solid residue was triturated with 20 mL of ether and part A compound (0.56 g, 77%) was obtained by filtration.

B

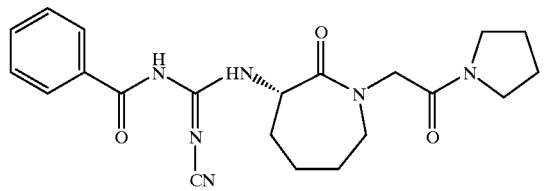

To Part A compound (153 mg, 0.50 mmol) in 5 mL of anhydrous DMF was added sodium hydride (33 mg, 1.1 mmol). The reaction mixture was stirred at room temperature for 30 min and then benzoic anhydride (124 mg, 0.55 mmol) was added. The reaction was stirred at room temperature for another 48 hours and then the solvent was removed by rotary evaporation. The Title compound (87 mg, 42%) was obtained after purification by preparative HPLC: LRMS (ESI) m/z 411 (M+H); HPLC (method A) $t_R$=2.9 min.

EXAMPLE 229

Using the same methodology described for title compound of Example 228, the following compound was prepared using 2-naphthoyl chloride.

| Example | Structure | Characterization |
|---|---|---|
| 229 | 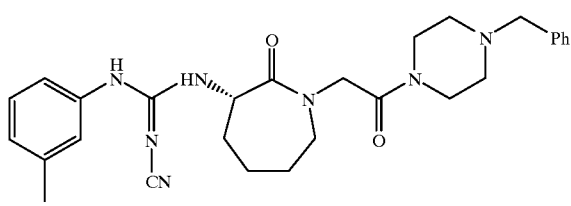 | HPLC (method A) $t_R$ = 3.5 min. LRMS (ESI) m/z 461 |

EXAMPLE 230

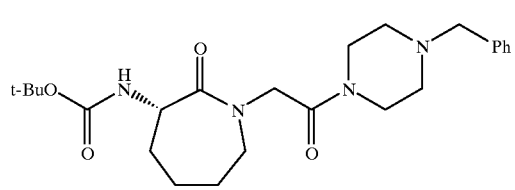

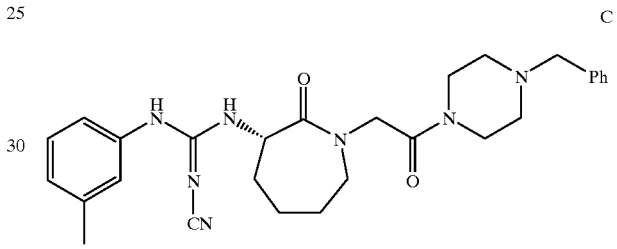

A

To a solution of bromoacetyl chloride (0.92 g, 5.7 mmol) in dichloromethane (30 mL) at 0° C. was added dropwise a solution of 1-benzylpiperazine (0.99 mL, 5.7 mmol) and triethylamine (0.74 mL, 6.8 mmol) in dichloromethane (20 mL) over 30 min. The reaction was stirred at room temperature for additional 16 h and was quenched with water. The organic phase was washed with HCl solution (0.5 N, 20 mL) and brine, dried over magnesium sulfate and filtered. The solvent was removed to afford a brown oil, which was chromatographed on silica gel to give part A compound (1.43 g, 85%).

B 1,1-Dimethylethyl [(3S)-hexahydro-2-oxo-1H-azepin-3-yl]carbamate (1.04 g, 4.58 mmol) was dissolved in 60 mL of dry THF and cooled to 0° C. Lithium bis(trimethylsilyl) amide (1.0 M in hexanes, 9.5 mL, 9.5 mmol) was added over 10 min. The mixture was warmed to room temperature and stirred for additional 1 h, at which time part A compound (1.43 g, 4.81 mmol) in 30 mL THF was added dropwise over 1 h. The reaction mixture was stirred at room temperature for additional 16 h. The reaction was quenched with saturated sodium bicarbonate solution and extracted with ethyl acetate (3×100 mL). The organic fractions were combined, washed with saturated sodium bicarbonate solution, dried over magnesium sulfate, filtered and the solvent was removed to provid part B compound as a brown oil.

C

To a solution of Part B compound (90 mg, 0.21 mmol) in dichloromethane (3 mL) was added trifluoroacetic acid (0.41 mL, 5.35 mmol). The reaction was stirred for 1.5 h. The solvent was removed and the residue was azeotroped with toluene (3×2 mL). The residue was dissolved in EtOH:CH$_3$CN (1:1, 1.5 mL), and triethylamine (0.059 mL, 0.43 mmol), N-cyano-N'-(3-methyl)phenyl-thiourea sodium salt (45 mg, 0.21 mmol) and WSC (52 mg, 0.27 mmol) were added. The reaction was stirred for 16 h and the solvent was removed. The residue was dissolved in CH$_2$Cl$_2$ (10 mL), washed with water (3 mL), saturated sodium chloride solution, dried over magnesium sulfate, filtered and concentrated in vacuo. Flash chromatography of the residue (silica, 10 % MeOH/ethyl acetate) gave title compound as a white solid (35 mg, 83 %): LRMS (ESI) m/z 502 (M+H); HPLC (method A) $t_R$=2.81 min.

EXAMPLES 231 to 234

Using the methodology described for preparing the Example 230 compound, the following compounds were prepared.

| Example | Structure | Characterization |
|---|---|---|
| 231 | 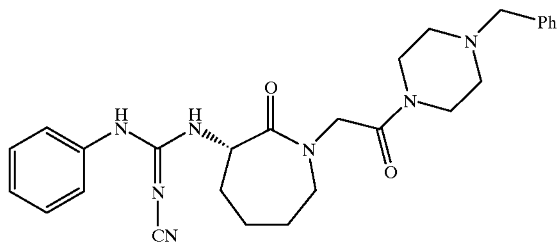 | HPLC (method A) $t_R$ = 2.62 min. LRMS (ESI) m/z 488 |
| 232 | 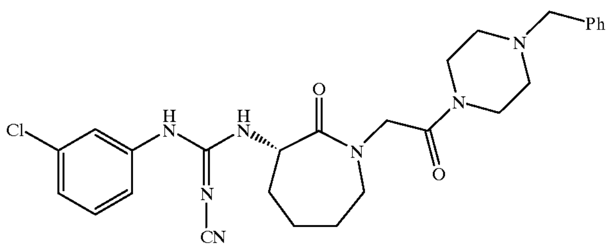 | HPLC (method A) $t_R$ = 3.02 min. LRMS (ESI) m/z 522 |
| 233 | 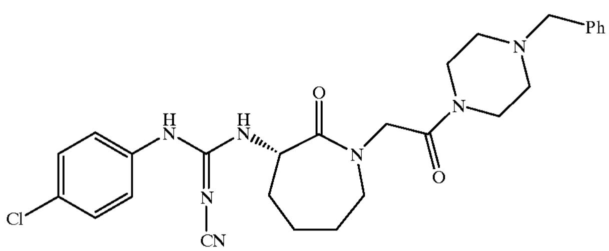 | HPLC (method A) $t_R$ = 2.99 min. LRMS (ESI) m/z 522 |
| 234 | 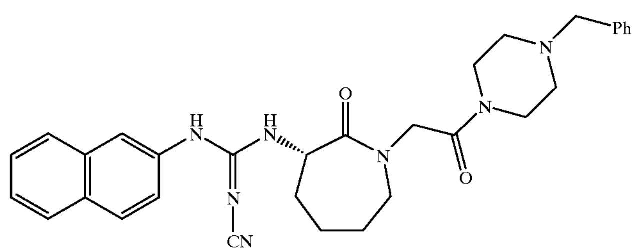 | HPLC (method A) $t_R$ = 3.18 min. LRMS (ESI) m/z 538 |

EXAMPLE 235

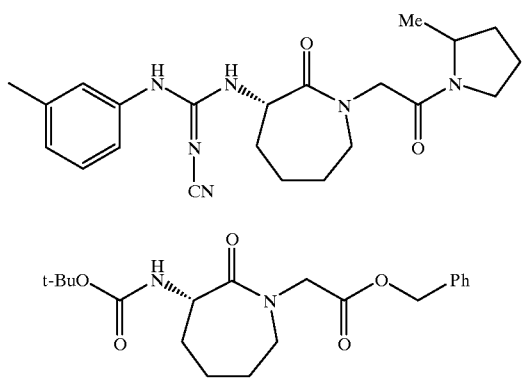

A 1,1-Dimethylethyl [(3S)-hexahydro-2-oxo-1H-azepin-3-yl]carbamate (10 g, 44 mmol) was dissolved in 600 mL of dry THF and cooled to 0° C. Lithium bis(trimethylsilyl) amide (1.0 M in hexanes, 90 mL, 90 mmol) was added over 1 h. The mixture was warmed to room temperature and stirred for additional 1 h, at which time benzyl bromoacetate (7.6 mL, 46 mmol) in 100 mL THF was added dropwise over 2 h. The reaction mixture was stirred at room temperature for additional 16 h. The reaction was quenched with saturated sodium bicarbonate solution and extracted with ethyl acetate (3×200 mL). The organic fractions were combined, washed with saturated sodium bicarbonate solution, dried over magnesium sulfate, filtered and concentrated in vacuo to provid a brown oil. Flash chromatography (silica, 5–30% ethyl acetate in hexanes) afforded part A compound as a yellow oil (7.05 g, 43%).

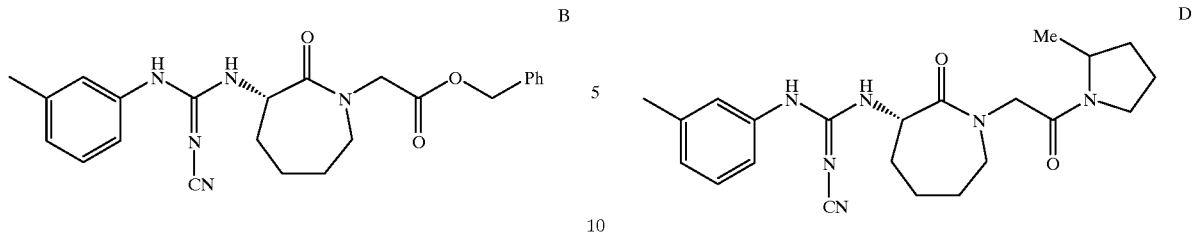

To a solution of Part A compound (2.15 g, 5.72 mmol) in dichloromethane (30 mL) was added trifluoroacetic acid (8.8 mL, 114 mmol). The reaction was stirred for 2 h. The solvent was removed and the residue was azeotroped with toluene (3×5 mL). The residue was dissolved in 10 mL of EtOH:CH$_3$CN (1:1), and triethylamine (1.75 mL, 12.6 mmol), N-cyano-N'-(3-methylphenyl)thiourea sodium salt (1.23 g, 5.72 mmol) and WSC (1.21 g, 6.29 mmol) were added. The reaction was stirred for 16 h and the solvent was removed in vacuo. The residue was dissolved in CH$_2$Cl$_2$ (50 mL); washed with water (20 mL) and saturated sodium chloride solution; dried over magnesium sulfate; filtered and concentrated in vacuo. Flash chromatography of the residue with ethyl acetate gave part B compound as a white solid (2.05 g, 83%): LRMS (ESI) m/z 433 (M+H); HPLC (method A) $t_R$=4.09 min.

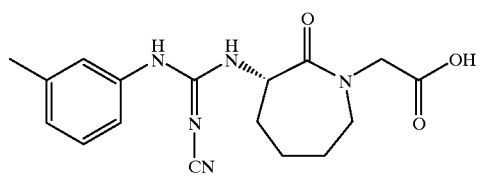

A mixture of Part B compound (2.00 g, 4.62 mmol) and palladium on active carbon (10% Pd, 0.5 g) in EtOH (20 mL) and THF (10 mL) was stirred at room temperature under an atmosphere of hydrogen for 3 h. The mixture was filtered through a pad of celite and concentrated to afford part C compound (1.6 g, 82%) as a white solid: LRMS (ESI pos. ion spectrum) m/z 343; HPLC (method A) $t_R$=3.21 min.

To Part C compound (15 mg, 0.044 mmol) and 2-methylpyrrolidine (36 mg, 0.44 mmol) in CH$_2$Cl$_2$ (1 mL) was added 4-(dimethylamino)pyridine (21 mg, 0.175 mmol) and WSC (34 mg, 0.175 mmol) in that order. The mixture was stirred at 50° C. under nitrogen for 3 h. The mixture was loaded on a silca gel column which was eluted with 50% ethyl acetate/hexanes and then 10% MeOH in ethyl acetate to give title compound (11 mg, 62%): LRMS (ESI) m/z 411 (M+H); HPLC (method A) $t_R$=3.65 min.

EXAMPLE 236

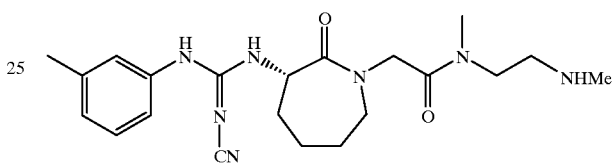

To a mixture of Example 235 Part C compound (13 mg, 0.038 mmol) and TFFH (11 mg, 0.040 mmol) in acetonitrile (0.5 mL) under nitrogen was added triethylamine (6 mL, 0.045 mmol). The resulting solution was stirred for 10 min at which time N,N'-dimethyl-ethylenediamine (10 mg, 0.11 mmol) was added. The reaction was stirred at room temperature for 2 h and concentrated in vacuo. The residue was purified by reverse phase HPLC to give the Title comound as the TFA salt (13 mg, 65%): LRMS (ESI) m/z 414 (M+H); HPLC (method A) $t_R$=2.66 min.

EXAMPLES 237 to 259

Using the methodology described for Examples 235 and 236, the following compounds were prepared.

| Example | Structure | Characterization |
|---|---|---|
| 237 | 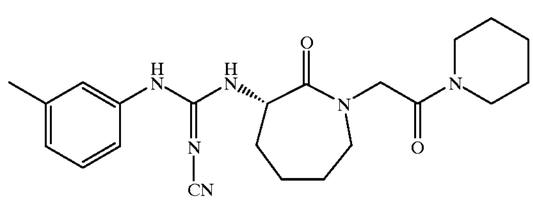 | HPLC (method A) $t_R$ = 3.67 min. LRMS (ESI) m/z 411 |
| 238 | 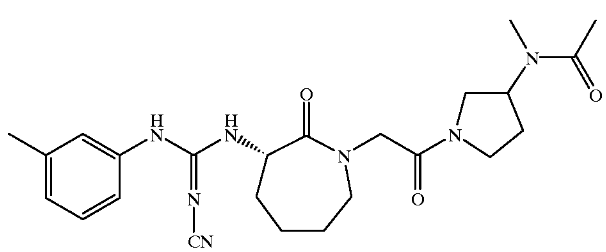 | HPLC (method A) $t_R$ = 3.19 min. LRMS (ESI) m/z 468 |

-continued

| Example | Structure | Characterization |
|---|---|---|
| 239 | 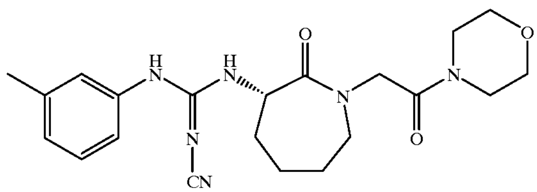 | HPLC (method A) $t_R$ = 3.20 min. LRMS (ESI) m/z 413 |
| 240 | 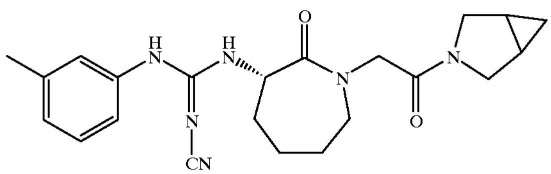 | HPLC (method A) $t_R$ = 3.59 min. LRMS (ESI) m/z 409 |
| 241 | 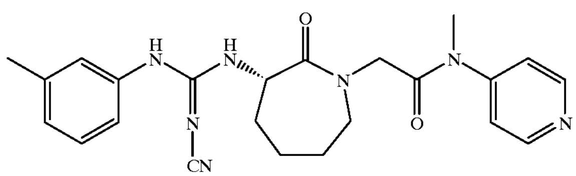 | HPLC (method A) $t_R$ = 2.71 min. LRMS (ESI) m/z 434 |
| 242 | 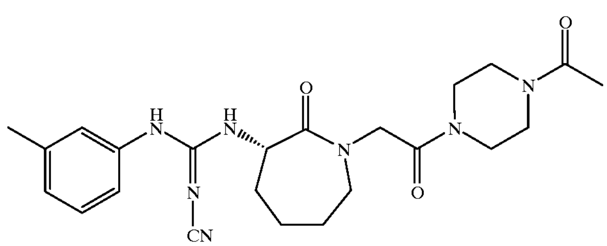 | HPLC (method A) $t_R$ = 3.10 min. LRMS (ESI) m/z 454 |
| 243 | 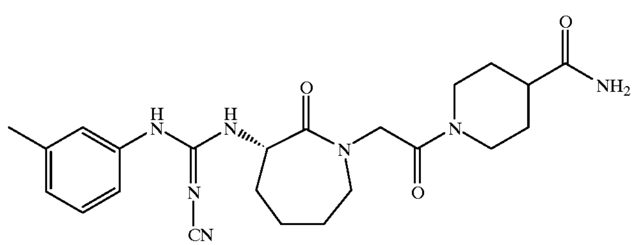 | HPLC (method A) $t_R$ = 3.11 min. LRMS (ESI) m/z 454 |
| 244 | 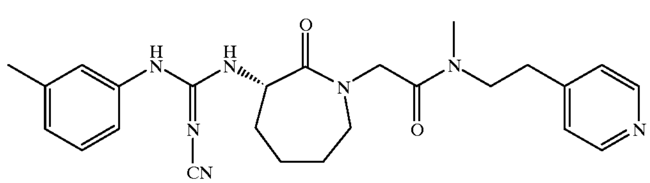 | HPLC (method A) $t_R$ = 2.62 min. LRMS (ESI) m/z 462 |
| 245 | 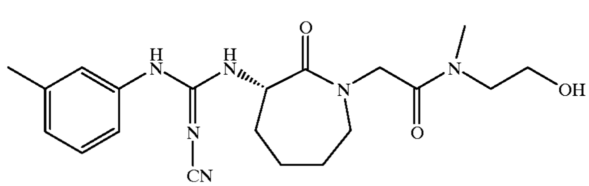 | HPLC (method A) $t_R$ = 3.11 min. LRMS (ESI) m/z 401 |

-continued

| Example | Structure | Characterization |
|---|---|---|
| 246 | 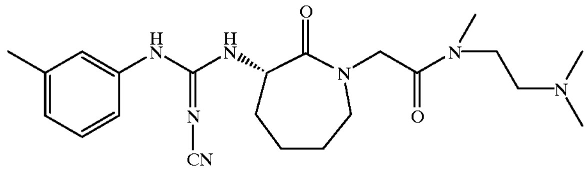 | HPLC (method A) $t_R$ = 2.61 min. LRMS (ESI) m/z 428 |
| 247 | 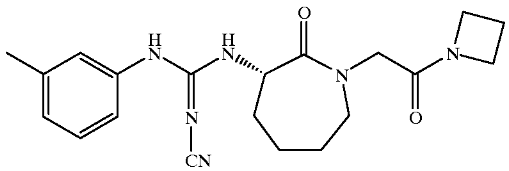 | HPLC (method A) $t_R$ = 3.24 min. LRMS (ESI) m/z 383 |
| 248 | 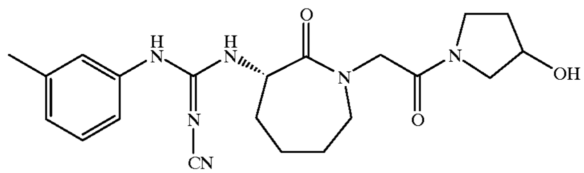 | HPLC (method A) $t_R$ = 3.13 min. LRMS (ESI) m/z 413 |
| 249 | 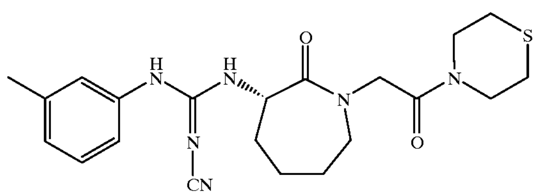 | HPLC (method A) $t_R$ = 3.55 min. LRMS (ESI) m/z 429 |
| 250 | 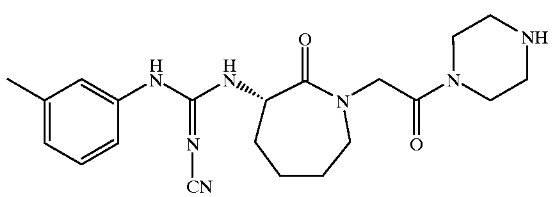 | HPLC (method A) $t_R$ = 2.56 min. LRMS (ESI) m/z 4121 |
| 251 | 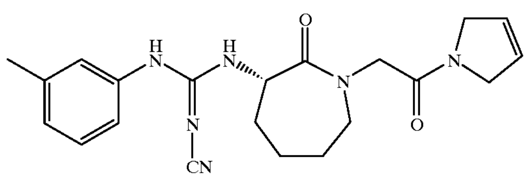 | HPLC (method A) $t_R$ = 3.41 min. LRMS (ESI) m/z 395 |
| 252 | 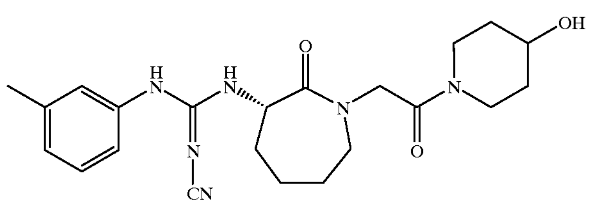 | HPLC (method A) $t_R$ = 3.18 min. LRMS (ESI) m/z 427 |
| 253 | 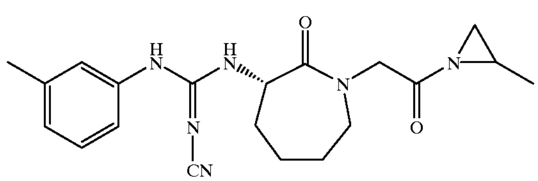 | HPLC (method A) $t_R$ = 3.12 min. LRMS (ESI) m/z 383 |

-continued
| Example | Structure | Characterization |
|---|---|---|
| 254 | 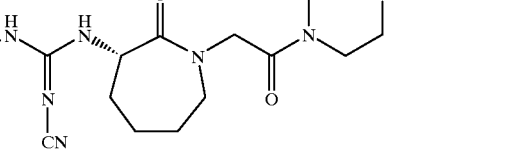 | HPLC (method A)<br>$t_R$ = 3.53 min.<br>LRMS (ESI) m/z<br>484 |
| 255 | 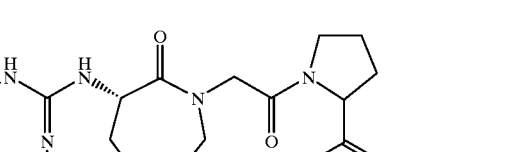 | HPLC (method A)<br>$t_R$ = 3.97 min.<br>LRMS (ESI) m/z<br>531 |
| 256 | 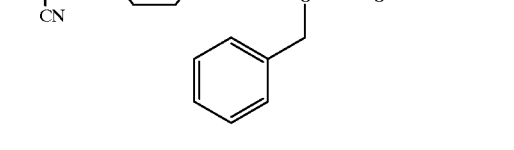 | HPLC (method A)<br>$t_R$ = 3.85 min.<br>LRMS (ESI) m/z<br>512 |
| 257 | 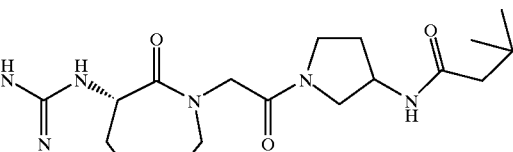 | HPLC (method A)<br>$t_R$ = 1.57 min.<br>LRMS (ESI) m/z<br>412 |
| 258 | 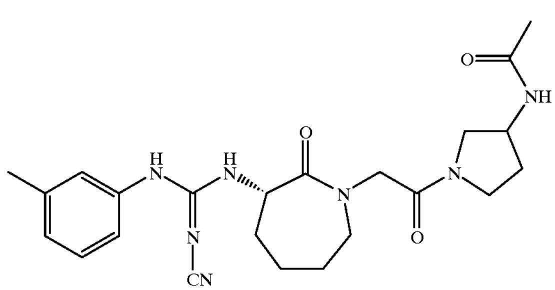 | HPLC (method A)<br>$t_R$ = 2.25 min.<br>LRMS (ESI) m/z<br>454 |
| 259 | 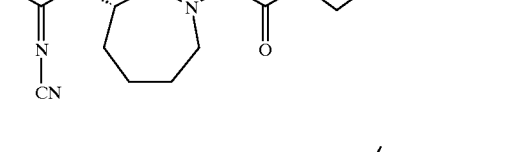 | HPLC (method A)<br>$t_R$ = 3.04 min.<br>LRMS (ESI) m/z<br>440 |

EXAMPLE 260

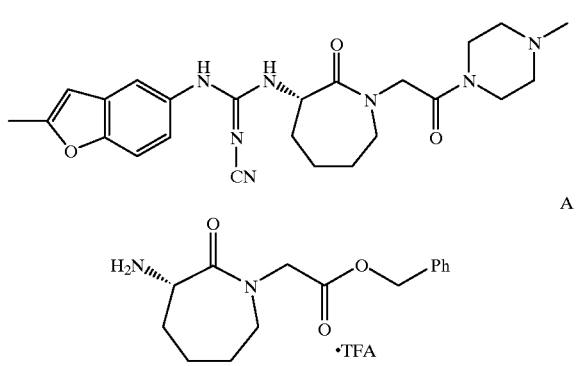

A

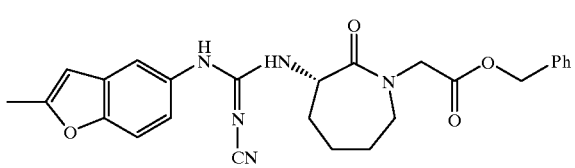

To a solution of Example 150 part A compound (2.58 g, 6.87 mmol) in dichloromethane (20 mL) was added trifluoroacetic acid (10.6 mL, 137 mmol). The reaction was stirred for 2 h. The solvent was removed and the residue was azeotroped with toluene (3×5 mL) to afford part A compound.

B

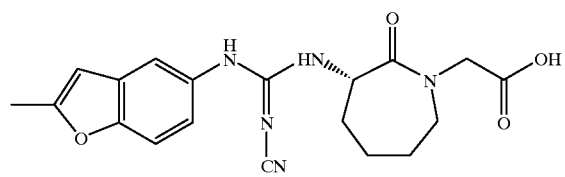

A mixture of diphenyl cyanocarbonimidate (1.64 g, 6.87 mmol), triethylamine (0.96 mL, 6.87 mmol) and 2-methyl-5-benzofuranamine hydrochloride (1.26 g, 6.87 mmol) in DMF (8 mL) was heated to 50° C. for 2 h. To this solution was added triethylamine (0.96 mL, 6.87 mmol) and Part A compound dissolved in DMF (5 mL). The mixture was heated to 50° C. for 2 days under nitrogen. The solvent was removed under high vacuum and the residue chromatographed (silica, 30% to 75% ethyl acetate in hexanes) to afford part B compound (2.75 g, 85%) as a white solid: LRMS (ESI) m/z 473; HPLC (method A) $t_R$ 4.32 min.

C

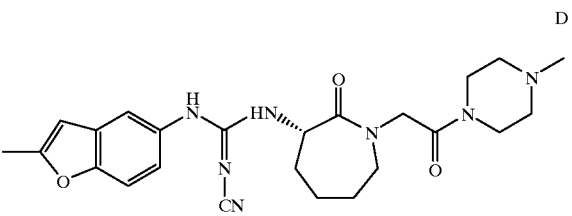

A solution of Part B compound (2.00 g, 4.23 mmol) in THF (30 mL) was cooled to 0° C. Aqueous KOH (1.0 N, 50 mL) was added slowly over 10 min. The mixture was stirred at 0° C. for 15 min and was warmed to room temperature. The mixture was washed with $CH_2Cl_2$ twice. The aqueous phase was then acidified with 1N HCl to pH 1 and was then extracted with ethyl acetate three times. The combined ethyl acetate extracts were dried over magnesium sulfate, filtered and concentrated to afford part C compound as a white solid: LRMS (ESI) m/z 383 (M+H); HPLC (method A) $t_R$=3.47 min.

D

To part C compound (15 mg, 0.039 mmol) and TFFH (10 mg, 0.040 mmol) in acetonitrile (0.5 mL) under nitrogen was added triethylamine (0.011 mL, 0.078 mmol). The resulting solution was stirred for 10 min at which time 1-methylpiperazine (7.8 mg, 0.078 mmol) was added. The reaction was stirred at room temperature for 2 h and concentrated. The mixture was purified by reverse phase HPLC to give title compound as a solid (12 mg, 66%): LRMS (ESI) m/z 466; HPLC (method A) $t_R$=2.91 min.

EXAMPLES 261 to 271

Using the methodology described in Example 260, the following compounds were prepared.

| Example | Structure | Characterization |
|---|---|---|
| 261 | 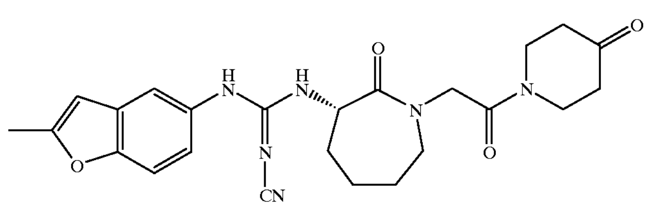 | HPLC (method A) $t_R$ = 3.40min. LRMS (ESI) m/z 465 |
| 262 | 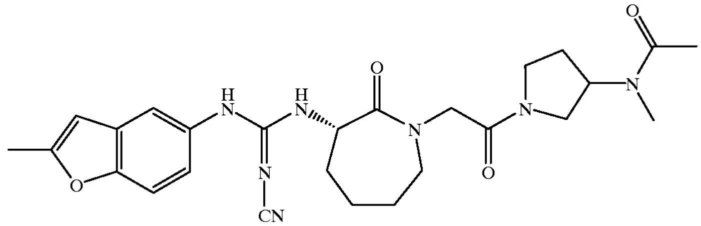 | HPLC (method A) $t_R$ = 3.39 min. LRMS (ESI) m/z 508 |

| Example | Structure | Characterization |
|---|---|---|
| 263 | 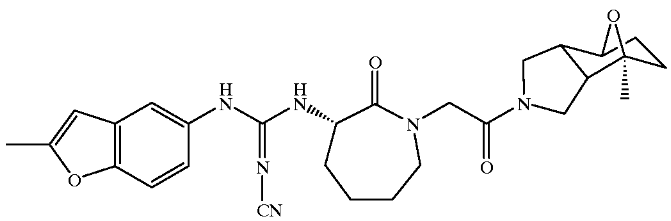 | HPLC (method A) $t_R$ = 3.71 min. LRMS (ESI) m/z 519 |
| 264 | 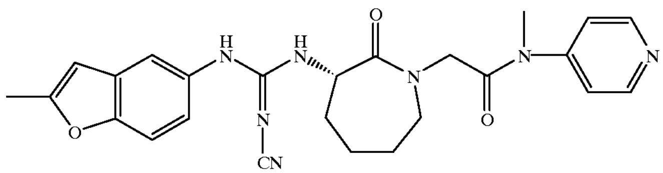 | HPLC (method A) $t_R$ = 2.93 min. LRMS (ESI) m/z 474 |
| 265 | 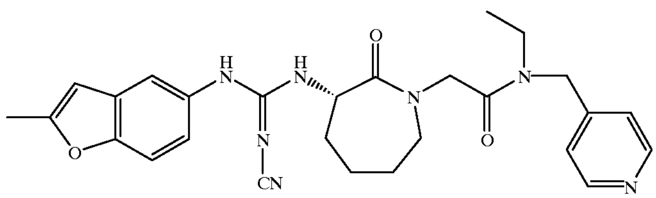 | HPLC (method A) $t_R$ = 3.03 min. LRMS (ESI) m/z 502 |
| 266 | 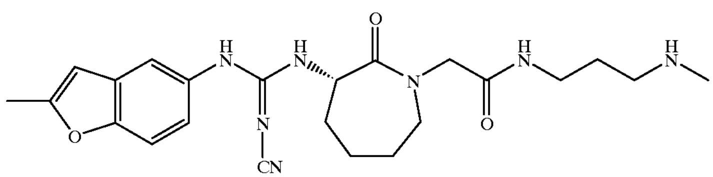 | HPLC (method A) $t_R$ = 2.88 min. LRMS (ESI) m/z 454 |
| 267 | 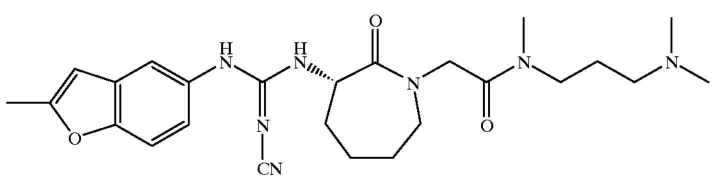 | HPLC (method A) $t_R$ = 2.90 min. LRMS (ESI) m/z 482 |
| 268 | 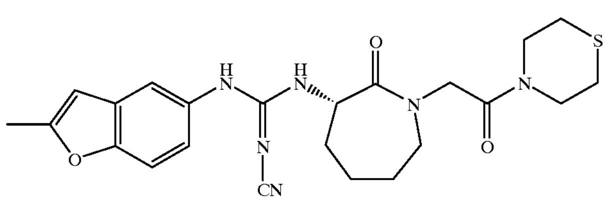 | HPLC (method A) $t_R$ = 3.71 min. LRMS (ESI) m/z 469 |
| 269 | 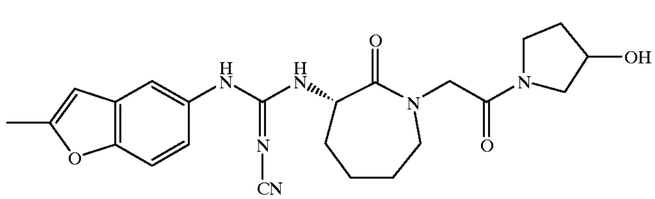 | HPLC (method A) $t_R$ = 3.34 min. LRMS (ESI) m/z 453 |

-continued

| Example | Structure | Characterization |
|---|---|---|
| 270 | 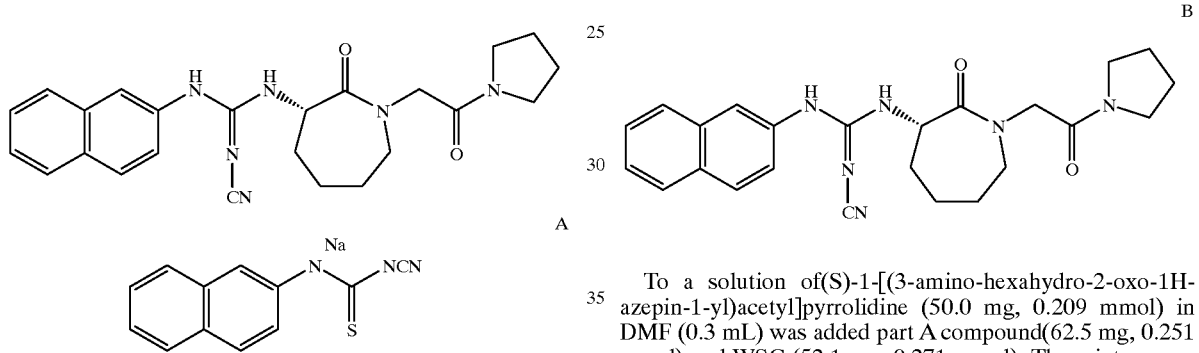 | HPLC (method A) $t_R$ = 3.42 min. LRMS (ESI) m/z 453 |
| 271 | 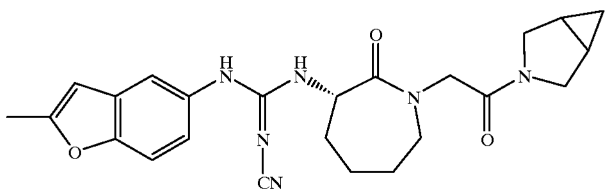 | HPLC (method A) $t_R$ = 3.71 min. LRMS (ESI) m/z 449 |

EXAMPLE 272

To sodium cyanamide (0.27 g, 4.2 mmol) in 3 mL of ethanol was added 2-naphthylisothiocyanate (0.77 g, 4.2 mmol). The reaction mixture was heated at 60° C. for 16 h. The white precipitate which formed was collected by filtration and then triturated with ether. The resultant solid was collected by filtration and washed with ethanol and ether and was then dried to give part A compound (0.90 g, 86%).

To a solution of(S)-1-[(3-amino-hexahydro-2-oxo-1H-azepin-1-yl)acetyl]pyrrolidine (50.0 mg, 0.209 mmol) in DMF (0.3 mL) was added part A compound(62.5 mg, 0.251 mmol) and WSC (52.1 mg, 0.271 mmol). The mixture was stirred for 24 h at room temperature. The reaction was then quenched by addition of water and was extracted with ethyl acetate. The organic layers were concentrated and the residue was purified by flash chromatography on silica (10% methanol/ethyl acetate) to give the Title compound as a white solid (39.8 mg, 44%): LRMS (ESI) m/z 433 (M+H); HPLC (method A) $t_R$=3.70 min.

EXAMPLES 273 to 290

Using the procedure in Example 272, the following compounds were prepared.

| Example | Structure | Characterization |
|---|---|---|
| 273 | 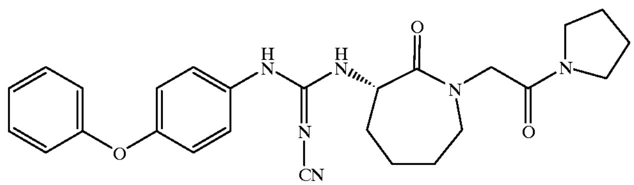 | HPLC (method A) $t_R$ = 3.96 min. LRMS (ESI) m/z 475 |

-continued

| Example | Structure | Characterization |
|---------|-----------|------------------|
| 274 | 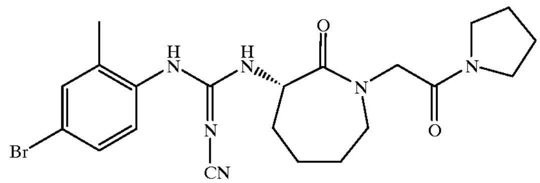 | HPLC (method A) $t_R$ = 3.71 min. LRMS (ESI) m/z 475 |
| 275 | 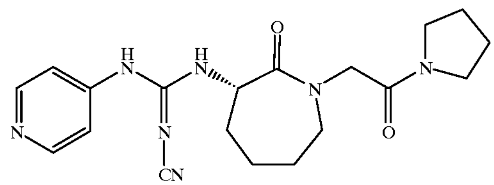 | HPLC (method A) $t_R$ = 1.87 min. LRMS (ESI) m/z 384 |
| 276 | 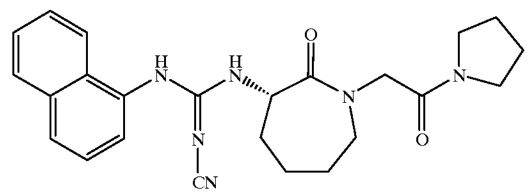 | HPLC (method A) $t_R$ = 3.55 min. LRMS (ESI) m/z 433 |
| 277 | 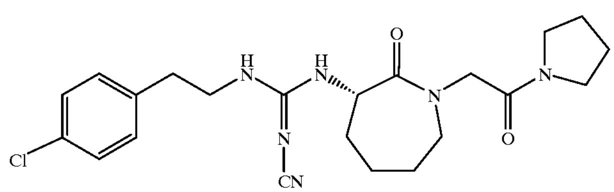 | HPLC (method A) $t_R$ = 3.83 min. LRMS (ESI) m/z 445 |
| 278 | 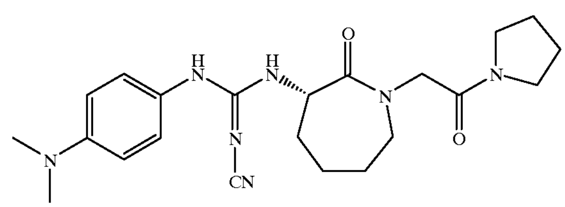 | HPLC (method A) $t_R$ = 2.90 min. LRMS (ESI) m/z 426 |
| 279 | 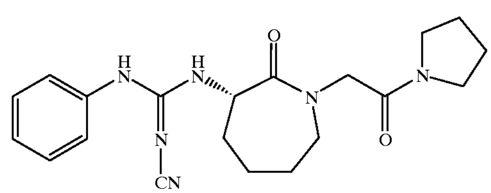 | HPLC (method A) $t_R$ = 3.17 min. LRMS (ESI) m/z 383 |
| 280 | 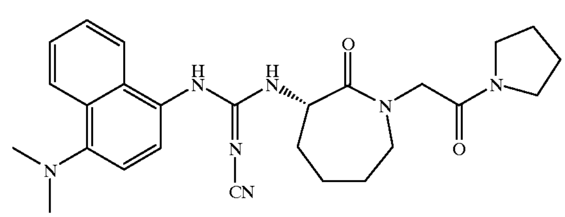 | HPLC (method A) $t_R$ = 2.91 min. LRMS (ESI) m/z 476 |

-continued

| Example | Structure | Characterization |
|---|---|---|
| 281 | 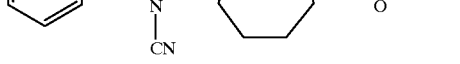 | HPLC (method A)<br>t$_R$ = 1.91 min.<br>LRMS (ESI) m/z<br>384 |
| 282 | 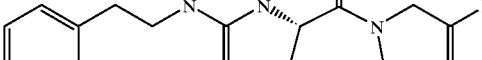 | HPLC (method A)<br>t$_R$ = 3.5 min.<br>LRMS (ESI) m/z<br>429 |
| 283 | 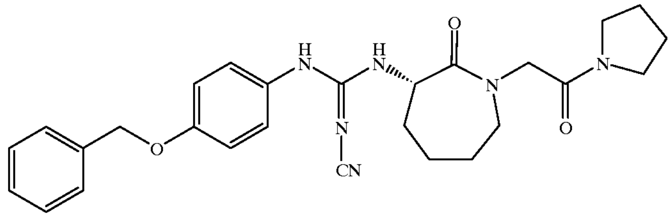 | HPLC (method A)<br>t$_R$ = 3.96 min.<br>LRMS (ESI) m/z<br>489 |
| 284 | 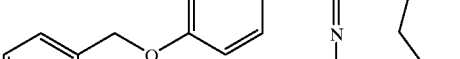 | HPLC (method A)<br>t$_R$ = 3.54 min.<br>LRMS (ESI) m/z<br>429 |
| 285 | 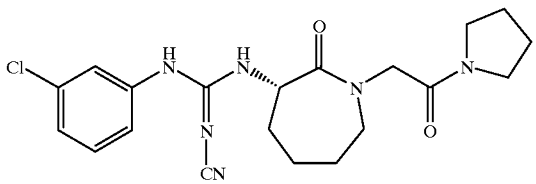 | HPLC (method A)<br>t$_R$ = 3.52 min.<br>LRMS (ESI) m/z<br>417 |
| 286 | 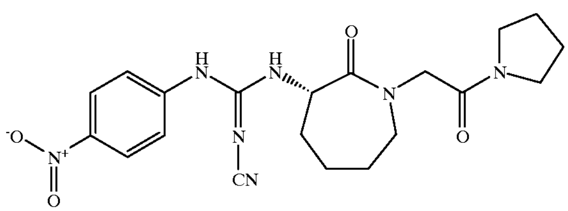 | HPLC (method A)<br>t$_R$ = 3.28 min.<br>LRMS (ESI) m/z<br>428 |
| 287 | 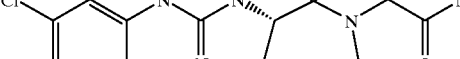 | HPLC (method A)<br>t$_R$ = 3.33 min.<br>LRMS (ESI) m/z<br>441 |

-continued

| Example | Structure | Characterization |
|---|---|---|
| 288 | 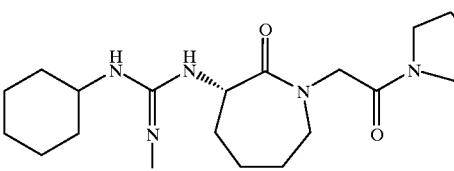 | HPLC (method A)<br>$t_R$ = 3.51 min.<br>LRMS (ESI) m/z<br>389 |
| 289 | 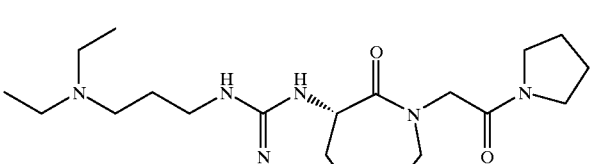 | HPLC (method A)<br>$t_R$ = 1.90 min.<br>LRMS (ESI) m/z<br>420 |
| 290 | 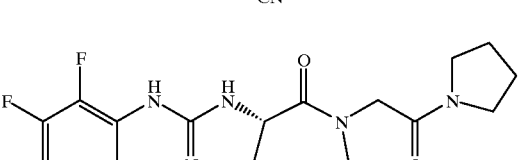 | HPLC (method A)<br>$t_R$ = 3.54 min.<br>LRMS (ESI) m/z<br>473 |

EXAMPLE 291

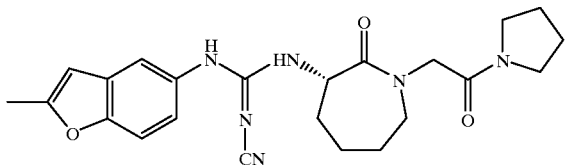

To a 0° C. slurry of sodium hydroxide (82 g, 2 mol) in DMF (1.5 L) was added acetone oxime (125 g, 1.7 mol). After stirring 45 min, 1-fluoro-4-nitrobenzene (218 g, 1.55 mol) was added over 45 min. After stirring at room temperature for 2.5 h, the reaction was poured into cold brine (4.5 L). The mixture was stirred at 0° C. for 2 h. The solid was collected by filtration, washed with water (4×1.5 L) and dried to provide 300 g (99%) of 2-propanone O-(4-nitrophenyl)oxime.

To 2.5 L of ethanol was added acetyl chloride (490 g, 6.2 mol) over 1.5 h. The oxime was then added and the reaction was stirred at reflux for 2.5 h. The reaction was cooled to room temperature and was then poured into ice water (2.5 L). After stirring for 1 h at room temperature and at 0° C. for 2 h, the precipitate was collected, washed and dried to provide 232 g (85%) of 2-methyl-5-nitrobenzofuran.

To a 35° C. mixture of 50 g of 2-methyl-5-nitrobenzofuran, ethanol (250 mL), THF (250 mL) and wet 10% Pd/C (4 g) was added ammonium formate (53.4 g, 0.85 mol) over 50 min. After an additional 4 h, the reaction was cooled to room temperature and filtered through Celite. The filtrate was concentrated and the residue was taken up in methyl t-butyl ether. This mixture was filtered, concentrated and dried to provide 2-methyl-5-benzofuranamine which was converted to its hydrochloride salt or its oxalate salt.

The oxalate was prepared as follows: To a solution of 2-methyl-5-benzofuranamine in TBME (415 mL) was added a solution of oxalic acid (25.4 g) in methanol (80 mL) dropwise. The precipitate was stirred for 2 h, collected, washed with methanol/TBME and dried to provide 2-methyl-5-benzofuranamine oxalate.

2-methyl-5-benzofuranamine hydrochloride (45.8 mg, 0.250 mmol) and diphenyl cyanocarbonimidate (49.8 mg, 0.209 mmol) were dissolved in DMF (0.3 mL). One drop (ca 0.05 mL) of triethylamine was added and the reaction mixture was heated at 50° C. for 8 h. (S)-1-[(3-Amino-hexahydro-2-oxo-1H-azepin-1-yl)acetyl]pyrrolidine (50.0 mg, 0.209 mmol) was added and the reaction mixture was heated at 50° C. for another 40 h. Flash chromatography on silica gel, eluting with ethyl acetate gave the Title compound as a white solid (45.0 mg, 49%): LRMS (ESI) m/z 437; HPLC (method A) $t_R$=3.60 min.

EXAMPLES 292 to 319

Using the procedure described in Example 291, the following compounds were prepared. In some cases DBU or diisopropylethyl amine were used rather than triethylamine. In some cases acetonitrile, ethyl acetate or ethanol were used as solvent in place of DMF. If the reactant amine was available in the free base form rather than as a salt, the added amine base was omitted.

| Example | Structure | Characterization |
|---|---|---|
| 292 | 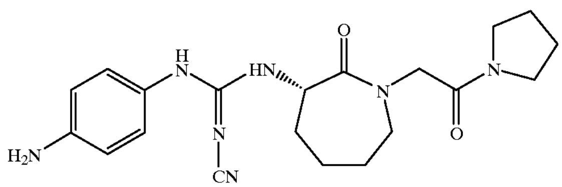 | HPLC (method A) $t_R$ = 2.09 min. LRMS (ESI) m/z 398 |
| 293 | 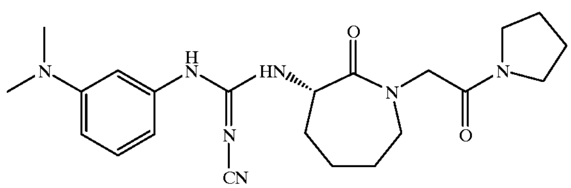 | HPLC (method A) $t_R$ = 2.88 min. LRMS (ESI) m/z 426 |
| 294 | 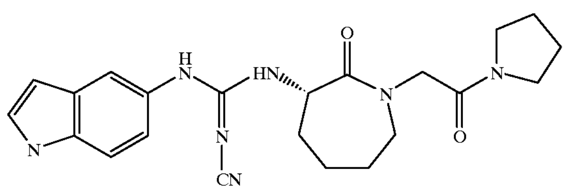 | HPLC (method A) $t_R$ = 3.10 min. LRMS (ESI) m/z 422 |
| 295 | 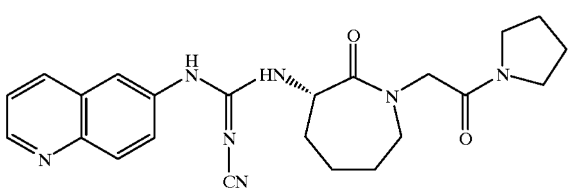 | HPLC (method A) $t_R$ = 2.22 min. LRMS (ESI) m/z 434 |
| 296 | 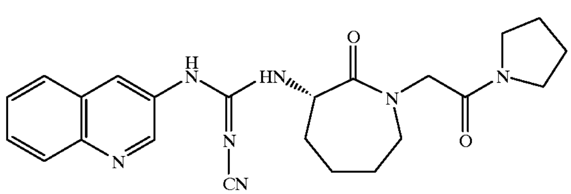 | HPLC (method A) $t_R$ = 2.77 min. LRMS (ESI) m/z 434 |
| 297 | 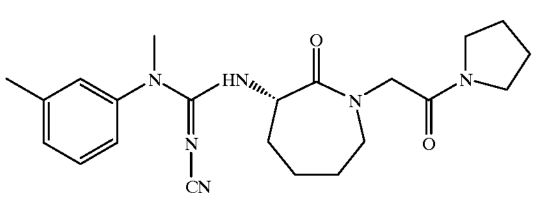 | HPLC (method A) $t_R$ = 3.50 min. LRMS (ESI) m/z 411 |
| 298 | 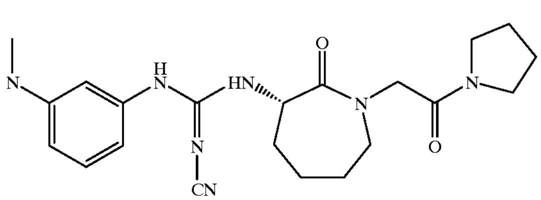 | HPLC (method A) $t_R$ = 2.33 min. LRMS (ESI) m/z 412 |

| Example | Structure | Characterization |
|---|---|---|
| 299 | 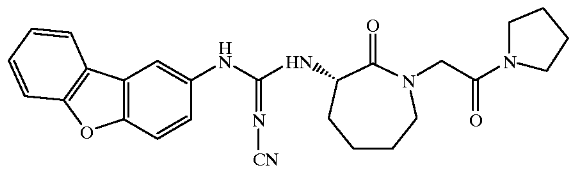 | HPLC (method A) $t_R$ = 3.97 min. LRMS (ESI) m/z 473 |
| 300 | 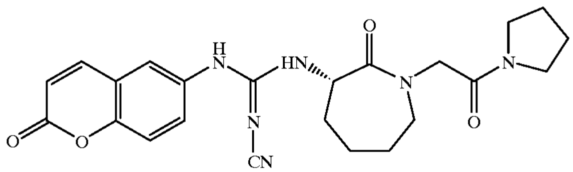 | HPLC (method A) $t_R$ = 2.98 min. LRMS (ESI) m/z 451 |
| 301 | 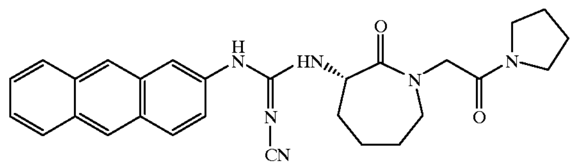 | HPLC (method A) $t_R$ = 4.17 min. LRMS (ESI) m/z 483 |
| 302 | 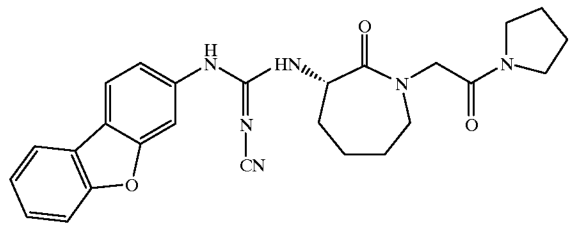 | HPLC (method A) $t_R$ = 4.0 min. LRMS (ESI) m/z 473 |
| 303 | 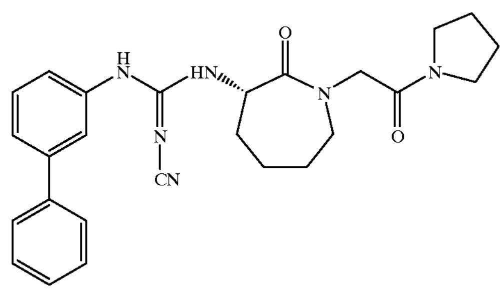 | HPLC (method A) $t_R$ = 3.96 min. LRMS (ESI) m/z 459 |
| 304 | 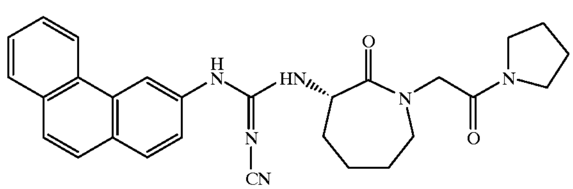 | HPLC (method A) $t_R$ = 4.12 min. LRMS (ESI) m/z 483 |
| 305 | 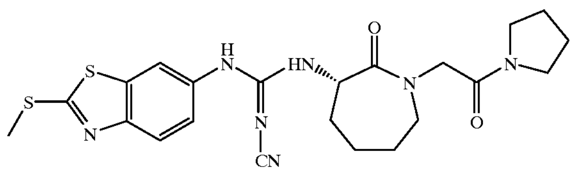 | HPLC (method A) $t_R$ = 3.59 min. LRMS (ESI) m/z 486 |

-continued

| Example | Structure | Characterization |
|---|---|---|
| 306 | 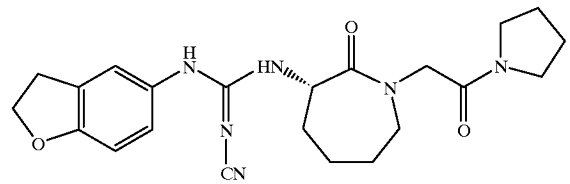 | HPLC (method A) $t_R$ = 3.34 min. LRMS (ESI) m/z 425 |
| 307 | 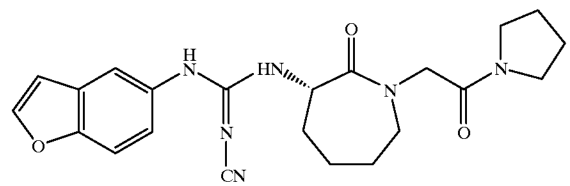 | HPLC (method A) $t_R$ = 3.34 min. LRMS (ESI) m/z 423 |
| 308 | 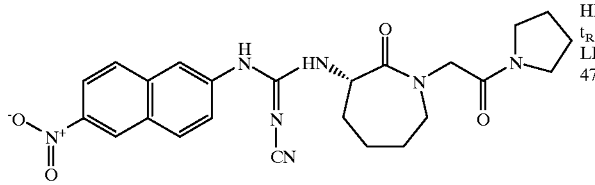 | HPLC (method A) $t_R$ = 3.73 min. LRMS (ESI) m/z 478 |
| 309 | 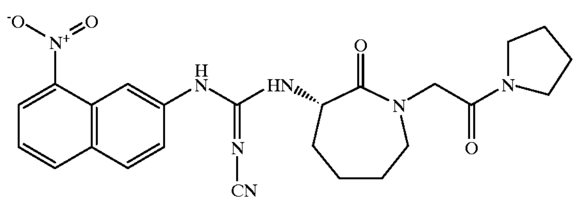 | HPLC (method A) $t_R$ = 3.60 min. LRMS (ESI) m/z 478 |
| 310 | 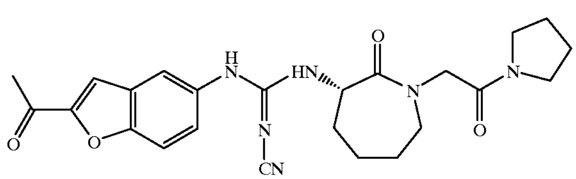 | HPLC (method A) $t_R$ = 3.21 min. LRMS (ESI) m/z 465 |
| 311 | 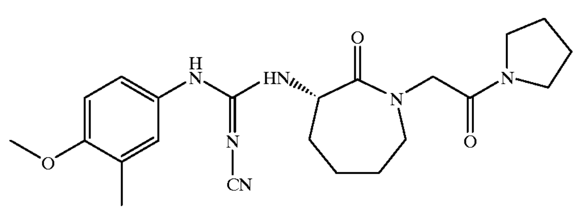 | HPLC (method A) $t_R$ = 3.52 min. LRMS (ESI) m/z 427 |
| 312 | 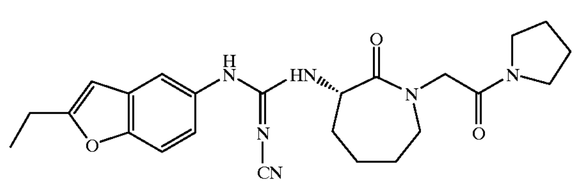 | HPLC (method A) $t_R$ = 3.91 min. LRMS (ESI) m/z 451 |

-continued

| Example | Structure | Characterization |
|---|---|---|
| 313 | 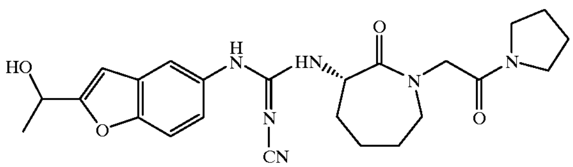 | HPLC (method A) $t_R$ = 3.25 min. LRMS (ESI) m/z 467 |
| 314 | 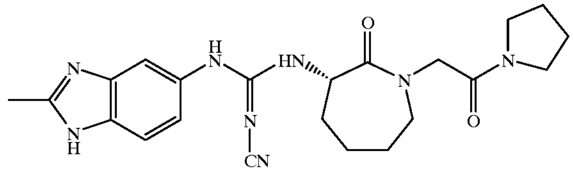 | HPLC (method A) $t_R$ = 2.25 min. LRMS (ESI) m/z 437 |
| 315 | 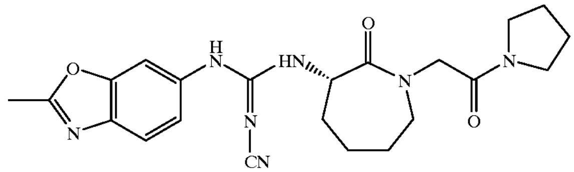 | HPLC (method A) $t_R$ = 3.11 min. LRMS (ESI) m/z 438 |
| 316 | 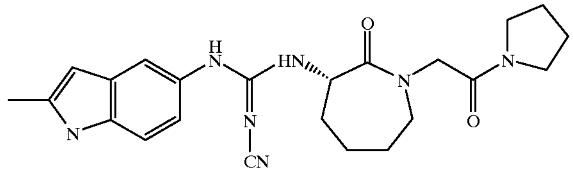 | HPLC (method A) $t_R$ = 3.39 min. LRMS (ESI) m/z 436 |
| 317 | 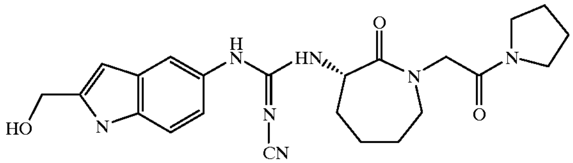 | HPLC (method A) $t_R$ = 2.99 min. LRMS (ESI) m/z 453 |
| 318 | 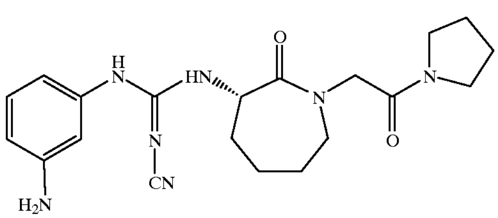 | HPLC (method A) $t_R$ = 2.18 min. LRMS (ESI) m/z 398 |
| 319 | 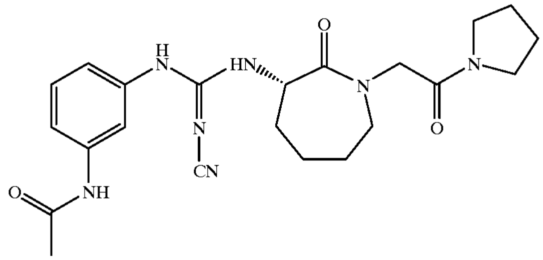 | HPLC (method A) $t_R$ = 2.87 min. LRMS (ESI) m/z 440 |

EXAMPLE 320

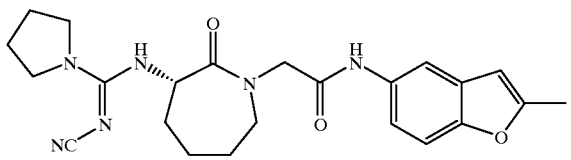

A

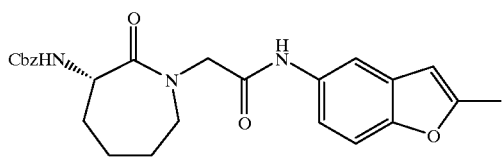

To a solution of (3S)-3-[[(phenylmethoxy)carbonyl]amino]hexahydro-2-oxo-1H-azepine-1-acetic acid (369 mg, 1.15 mmol) in DMF (2 mL) was added WSC (221 mg, 1.15 mmol) and 5-amino-2-methylbenzofuran (169 mg, 1.15 mmol). After stirring for 11 hours at room temperature, the mixture was diluted with ethyl acetate (20 mL) and washed with water (5×20 mL). The combined organic layers were dried over magnesium sulfate, and concentrated in vacuo. Flash chromatography (silica gel, 25 mm dia. column, 1% methanol/chloroform) provided part A compound (495 mg, 96%) as a tan foam: LCMS (ESI, positive ion spectrum, HPLC method F), m/z 450 (M+H), $t_R$=3.7 min.

B

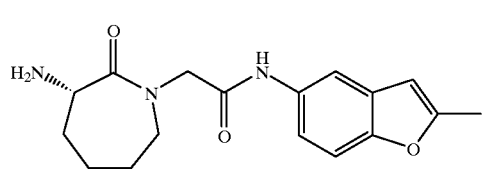

To a solution of part A compound (385 mg, 0.86 mmol) in a mixture of ethanol (20 mL), ethyl acetate (5 mL), and acetic acid (0.2 mL), was added Pd(OH)$_2$/carbon (40 mg). The mixture was placed under an atmosphere of hydrogen at 40 psi on a Parr shaker. After 1.5 hours, the mixture was filtered through Celite 545 using methanol (12 mL) to rinse the pad. The solvent was removed in vacuo and the residue partitioned between chloroform (2 mL) and water (1 mL). The aqueous phase was adjusted to pH 10 with sodium carbonate and the aqueous phase extracted with chloroform (3×2 mL). The combined organic extracts were concentrated in vacuo and the residue was purified by passing through a 10 g C-18 cartridge, eluting with 50% methanol/water. This provided the part B compound (239 mg, 88%) as an off-white solid: LCMS (ESI, positive ion spectrum, HPLC method F), m/z 316 (M+H), $t_R$=2.5 min.

C

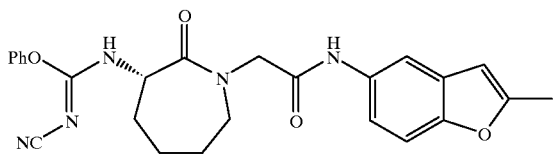

To a suspension of part B compound (95 mg, 0.30 mmol) in ethyl acetate (0.5 mL) was added diphenyl cyanocarbonimidate (71 mg, 0.30 mmol). The mixture was placed in a 70° C. bath. The mixture became transiently homogeneous and then a thick, white precipitate formed. The reaction mixture was removed from the bath after 5 minutes. Ethyl acetate (0.5 mL) was added to aid in stirring. The solid was collected by filtration, rinsed with ethyl acetate (0.5 mL) and dried to provide part C compound (118 mg, 86%) as a white, crystalline solid: LCMS (ESI, positive ion spectrum, HPLC method F), m/z 460 (M+H), $t_R$=3.5 min.

D

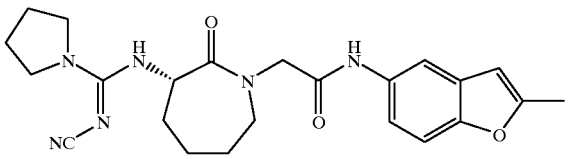

To a suspension of part C compound (46 mg, 0.1 mmol) in ethyl acetate (0.3 mL) was added pyrrolidine (14 mg, 0.2 mmol). The mixture was placed in a 70° C. bath. After 1 hour, the reaction mixture was removed from the bath and the solvent removed in vacuo. The product was purified by passing through a 2 g C-18 cartridge and eluting with 60% methanol/water to provide Title compound Title compound (36 mg, 83%) as a tan powder: LCMS (ESI, positive ion spectrum, HPLC method F), m/z 437 (M+H), $t_R$=3.3 min.

EXAMPLE 321

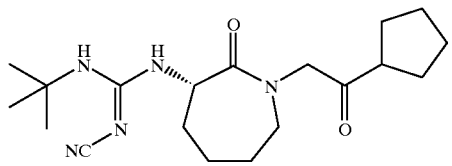

A

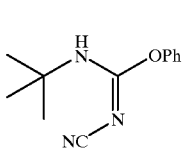

To a slurry of diphenyl cyanocarbonimidate (476 mg, 2.0 mmol) in ethyl acetate (1.5 mL) was added t-butylamine (146 mg, 2.0 mmol). The mixture was heated briefly at 80° C. (5 mn). Upon cooling to room temperature, a thick white slurry had formed. This was filtered and washed with ethyl acetate (0.5 mL) and then hexane (3×1 mL) to yield part A compound (284 mg, 66%) as a white solid.

B

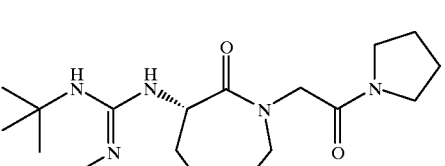

To a slurry of part A compound (85 mg, 0.39 mmol) in ethyl acetate (1 mL) was added (S)-1-[(3-amino-hexahydro-2-oxo-1H-azepin-1-yl)acetyl]pyrrolidine (94 mg, 0.39 mmol). The mixture was heated at 80° C. which led to a complete dissolution of the solids. After 23 hours at 80° C., the product was purified by flash chromatography (silica, 40 mm dia column, 2% methanol/chloroform) to yield Title compound (79 mg, 59%) as a white foam: LCMS (ESI, positive ion spectrum, HPLC method F), m/z 363 (M+H), $t_R$=2.4 min.

EXAMPLE 322

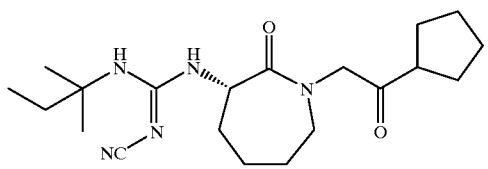

Using the methods described for Example 321, Title compound was prepared (102 mg, 59%) as a white foam: LCMS (ESI, positive ion spectrum, HPLC method F), m/z 377 (M+H), $t_R$=2.7 min.

EXAMPLE 323

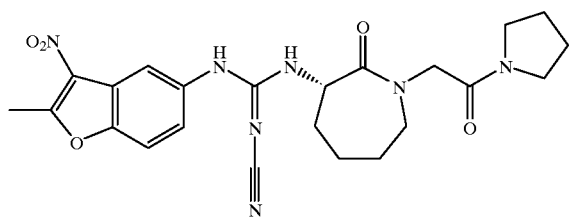

A

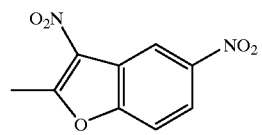

To a solution of 2-methyl-5-nitrobenzofuran (9.14 g, 51.6 mmol) in 200 mL of acetic anhydride at 5° C. was added fuming nitric acid (5.42 g, d=1.52) and then concentrated sulfuric acid (1.7 mL, d=1.84) dropwise. The temperature of the reaction mixture was kept between 0° C. to 10° C. during the addition. The reaction was stirred for 3 hours while keeping the temperature between 0° C. and 10° C. The reaction was poured into 150 mL of ice, and the mixture was extracted with dichloromethane (3×200 mL). The organic phases were dried over magnesium sulfate and concentrated. The residue was chromatographed (silica, 50–70% dichloromethane in hexanes) to give part A compound as a white solid (5.7 g, 50%): $^1$H-NMR (270 MHz, CDCl$_3$) δ 9,04 (d, 1H, J=2 Hz), 8.35 (dd, 1H, J=9.0, 2 Hz), 7.63 (d, 1H, J=9 Hz), 3.0 (s, 3H); HPLC (Method A) $t_R$=3.8 min.

B

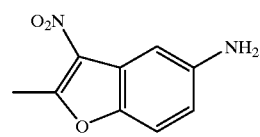

To a solution of 2-methyl-3,5-dinitrobenzofuran (4.4 g, 19.8 mmol) in ethyl acetate (250 mL) was added stannous chloride (dihydrate, 8.99 g, 39.8 mmol). The mixture was stirred at room temperature for 70 hours. Water (100 mL) and 1N NaOH (100 mL) were added. The mixture was extracted with ethyl acetate (4×150 mL). The combined organic layers were dried over magnesium sulfate. The solvent was removed in vacuo and the residue was chromatographed (silica, 20–30% ethyl acetate in hexanes) to give 2-methyl-3-nitro-5-benzofuranamine as a yellow solid (1.71 g, 45%): $^1$H-NMR (270 MHz, CDCl3) δ 7.38 (d, 1H, J=2.8 Hz), 7.25 (d, 1H, J=8.8 Hz), 6.72 (dd, 1H, J=8.8, 2.8 Hz), 2.87 (s, 3H); HPLC (Method A) $t_R$=1.36 min.

C

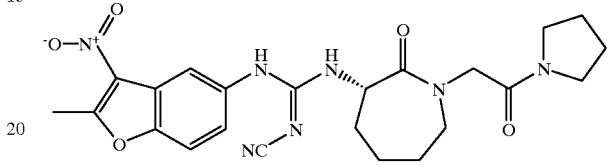

Using the procedure described in Example 291, the Title compound was prepared from part B compound. Because part B compound is not a hydrochloride salt, triethylamine was omitted: LRMS (ESI) m/z 482 (M+H); HPLC (Method A) $t_R$=3.5 min.

EXAMPLE 324

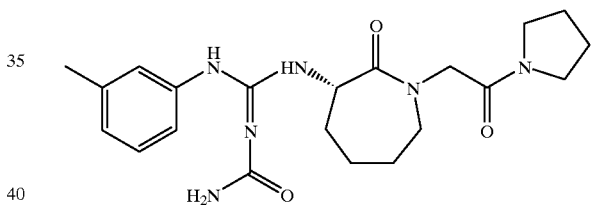

To a solution of Example 27 compound (93 mg, 0.23 mmol) in 5 mL of THF, was added 5 mL of 2 N HCl. The reaction was stirred at 60° C. for 8 h. The reaction mixture was concentrated by rotary evaporation and the residue was dissolved in 20 mL of ethyl acetate. The organic solution was washed with 20 mL of saturated NaHCO$_3$, 20 mL of brine, dried and concentrated. The residue was purified by preparative HPLC (YMC ODS-A C-18 reverse phase column; linear gradient elution: solvent A: 90:10 H$_2$O:MeOH+ 0.2% TFA and solvent B: 10:90 H$_2$O:MeOH+0.2% TFA) to give title compound (37 mg, 39%): LRMS (ESI) m/z 415; HPLC (method B) $t_R$=3.2 min.

EXAMPLES 325 to 332

Using the same methodology described for preparing the Example 324 compound, the following compounds were prepared.

| Example | Structure | Characterization |
|---------|-----------|------------------|
| 325 | 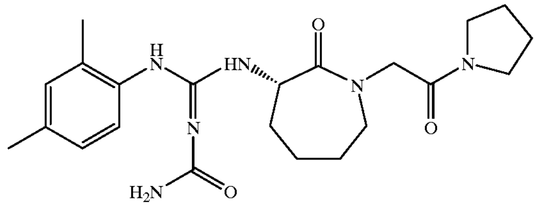 | HPLC (method C) $t_R$ = 4.6 min. LRMS (ESI) m/z 429 |
| 326 | 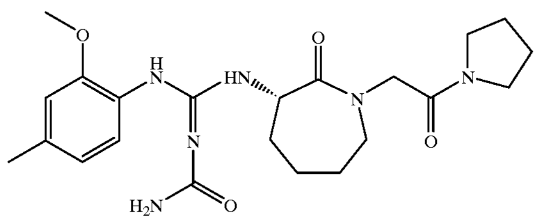 | HPLC (method C) $t_R$ = 4.5 min. LRMS (ESI) m/z 445 |
| 327 | 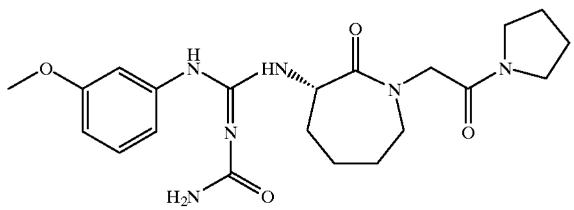 | HPLC (method B) $t_R$ = 3.0 min. LRMS (ESI) m/z 431 |
| 328 | 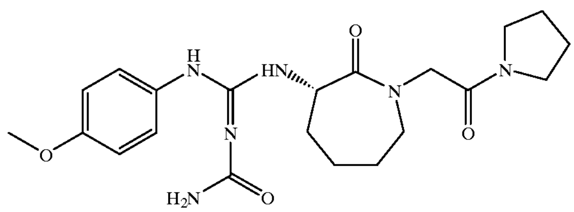 | HPLC (method A) $t_R$ = 1.6 min. LRMS (ESI) m/z 431 |
| 329 | 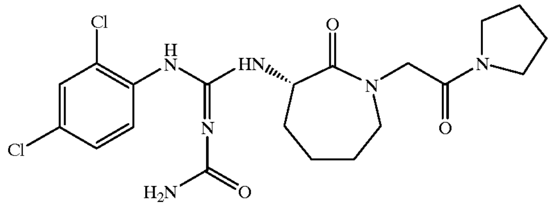 | HPLC (method A) $t_R$ = 2.66 min. LRMS (ESI) m/z 469 |
| 330 | 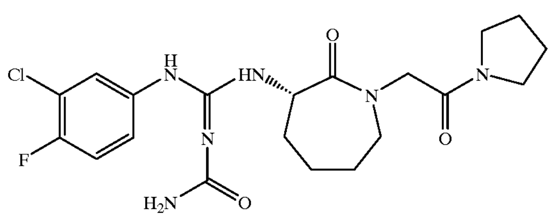 | HPLC (method A) $t_R$ = 2.48 min. LRMS (ESI) m/z 453 |
| 331 | 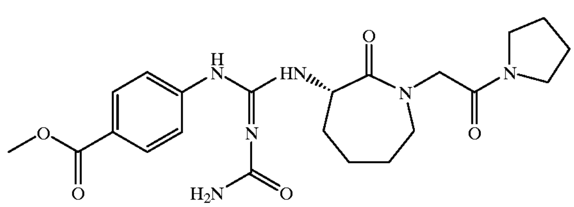 | HPLC (method A) $t_R$ = 2.31 min. LRMS (ESI) m/z 459 |

| Example | Structure | Characterization |
|---|---|---|
| 332 | 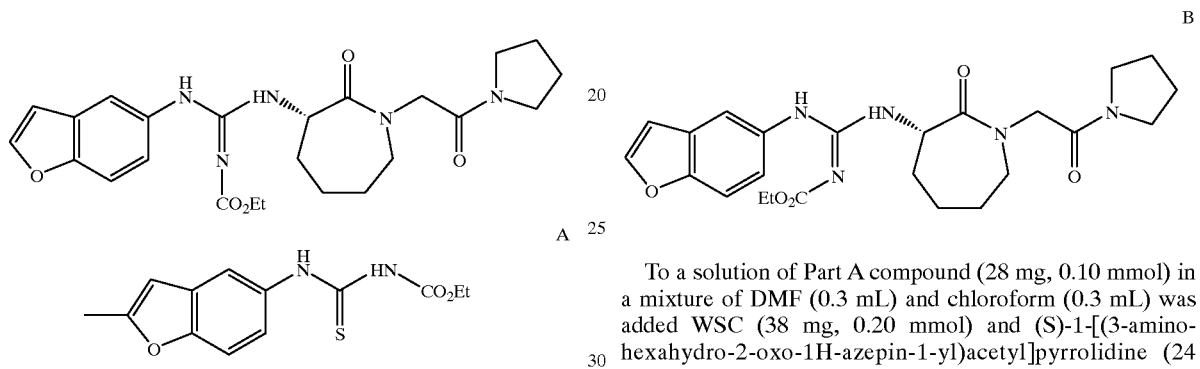 | HPLC (method A) $t_R$ = 2.39 min. LRMS (ESI) m/z 455 |

EXAMPLE 333

To a solution of 2-methyl-5-benzofuranamine (74 mg, 0.50 mmol) in chloroform (1 mL) at room temperature was added ethoxycarbonyl isothiocyanate (72 mg, 0.55 mmol). A precipitate began to form within 5 minutes. After 12 hours, the solids were collected by filtration. The filtrate was concentrated in vacuo and the residue was triturated with hexanes. The solids were combined to provide 124 mg (78%) of title compound: LC-MS (HPLC method F, ESI) m/z 278 (M+H), $t_R$=3.8 min.

To a solution of Part A compound (28 mg, 0.10 mmol) in a mixture of DMF (0.3 mL) and chloroform (0.3 mL) was added WSC (38 mg, 0.20 mmol) and (S)-1-[(3-amino-hexahydro-2-oxo-1H-azepin-1-yl)acetyl]pyrrolidine (24 mg, 0.10 mmol). After stirring overnight at room temperature, the reaction mixture was washed with water (2×2 mL) and concentrated in vacuo. The residue was then chromatographed (silica, 2% methanol in chloroform). The product-containing fractions were combined and concentrated in vacuo. Further purification of the residue (Varian Megabond Elute C-18, 70% methanol in water) yielded title compound (18 mg, 37%): LC-MS (HPLC method F, ESI) m/z 484 (M+H), $t_R$=3.1 min.

EXAMPLE 334

The following compound was prepared from benzoyl isothiocyanate using the methodology described in Example 333.

| Example | Structure | Characterization |
|---|---|---|
| 334 | 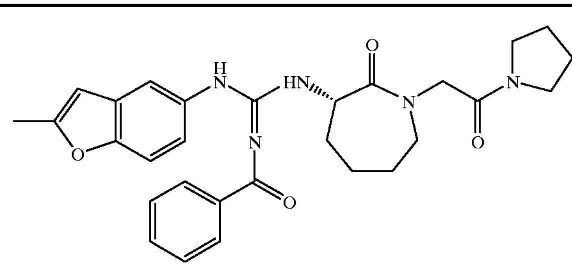 | HPLC (method A) $t_R$ = 3.3 min. LRMS (ESI) m/z 516 |

EXAMPLE 335

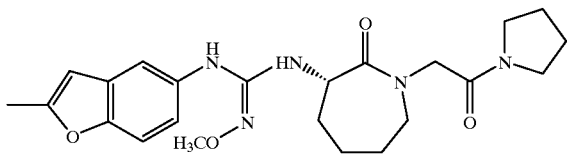

A

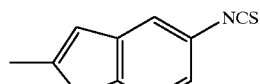

To a solution of 2-methyl-5-benzofuranamine (190 mg, 1.29 mmol) in dichloromethane (2 mL) at room temperature was added 1,1'-carbonothioylbis-2(1H)-pyridinone (300 mg, 1.29 mmol). After 60 minutes, the reaction mixture was passed through a column of silica by elution with chloroform and the product-containing fractions were combined and concentrated to provide part A compound (222 mg, 91%).

B

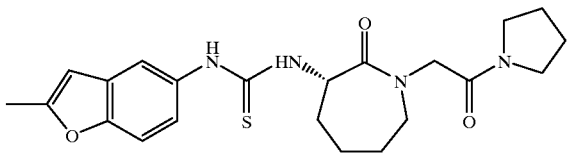

To a solution of Part A compound (72 mg, 0.38 mmol) in chloroform (2 mL) was added (S)-1-[(3-amino-hexahydro-2-oxo-1H-azepin-1-yl)acetyl]pyrrolidine (100 mg, 0.42 mmol). The mixture heated at 60° C. for 50 minutes. The reaction mixture was then placed on a silica column and eluted with 5% methanol in chloroform. The product-containing fractions were combined, concentrated, and then further purified by elution through a reverse phase column (Varian MegaBond Elute C-18, 70% methanol in water). This provided part B compound as a white solid (141 mg, 87%): LC-MS (HPLC method F, ESI) m/z 429 (M+H), $t_R$=3.4 min.

C

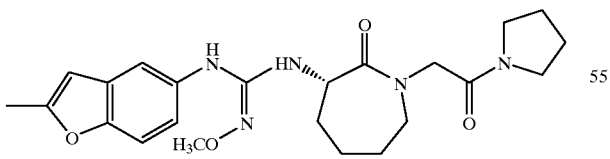

To a suspension of methoxylamine hydrochloride (167 mg, 2.00 mmol) in 1,2-dichloroethane (2 mL) was added triethylamine (404 mg, 4.00 mmol). After stirring at room temperature for 5 minutes, the slurry was filtered. The filtrate was added to a chloroform solution (1 mL) of Part B compound (56 mg, 0.13 mmol) and WSC (54 mg, 0.28 mmol). The mixture was heated at 60° C. for 2 hours. The reaction mixture was placed directly on a silica gel column and eluted with 5% methanol in chloroform. The product-containing fractions were combined, concentrated, and further purfied on a reverse phase cartridge (Varian MegaBond Elute C-18, 70% methanol in water). The product-containing fractions were combined and concentrated to yield the Title compound (10 mg, 17%): LC-MS (ESI) m/z 442 (M+H), $t_R$=3.0 min.

EXAMPLE 336

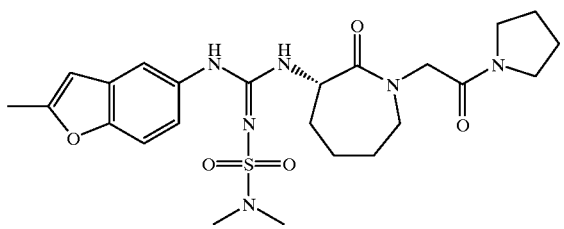

To a solution of N,N-dimethylsulfamide(60 mg, 0.56 mmol) in DMF (2 mL) was added NaH (95%, 21 mg, 0.84 mmol). The resulting mixture was stirred for 10 min and 2-methyl-5-isothiocyanatobenzofuran (84 mg, 0.45 mmol) was added. The reaction was stirred at room temperature for 1 h and (S)-1-[(3-amino-hexahydro-2-oxo-1H-azepin-1-yl)acetyl]pyrrolidine (133 mg, 0.56 mmol) and WSC (107 mg, 0.56 mmol) were added in that order. After stirring at room temperature overnight, the reaction was quenched with water (1 mL), extracted with ethyl acetate (3×10 mL), dried over MgSO$_4$ and filtered. The solvent was then removed and the residue was purified by preparative HPLC (C-18 reverse phase column; solvent A: 90:10 H$_2$O:MeOH+0.1% TFA, solvent B: 10:90 H$_2$O:MeOH+0.1% TFA) to give Title compound (173 mg, 75%): LRMS (ESI) m/z 519 (M+H); HPLC (Method A) $t_R$=3.8 min.

EXAMPLES 337 to 343

Using the procedure described in Example 336, the following compounds were prepared

| Example | structure | characterization |
|---|---|---|
| 337 | 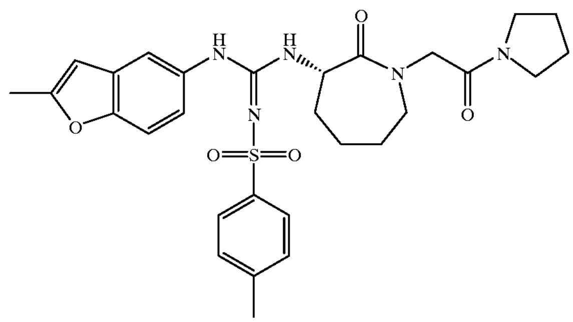 | HPLC (method A)<br>$t_R$ = 4.1 min<br>LRMS (ESI) m/z<br>566 (M + H) |
| 338 | 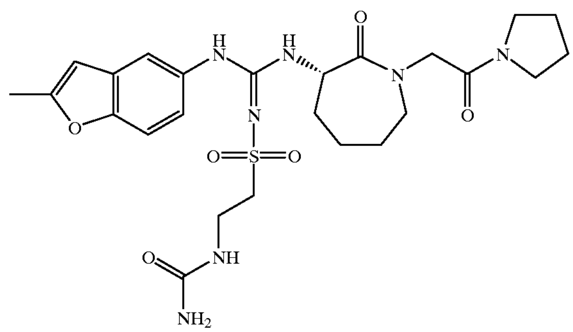 | HPLC (method A)<br>$t_R$ = 3.4 min<br>LRMS (ESI) m/z<br>562 (M + H) |
| 339 | 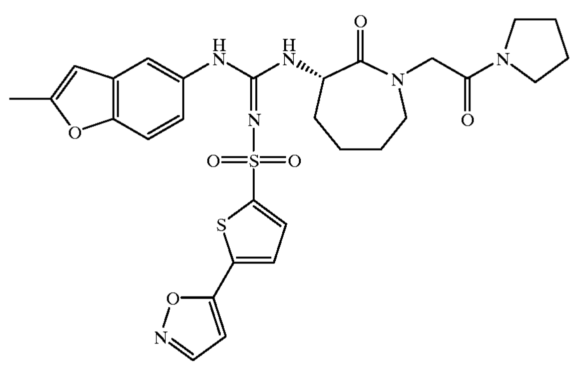 | HPLC (method A)<br>$t_R$ = 4.0 min<br>LRMS (ESI) m/z<br>625 (M + H) |
| 340 | 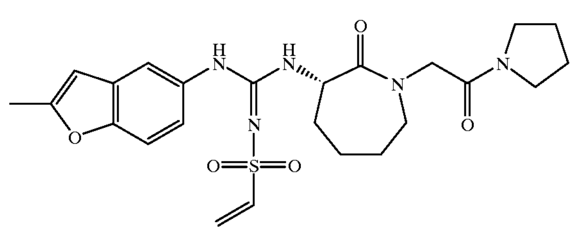 | HPLC (method A)<br>$t_R$ = 3.7 min<br>LRMS (ESI) m/z<br>502 (M + H) |
| 341 | 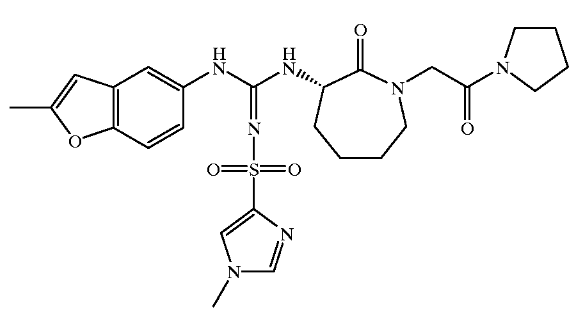 | HPLC (method A)<br>$t_R$ = 3.5 min<br>LRMS (ESI) m/z<br>556 (M + H) |

-continued

| Example | structure | characterization |
|---|---|---|
| 342 | 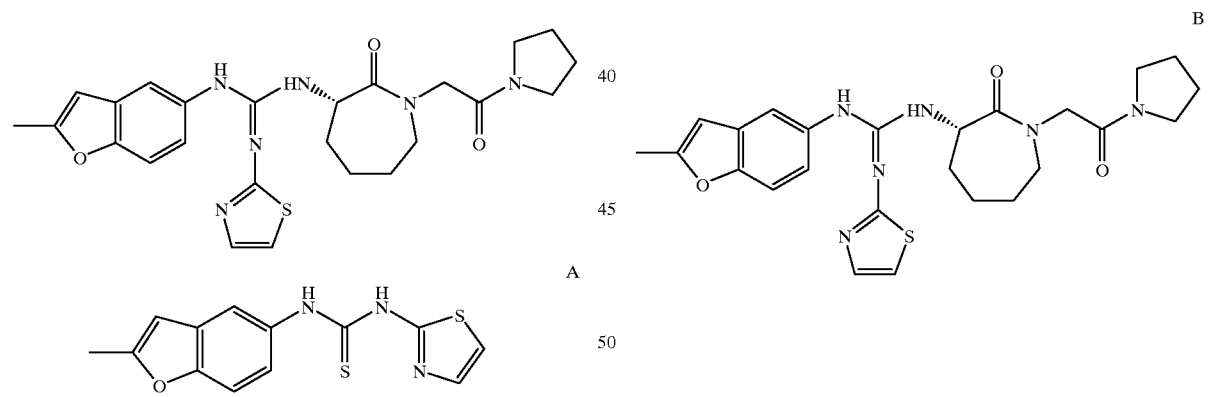 | HPLC (method A)<br>$t_R$ = 3.2 min<br>LRMS (ESI) m/z<br>679 (M + H) |
| 343 | 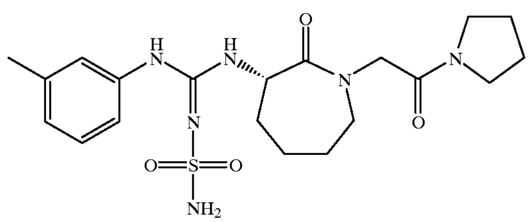 | HPLC (method A)<br>$t_R$ = 3.3 min<br>LRMS (ESI) m/z<br>451 (M + H) |

EXAMPLE 344

To a solution of 2-methyl-5-isothiocyanatobenzofuran (38 mg, 0.20 mmol) in chloroform (1 mL) was added 2-aminothiazole (24 mg, 0.24 mmol). The heterogeneous mixture was heated at 60° C. for 28 hours. After washing the reaction mixture with water (2 mL), drying with magnesium sulfate, and concentration, the residue was passed thru a silica column and eluting with 5% methanol in chloroform to yield part A compound (21 mg, 36%): LC-MS (HPLC method F, ESI) m/z 290 (M+H), $t_R$=3.7 min.

A mixture of Part A compound (21 mg, 0.073 mmol), (S)-1-[(3-amino-hexahydro-2-oxo-1H-azepin-1-yl)acetyl] pyrrolidine (17 mg, 0.073 mmol), and WSC (28 mg, 0.146 mmol) were dissolved in DMF (0.4 mL) and stirred at room temperature for 30 hours. Ethyl acetate (2 mL) was added and the mixture washed with water (5×1 mL), dried with magnesium sulfate, and then concentrated. The residue was purified by silica gel chromatography (eluting with 2% methanol in chloroform) and then by reverse phase chromatography (Varian MegaBond Elute cartridge C-18) eluting with 70% methanol in water to provide the Title compound (8 mg, 22%): LC-MS (HPLC method F, ESI) m/z 495 (M+H) $t_R$=3.2 min.

EXAMPLE 345

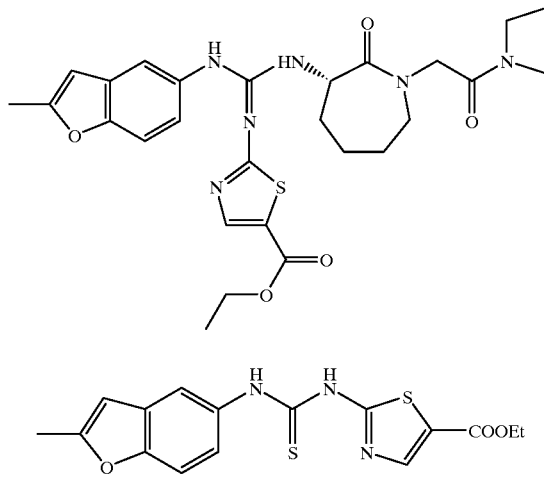

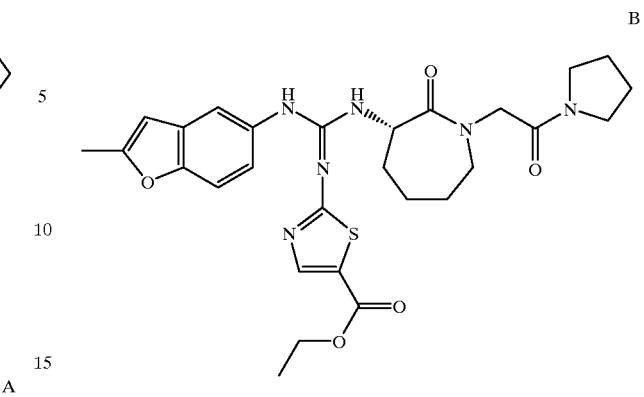

To a solution of ethyl 2-amino-5-thiazolecarboxylate (344 mg, 2.0 mmol) in DMF (1 mL) was added sodium hydride (60% in mineral oil, 96 mg, 2.4 mmol). After stirring at room temperature for 20 minutes, 5-isothiocyanato-2-methylbenzofuran (378 mg, 2.0 mmol) was added to the reaction mixture. The reaction was stirred at room temperature for 1 hour. The reaction was diluted with 50 mL of ethyl acetate and the organic solution was washed with brine (2×40 mL). The organic layer was dried over sodium sulfate and concentrated to give 678 mg (94%) of part A compound: LCMS (ESI) m/z 362 (M+H)

A mixture of part A compound (108 mg, 0.30 mmol), (S)-1-[(3-amino-hexahydro-2-oxo-1H-azepin-1-yl)acetyl]pyrrolidine (72 mg, 0.30 mmol), and WSC (58 mg, 0.30 mmol) was dissolved in DMF (1 mL) and stirred at room temperature for 16 hours. Ethyl acetate (25 mL) was added and the mixture washed with brine (2×20 mL), dried with sodium sulfate, and then concentrated. The residue was purified by preparative HPLC (C-18 reverse phase column; solvent A: 90:10 $H_2O$:MeOH+0.1% TFA, solvent B: 10:90 $H_2O$:MeOH+0.1% TFA) to provide (73 mg, 43%) the Title compound: HPLC (method D) $t_R$=3.8; LCMS (ESI) m/z 567 (M+H)

EXAMPLE 346

Using the procedure described in Example 345, the following compound was prepared.

| Example | structure | characterization |
|---|---|---|
| 346 | (structure shown) | HPLC (method D) $t_R$ = 3.4 min LRMS (ESI) m/z 567 (M + H) |

EXAMPLE 347

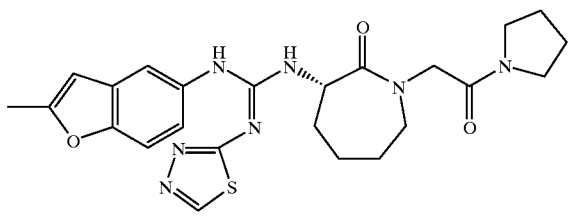

To a solution of Example 335 part B compound (21 mg, 0.049 mmol) in acetonitrile (0.3 mL) was added 1,1',1"[(1, 1-dimethylethyl)phosphinimylidyne]trispyrrolidine (18 mg, 0.058 mmol). After stirring the mixture for 5 days, the product was isolated by preparative TLC (500 μm silica plate, 5% methanol/chloroform, $R_f$=0.2). The Title compound was isolated as a light brown oil (5 mg, 21%): LCMS (ESI, positive ion spectrum, HPLC method F), m/z 496 (M+H), $t_R$=3.0 min.

EXAMPLE 348

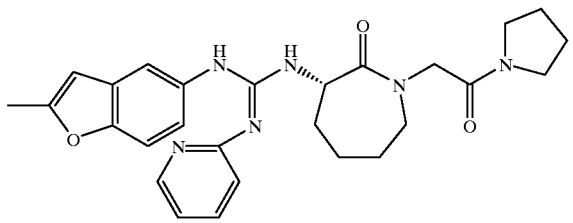

A

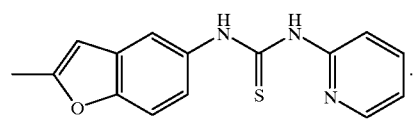

To a solution of 2-methyl-5-isothiocyanatobenzofuran (189 mg, 1.0 mmol) in chloroform (2 mL) was added 2-aminopyridine (104 mg, 1.1 mmol). The mixture was heated at 60° C. for 26 hours. Flash chromatography (silica, 40 mm dia. column, 2% methanol/chloroform) provided part A compound as a white solid (156 mg, 55%): LCMS (ESI, positive ion spectrum, HPLC method F), m/z 284 (M+H), $t_R$=3.7 min.

B

To a solution of (S)-1-[(3-amino-hexahydro-2-oxo-1H-azepin-1-yl)acetyl]pyrrolidine (24 mg, 0.10 mmol) in DMF (0.6 mL) was added part A compound (28 mg, 0.10 mmol) and WSC (38 mg, 0.20 mmol). The mixture was heated at 60° C. for 2 hours. The reaction mixture was diluted with ethyl acetate (5 mL) and then washed with water (5×5 mL). The organic layer was dried with magnesium sulfate and concentrated in vacuo. The residue was passed through a 2 g C-18 cartridge eluting the product with 70% methanol/water. This provided the Title compound (18 mg, 37%) as an off-white powder: LCMS (ESI, positive ion spectrum, HPLC method F), m/z 489 (M+H), $t_R$=3.3 min.

EXAMPLE 349

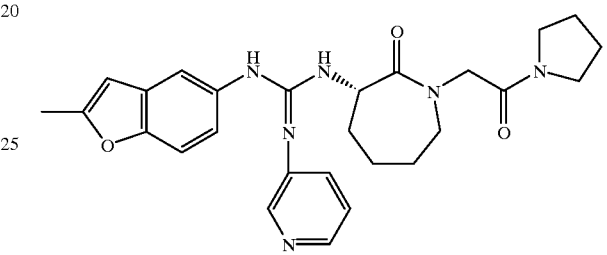

To a solution of 3-pyridinamine (38 mg, 0.40 mmol) in DMF (0.5 mL) was added sodium hydride (60% in mineral oil, 19 mg, 0.48 mmol). After stirring at room temperature for 30 minutes, 5-isothiocyanato-2-methylbenzofuran (76 mg, 0.40 mmol) was added to the reaction mixture. Then the reaction mixture was stirred at room temperature for 5 hour. (S)-1-[(3-amino-hexahydro-2-oxo-1H-azepin-1-yl)acetyl] pyrrolidine (96 mg, 0.40 mmol), and WSC (77 mg, 0.40 mmol) were added and the reaction mixture was stirred at room temperature for 16 hours. Ethyl acetate (25 mL) was added and the mixture waswashed with brine (2×20 mL), dried with sodium sulfate, and then concentrated. The residue was purified by preparative HPLC (C-18 reverse phase column; solvent A: 90:10 $H_2O$:MeOH+0.1% TFA, solvent B: 10:90 $H_2O$:MeOH+0.1% TFA) to provide the Title compound (60 mg, 31%): HPLC (method D) $t_R$=2.5 min; LCMS (ESI) m/z 489 (M+H)

EXAMPLES 350 to 368

Using the procedure described in Example 349, the following compounds were prepared.

| Example | structure | characterization |
|---|---|---|
| 350 | 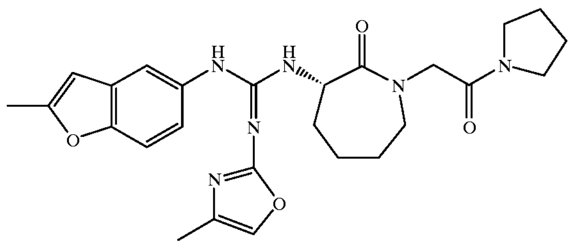 | HPCL (method A)<br>$t_R$ = 3.4 min<br>LCMS (ESI) m/z<br>493 (M + H) |
| 351 | 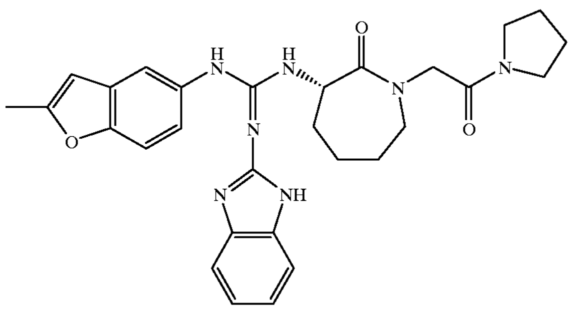 | HPCL (method D)<br>$t_R$ = 3.3 min<br>LCMS (ESI) m/z<br>528 (M + H) |
| 352 | 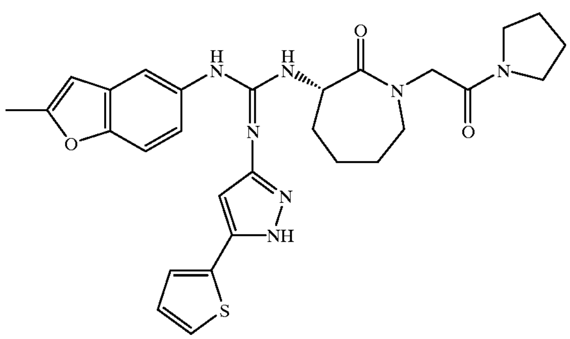 | HPCL (method D)<br>$t_R$ = 3.5 min<br>LCMS (ESI) m/z<br>560 (M + H) |
| 353 | 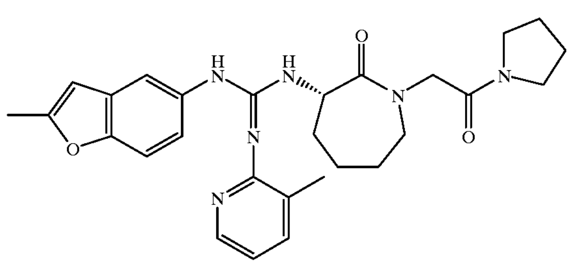 | HPCL (method D)<br>$t_R$ = 3.2 min<br>LCMS (ESI) m/z<br>503 (M + H) |
| 354 | 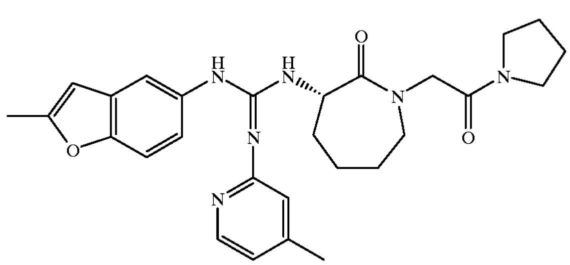 | HPCL (method D)<br>$t_R$ = 3.4 min<br>LCMS (ESI) m/z<br>503 (M + H) |

-continued

| Example | structure | characterization |
|---|---|---|
| 355 | 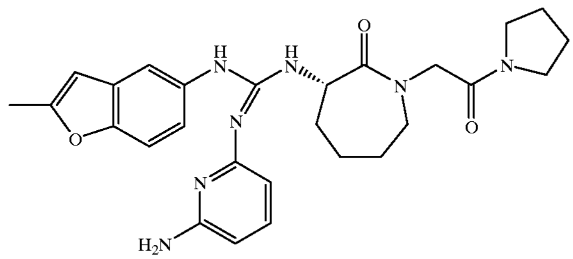 | HPCL (method D)<br>$t_R$ = 3.1 min<br>LCMS (ESI) m/z<br>504 (M + H) |
| 356 | 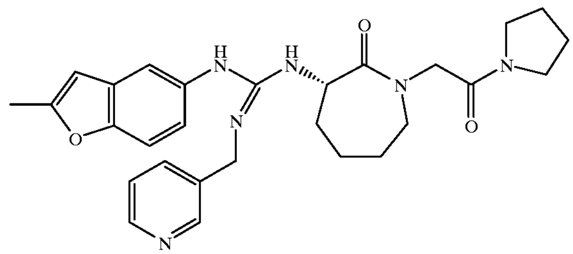 | HPCL (method D)<br>$t_R$ = 2.3 min<br>LCMS (ESI) m/z<br>503 (M + H) |
| 357 | 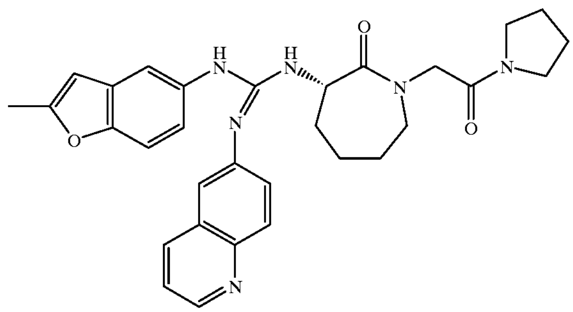 | HPCL (method D)<br>$t_R$ = 2.5 min<br>LCMS (ESI) m/z<br>539 (M + H) |
| 358 | 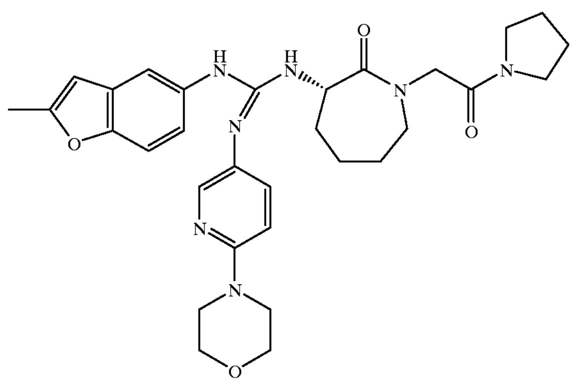 | HPCL (method D)<br>$t_R$ = 2.7 min<br>LCMS (ESI) m/z<br>574 (M + H) |
| 359 | 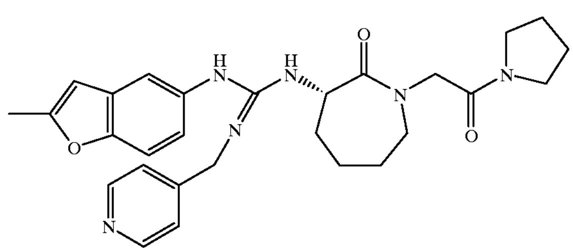 | HPCL (method D)<br>$t_R$ = 2.3 min<br>LCMS (ESI) m/z<br>503 (M + H) |

-continued

| Example | structure | characterization |
|---|---|---|
| 360 | 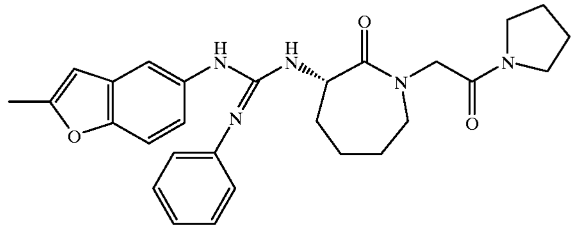 | HPCL (method D) $t_R$ = 3.2 min LCMS (ESI) m/z 488 (M + H) |
| 361 | 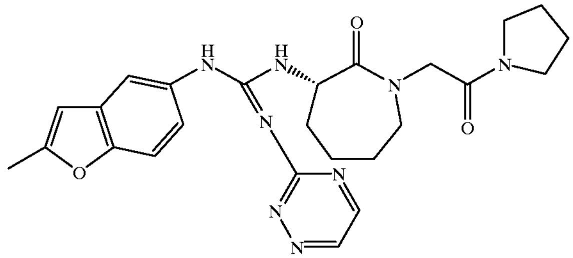 | HPCL (method D) $t_R$ = 2.8 min LCMS (ESI) m/z 491 (M + H) |
| 362 | 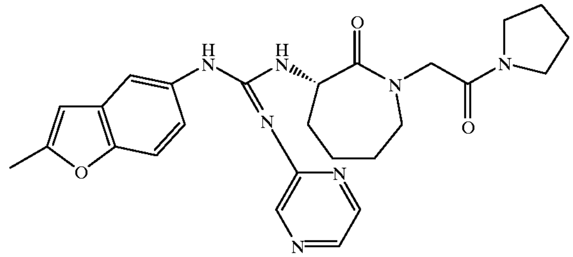 | HPCL (method D) $t_R$ = 2.9 min LCMS (ESI) m/z 490 (M + H) |
| 363 | 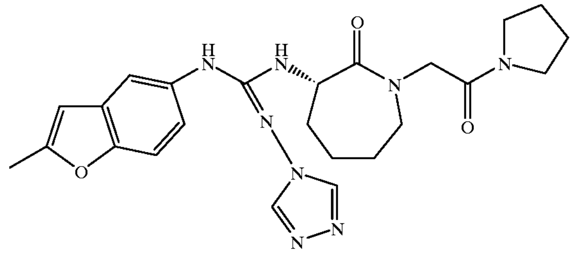 | HPCL (method D) $t_R$ = 2.9 min LCMS (ESI) m/z 479 (M + H) |
| 364 | 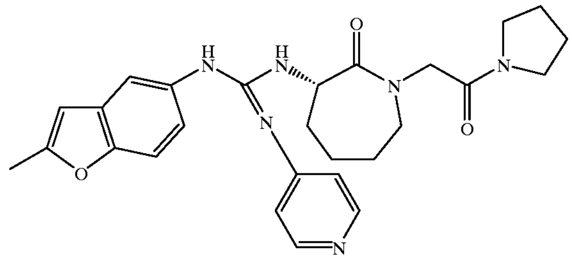 | HPCL (method D) $t_R$ = 2.2 min LCMS (ESI) m/z 489 (M + H) |

-continued

| Example | structure | characterization |
|---|---|---|
| 365 | 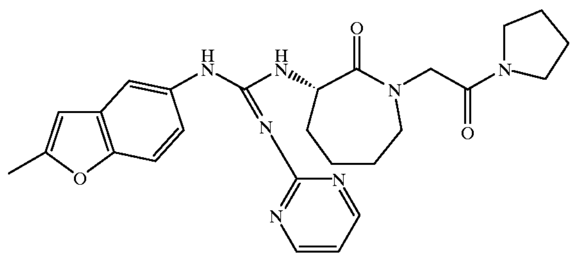 | HPCL (method D)<br>$t_R$ = 2.9 min<br>LCMS (ESI) m/z<br>490 (M + H) |
| 366 | 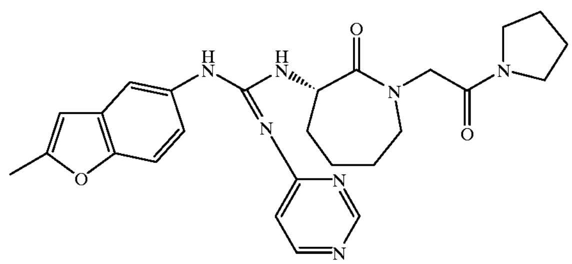 | HPCL (method D)<br>$t_R$ = 2.9 min<br>LCMS (ESI) m/z<br>490 (M + H) |
| 367 | 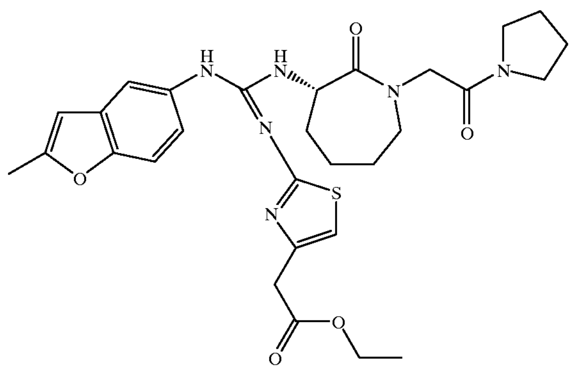 | HPCL (method D)<br>$t_R$ = 3.3 min<br>LCMS (ESI) m/z<br>581 (M + H) |
| 368 | 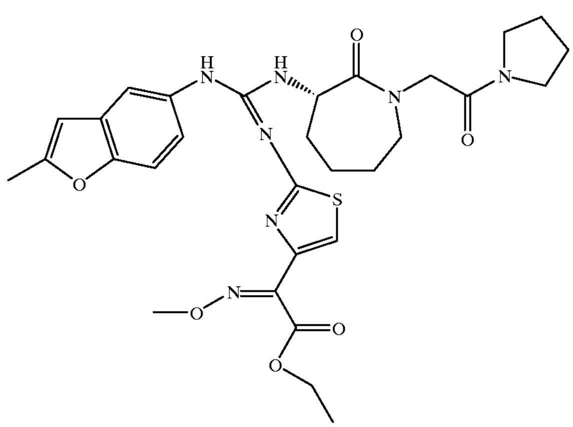 | HPCL (method D)<br>$t_R$ = 3.6 min<br>LCMS (ESI) m/z<br>624 (M + H) |

EXAMPLE 369

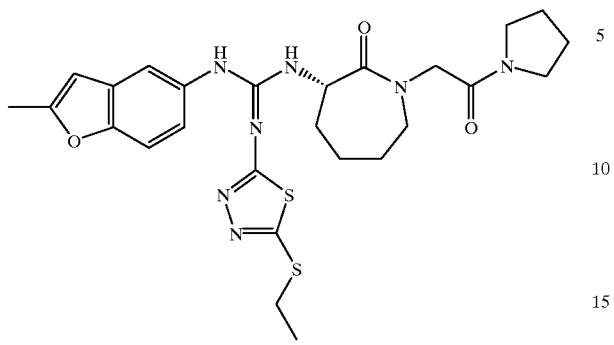

A mixture of 335 part B compound (86 mg, 0.20 mmol), 5-(ethylthio)-1,3,4-thiadiazol-2-amine (32 mg, 0.20 mmol) and 2-[(1,1-dimethylethyl)imino]-N,N-diethyl-2,2,3,4,5,6-hexahydro-1,3-dimethyl-1,3,2-diazaphosphorin-2(1H)-amine (BEMP) (0.29 mL, 1.0 mmol) was dissolved in $CH_3CN$ (0.5 mL). The reaction mixture was stirred at 80° C. for 24 hours, and an additional portion of BEMP (42 mg, 0.2 mmol) was added. The reaction mixture was stirred for another 40 hours. Ethyl acetate (25 mL) was added and the mixture washed with brine (2×20 mL), dried with sodium sulfate, and then concentrated. The residue was purified by preparative HPLC (C-18 reverse phase column; solvent A: 90:10 $H_2O$:MeOH+0.1% TFA and solvent B: 10:90 $H_2O$:MeOH+0.1% TFA) to provide 24 mg (22%) of the title compound: HPLC (method D) $t_R$=3.8 min; LCMS (ESI) m/z 556 (M+H)

EXAMPLE 370

Using the procedure described in Example 369, the following compound was prepared.

EXAMPLE 371

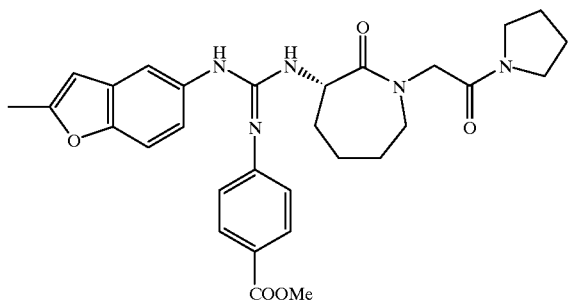

To a solution of 2-methyl-5-benzofuranamine (74 mg, 0.50 mmol) in DMF (1 mL) was added sodium hydride (60% in mineral oil, 24 mg, 0.6 mmol). After stirring at room temperature for 30 minutes, methyl 4-isothiocyanatobenzoate (97 mg, 0.50 mmol) was added to the reaction mixture. The reaction mixture was stirred at room temperature for 5 hour at which time (S)-1-[(3-amino-hexahydro-2-oxo-1H-azepin-1-yl)acetyl]pyrrolidine (120 mg, 0.50 mmol), and WSC (96 mg, 0.50mmol) were added. The reaction mixture was stirred at room temperature for 16 hours. Ethyl acetate (25 mL) was added and the mixture was washed with brine (20 mL×2), dried with sodium sulfate, and then concentrated. The residue was purified by preparative HPLC (C-18 reverse phase column; solvent A: 90:10 $H_2O$:MeOH+0.1% TFA, solvent B: 10:90 $H_2O$:MeOH+0.1% TFA) to provide 51 mg (19%) of the Title compound: HPLC (method D) $t_R$=3.2 min; LCMS (ESI) m/z 546 (M+H).

| Example | structure | characterization |
|---|---|---|
| 370 | 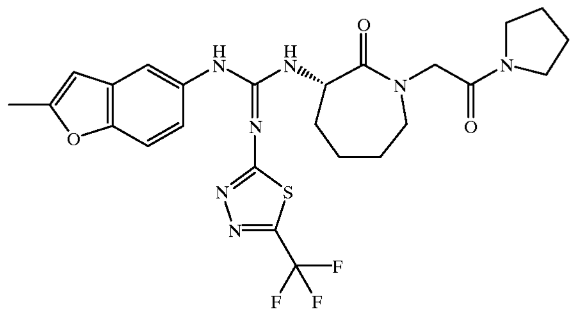 | HPLC (method D) $t_R$ = 4.5 min LCMS (ESI) m/z 564 (M + H) |

EXAMPLE 372

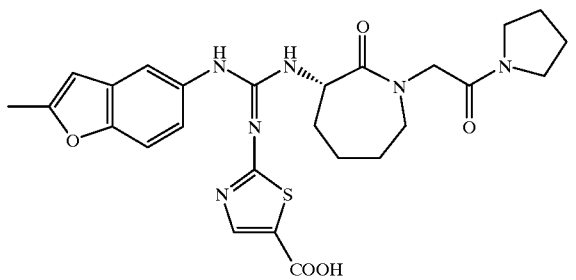

EXAMPLE 375

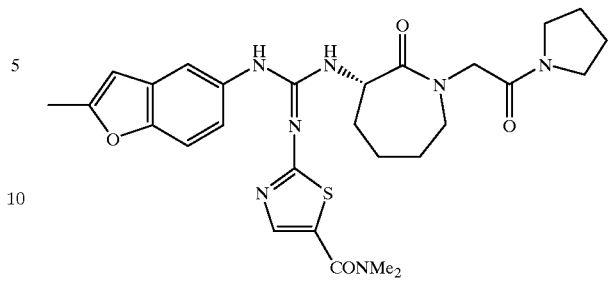

Example 345 compound (895 mg, 1.58 mmol) was dissolved in THF (5 mL) and 5 mL of 2 M LiOH aqueous solution was added. The reaction mixture was stirred at room temperature for 24 hours. The reaction mixture was concentrated by rotary evaporation and the residue was dissolved in methylene chloride. The organic mixture was extracted with 2×25 mL of water. The combined aqueous layers were acidified with 1 N HCl to pH 4. The aqueous solution then was extracted 2×25 mL with ethyl acetate. The combined ethyl acetate layers were dried over $Na_2SO_4$ and concentrated to give the Title compound (414 mg, 46%) as yellow solid: HPLC (method D) $t_R$=3.2 min; LCMS (ESI) m/z 539 (M+H)

EXAMPLES 373–374

Using the procedure described in Example 372, the following compounds were prepared To a solution of Example 372 compound (54 mg, 0.10 mmol) in 1 mL of DMF were added TFFH (29 mg, 0.11 mmol) and triethylamine (0.03 mL, 0.20 mmol). The reaction mixture was stirred at room temperature for 30 min at which time 2 M dimethylamine in THF (0.06 mL, 0.12 mmol) was added. The reaction mixture was stirred at room temperature for another 2 hours. The reaction mixture was diluted with 20 mL of ethyl acetate. The organic solution was washed with brine (20 mL×2), and concentrated. The residue was purified by preparative HPLC (C-18 reverse phase column; solvent A: 90:10 $H_2O$:MeOH+0.1% TFA, solvent B: 10:90 $H_2O$:MeOH+0.1% TFA) to provide the Title compound (17 mg, 30%) as a yellow solid: HPLC (method D) $t_R$=3.1 min; LCMS (ESI) m/z 566 (M+H).

EXAMPLES 376 to 378

Using the procedure described in Example 375, the following compounds were prepared.

| Example | structure | characterization |
|---|---|---|
| 373 | 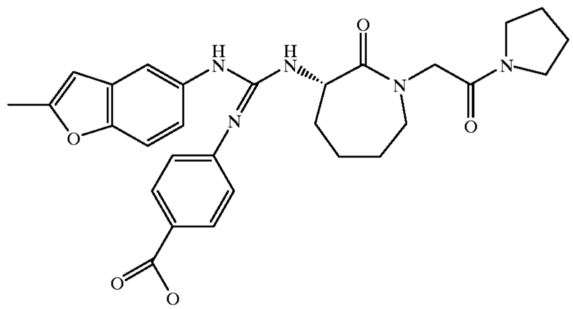 | HPCL (method D) $t_R$ = 3.0 min LCMS (ESI) m/z 532 (M + H) |
| 374 | 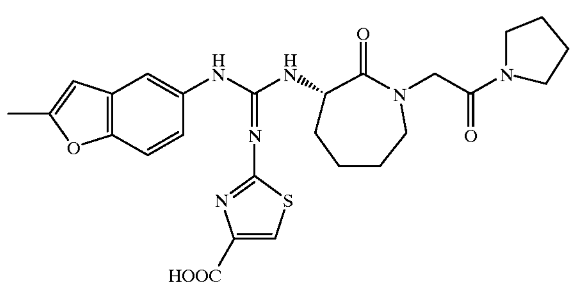 | HPCL (method D) $t_R$ = 3.1 min LCMS (ESI) m/z 539 (M + H) |

| Example | structure | characterization |
|---|---|---|
| 376 | 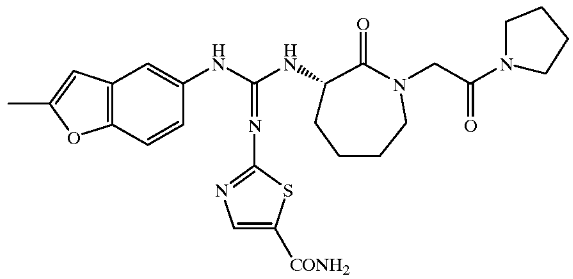 | HPCL (method C)<br>$t_R$ = 3.0 min<br>LCMS (ESI) m/z<br>538 (M + H) |
| 377 | 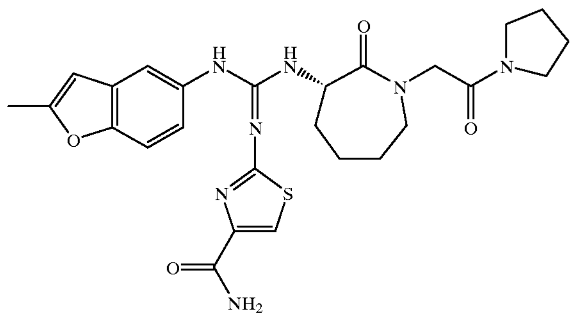 | HPCL (method C)<br>$t_R$ = 3.0 min<br>LCMS (ESI) m/z<br>538 (M + H) |
| 378 | 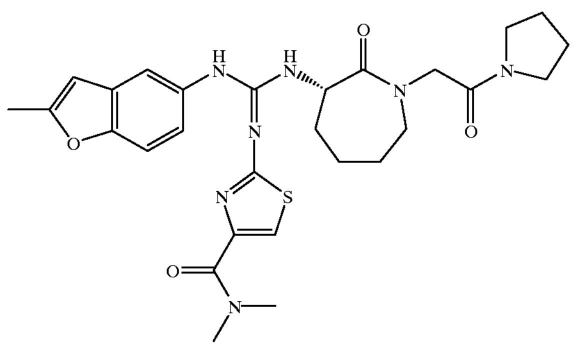 | HPCL (method C)<br>$t_R$ = 3.0 min<br>LCMS (ESI) m/z<br>566 (M + H) |

EXAMPLE 379

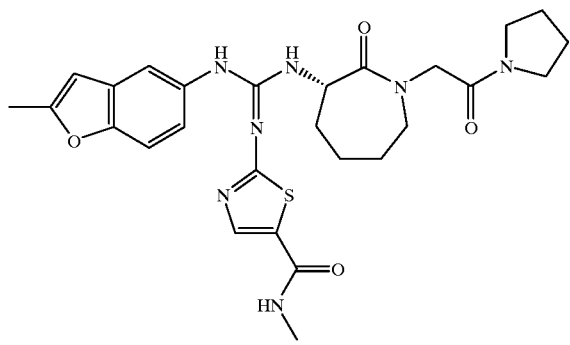

Example 372 compound (54 mg, 0.10 mmol), HOBT (14 mg, 0.10 mmol) and WSC (19 mg, 0.10 mmol) were dissolved in 1 mL of methylene chloride. The reaction mixture was stirred at room temperature for 30 min at which time 2 M methylamine in THF (0.05 mL, 0.10 mmol) was added. The reaction mixture was stirred at room temperature for another 2 hours. The reaction mixture was concentrated and the residue was purified by preparative HPLC (C-18 reverse phase column; solvent A: 90:10 $H_2O$:MeOH+0.1% TFA, solvent B: 10:90 $H_2O$:MeOH+0.1% TFA) to provide the Title compound (21 mg, 38%) as a white solid: HPLC (method D) $t_R$=3.1 min; LCMS (ESI) m/z 552 (M+H).

EXAMPLES 380 to 384

Using the procedure described in Example 379, the following compounds were prepared.

| Example | structure | characterization |
|---|---|---|
| 380 | 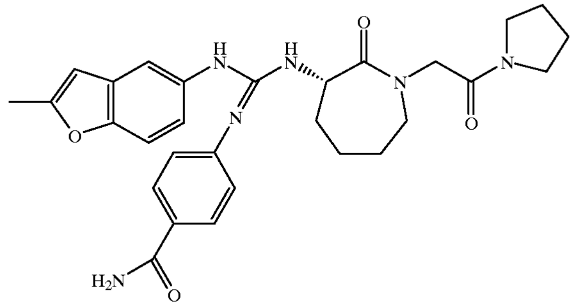 | HPCL (method C)<br>$t_R$ = 2.8 min<br>LCMS (ESI) m/z<br>531 (M + H) |
| 381 | 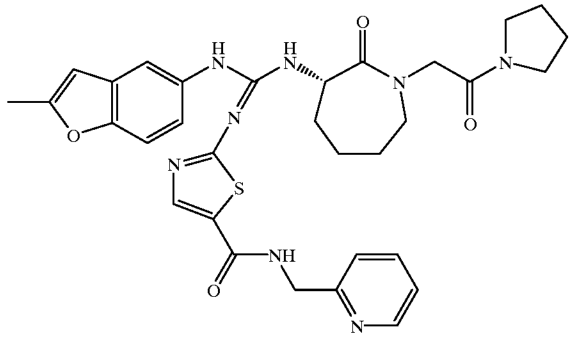 | HPCL (method C)<br>$t_R$ = 2.9 min<br>LCMS (ESI) m/z<br>629 (M + H) |
| 382 | 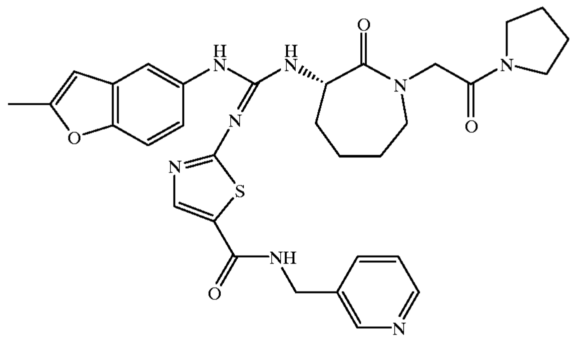 | HPCL (method C)<br>$t_R$ = 2.8 min<br>LCMS (ESI) m/z<br>629 (M + H) |
| 383 | 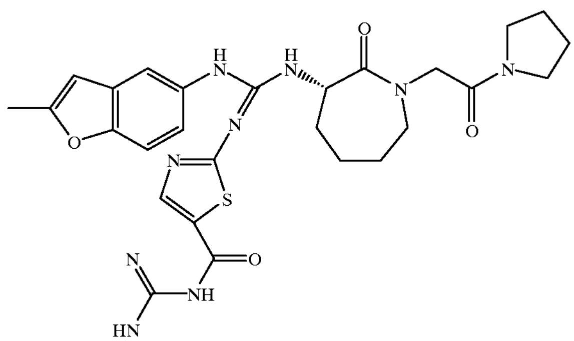 | HPCL (method C)<br>$t_R$ = 3.1 min<br>LCMS (ESI) m/z<br>580 (M + H) |

-continued

| Example | structure | characterization |
|---|---|---|
| 384 | 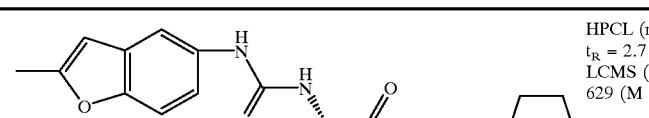 | HPCL (method C)<br>$t_R$ = 2.7 min<br>LCMS (ESI) m/z<br>629 (M + H) |

EXAMPLE 385

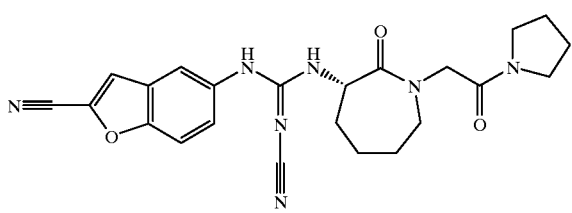

Example 83 compound (45 mg, 0.10 mmol) and Burgess' reagent (95 mg, 0.40 mmol) were dissolved in 2.5 mL of anhydrous methylene chloride. The reaction was stirred at room temperature under argon atmosphere for 2 hours. The reaction mixture was concentrated and the residue was purified by preparative HPLC (C-18 reverse phase column; solvent A: 90:10 H$_2$O:MeOH+0.1% TFA, solvent B: 10:90 H$_2$O:MeOH+0.1% TFA) to provide the Title compound (9.0 mg, 20%): HPLC (method D) $t_R$=3.3 min; LRMS (ESI) m/z 448 (M+H).

EXAMPLE 386

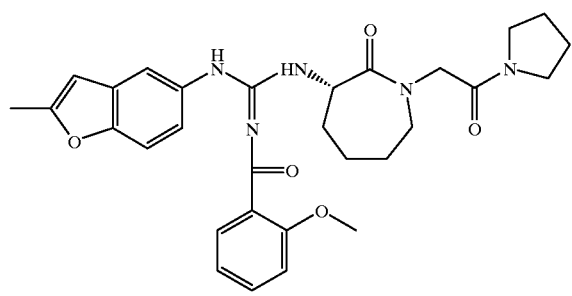

To 2-Methoxybenzamide (26.3 mg, 0.174 mmol) dissolved in 0.5 mL of THF was added NaH (6 mg, 0.26 mmol). Additional (0.5 mL) DMF was added to dissolve the precipitate which formed. 2-Methyl-isothiocyanatobenzofuran (29.5 mg, 0.156 mmol) was added and the reaction mixture was the heated at 50° C. for 16 h. (S)-1-[(3-amino-hexahydro-2-oxo-1H-azepin-1-yl)acetyl]pyrrolidine (41.6 mg, 0.174 mmol) and HgCl$_2$ (47.1 mg, 0.174 mmol) were added. The reaction mixture was stirred at room temperature for 10 minutes. The reaction was then quenched by addition of water and extracted three times with ethyl acetate. The combined organic fractions were washed once with brine, dried over MgSO$_4$ and evaporated. The residue was purified by preparative HPLC (YMC ODS-A C-18 reverse phase column; linear gradient elution: solvent A: 90:10 H$_2$O:MeOH+0.1% TFA and solvent B: 10:90 H$_2$O:MeOH+0.1% TFA) and then by flash chromatography (silica, 10% methanol/ethyl acetate) to give the Title compound as a white solid (27 mg, 28%): LRMS (ESI) m/z 546 (M+H); HPLC (method A) $t_R$=3.48 min.

EXAMPLE 387

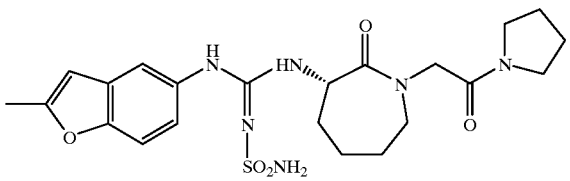

To a solution of sulfamide (30 mg, 0.31 mmol) in DMF-THF (1:1, 2 mL) was added NaH (14 mg, 0.55 mmol). The resulting mixture was stirred for 5 min and 2-methyl-5-isothiocyanatobenzofuran (45.3 mg, 0.2 mmol) was added. The reaction was then heated in a 60° C. bath for 14 h and then allowed to cool to room temperature. (S)-1-[(3-Amino-hexahydro-2-oxo-1H-azepin-1-yl)acetyl]pyrrolidine (57.4 mg, 0.24 mmol) and WSC (46 mg, 0.24 mmol) were added in that order. After stirring at room temperature for 3 h, the reaction was quenched with water (1 mL), extracted with ethyl acetate (3×10 mL). The combined organic layers were dried over MgSO$_4$. The solvent was the removed in vacuo and the residue was purified by chromatography (silica, step gradient of 5–10% MeOH in ethyl acetate) to provide Title compound as a white solid (33 mg, 30% yield): LRMS (ESI) m/z 491 (M+H); HPLC (method A) $t_R$=3.4 min.

EXAMPLE 388

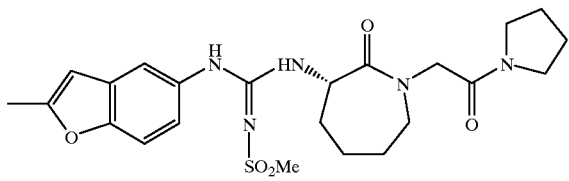

To a solution of methanesulfonamide (19 mg, 0.20 mmol) in DMF (1 mL) was added NaH (95%, 6.1 mg, 0.22 mmol) and the resulting mixture was stirred for 5 min. 2-Methyl-5-isothiocyanatobenzofuran (34 mg, 0.18 mmol) was added and the reaction was heated in a 60° C. bath for 1 h. After cooling the reaction to room temperature, (S)-1-[(3-amino-hexahydro-2-oxo-1H-azepin-1-yl)acetyl]pyrrolidine (47.8 mg, 0.20 mmol) and HgCl$_2$ (54.2 mg, 0.2 mmol) were added in that order. After stirring at room temperature for 10 min, the reaction was quenched with water (1 mL), extracted with ethyl acetate (3×10 mL), dried over MgSO$_4$ and filtered through Celite. The solvent was then removed and the residue was chromatographed (silica, ethyl acetate and then 5% MeOH in ethyl acetate) to provide Title compound as a white solid (50 mg, 57%): LRMS (ESI) m/z 491 (M+H); HPLC (method A) t$_R$=3.96 min.

EXAMPLE 389

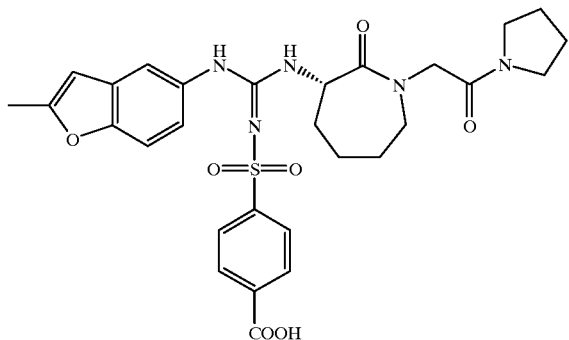

To a solution of 4-(aminosulfonyl)benzoic acid (40.2 mg, 0.20 mmol) in DMF (1 mL) was added NaH (95%, 13 mg, 0.5 mmol). The resulting mixture was stirred for 10 min and 2-methyl-5-isothiocyanatobenzofuran (34 mg, 0.18 mmol) was added. The reaction was heated in a 60° C. bath for 1 h. After cooling the reaction to room temperature, (S)-1-((3-amino-hexahydro-2-oxo-1H-azepin-1-yl)acetyl]pyrrolidine (47.8 mg, 0.20 mmol) and HgCl$_2$ (54.2 mg, 0.2 mmol) were added in that order. After stirring at room temperature overnight, the reaction was quenched with water (1 mL), extracted with ethyl acetate (3×10 mL), dried over MgSO$_4$ and filtered through Celite. The solvent was then removed and the residue was purified by preparative HPLC to give Title compound (15.5 mg, 15%): LRMS (ESI) m/z 596 (M+H); HPLC (Method A) t$_R$=3.8 min.

EXAMPLE 390

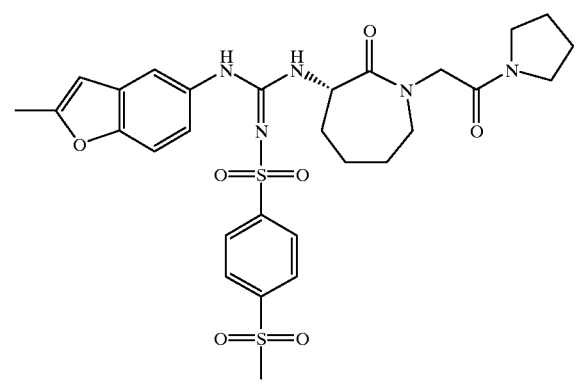

To a suspension of (4-methylsulphonyl)-benzenesulfonamide (100 mg, 0.425 mmol) in DMF (1 mL) was added NaH (95%, 15.3 mg, 0.605 mmol). The mixture was stirred 5 min at room temperature at which time, 2-methyl-5-isothiocyanatobenzofuran (64.3 mg, 0.34 mmol) was added in one portion. The flask was heated at 50° C. for 30 min at which time (S)-1-[(3-amino-hexahydro-2-oxo-1H-azepin-1-yl)acetyl]pyrrolidine (97.5 mg, 0.408 mmol), WSC (78.3 mg, 0.408 mmol) and 4-(dimethylamino)pyridine (cat.) were added in that order. The reaction mixture was stirred at room temperature overnight. The reaction was then quenched by addition of water and extracted with ethyl acetate three times. The combined organic fractions were washed once with brine, dried over MgSO$_4$ and evaporated. The residue was purified by flash chromatography (silica, 5% methanol in ethyl acetate) to give the Title compound as a white solid (149 mg, 70%): HPLC (method A) t$_R$=3.65 min; LRMS (ESI) m/z 630 (M+H)

EXAMPLES 391–395

Using the procedure described Example 390, the following compounds were prepared.

| Example | structure | characterization |
|---|---|---|
| 391 | 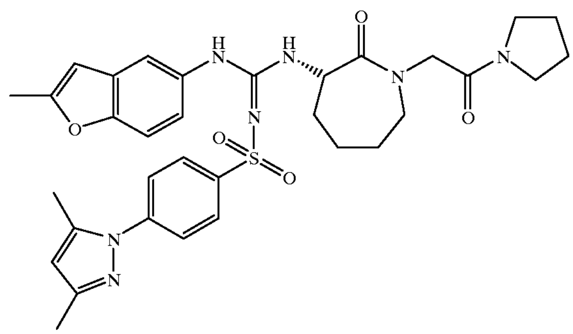 | HPCL (method A)<br>$t_R$ = 4.15 min<br>LCMS (ESI) m/z<br>646 (M + H) |
| 392 | 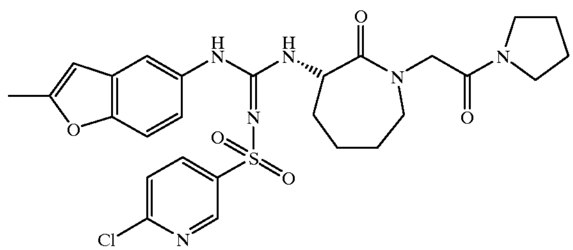 | HPCL (method A)<br>$t_R$ = 3.99 min<br>LCMS (ESI) m/z<br>588 (M + H) |
| 393 | 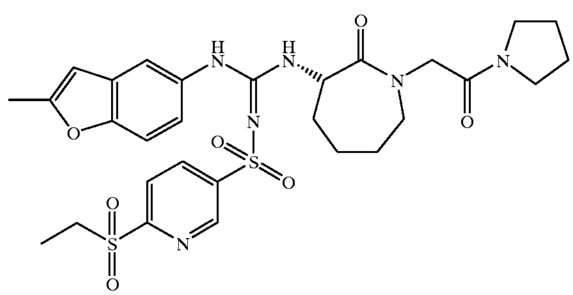 | HPCL (method A)<br>$t_R$ = 3.74 min<br>LCMS (ESI) m/z<br>645 (M + H) |
| 394 | 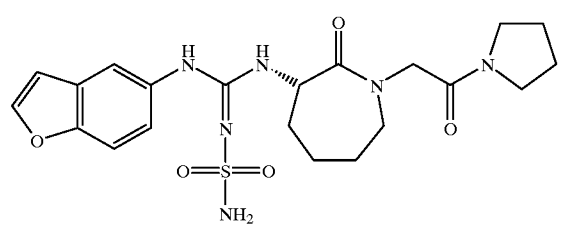 | HPCL (method A)<br>$t_R$ = 2.8 min<br>LCMS (ESI) m/z<br>477 (M + H) |
| 395 | 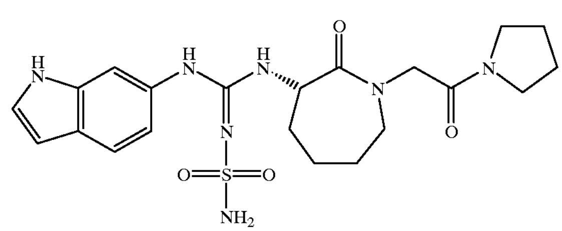 | HPCL (method A)<br>$t_R$ = 2.9 min<br>LCMS (ESI) m/z<br>476 (M + H) |

EXAMPLE 396

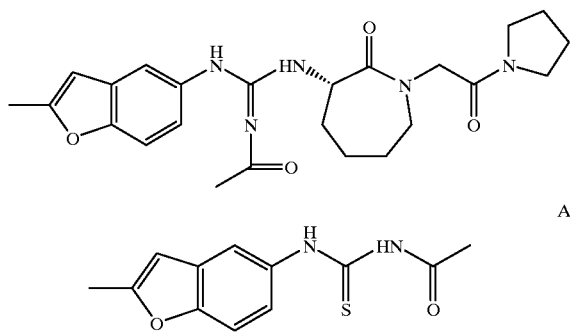

A.

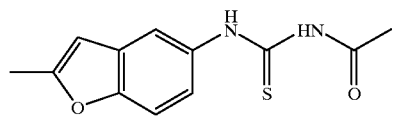

A mixture of potassium thiocyanate (200 mg, 2.06 mmol) and acetyl chloride (0.13 mL, 1.83 mmol) in acetone (8.0 mL) was stirred at room temperature for 30 minutes and then at reflux for additional 30 minutes. The mixture was cooled to 0° C. and a solution of 2-methyl-5-benzofuranamine (269 mg, 1.83 mmol) in acetone (3.0 mL) was added dropwise. The resulting mixture was then stirred at room temperature for 2 hours. The precipitate was removed by filtration and the filtrate was concentrated to give a yellow residue which was washed thoroughly with MeOH to yield part A compound as a yellow solid (181 mg, 40%).

B.

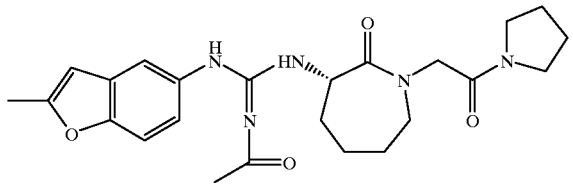

To a solution of Part A compound (41 mg, 0.16 mmol), (S)-1-[(3-amino-hexahydro-2-oxo-1H-azepin-1-yl)acetyl]pyrrolidine (43 mg, 0.18 mmol), and triethylamine (0.06 mL, 0.43 mmol) in DMF (0.8 mL) at 0° C. was added $HgCl_2$ (49 mg, 0.18 mmol). The resulting mixture was stirred at 0° C. for 30 minutes and at room temperature for 2 hours. The resulting dark mixture was diluted with ethyl acetate and filtered through Celite. The filtrate was washed with water and saturated aqueous NaCl solution, dried ($Na_2SO_4$) and concentrated. The residue was purified by flash chromatography (silica, dichloromethane then 3% MeOH in $CH_2Cl_2$) to give Title compound as a white solid (45 mg, 61%): LRMS (ESI) m/z 454 (M+H); HPLC (method A) $t_R$=2.77 min.

EXAMPLES 397 to 399

Using the methodology described for the Example 396 Title compound, the following compounds were prepared.

| Example | Structure | Characterization |
|---|---|---|
| 397 | 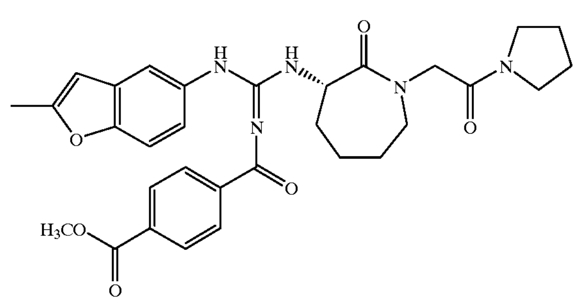 | HPCL (method A) $t_R$ = 4.04 min LCMS (ESI) m/z 574 |
| 398 | 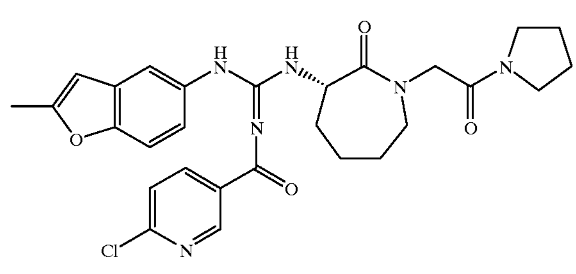 | HPCL (method A) $t_R$ = 4.32 min LCMS (ESI) m/z 551 |

| Example | Structure | Characterization |
|---|---|---|
| 399 | 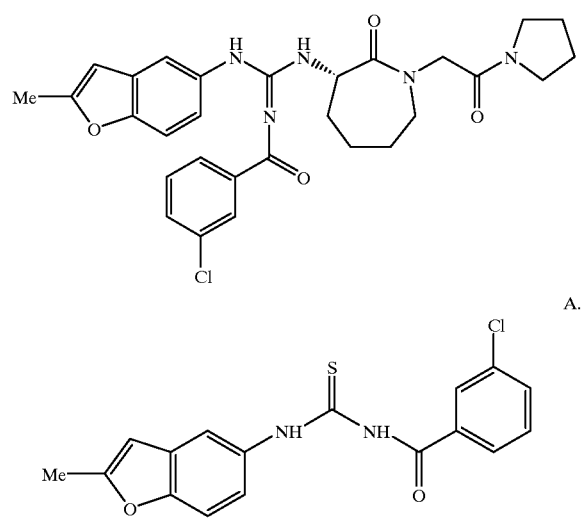 | HPCL (method A) $t_R$ = 3.6 min LCMS (ESI) m/z 521 (M + H) |

EXAMPLE 400

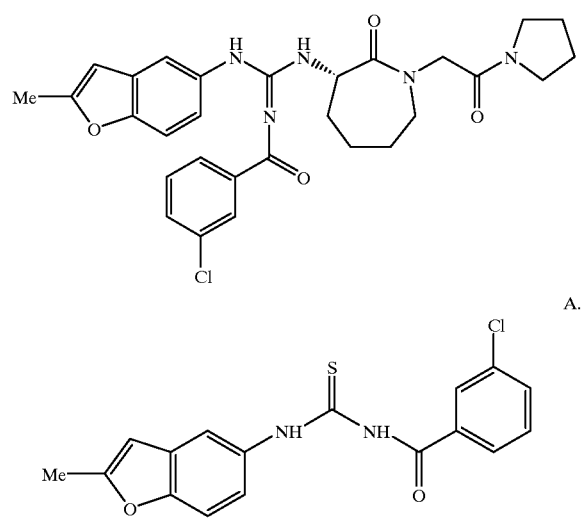

A.

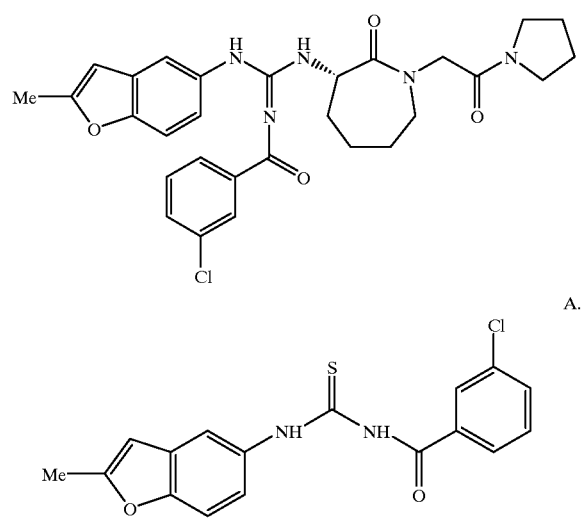

A mixture of 3-chlorobenzoyl isothiocyanate (102 mg, 0.52 mmol) and 2-methyl-5-benzofuranamine (76 mg, 0.52 mmol) in acetonitrile (2.5 mL) was stirred at room temperature for 2 h and concentrated. The residue was purified by flash chromatography (silica, 1:1 hexanes:methylene chloride, and then 100% methylene chloride) to afford part A compound (175 mg, 98%) as an off-white solid.

B.

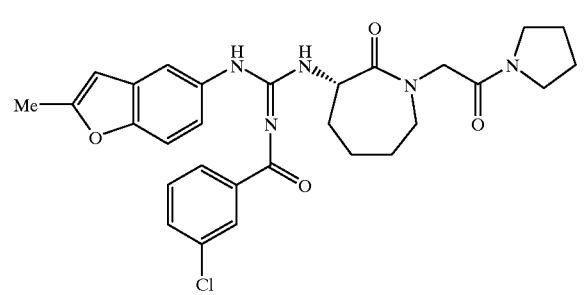

To a mixture of part A compound (56 mg, 0.16 mmol), (S)-1-[(3-amino-hexahydro-2-oxo-1H-azepin-1-yl)acetyl] pyrrolidine (39 mg, 0.16 mmol), and triethylamine (0.06 mL, 0.43 mmol) in DMF (1.0 mL) at room temperature was added $HgCl_2$ (49 mg, 0.18 mmol). The resulting mixture was stirred at room temperature for 30 min, then diluted with EtOAc and filtered through Celite. The filtrate was washed with water and brine, dried ($Na_2SO_4$) and concentrated. The residue was purified by flash chromatography (silica gel, 2% methanol in methylene chloride) to afford Title compound (75 mg, 84%) as a white solid: HPLC (method A) $t_R$=4.3 min; LRMS (ESI) m/z 551 (M+H).

EXAMPLE 401

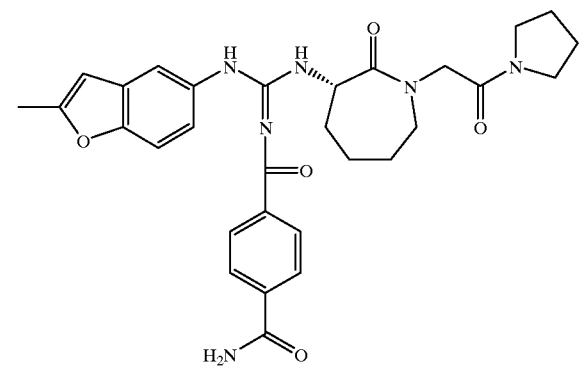

To a suspension of benzenedicarboxamide (312 mg, 1.90 mmol) in DMF (10 mL) was added NaH (95%, 60 mg, 2.4 mmol). The mixture was stirred 5 min at room temperature at which time 2-methyl-5-isothiocyanatobenzofuran (300 mg, 1.59 mmol) was added in one portion. The mixture was heated at 50° C. for 30 min at which time (S)-1-[(3-amino-hexahydro-2-oxo-1H-azepin-1-yl)acetyl]pyrrolidine (455 mg, 1.90 mmol), WSC (516 mg, 1.90 mmol) and 4-(dimethylamino)pyridine (cat.) were added in that order. The reaction mixture was stirred at room temperature overnight. The reaction was then quenched by addition of water and extracted with ethyl acetate three times. The combined organic fractions were washed once with brine, dried over $MgSO_4$ and evaporated. The residue was purified by flash chromatography on silica (5% methanol in ethyl acetate) to give the Title compound as a white solid (550 mg, 62%): HPLC (method A) $t_R$=3.37 min; LRMS (ESI) m/z 559 (M+H)

EXAMPLES 402 to 431

Using the procedure described in Example 401, the following compounds were prepared

| Example | structure | characterization |
|---|---|---|
| 402 | 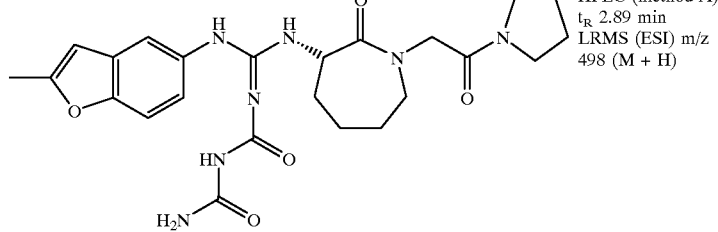 | HPLC (method A) $t_R$ 2.89 min LRMS (ESI) m/z 498 (M + H) |
| 403 | 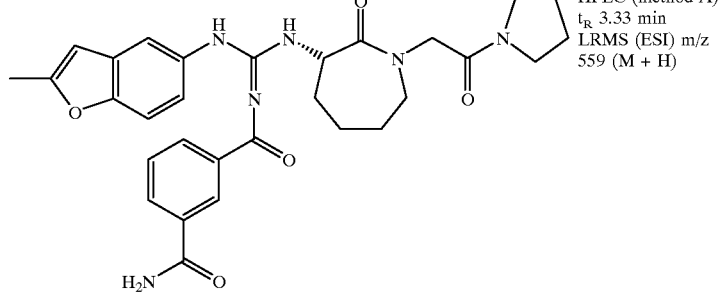 | HPLC (method A) $t_R$ 3.33 min LRMS (ESI) m/z 559 (M + H) |
| 404 | 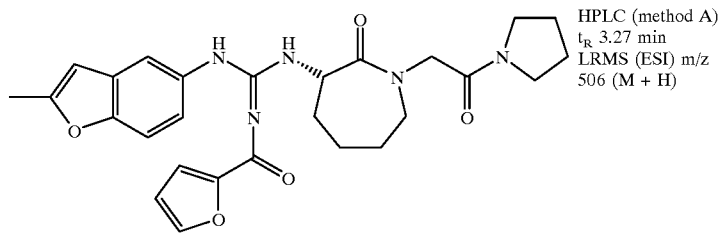 | HPLC (method A) $t_R$ 3.27 min LRMS (ESI) m/z 506 (M + H) |
| 405 | 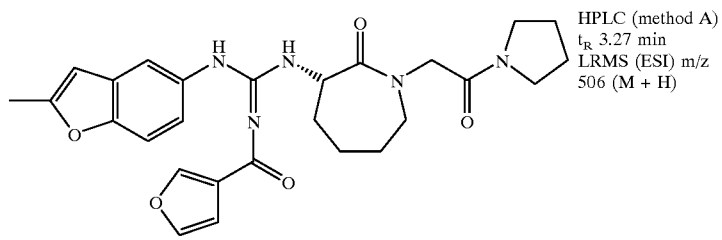 | HPLC (method A) $t_R$ 3.27 min LRMS (ESI) m/z 506 (M + H) |
| 406 | 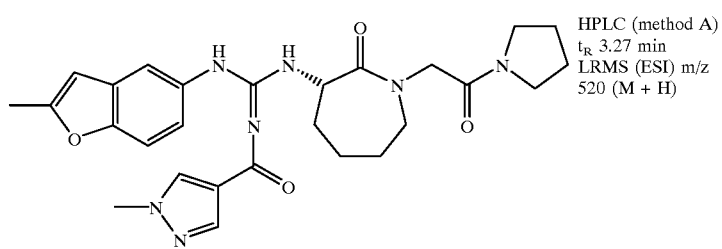 | HPLC (method A) $t_R$ 3.27 min LRMS (ESI) m/z 520 (M + H) |

| Example | structure | characterization |
|---|---|---|
| 407 | 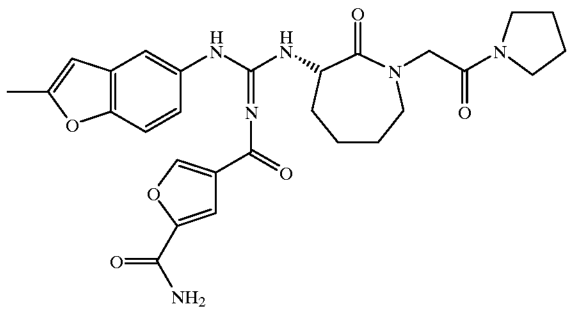 | HPLC (method A) $t_R$ 3.44 min<br>LRMS (ESI) m/z 549 (M + H) |
| 408 | 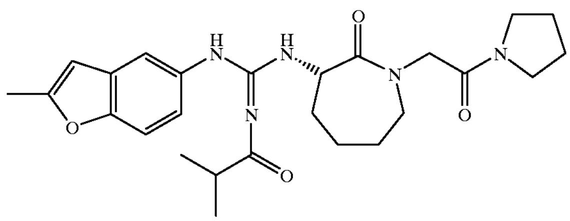 | HPLC (method A) $t_R$ 2.93 min<br>LRMS (ESI) m/z 483 (M + H) |
| 409 | 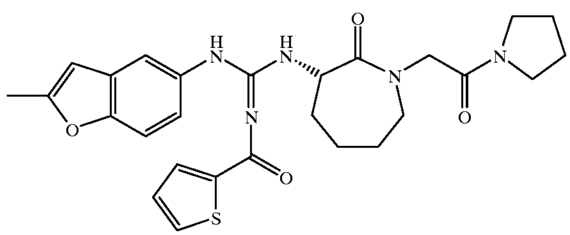 | HPLC (method A) $t_R$ 3.90 min<br>LRMS (ESI) m/z 522 (M + H) |
| 410 | 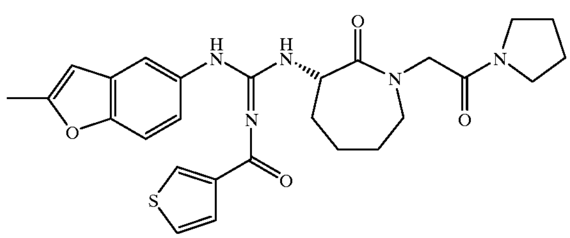 | HPLC (method A) $t_R$ 3.41 min<br>LRMS (ESI) m/z 522 (M + H) |
| 411 | 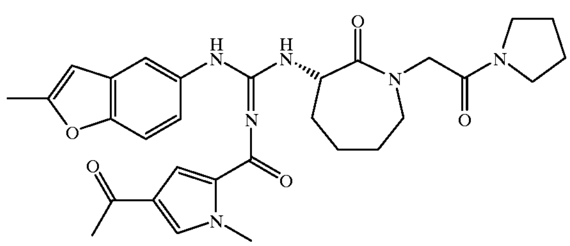 | HPLC (method A) $t_R$ 3.35 min<br>LRMS (ESI) m/z 561 (M + H) |
| 412 | 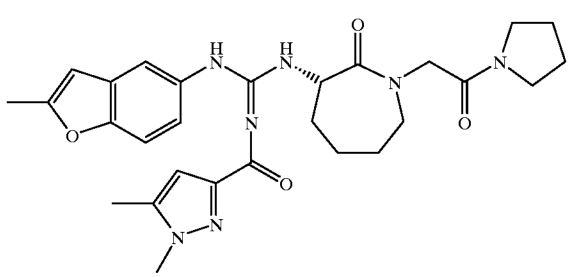 | HPLC (method A) $t_R$ 3.33 min<br>LRMS (ESI) m/z 534 (M + H) |

-continued

| Example | structure | characterization |
|---|---|---|
| 413 | 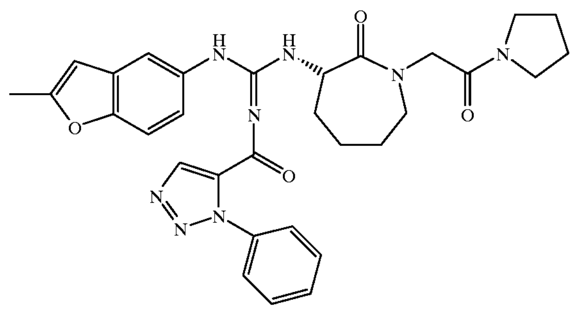 | HPLC (method A) $t_R$ 4.28 min LRMS (ESI) m/z 583 (M + H) |
| 414 | 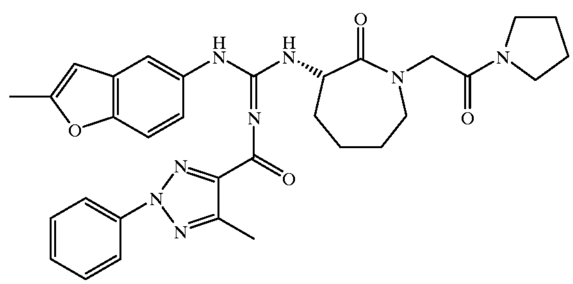 | HPLC (method A) $t_R$ 4.09 min LRMS (ESI) m/z 597 (M + H) |
| 415 | 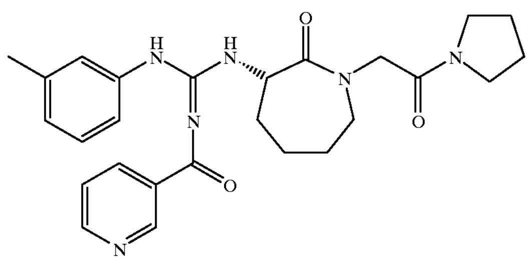 | HPLC (method A) $t_R$ 3.48 min LRMS (ESI) m/z 477 (M + H) |
| 416 | 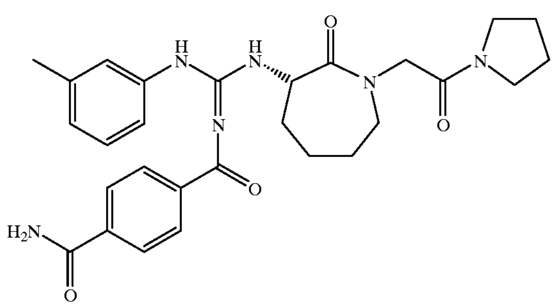 | HPLC (method A) $t_R$ 3.21 min LRMS (ESI) m/z 519 (M + H) |
| 417 | 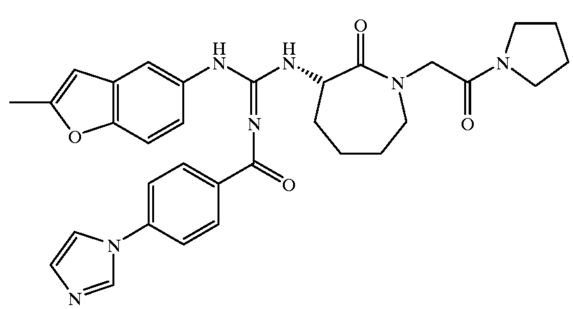 | HPLC (method A) $t_R$ 3.16 min LRMS (ESI) m/z 582 (M + H) |

-continued

| Example | structure | characterization |
|---|---|---|
| 418 | 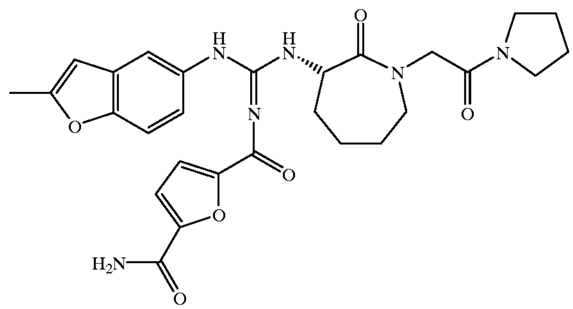 | HPLC (method A) $t_R$ 3.48 min LRMS (ESI) m/z 549 (M + H) |
| 419 | 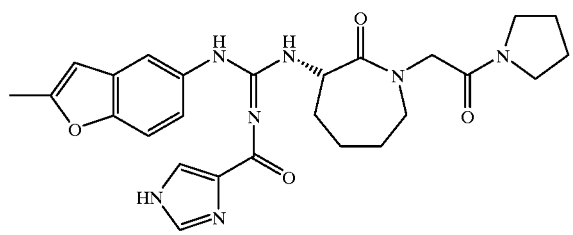 | HPLC (method A) $t_R$ 3.21 min LRMS (ESI) m/z 506 (M + H) |
| 420 | 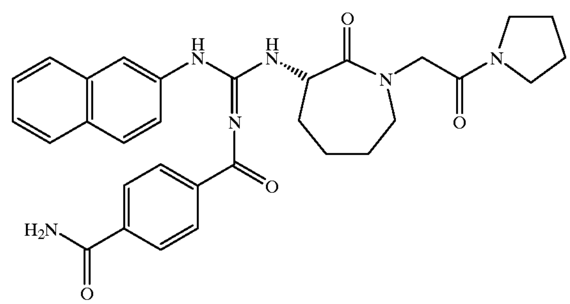 | HPLC (method A) $t_R$ 3.45 min LRMS (ESI) m/z 555 (M + H) |
| 421 | 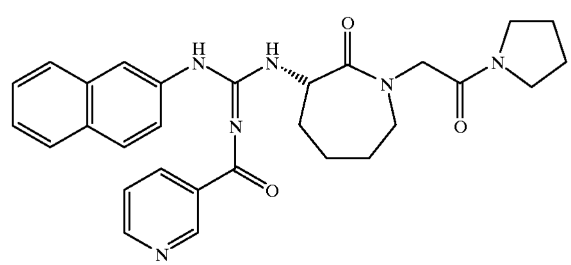 | HPLC (method A) $t_R$ 3.67 min LRMS (ESI) m/z 513 (M + H) |
| 422 | 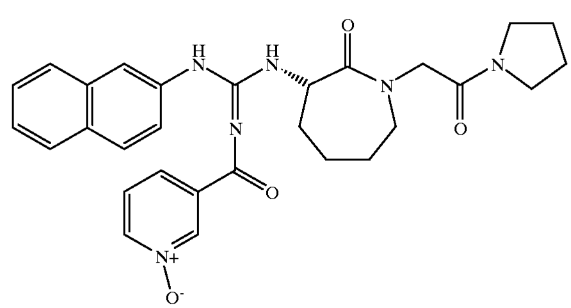 | HPLC (method A) $t_R$ 3.58 min LRMS (ESI) m/z 529 (M + H) |

-continued

| Example | structure | characterization |
|---|---|---|
| 423 | 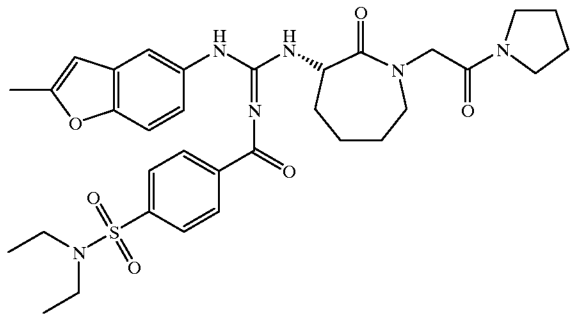 | HPLC (method A) $t_R$ 4.21 min LRMS (ESI) m/z 651 (M + H) |
| 424 | 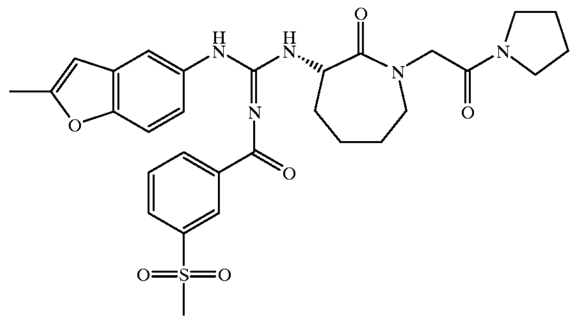 | HPLC (method A) $t_R$ 3.83 min LRMS (ESI) m/z 594 (M + H) |
| 425 | 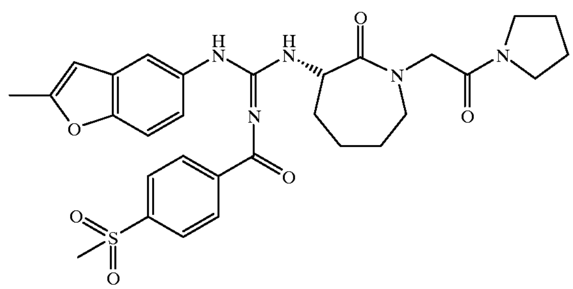 | HPLC (method A) $t_R$ 3.77 min LRMS (ESI) m/z 594 (M + H) |
| 426 | 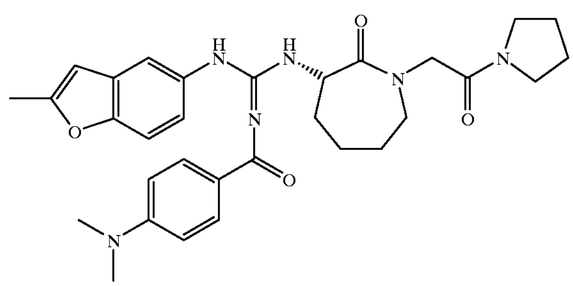 | HPLC (method A) $t_R$ 3.56 min LRMS (ESI) m/z 559 (M + H) |
| 427 | 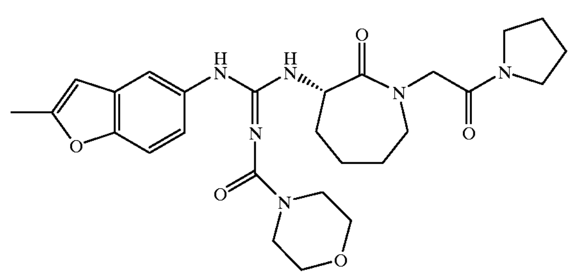 | HPLC (method D) $t_R$ 2.9 min LCMS (ESI) m/z 525 (M + H) |

-continued

| Example | structure | characterization |
|---|---|---|
| 428 | 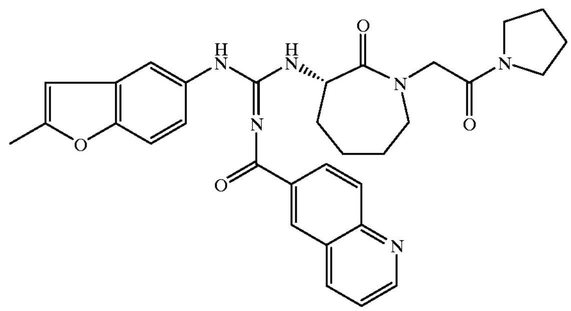 | HPLC (method D) $t_R$ 3.6 min<br>LCMS (ESI) m/z 567 (M + H) |
| 429 | 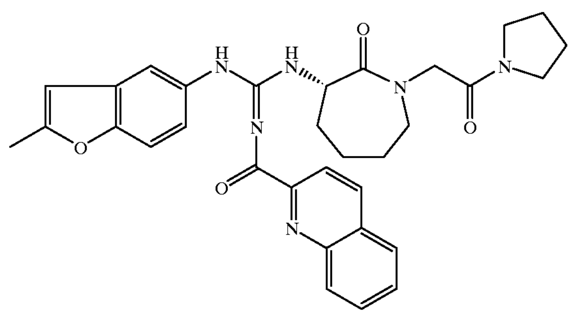 | HPLC (method D) $t_R$ 3.6 min<br>LCMS (ESI) m/z 567 (M + H) |
| 430 | 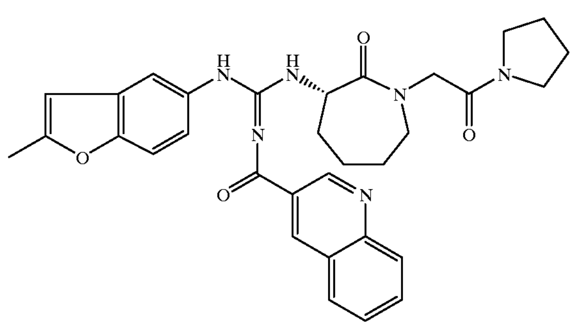 | HPLC (method D) $t_R$ 4.0 min<br>LCMS (ESI) m/z 567 (M + H) |
| 431 | 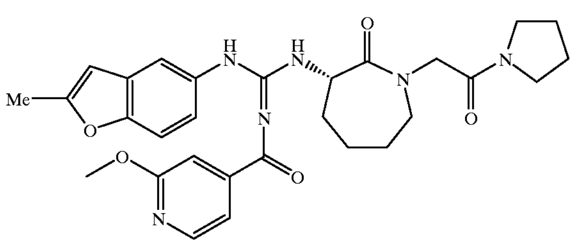 | HPLC (method A) $t_R$ = 4.6 min<br>LCMS (ESI) m/z 547 (M + H) |

EXAMPLE 432

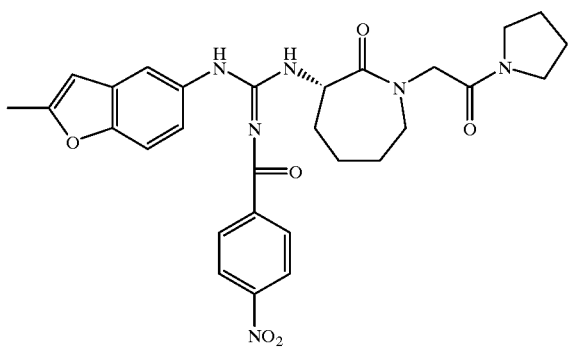

A mixture of potassium thiocyanate (0.108 g, 1.11 mmol) and 4-nitrobenzoyl chloride (0.185 g, 0.996 mmol) in acetonitrile (2 mL) was stirred at room temperature for 30 minutes and at reflux for additional 30 minutes. 2-Methyl-5-benzofuranamine (0.175 g, 1.195 mmol) was added slowly. The resulting mixture was then stirred at 60° C. for one hour at which time (S)-1-[(3-amino-hexahydro-2-oxo-1H-azepin-1-yl)acetyl]pyrrolidine (0.285 g, 1.195 mmol), WSC (0.323 mg, 1.195 mmol) and 4-(dimethylamino) pyridine (cat.) were added in that order. The reaction mixture was stirred at room temperature overnight. The reaction was then quenched by addition of water and extracted with ethyl acetate three times. The combined organic fractions were washed once with brine, dried over $MgSO_4$ and evaporated. The residue was purified by flash chromatography on silica gel (5% methanol in ethyl acetate) to give the Title compound as white solid (340 mg, 62%): HPLC (method A) $t_R$=4.42 min; LRMS (ESI) m/z 561 (M+H).

EXAMPLES 433 to 468

Using the procedure described in Example 432, the following compounds were prepared.

| Example | structure | characterization |
|---|---|---|
| 433 | 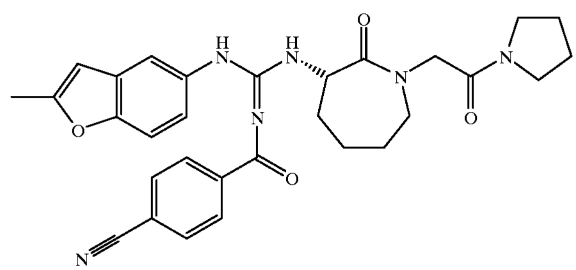 | HPLC (method A) $t_R$ 4.14 min LRMS (ESI) m/z 541 (M + H) |
| 434 | 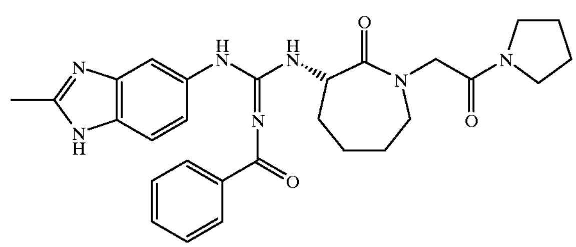 | HPLC (method A) $t_R$ 2.33 min LRMS (ESI) m/z 516 (M + H) |
| 435 | 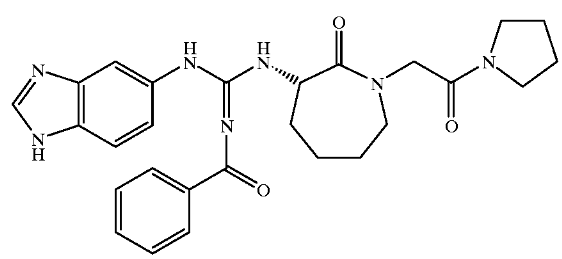 | HPLC (method A) $t_R$ 2.30 min LRMS (ESI) m/z 502 (M + H) |

| Example | structure | characterization |
|---|---|---|
| 436 | 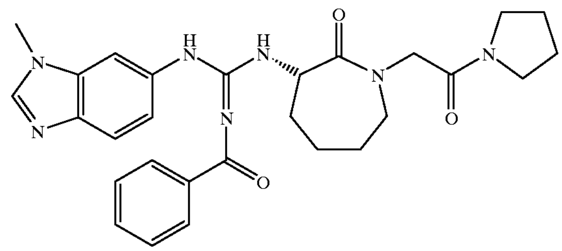 | HPLC (method A)<br>t_R 2.25 min<br>LRMS (ESI) m/z<br>516 (M + H) |
| 437 | 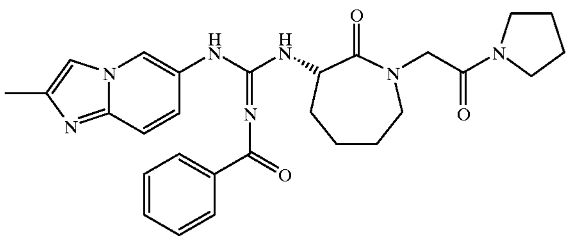 | HPLC (method A)<br>t_R 2.74 min<br>LRMS (ESI) m/z<br>516 (M + H) |
| 438 | 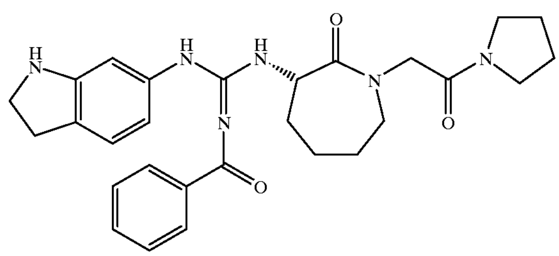 | HPLC (method A)<br>t_R 3.11 min<br>LRMS (ESI) m/z<br>503 (M + H) |
| 439 | 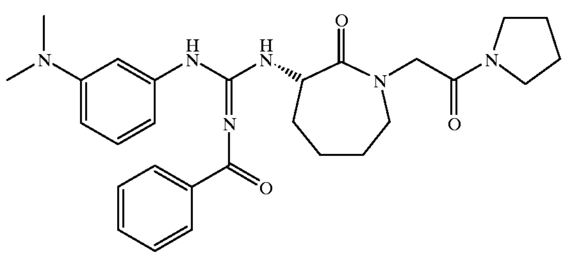 | HPLC (method A)<br>t_R 3.73 min<br>LRMS (ESI) m/z<br>505 (M + H) |
| 440 | 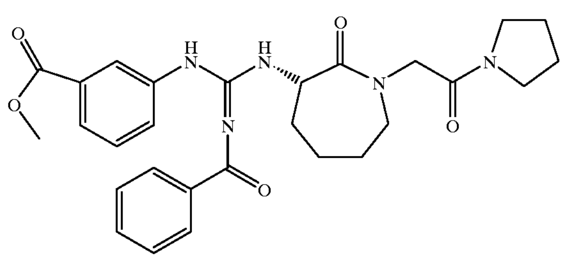 | HPLC (method A)<br>t_R 3.73 min<br>LRMS (ESI) m/z<br>520 (M + H) |

-continued

| Example | structure | characterization |
|---|---|---|
| 441 | 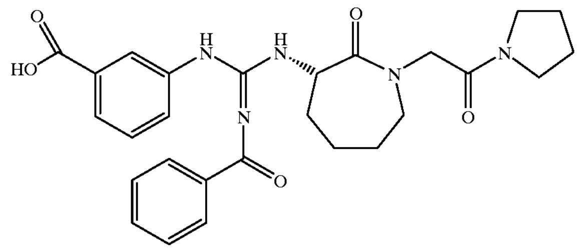 | HPLC (method A) $t_R$ 3.60 min LRMS (ESI) m/z 506 (M + H) |
| 442 | 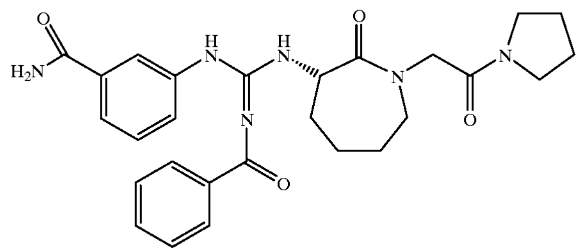 | HPLC (method A) $t_R$ 3.78 min LRMS (ESI) m/z 505 (M + H) |
| 443 | 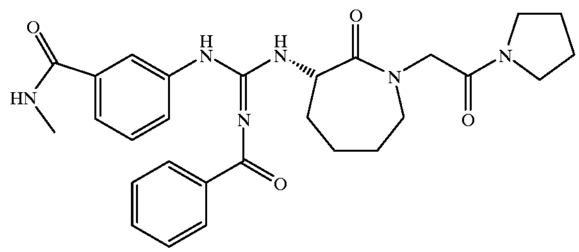 | HPLC (method A) $t_R$ 2.79 min LRMS (ESI) m/z 519 (M + H) |
| 444 | 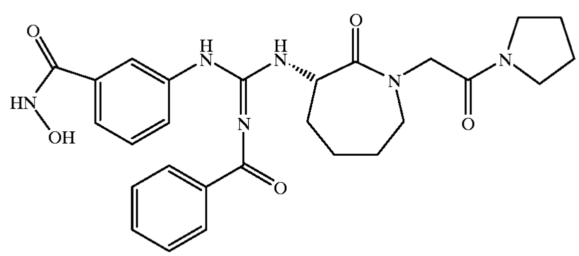 | HPLC (method A) $t_R$ 2.80 min LRMS (ESI) m/z 521 (M + H) |
| 445 | 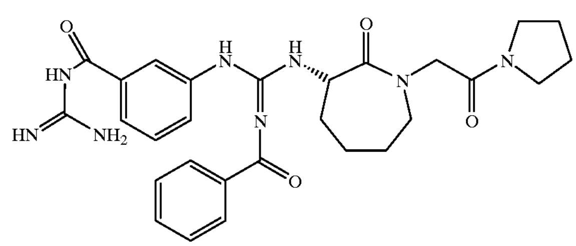 | HPLC (method A) $t_R$ 3.05 min LRMS (ESI) m/z 547 (M + H) |
| 446 | 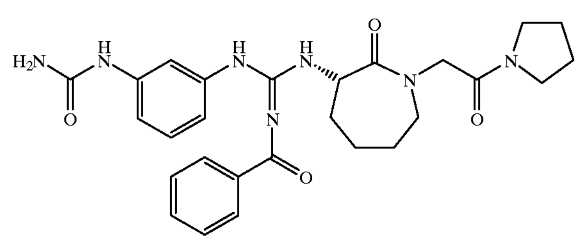 | HPLC (method A) $t_R$ 2.90 min LRMS (ESI) m/z 520 (M + H) |

-continued
| Example | structure | characterization |
|---|---|---|
| 447 | 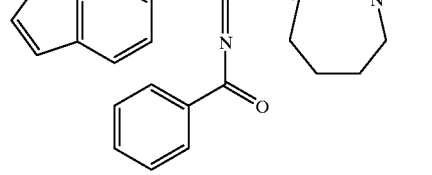 | HPLC (method A) $t_R$ 3.50 min LRMS (ESI) m/z 515 (M + H) |
| 448 | 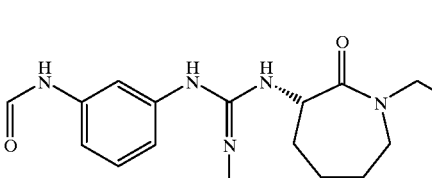 | HPLC (method A) $t_R$ 3.20 min LRMS (ESI) m/z 505 (M + H) |
| 449 | 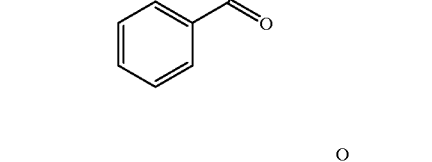 | HPLC (method A) $t_R$ 3.10 min LRMS (ESI) m/z 535 (M + H) |
| 450 | 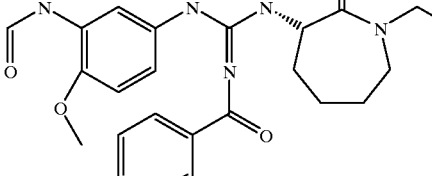 | HPLC (method A) $t_R$ 3.0 min LRMS (ESI) m/z 531 (M + H) |
| 451 | 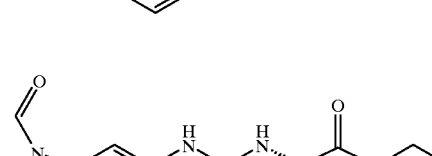 | HPLC (method A) $t_R$ 2.9 min LRMS (ESI) m/z 519 (M + H) |

-continued

| Example | structure | characterization |
|---|---|---|
| 452 | 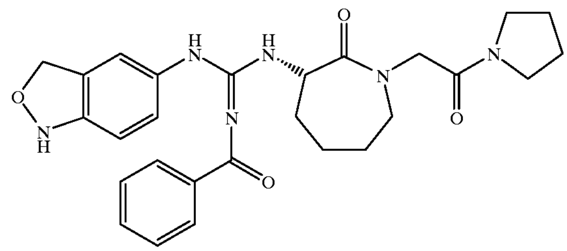 | HPLC (method A)<br>$t_R$ 2.7 min<br>LRMS (ESI) m/z<br>505 (M + H) |
| 453 | 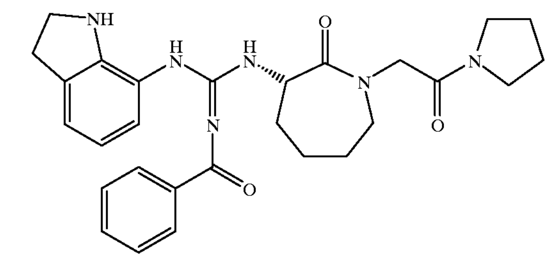 | HPLC (method A)<br>$t_R$ 2.9 min<br>LRMS (ESI) m/z<br>503 (M + H) |
| 454 | 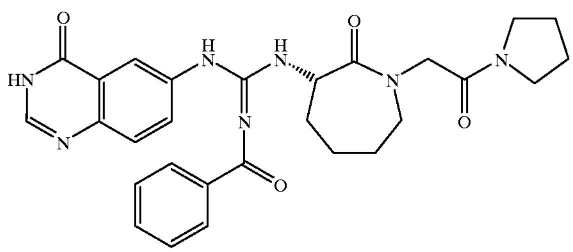 | HPLC (method A)<br>$t_R$ 2.76 min<br>LRMS (ESI) m/z<br>530 (M + H) |
| 455 | 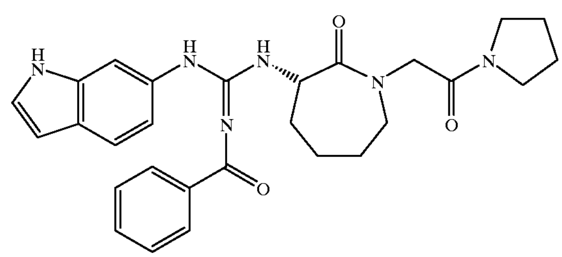 | HPLC (method A)<br>$t_R$ 3.2 min<br>LRMS (ESI) m/z<br>501 (M + H) |
| 456 | 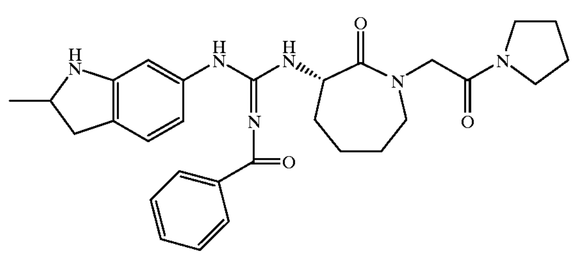 | HPLC (method A)<br>$t_R$ = 2.8 min<br>LRMS (ESI) m/z<br>517 (M + H) |
| 457 | 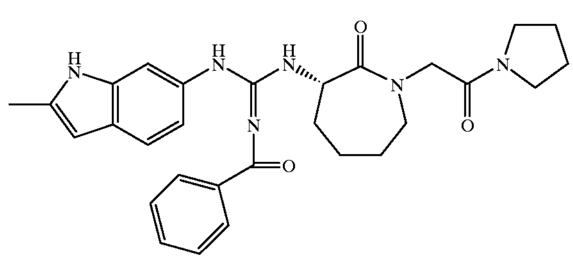 | HPLC (method A)<br>$t_R$ = 3.4 min<br>LRMS (ESI) m/z<br>515 (M + H) |

-continued

| Example | structure | characterization |
|---|---|---|
| 458 | 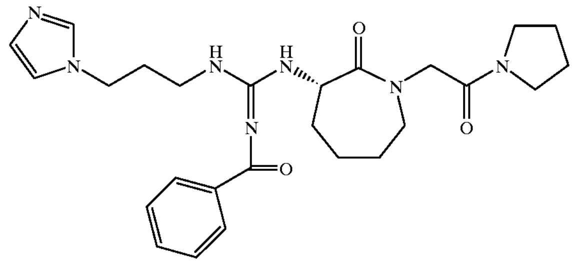 | HPLC (method A) $t_R$ = 2.0 min LRMS (ESI) m/z 494 (M + H) |
| 459 | 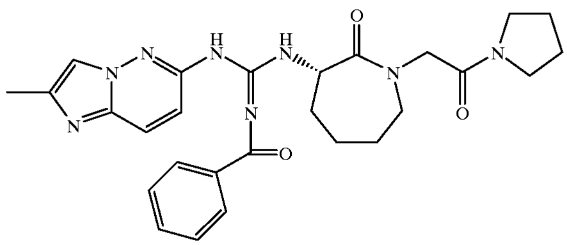 | HPLC (method A) $t_R$ = 3.9 min LRMS (ESI) m/z 517 (M + H) |
| 460 | 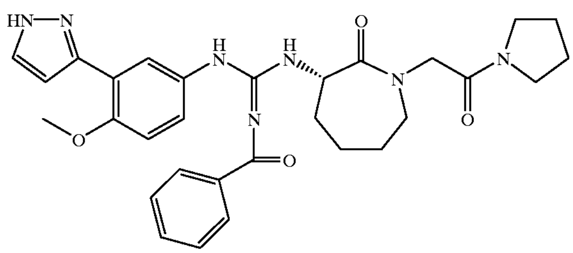 | HPLC (method A) $t_R$ = 3.3 min LRMS (ESI) m/z 558 (M + H) |
| 461 | 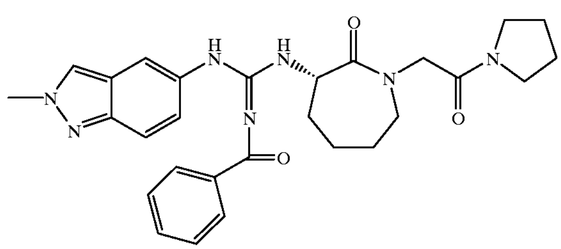 | HPLC (method A) $t_R$ = 3.4 min LRMS (ESI) m/z 516 (M + H) |
| 462 | 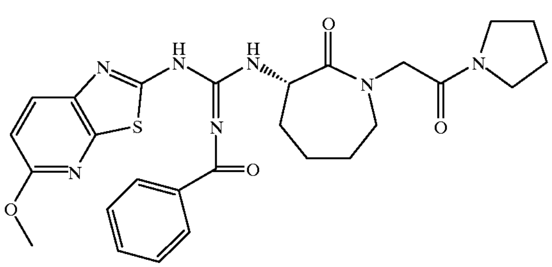 | HPLC (method A) $t_R$ = 4.4 min LRMS (ESI) m/z 550 (M + H) |

-continued

| Example | structure | characterization |
|---------|-----------|------------------|
| 463 | 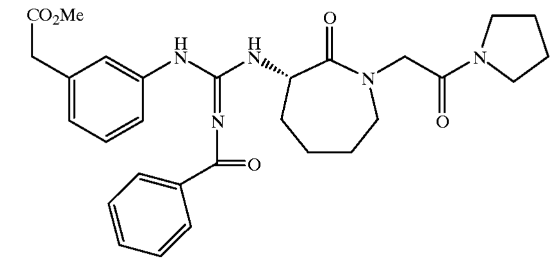 | HPLC (method A) $t_R$ = 3.4 min LRMS (ESI) m/z 534 (M + H) |
| 464 | 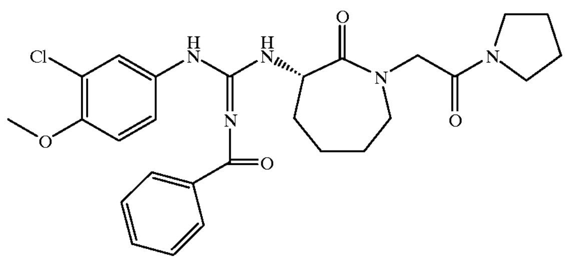 | HPLC (method A) $t_R$ = 3.6 min LRMS (ESI) m/z 527 (M + H) |
| 465 | 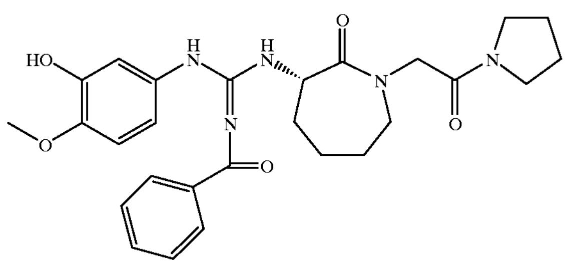 | HPLC (method A) $t_R$ = 3.0 min LRMS (ESI) m/z 508 (M + H) |
| 466 | 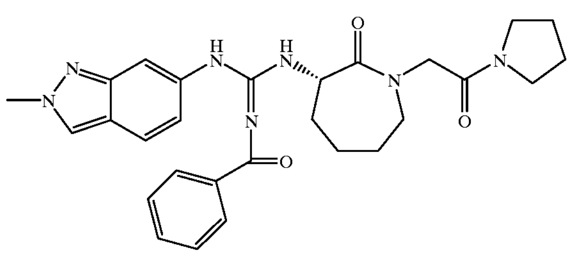 | HPLC (method A) $t_R$ = 3.2 min LRMS (ESI) m/z 516 (M + H) |
| 467 | 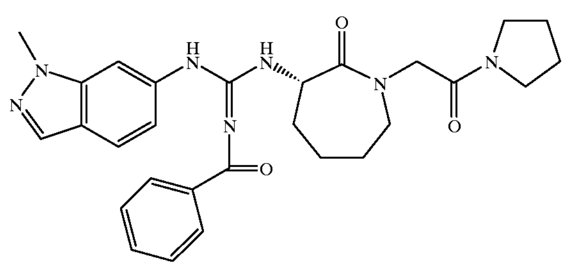 | HPLC (method A) $t_R$ = 3.2 min LRMS (ESI) m/z 516 (M + H) |

| Example | structure | characterization |
|---------|-----------|------------------|
| 468 | 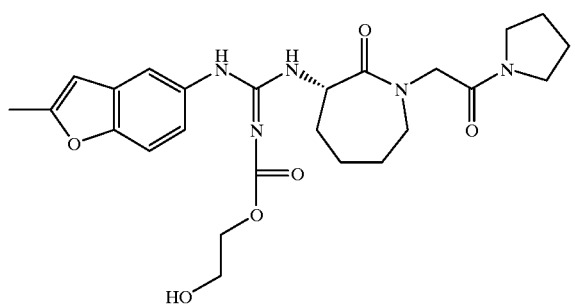 | HPLC (method A)<br>$t_R$ = 3.0 min<br>LRMS (ESI) m/z<br>517 (M + H) |

EXAMPLE 469

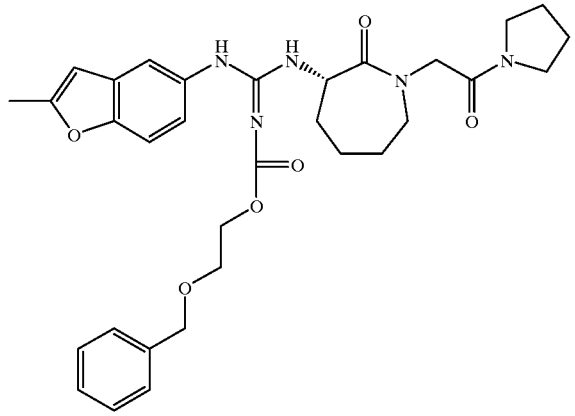

A.

To 2-benzyloxyethanol (140 mg, 0.919 mmol) was added phosgene (0.49 mL, 20% in Toluene). The reaction was stirred at room temperature for 30 minutes and then heated at 60° C. for another 30 min. The solvent was evaporated and acetonitrile (2 mL) was added. Potassium thiocyanate (98.3 mg, 1.01 mmol) was added and the reaction mixture was stirred at room temperature for 30 minutes and at reflux for additional 30 minutes. 2-Methyl-5-benzofuranamine (162 mg, 1.10 mmol) was added slowly. The resulting mixture was then stirred at 60° C. for another one hour at which time (S)-1-[(3-amino-hexahydro-2-oxo-1H-azepin-1-yl)acetyl]pyrrolidine (264 mg, 1.10 mmol), WSC (422.4 mg, 1.90 mmol) and 4-(dimethylamino)pyridine (cat.) were added in that order. The reaction mixture was stirred at room temperature overnight. The reaction was then quenched by addition of water and extracted with ethyl acetate three times. The combined organic fractions were washed once with brine, dried over $MgSO_4$ and evaporated. The residue was purified by flash chromatography on silica gel (5% methanol in ethyl acetate) to give part A compound as a white solid (335 mg, 62%): HPLC (method A) $t_R$=3.65 min; LRMS (ESI) m/z 590 (M+H).

B.

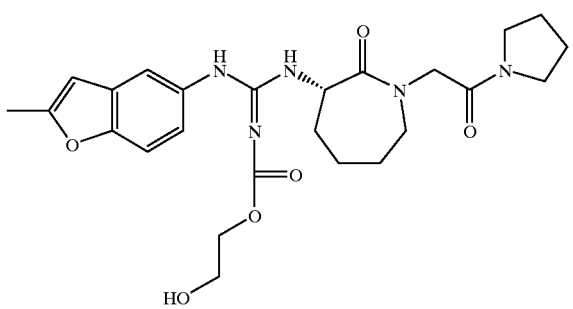

A mixture of part A compound (100 mg, 0.169 mmol) and palladium on active carbon (10% Pd) in methanol was stirred at room temperature under an atmosphere of hydrogen for 3 h. The mixture was filtered through a pad of Celite and concentrated. The residue was purified by flash chromatography on silica gel (5% methanol in ethyl acetate) give the Title compound as a white solid (62.4 mg, yield: 74%). HPLC (method A): $t_R$=2.75 min. LRMS (ESI) m/z=500 (M+H).

EXAMPLES 470 to 474

Using the procedures described in Example 469, the following compounds were prepared.

| Example | structure | characterization |
|---|---|---|
| 470 | 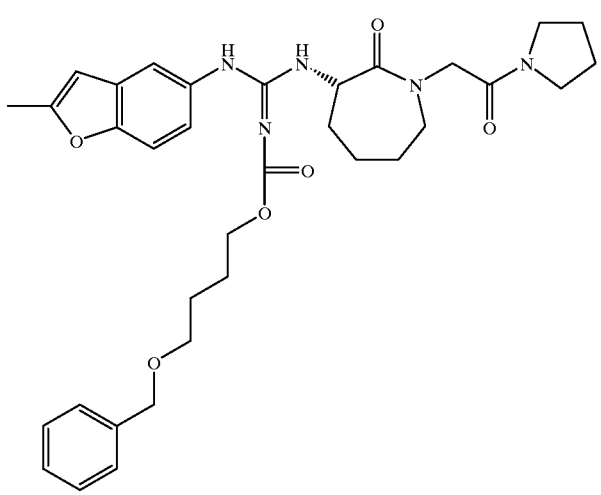 | HPLC (method A)<br>$t_R$ 3.85 min<br>LRMS (ESI) m/z<br>618 (M + H) |
| 471 | 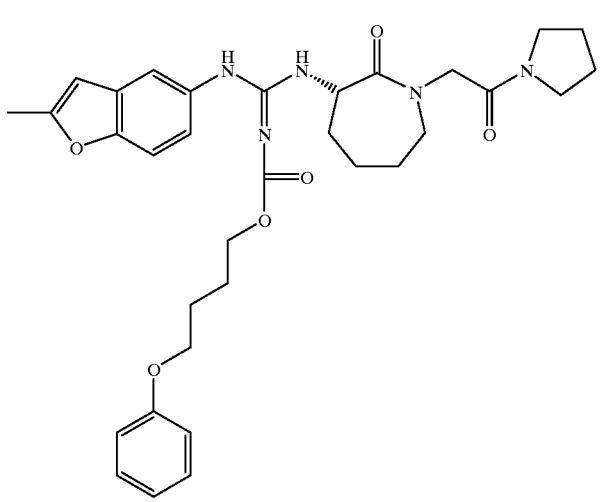 | HPLC (method A)<br>$t_R$ 3.68 min<br>LRMS (ESI) m/z<br>604 (M + H) |
| 472 | 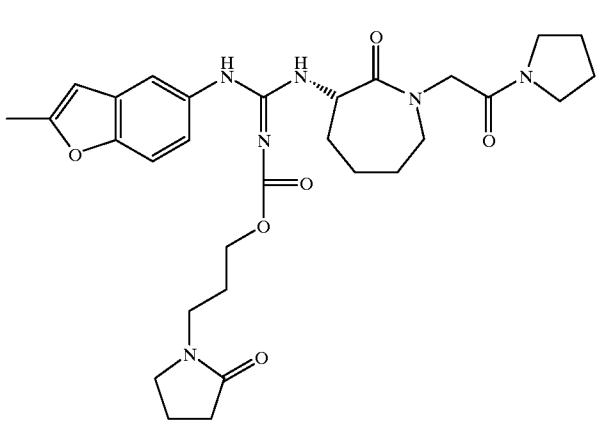 | HPLC (method A)<br>$t_R$ 2.96 min<br>LRMS (ESI) m/z<br>581 (M + H) |

| Example | structure | characterization |
|---------|-----------|------------------|
| 473 | 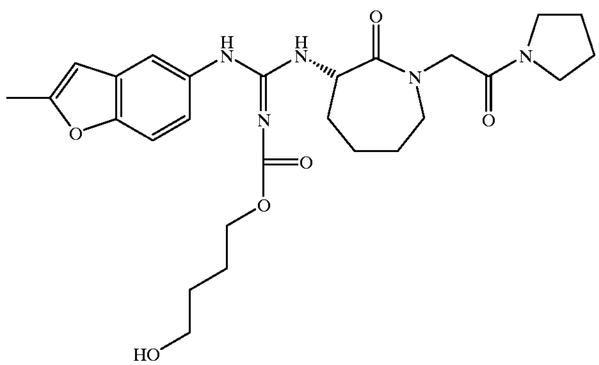 | HPLC (method A)<br>$t_R$ 2.95 min<br>LRMS (ESI) m/z<br>523 (M + H) |
| 474 | 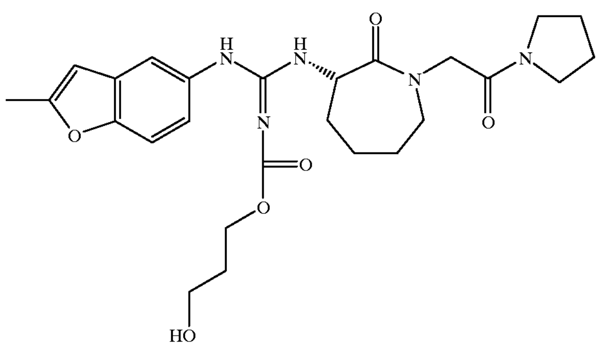 | HPLC (method A)<br>$t_R$ 2.84 min<br>LRMS (ESI) m/z<br>514 (M + H) |

EXAMPLE 475

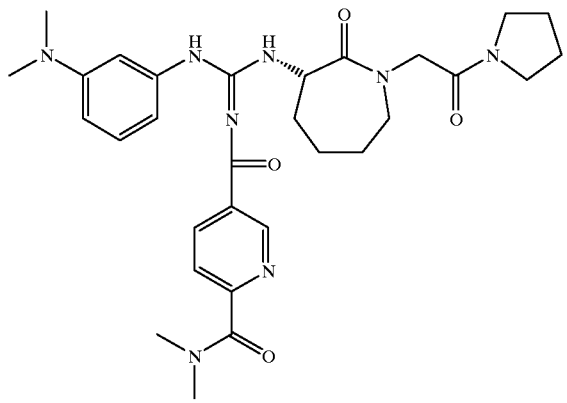

To a suspension of 6-[(dimethylamino)carbonyl]-3-pyridine carboxylic acid (52.4 mg, 0.27 mmol) in dichloromethane (1.5 mL) was added oxalyl chloride (0.04 mL, 0.5 mmol) and a small drop dry DMF. The reaction mixture was stirred at room temperature until it became a clear solution (about 1 hour). The solvent removed in vacuo and dry acetonitrile (1.5 mL) and potassium thiocyanate (27 mg, 0.23 mmol) was then added to the residue. The brown to black mixture was stirred at 60° C. for 1 hour at which time N,N-dimethylbenzenediamine (43.4 mg, 0.32 mmol) was then added. After stirring at 70° C. for 1 hour, the reaction was allowed to cool to room temperature. (S)-1-[(3-Amino-hexahydro-2-oxo-1H-azepin-1-yl)acetyl]pyrrolidine (65 mg, 0.27 mmol), WSC (62 mg, 0.32 mmol) and 4-(dimethylamino)pyridine (cat.) were added in that sequence. The reaction mixture was stirred at room temperature overnight. The reaction was then quenched by addition of water and extracted with ethyl acetate three times. The combined organic fractions were washed once with brine, dried over MgSO$_4$ and evaporated. The residue was purified by flash chromatography on silica gel (5% methanol in ethyl acetate) to give the Title compound as a white solid (70 mg, 45%); HPLC (method A) $t_R$=3.29 min; LRMS (ESI) m/z 577 (M+H).

EXAMPLES 476 to 478

Using the procedure described in preparation 475, the following compounds were prepared.

| Example | structure | characterization |
|---|---|---|
| 476 | 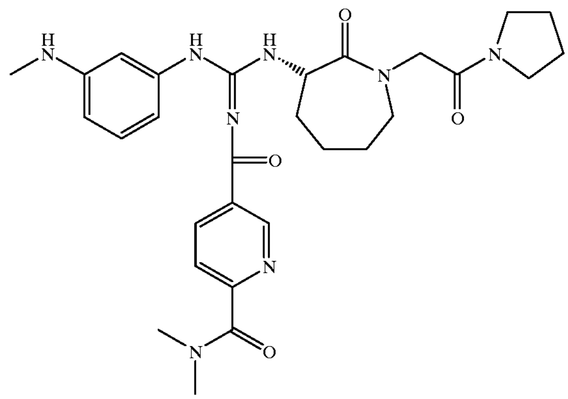 | HPLC (method A)<br>t_R 3.02 min<br>LRMS (ESI) m/z<br>563 (M + H) |
| 477 | 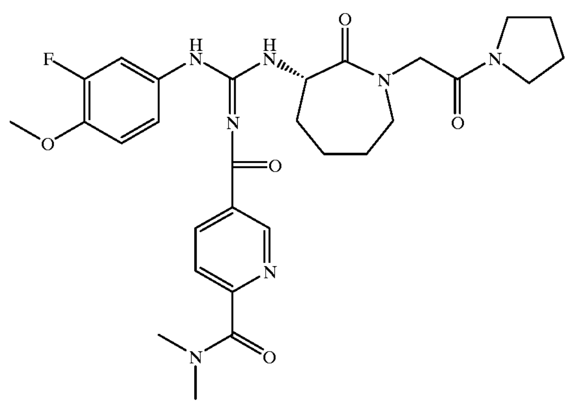 | HPLC (method A)<br>t_R 3.8 min<br>LRMS (ESI) m/z<br>582 (M + H) |
| 478 | 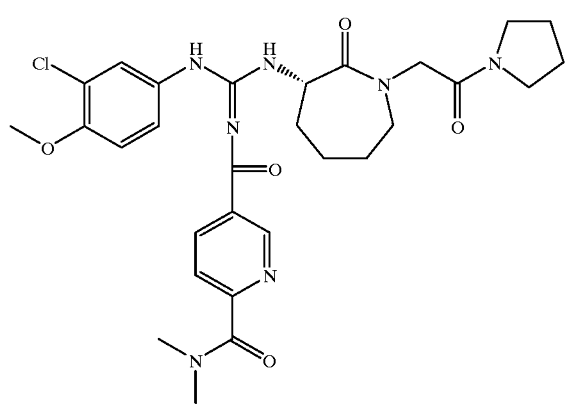 | HPLC (method A)<br>t_R = 3.5 min<br>LRMS (ESI) m/z<br>598 (M + H) |

EXAMPLE 479

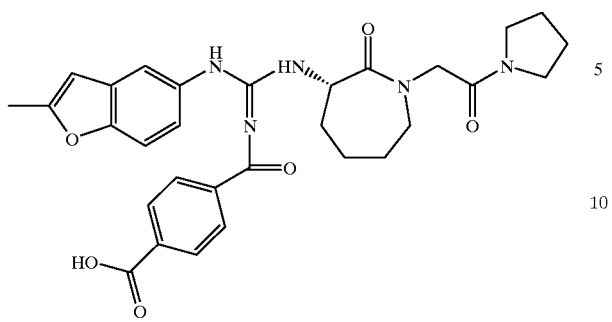

A solution of lithium hydroxide monohydrate (18 mg, 0.43 mmol) in water (0.2 mL) was added dropwise to a solution of Example 397 Title compound (25 mg, 0.044 mmol) in THF (1.0 mL) at 0° C. The resulting mixture was then stirred at room temperature for 18 hours. The pH of the solution was adjusted to 2–3 using 1 N aqueous HCl. The resulting mixture was extracted twice with ethyl acetate, and the organic layer was washed with saturated aqueous NaCl solution, dried (Na$_2$SO$_4$) and concentrated to furnish the Title compound as a white solid (22 mg, 90%): LRMS (ESI) m/z 560; HPLC (method A) $t_R$=3.73 min.

EXAMPLES 480 to 481

Using the method described in Example 479, the following compounds were prepared. The hydrolysis time was variable so the reactions were monitored by HPLC or TLC.

EXAMPLE 482

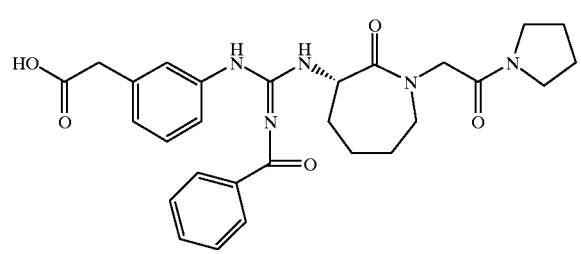

A solution of Example 463 compound (869 mg, 1.63 mmol) and lithium hydroxide in 25 mL tetrahydrofuran and 10 ml of water was stirred at room temperature for 90 min. The reaction was acidified to pH 1 with 1 N HCl and was then extracted with chloroform (4×30 ml). The combined organic layers were dried over MgSO$_4$ and filtered. The solvent was then removed to afford the Title compound (843 mg, 99%): LRMS (ESI, neg. ion spectrum) m/z 518 (M–H); HPLC (Method A) $t_R$=3.9 min.

| Example | structure | characterization |
|---|---|---|
| 480 | 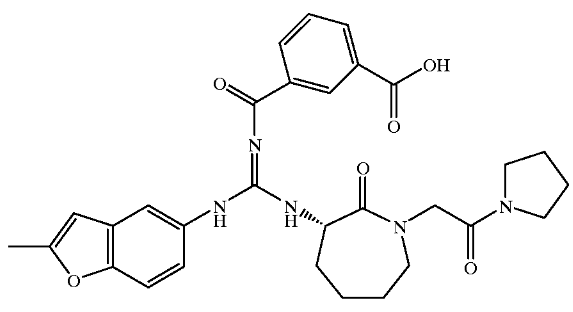 | HPLC (method A) $t_R$ = 3.8 min LRMS (ESI) m/z 560 (M + H) |
| 481 | 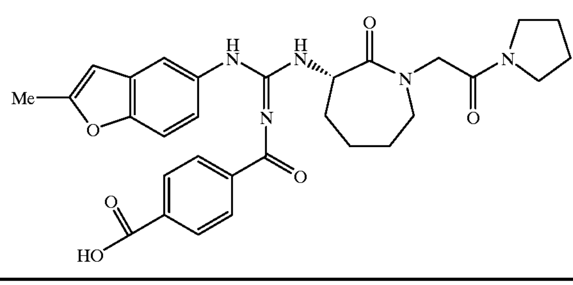 | LRMS (ESI) m/z 561 (M + H) HPLC (method A) $t_R$ = 4.0 min |

EXAMPLE 483

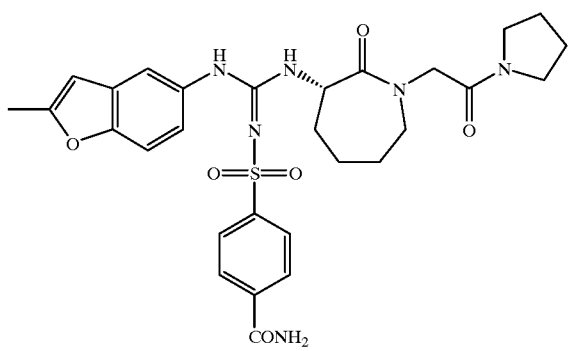

To acid Example 389 compound (4 mg, 0.007 mmol) and TFFH (2.6 mg, 0.009 mmol) in acetonitrile (0.5 mL) under nitrogen was added triethylamine (0.005 mL, 0.036 mmol). The resulting solution was stirred for 10 min at which time a solution of ammonia in methanol (7N, 0.2 ml) was added. After stirring at room temperature for 2 h the solvent was removed. The mixture was purified by reverse phase HPLC to give the Title compound as the TFA salt (1.1 mg, 28%): LRMS (ESI) m/z 595 (M+H); HPLC (Method A) $t_R$=3.6 min.

EXAMPLE 484

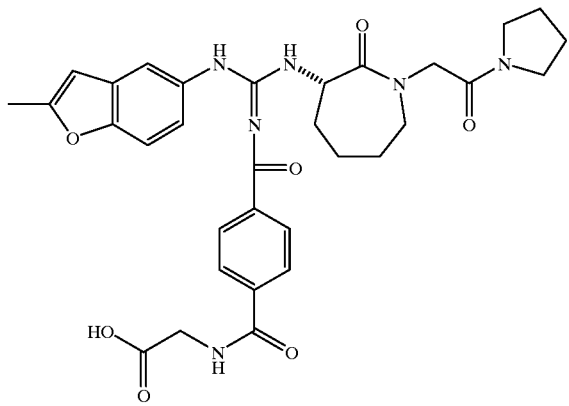

A.

To Example 479 compound (87 mg, 0.155 mmol) in dichloromethane (2 mL) was added benzyl glycinate (62.5 mg, 0.309 mmol), WSC (119 mg, 0.619 mmol), and 4-(dimethylamino)pyridine in that order. The resulting solution was stirred at room temperature overnight. The reaction was then quenched by addition of water and extracted with ethyl acetate three times. The combined organic fractions were washed once with brine, dried over $MgSO_4$ and evaporated. The residue was purified by flash chromatography on silica gel (5% methanol in ethyl acetate) to give part A compound as a white solid (109 mg, 62%): HPLC (method A) $t_R$=3.99 min; LRMS (ESI) m/z 707 (M+H).

B.

A mixture of part A compound (80 mg, 0.113 mmol) and palladium on active carbon (10% Pd) in methanol was stirred at room temperature under an atmosphere of hydrogen for 3 h. The mixture was filtered through a pad of Celite and concentrated. The residue was purified by flash chromatography on silica gel (5% methanol in ethyl acetate) to give the Title compound as a white solid (559 mg, 80%); HPLC (method A) $t_R$=3.33 min; LRMS (ESI) m/z 617 (M+H).

EXAMPLES 485 to 489

Using the procedure described in Example 484, the following compounds were prepared.

| Example | structure | characterization |
|---|---|---|
| 485 | 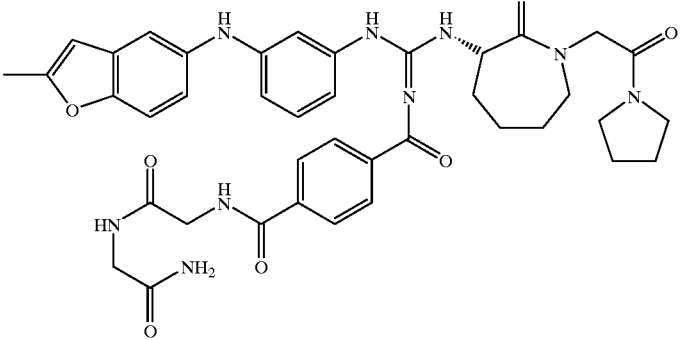 | HPLC (method A)<br>$t_R$ 3.20 min<br>LRMS (ESI) m/z<br>673 (M + H) |
| 486 | 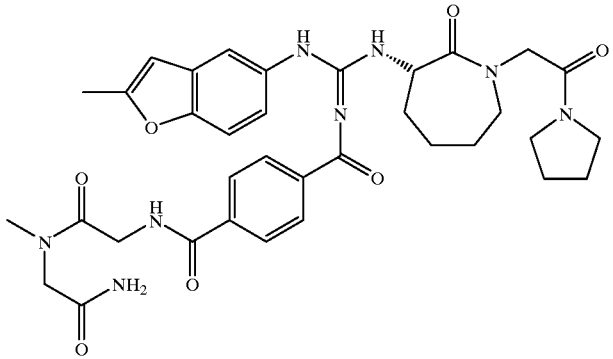 | HPLC (method A)<br>$t_R$ 3.23 min<br>LRMS (ESI) m/z<br>687 (M + H) |
| 487 | 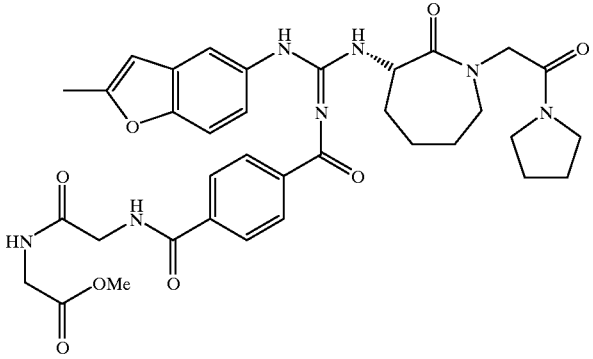 | HPLC (method A)<br>$t_R$ 3.36 min<br>LRMS (ESI) m/z<br>688 (M + H) |
| 488 | 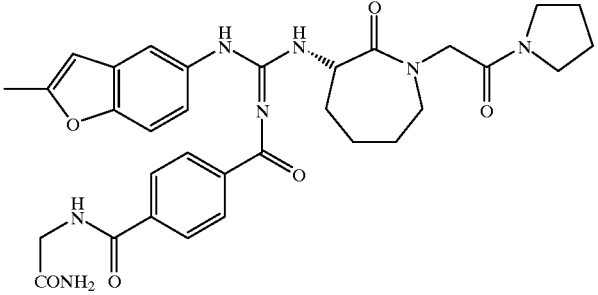 | HPLC (method A)<br>$t_R$ 3.22 min<br>LRMS (ESI) m/z<br>616 (M + H) |

| Example | structure | characterization |
|---|---|---|
| 489 | 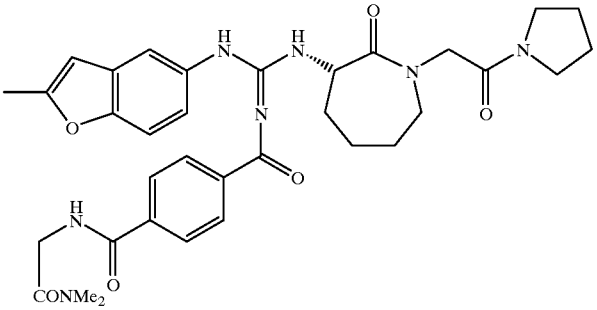 | HPLC (method A) $t_R$ 3.40 min LMRS (ESI) m/z 644 (M + H) |

EXAMPLE 490

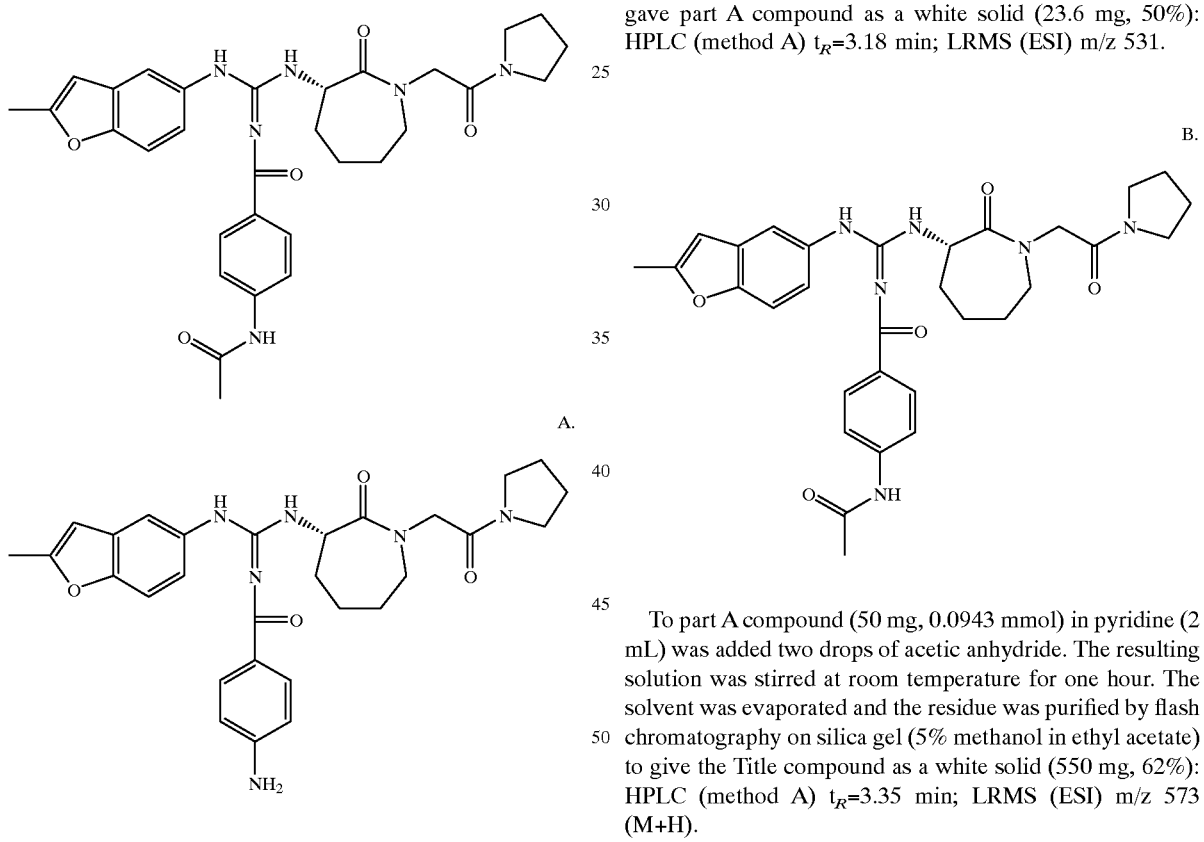

A mixture of Example 432 compound (50 mg, 0.089 mmol) and palladium on active carbon (10% Pd) in methanol was stirred at room temperature under an atmosphere of hydrogen for 3 h. The mixture was filtered through a pad of Celite and concentrated. The residue was purified by flash chromatography on silica gel (5% methanol in ethyl acetate) gave part A compound as a white solid (23.6 mg, 50%): HPLC (method A) $t_R$=3.18 min; LRMS (ESI) m/z 531.

To part A compound (50 mg, 0.0943 mmol) in pyridine (2 mL) was added two drops of acetic anhydride. The resulting solution was stirred at room temperature for one hour. The solvent was evaporated and the residue was purified by flash chromatography on silica gel (5% methanol in ethyl acetate) to give the Title compound as a white solid (550 mg, 62%): HPLC (method A) $t_R$=3.35 min; LRMS (ESI) m/z 573 (M+H).

EXAMPLES 491 to 493

Using the procedures described in Example 490, the following compounds were prepared.

| Example | structure | characterization |
|---|---|---|
| 491 | 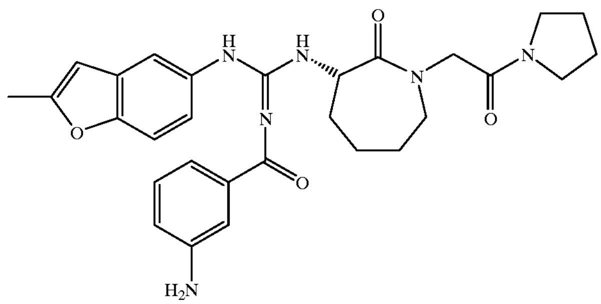 | HPLC (method A)<br>$t_R$ = 3.08 min<br>LRMS (ESI) m/z<br>531 (M + H) |
| 492 | 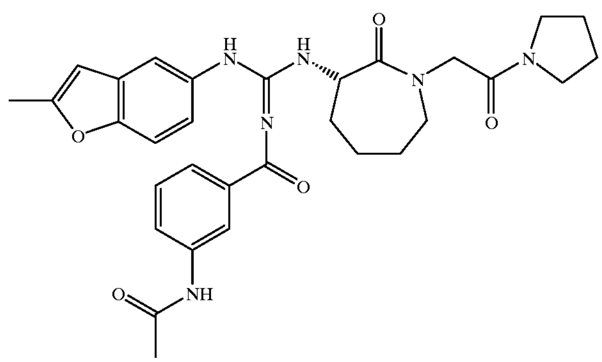 | HPLC (method A)<br>$t_R$ = 3.32 min<br>LRMS (ESI) m/z<br>573 (M + H) |
| 493 | 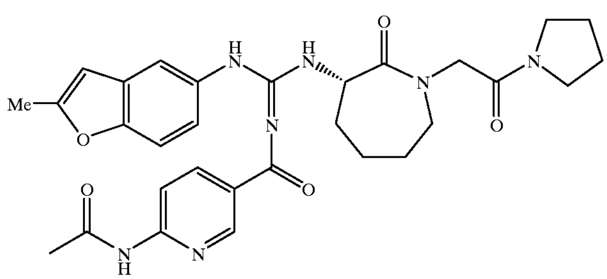 | HPLC (method A)<br>$t_R$ = 3.7 min.<br>LRMS (ESI) m/z<br>574 (M + H) |

EXAMPLE 494

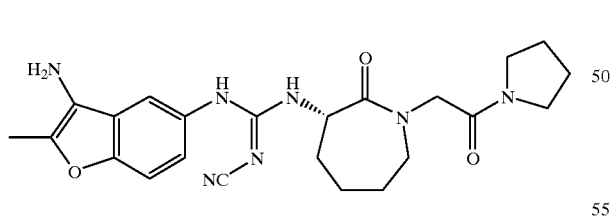

A mixture of Example 323 Title compound (10 mg) in methanol (1 mL) and 10% palladium on activated carbon (5 mg) was stirred under one atmosphere of hydrogen for 1.5 h. The reaction was filtered through a plug of Celite 545 and concentrated to afford 8 mg (87%) of Title compound as a white solid: LRMS (ESI) m/z 452 (M+H); HPLC (Method A) $t_R$=2.8 min.

EXAMPLE 495

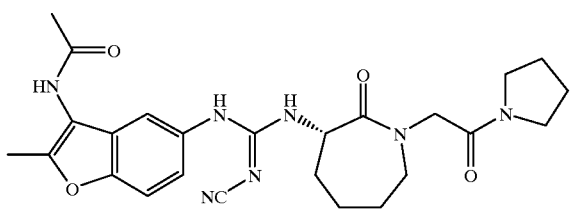

A dichloromethane solution containing Example 494 compound (14 mg), acetic anhydride (0.020 mL) and pyridine (0.018 mL) was stirred for 1 hour. The solvent was removed in vacuo and the residue was chromatographed (silica) to give Title compound as a pale yellow solid (10 mg, 65%): LRMS (ESI) m/z 494 (M+H); HPLC (Method A) $t_R$=3.2 min.

EXAMPLE 496

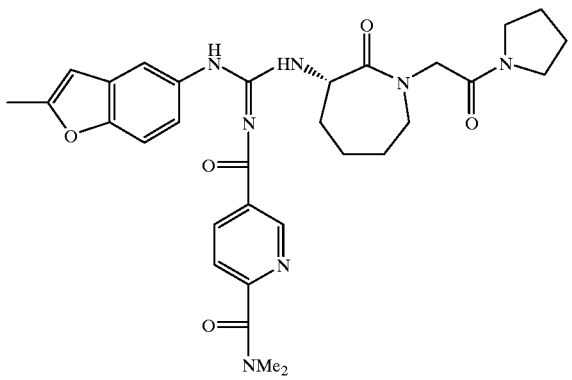

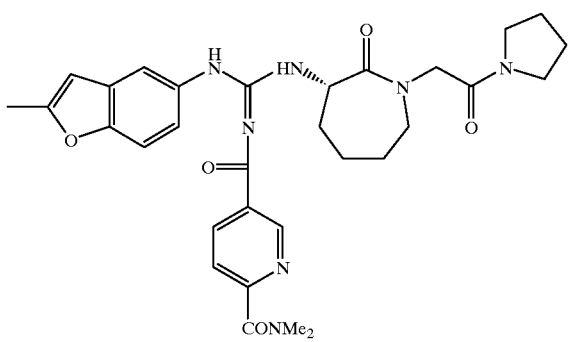

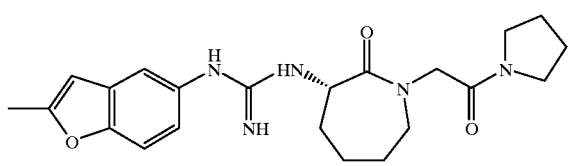

A.

To a solution of Example 335 compound B (180 mg, 0.42 mmol) in 7 M ammonia/methanol (5 mL) was added mercuric oxide (red, 900 mg, 0.42 mmol). The reaction was stirred at room temperature for 35 min and then filtered through Celite AFA. The filter pad was rinsed with methanol (4×5 mL) and the combined filtrates were concentrated in vacuo to provide 170 mg of a yellow foam: HPLC (method A) $t_R$=2.6 min.

B. Preparation of 6-[(dimethylamino)carbonyl]-3-pyridine carboxylic acid. To a 2° C. slurry of dimethyl 2,5-pyridinedicarboxylate (50 g, 0.256 mol) in THF (700 mL) was added magnesium chloride (26.8 g, 0.282 mol). After stirring for 15 min, dimethylamine (2 M in THF, 256 mL, 0.512 mol) was added dropwise over 40 min. The mixture was stirred for 30 min at 2° C. and then at room temperature for 1 h. To the mixture was added water (100 mL) and 1 N HCl (300 mL). The mixture was extracted with ethyl acetate (4×400 mL). The combined organic layers were dried (MgSO$_4$) and concentrated in vacuo to provide 53 g (100%) of methyl 6-[(dimethylamino)carbonyl]-3-pyridine carboxylate a pale yellow solid.

To a 5° C. mixture of methyl 6-[(dimethylamino) carbonyl]-3-pyridine carboxylate (52.5 g, 0.252 mol) and THF (390 mL) was added a solution of lithium hydroxide (trihydrate, 11.6 g, 0.277 mol) in water (60 mL) over 6 minutes. After stirring for 1 h, 2 N HCl (145 mL) was added over a 15-min period. Toluene (200 mL) was added and the organic solvents were removed in vacuo. The slurry was filtered, and the solids were washed with water (2×20 mL) and dried at 75° C. in vacuo to provide 47 g (96%) of 6-[(dimethylamino)carbonyl]-3-pyridine carboxylic acid.

To a solution of 6-[(dimethylamino)carbonyl]-3-pyridinecarboxylic acid, (75 mg, 0.39 mmol) in DMF (0.9 mL) was added 1,1'-carbonyldiimidazole (63 mg, 0.39 mmol). After stirring at ambient temperature for 30 min, the part A compound (106 mg, 0.26 mmol) was added. After stirring at ambient temperature for 4 h and at 45° C. for 19 h, the reaction was diluted with ethyl acetate and transferred to a separatory funnel. The mixture was washed with saturated NaHCO$_3$, brine, and dried over MgSO$_4$ to afford 175 mg of crude product after evaporation of the solvent. Flash chromatography (silica gel, 15 mm dia column, 5% MeOH/CH$_2$Cl$_2$) afforded 115 mg (75%) of the title compound: HPLC (method A) $t_R$=3.7 min; LRMS (ESI) m/z 588 (M+H).

Alternate Synthesis Of The Title Compound

D.

To a 0° C. slurry of sodium hydroxide (82 g, 2 mol) in DMF (1.5 L) was added acetone oxime (125 g, 1.7 mol). After stirring 45 min, 1-fluoro-4-nitrobenzene (218 g, 1.55 mol) was added over 45 min. After stirring at room temperature for 2.5 h, the reaction was poured into cold brine (4.5 L). The mixture was stirred at 0° C. for 2 h. The solid was collected by filtration, washed with water (4×1.5 L) and dried to provide 300 g (99%) of 2-propanone O-(4-nitrophenyl)oxime.

To 2.5 L of ethanol was added acetyl chloride (490 g, 6.2 mol) over 1.5 h. The oxime was then added and the reaction was stirred at reflux for 2.5 h. The reaction was cooled to room temperature and was then poured into ice water (2.5 L). After stirring for 1 h at room temperature and at 0° C. for 2 h, the precipitate was collected, washed and dried to provide 232 g (85%) of 2-methyl-5-nitrobenzofuran.

To a 35° C. mixture of 50 g of 2-methyl-5-nitrobenzofuran, ethanol (250 mL), THF (250 mL) and wet 10% Pd/C (4 g) was added ammonium formate (53.4 g, 0.85 mol) over 50 min. After an additional 4 h, the reaction was cooled to room temperature and filtered through Celite. The filtrate was concentrated and the residue was taken up in methyl t-butyl ether (415 mL). This mixture was filtered and a solution of oxalic acid (25.4 g) in methanol (80 mL) was added dropwise. The precipitate was stirred for 2 h, collected, washed with methanol/TBME and dried to provide 2-methyl-5-benzofuranamine oxalate.

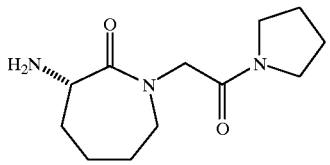

E.

To a 0° C. solution of (3S)-aminohexahydro-2H-azapin-2-one (200 g, 1.56 mol) in 2 N NaOH (2 L) was added benzyl chloroformate (272 mL, 1.81 mol) over 2 h. After stirring 1 h at 0° C. and at room temperature for 1 h, the precipitate was collected by filtration, washed with water (4×2 L), heptane (4×5 L) and dried to provide 396 g, 100%) of [(3S)-hexahydro-2-oxo-1H-azapin-3yl]carbamic acid phenylmethyl ester.

To a −10° C. solution of [(3S)-hexahydro-2-oxo-1H-azapin-3-yl]carbamic acid phenylmethyl ester (1 kg, 3.8 mol) in THF (10 L) was added lithium hexamethyldisilamide (1 N in THF, 5 L). After 30 min, methyl bromoacetate (4.3 mol) was added. After 1 h, pyrrolidine (7.3 mol) was added. The reaction was stirred overnight at room temperature. Over 30 min, 2 N HCl (2 L) was added. In vacuo, 7.5 L of solvent was removed. Ethyl acetate (7.5 L) was added. The organic layer was washed with 2 N HCl. The combined aqueous layers were extracted with ethyl acetate (2×1 L). The combined organic layers were washed with saturated sodium bicarbonate (2×1.5 L) and were then concentrated. The residue was crystallized from ethyl acetate/heptane to provide 1.1 kg (75%) of 1-[((3S)-3-[(phenylmethoxy)carbonyl]amino-hexahydro-2-oxo-1H-azepin-1-yl)acetyl]pyrrolidine.

To a 30° C. mixture of 1-[((3S)-3-[(phenylmethoxy)carbonyl]amino-hexahydro-2-oxo-1H-azepin- 1-yl)acetyl]pyrrolidine (20 g, 54 mmol), ethanol (100 mL), THF (100 mL) and wet 10% Pd/C (4 g) was added ammonium formate (5.1 g, 81 mmol) over 45 min. After stirring for 3 h, the reaction was cooled to room temperature and filtered. The filtrate was concentrated, taken up in TBME (150 mL) and filtered again. The filtrate was concentrated in vacuo to provide 12.3 g (95%) of (S)-1-[(3-amino-hexahydro-2-oxo-1H-azepin-1-yl)acetyl]pyrrolidine.

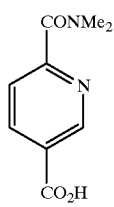

F.

To a 2° C. slurry of dimethyl 2,5-pyridinedicarboxylate (50 g, 0.256 mol) in THF (700 mL) was added magnesium chloride (26.8 g, 0.282 mol). After stirring for 15 min, dimethylamine (2 M in THF, 256 mL, 0.512 mol) was added dropwise over 40 min. The mixture was stirred for 30 min at 2° C. and then at room temperature for 1 h. To the mixture was added water (100 mL) and 1 N HCl (300 mL). The mixture was extracted with ethyl acetate (4×400 mL). The combined organic layers were dried (MgSO4) and concentrated in vacuo to provide 53 g (100%) of methyl 6-[(dimethylamino)carbonyl]-3-pyridine carboxylate a pale yellow solid.

To a 5° C. mixture of the ester (52.5 g, 0.252 mol) and THF (390 mL) was added a solution of lithium hydroxide (trihydrate, 11.6 g, 0.277 mol) in water (60 mL) over 6 minutes. After stirring for 1 h, 2 N HCl (145 mL) was added over a 15-min period. Toluene (200 mL) was added and the organic solvents were removed in vacuo. The slurry was filtered, and the solids were washed with water (2×20 mL) and dried at 75° C. in vacuo to provide 47 g (96%) of 6-[(dimethylamino)carbonyl]-3-pyridine carboxylic acid.

G. To a 15° C. mixture of 6-[(dimethylamino)carbonyl]-3-pyridine carboxylic acid (39.3 g, 0.202 mol), DMF (0.25 mL) and dichloromethane was added dropwise over 30 min oxalyl chloride (17.8 mL, 0.204 mol). The reaction was stirred for 15 min at 15° C. and 30 min at 20° C. The reaction was distilled at 30° C. under reduced pressure while acetone (800 mL) was added dropwise to keep the reaction volume constant. After 800 mL of distillate had been collected normal pressure was restored and the reaction was brought to 15° C. Potassium thiocyanate was added to the reaction. The reaction was stirred at 20° C. for 2 h. To the reaction was added 2-methyl-5-benzofuranamine oxalate (52.8 g, 0.223 mol). After stirring 2.5 h, the reaction was distilled at reduced pressure while water (800 mL) was added to keep the volume constant. To the reaction was added potassium carbonate (97.9 g, 0.708 mol) over 5 min. After stirring 10 min, the solid was collected by filtration, washed with water (2.4 L) and vacuum dried to provide 66.3 g (86%) of a green-brown solid. This material was suspended in DMF (660 mL) and heated to 82° C. to effect solution. After 30 min, water (130 mL) was added over a 30 min period. The reaction was slowly cooled to room temperature and then to 0° C. The solids were collected by filtration, washed with methyl t-butyl ether (250 mL) and vacuum dried at 50° C. to provide 50.5 g (65%) of product. To a slurry of a portion of this material (10 g, 26.2 mmol), and (S)-1-[(3-amino-hexahydro-2-oxo-1H-azepin-1-yl)acetyl]pyrrolidine (6.88 g, 28.8 mmol) in THF (93 mL) was added triethylamine (16 mL, 115 mmol) and WSC (7.72 g, 40.3 mmol). The slurry was stirred for 15 h. Ethyl acetate (500 mL)was added and the mixture was washed with 1 N HCl (73 mL). The organic layer was washed with sodium dihydrogenphosphate (5% aqueous, 2×100 mL), brine (100 mL), dried (MgSO$_4$) and concentrated in vacuo to provide 15 g (98%) of Title compound as a grey solid.

EXAMPLES 497 to 575

Using the procedure described in Example 496, the following compounds were prepared in DMF or acetonitrile. In some cases, preparative HPLC (C-18 reverse phase column; solvent A: 90:10 H$_2$O:MeOH+0.1% TFA, solvent B: 10:90 H$_2$O:MeOH+0.1% TFA) was used to purify the products.

| Example | Structure | Characterization |
|---|---|---|
| 497 | 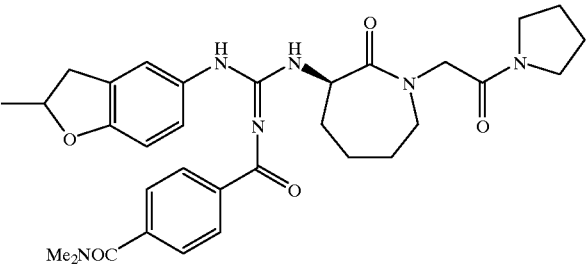 | HPLC (method A)<br>$t_R$ = 3.5 min<br>LRMS (ESI) m/z<br>588 |
| 498 | 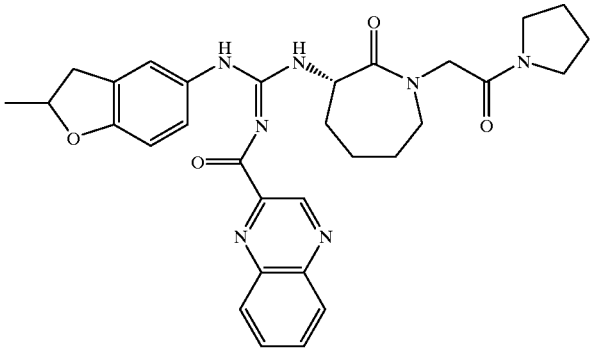 | HPLC (method D)<br>$t_R$ = 3.4 min<br>LCMS (ESI) m/z<br>568 (M + H) |
| 499 | 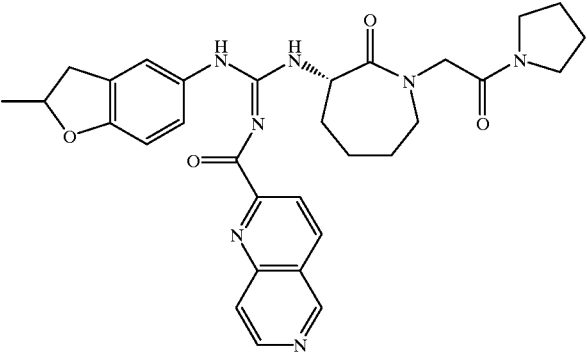 | HPLC (method D)<br>$t_R$ = 2.7 min<br>LCMS (ESI) m/z<br>568 (M + H) |
| 500 | 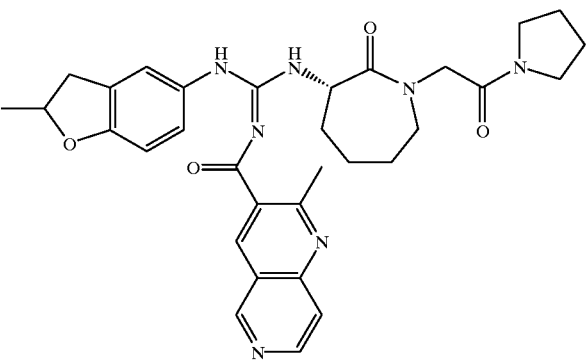 | HPLC (method D)<br>$t_R$ = 3.4 min<br>LCMS (ESI) m/z<br>582 (M + H) |

-continued

| Example | Structure | Characterization |
|---------|-----------|------------------|
| 501 | 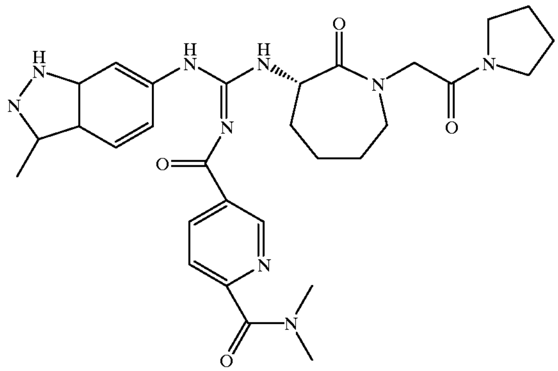 | HPLC (method D)<br>$t_R$ = 3.3 min<br>LCMS (ESI) m/z<br>588 (M + H) |
| 502 | 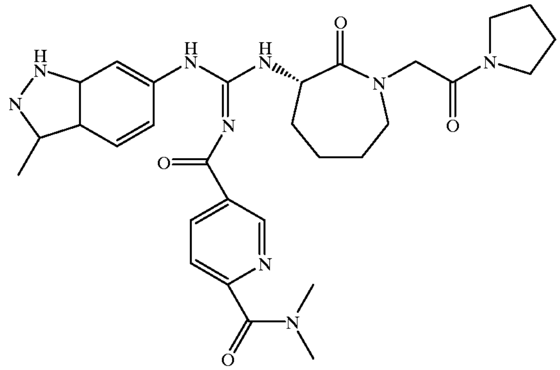 | HPLC (method D)<br>$t_R$ = 2.5 min<br>LCMS (ESI) m/z<br>574 (M + H) |
| 503 | 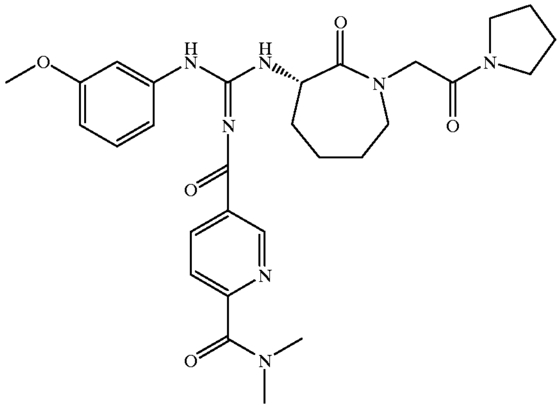 | HPLC (method D)<br>$t_R$ = 3.4 min<br>LCMS (ESI) m/z<br>564 (M + H) |

-continued
| Example | Structure | Characterization |
|---|---|---|
| 504 | 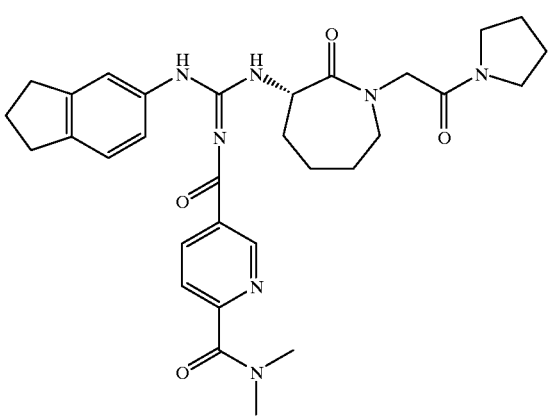 | HPLC (method D)<br>$t_R$ = 3.8 min<br>LCMS (ESI) m/z<br>574 (M + H) |
| 505 | 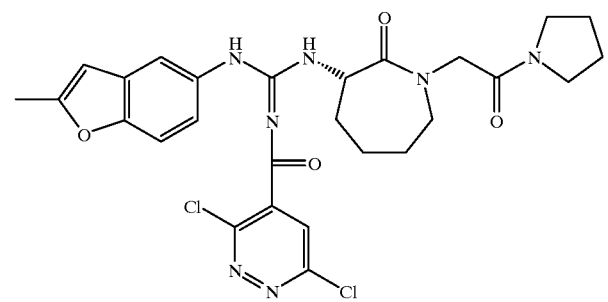 | HPLC (method A)<br>$t_R$ = 4.22 min<br>LCMS (ESI) m/z<br>587 (M + H) |
| 506 | 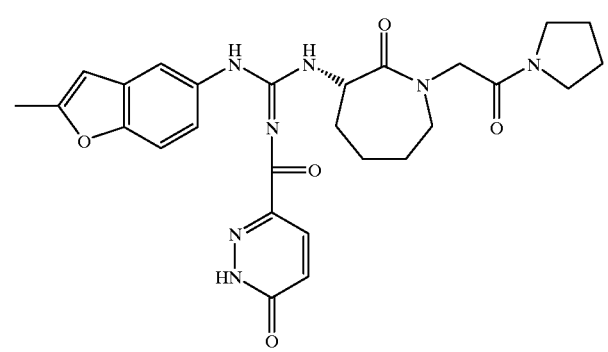 | HPLC (method A)<br>$t_R$ = 2.93 min<br>LCMS (ESI) m/z<br>534 (M + H) |
| 507 | 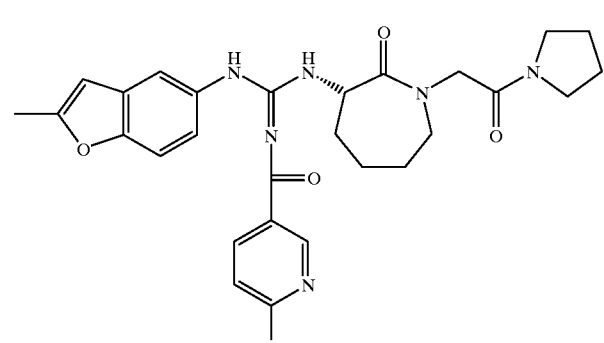 | HPLC (method A)<br>$t_R$ = 3.44 min<br>LCMS (ESI) m/z<br>533 (M + H) |

-continued

| Example | Structure | Characterization |
|---|---|---|
| 508 | 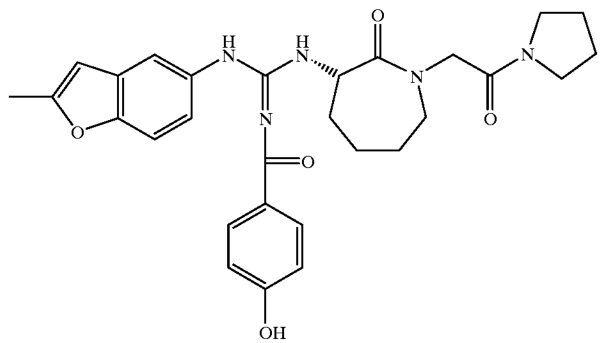 | HPLC (method A) t_R = 3.44 min LCMS (ESI) m/z 532 (M + H) |
| 509 | 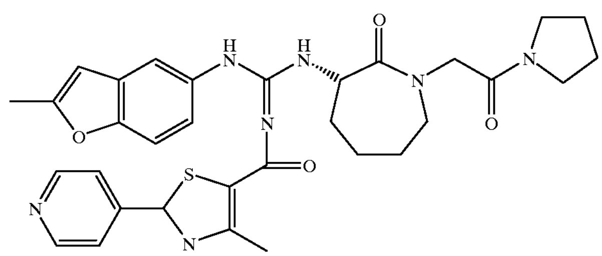 | HPLC (method A) t_R = 4.48 min LCMS (ESI) m/z 614 (M + H) |
| 510 | 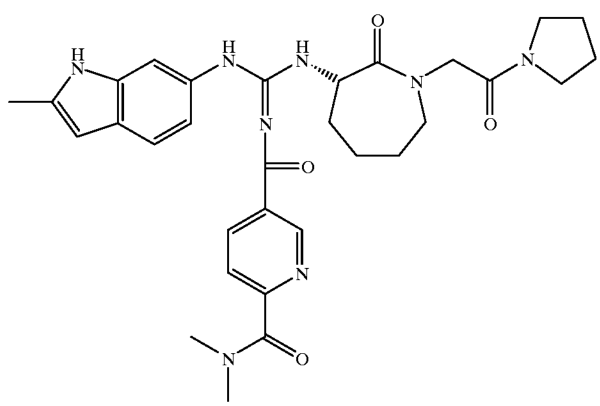 | HPLC (method A) t_R = 3.74 min LRMS (ESI) m/z 587 (M + H) |
| 511 | 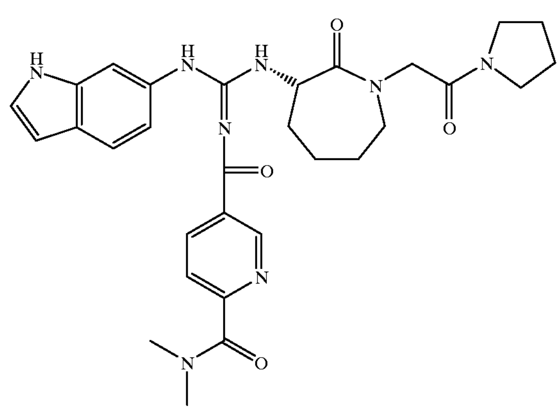 | HPLC (method A) t_R = 3.67 min LRMS (ESI) m/z 573 (M + H) |

| Example | Structure | Characterization |
|---|---|---|
| 512 | 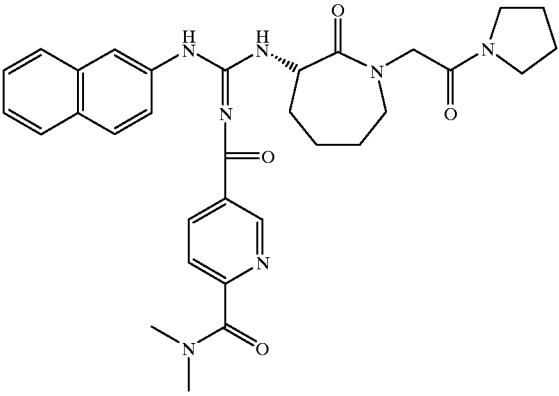 | HPLC (method A)<br>$t_R$ = 4.22 min<br>LRMS (ESI) m/z<br>584 (M + H) |
| 513 | 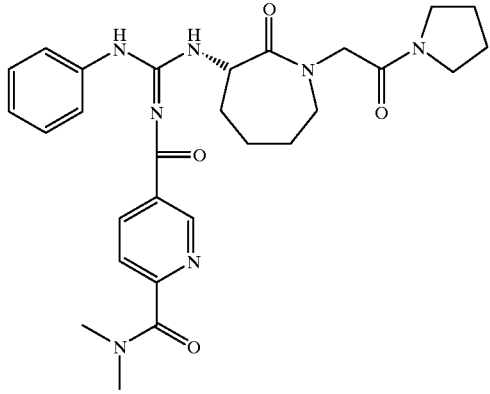 | HPLC (method A)<br>$t_R$ = 3.61 min<br>LRMS (ESI) m/z<br>534 (M + H) |
| 514 | 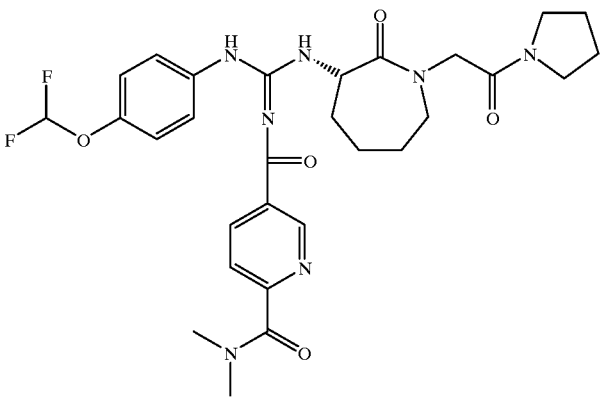 | HPLC (method A)<br>$t_R$ = 3.89 min<br>LRMS (ESI) m/z<br>600 (M + H) |

-continued

| Example | Structure | Characterization |
|---------|-----------|------------------|
| 515 | 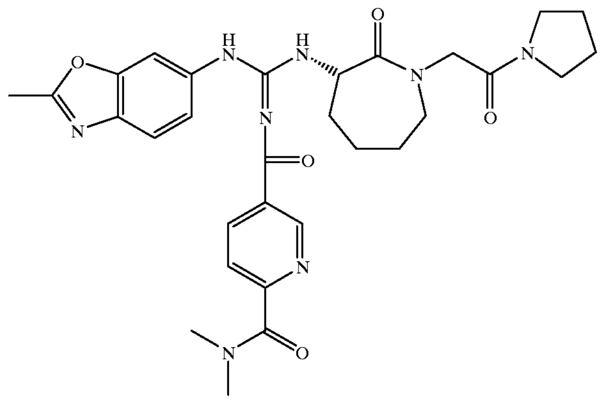 | HPLC (method A)<br>$t_R$ = 3.52 min<br>LRMS (ESI) m/z<br>589 (M + H) |
| 516 | 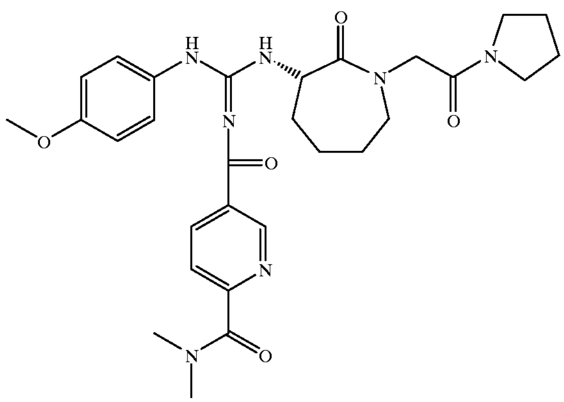 | HPLC (method A)<br>$t_R$ = 3.58 min<br>LRMS (ESI) m/z<br>564 (M + H) |
| 517 | 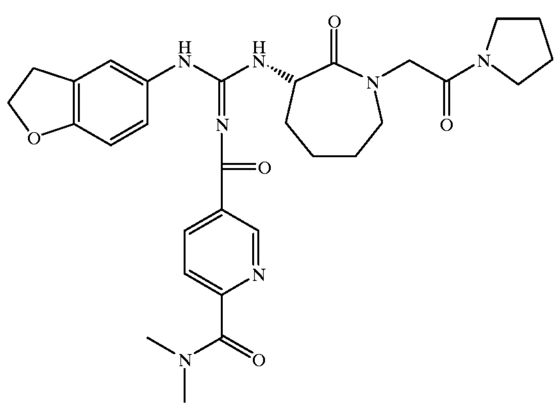 | HPLC (method A)<br>$t_R$ = 3.57 min<br>LRMS (ESI) m/z<br>576 (M + H) |

-continued

| Example | Structure | Characterization |
|---------|-----------|------------------|
| 518 | 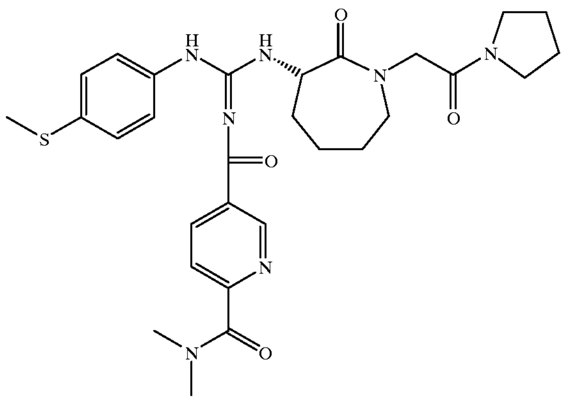 | HPLC (method A) $t_R$ = 3.96 min LRMS (ESI) m/z 580 (M + H) |
| 519 | 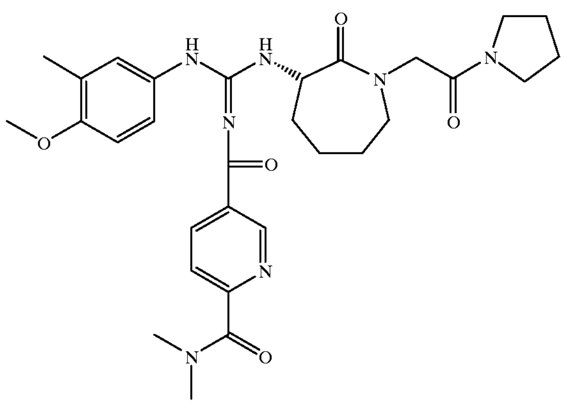 | HPLC (method A) $t_R$ = 4.05 min LRMS (ESI) m/z 578 (M + H) |
| 520 | 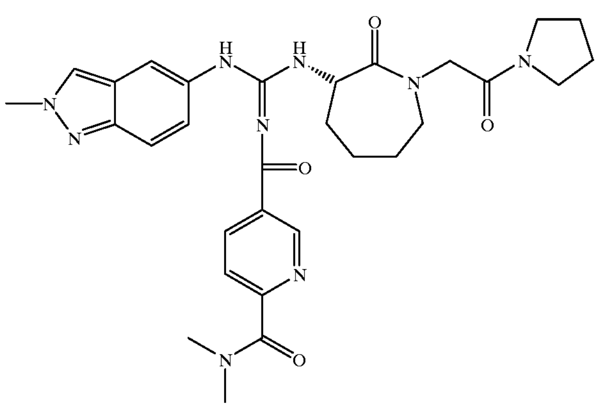 | HPLC (method A) $t_R$ = 3.11 min LRMS (ESI) m/z 588 (M + H) |

-continued

| Example | Structure | Characterization |
|---|---|---|
| 521 | 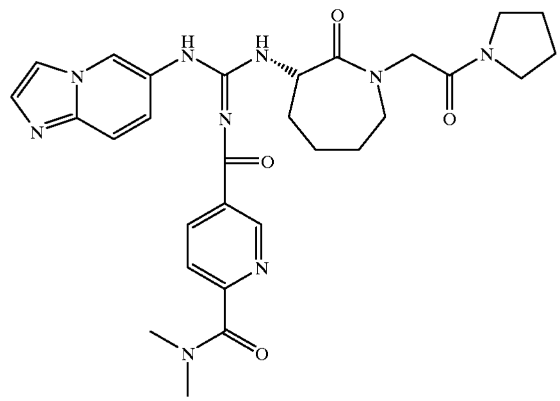 | HPLC (method A) $t_R$ = 2.32 min<br>LRMS (ESI) m/z<br>574 (M + H) |
| 522 | 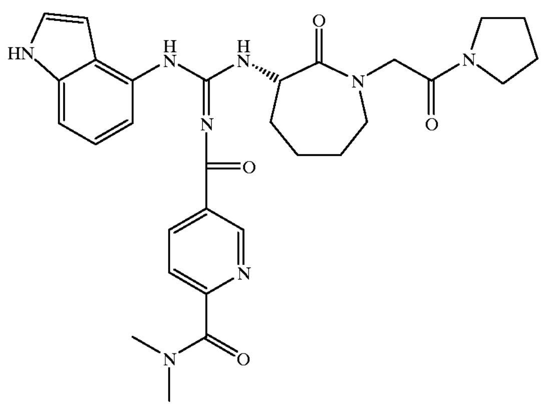 | HPLC (method A) $t_R$ = 2.90 min<br>LRMS (ESI) m/z<br>573 (M + H) |
| 523 | 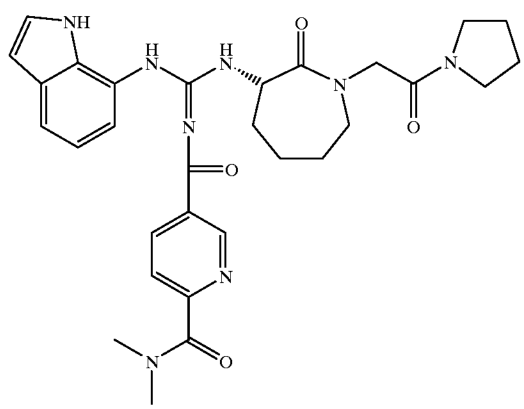 | HPLC (method A) $t_R$ = 3.20 min<br>LRMS (ESI) m/z<br>573 (M + H) |

-continued

| Example | Structure | Characterization |
|---|---|---|
| 524 | 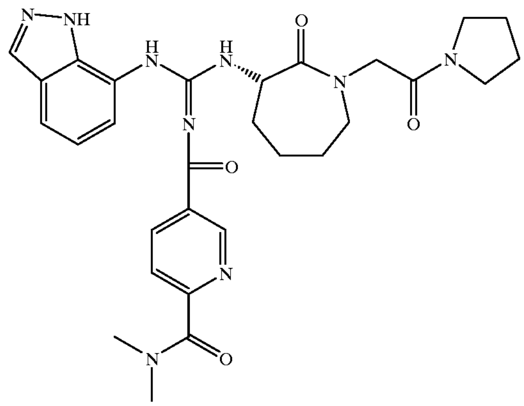 | HPLC (method A) $t_R$ = 2.90 min LRMS (ESI) m/z 574 (M + H) |
| 525 | 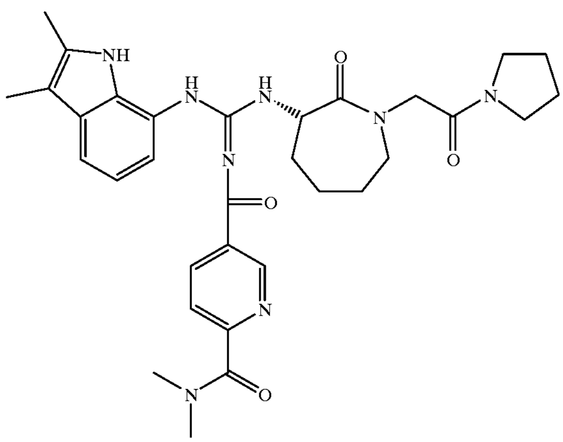 | HPLC (method A) $t_R$ = 3.6 min LRMS (ESI) m/z 601 (M + H) |
| 526 | 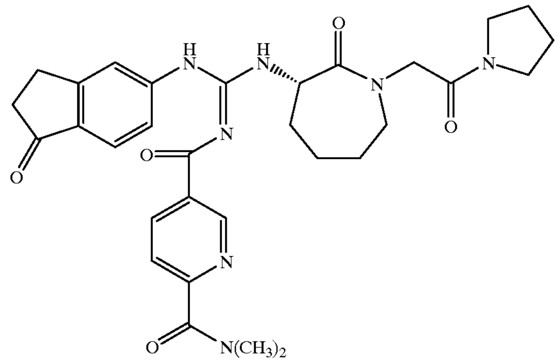 | LCMS (ESI, positive ion spectrum, HPLC method F), m/z 588 (M + H), $t_R$ = 2.7 min. |
| 527 | 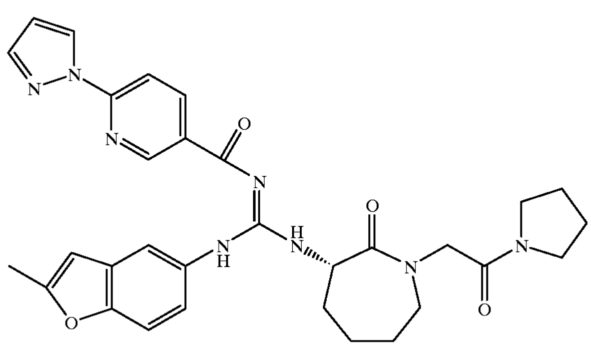 | HPLC (method A) $t_R$ = 4.3 min LRMS (ESI) m/z 583 (M + H) |

-continued

| Example | Structure | Characterization |
|---|---|---|
| 528 | 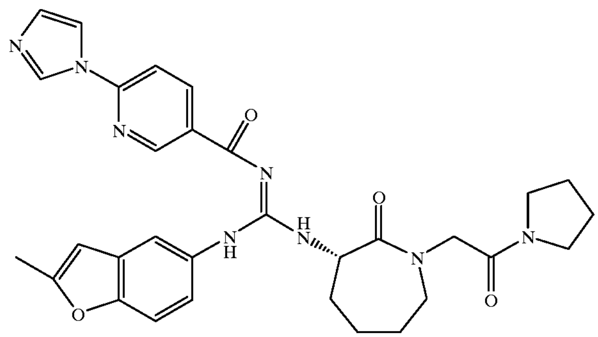 | HPLC (method A)<br>$t_R$ = 3.5 min<br>LRMS (ESI) m/z<br>583 (M + H) |
| 529 | 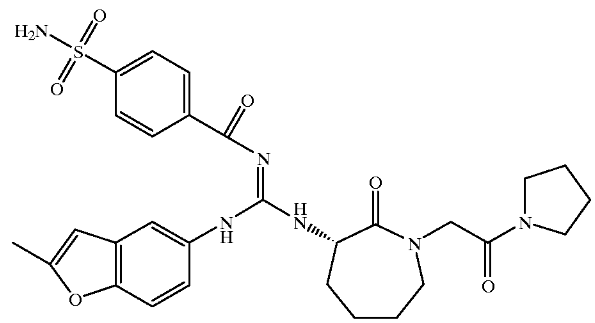 | HPLC (method A)<br>$t_R$ = 3.5 min<br>LRMS (ESI) m/z<br>595 (M + H) |
| 530 | 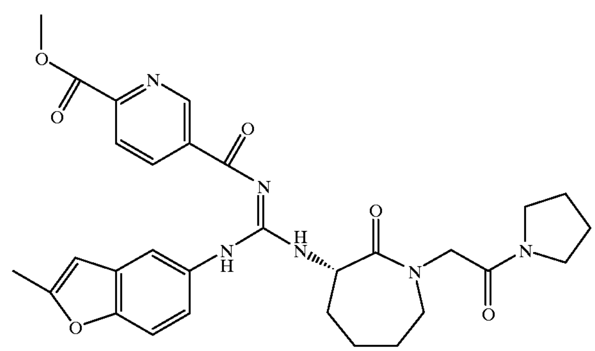 | HPLC (method A)<br>$t_R$ = 4.2 min<br>LRMS (ESI) m/z<br>575 (M + H) |
| 531 | 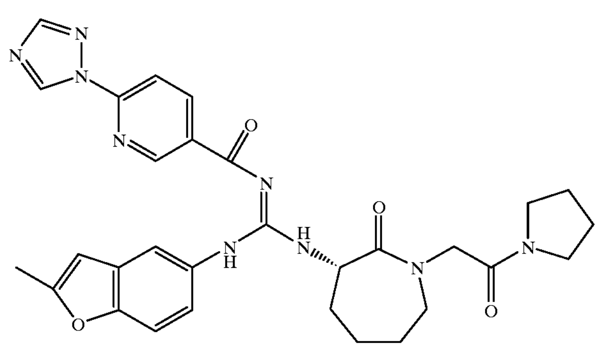 | HPLC (method A)<br>$t_R$ = 4.3 min<br>LRMS (ESI) m/z<br>584 (M + H) |

-continued

| Example | Structure | Characterization |
|---------|-----------|------------------|
| 532 | 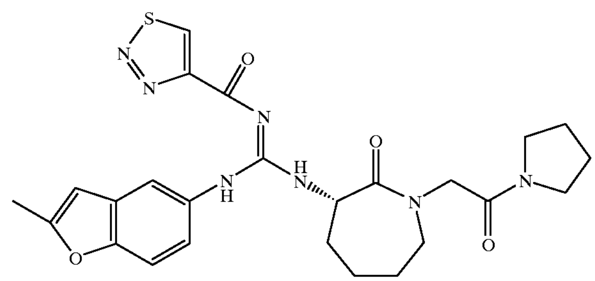 | HPLC (method A) $t_R$ = 3.4 min LRMS (ESI) m/z 524 (M + H) |
| 533 | 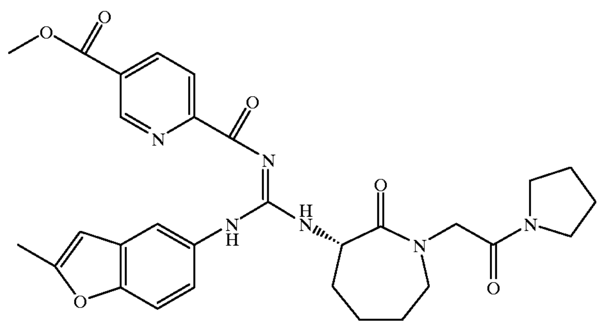 | HPLC (method A) $t_R$ = 3.5 min LRMS (ESI) m/z 575 (M + H) |
| 534 | 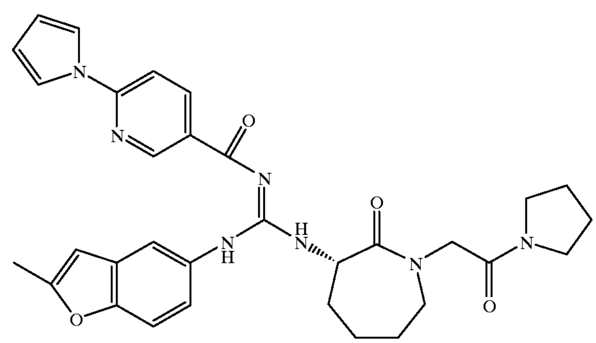 | HPLC (method A) $t_R$ = 4.4 min LRMS (ESI) m/z 581 (M + H) |
| 535 | 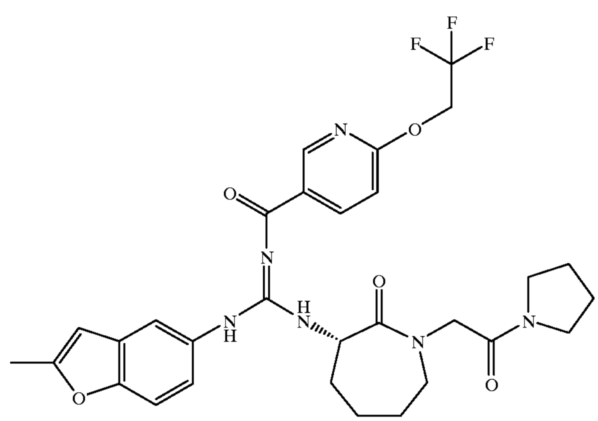 | HPLC (method A) $t_R$ = 4.4 min LRMS (ESI) m/z 615 (M + H) |

-continued
| Example | Structure | Characterization |
|---|---|---|
| 536 | 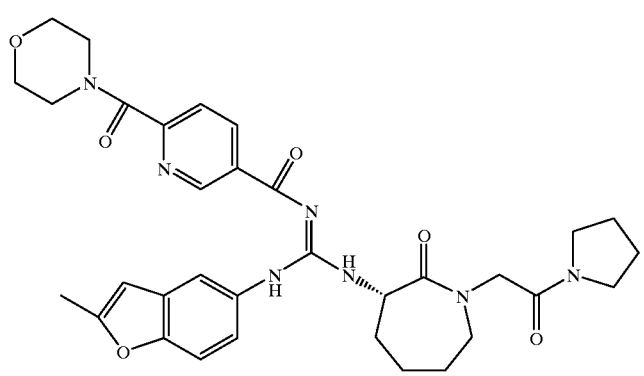 | HPLC (method A)<br>$t_R$ = 3.8 min<br>LRMS (ESI) m/z<br>630 (M + H) |
| 537 | 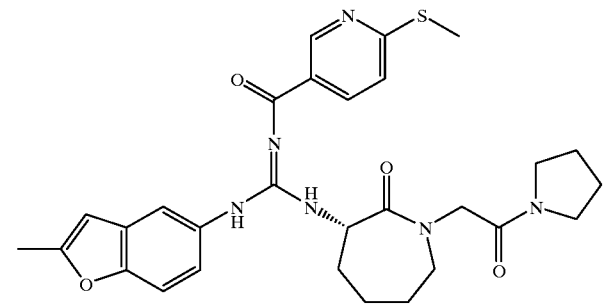 | HPLC (method A)<br>$t_R$ = 4.3 min<br>LRMS (ESI) m/z<br>563 (M + H) |
| 538 | 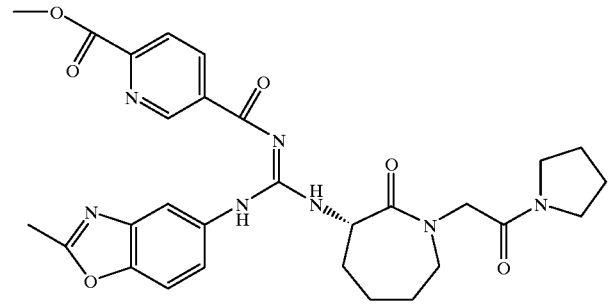 | HPLC (method A)<br>$t_R$ = 4.2 min<br>LRMS (ESI) m/z<br>576 (M + H) |
| 539 | 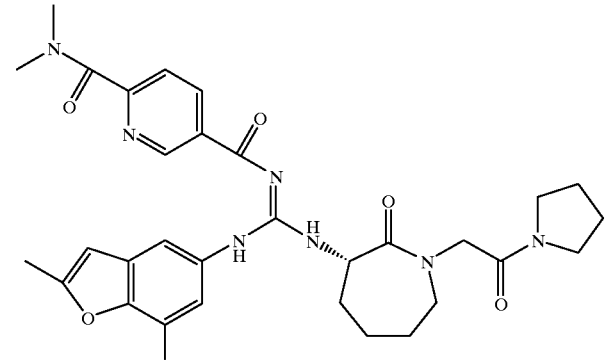 | HPLC (method A)<br>$t_R$ = 4.4 min<br>LRMS (ESI) m/z<br>606 (M + H) |

-continued

| Example | Structure | Characterization |
|---|---|---|
| 540 | 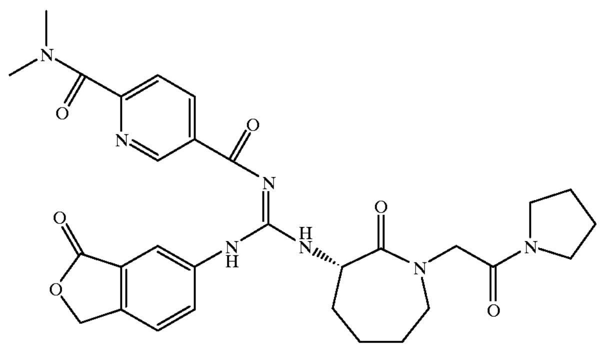 | HPLC (method A)<br>$t_R$ = 3.3 min<br>LRMS (ESI) m/z<br>590 (M + H) |
| 541 | 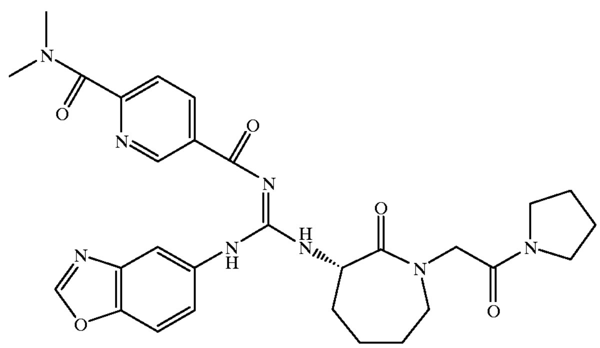 | HPLC (method A)<br>$t_R$ = 3.2 min<br>LRMS (ESI) m/z<br>575 (M + H) |
| 542 | 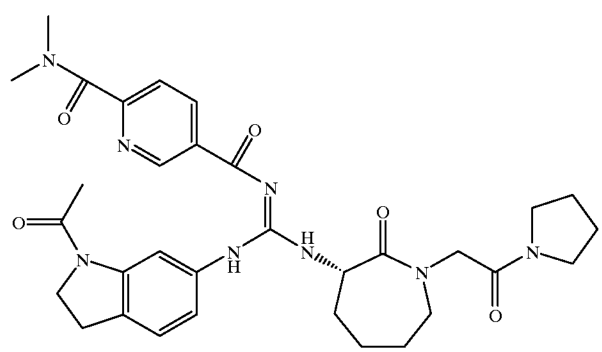 | HPLC (method A)<br>$t_R$ = 3.2 min<br>LRMS (ESI) m/z<br>617 (M + H) |
| 543 | 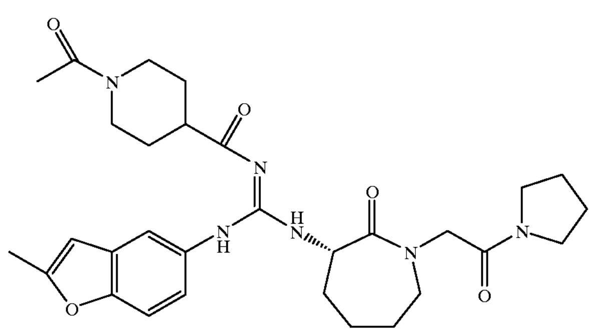 | HPLC (method A)<br>$t_R$ = 3.0 min<br>LRMS (ESI) m/z<br>565 (M + H) |

-continued

| Example | Structure | Characterization |
|---|---|---|
| 544 | 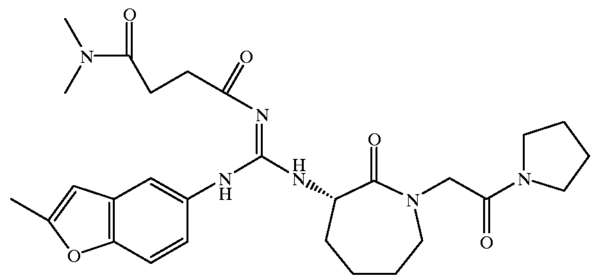 | HPLC (method A)<br>$t_R$ = 2.8 min<br>LRMS (ESI) m/z<br>539 (M + H) |
| 545 | 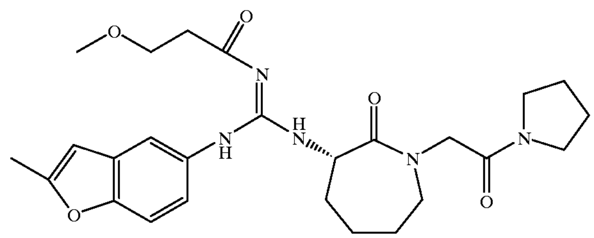 | HPLC (method A)<br>$t_R$ = 2.9 min<br>LRMS (ESI) m/z<br>498 (M + H) |
| 546 | 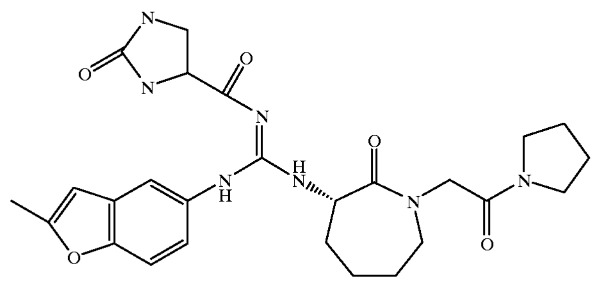 | HPLC (method A)<br>$t_R$ = 2.5 min<br>LRMS (ESI) m/z<br>524 (M + H) |
| 547 | 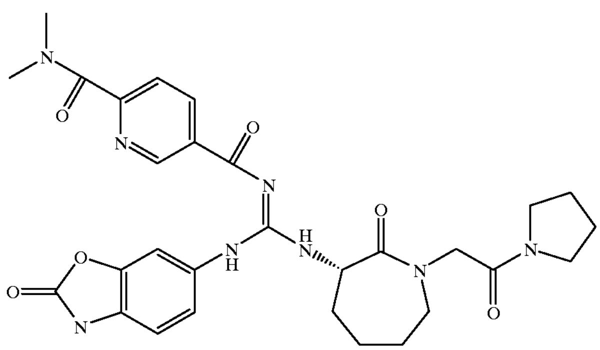 | HPLC (method A)<br>$t_R$ = 2.8 min<br>LRMS (ESI) m/z<br>591 (M + H) |
| 548 | 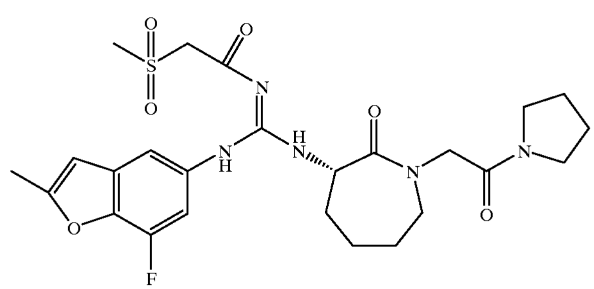 | HPLC (method A)<br>$t_R$ = 2.9 min<br>LRMS (ESI) m/z<br>550 (M + H) |

-continued

| Example | Structure | Characterization |
|---|---|---|
| 549 | 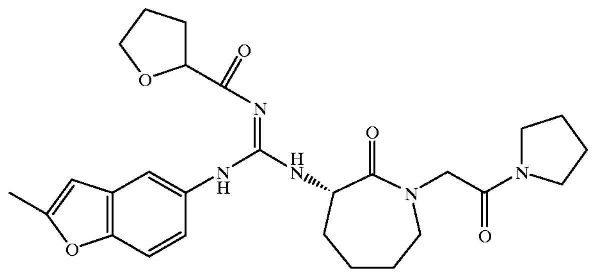 | HPLC (method A)<br>$t_R$ = 2.7 min<br>LRMS (ESI) m/z<br>510 (M + H) |
| 550 | 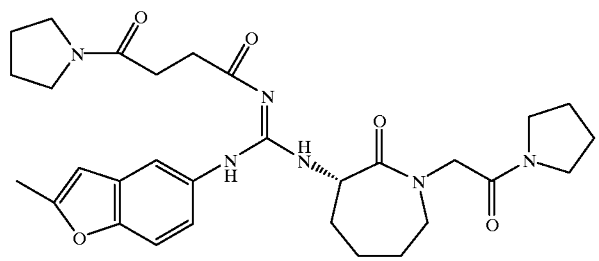 | HPLC (method A)<br>$t_R$ = 3.0 min<br>LRMS (ESI) m/z<br>565 (M + H) |
| 551 | 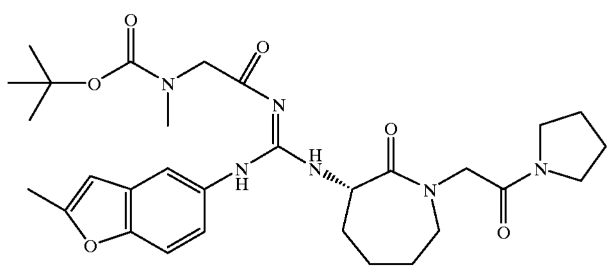 | HPLC (method A)<br>$t_R$ = 3.4 min<br>LRMS (ESI) m/z<br>583 (M + H) |
| 552 | 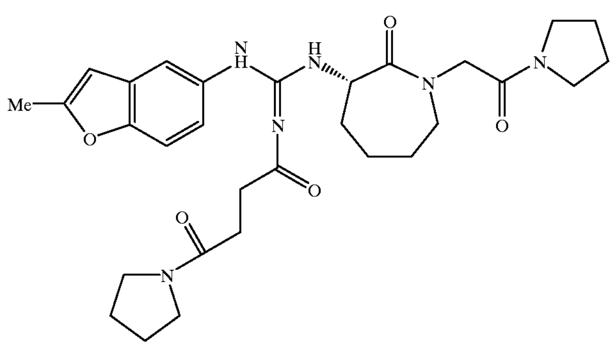 | HPLC (method A)<br>$t_R$ = 3.0 min<br>LRMS (ESI) m/z<br>565 (M + H) |
| 553 | 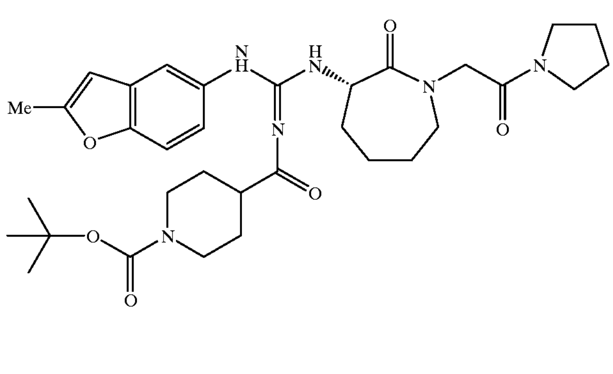 | HPLC (method D)<br>$t_R$ = 3.6 min<br>LRMS (ESI) m/z<br>623 (M + H) |

-continued
| Example | Structure | Characterization |
|---|---|---|
| 554 | 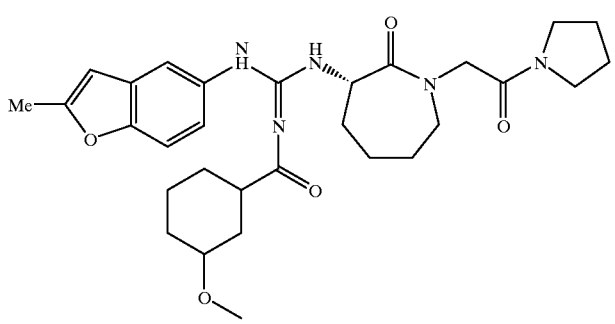 | HPLC (method A)<br>$t_R$ = 3.0 min<br>LRMS (ESI) m/z<br>552 (M + H) |
| 555 | 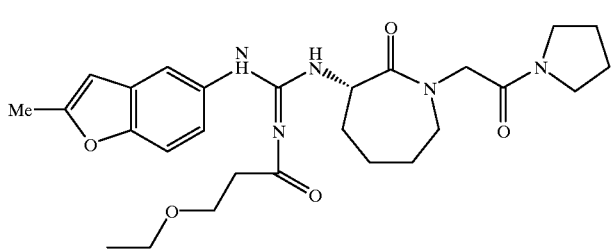 | HPLC (method A)<br>$t_R$ = 2.8 min<br>LRMS (ESI) m/z<br>512 (M + H) |
| 556 | 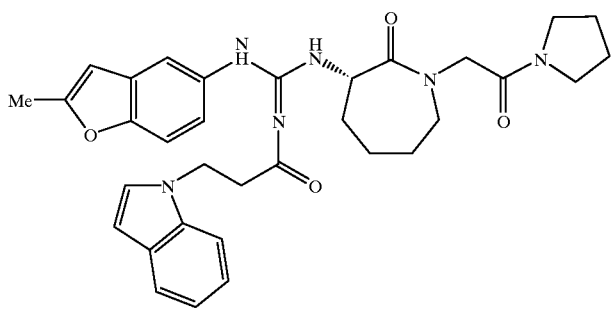 | HPLC (method A)<br>$t_R$ = 3.2 min<br>LRMS (ESI) m/z<br>583 (M + H) |
| 557 | 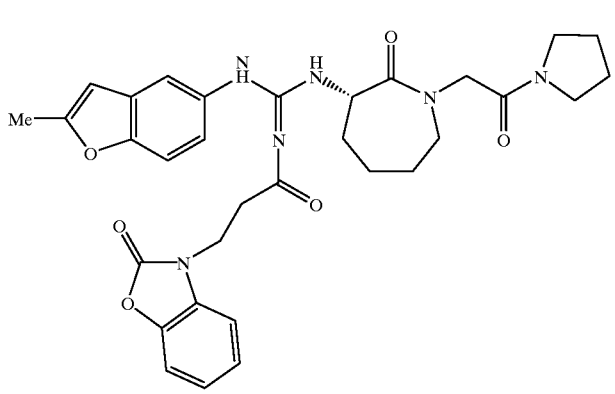 | HPLC (method A)<br>$t_R$ = 3.1 min<br>LRMS (ESI) m/z<br>601 (M + H) |

-continued
| Example | Structure | Characterization |
|---|---|---|
| 558 | 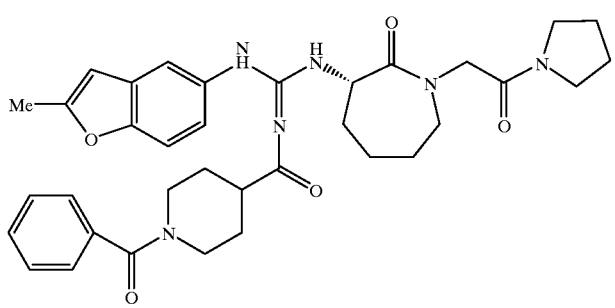 | HPLC (method A) $t_R$ = 3.0 min LRMS (ESI) m/z 627 (M + H) |
| 559 | 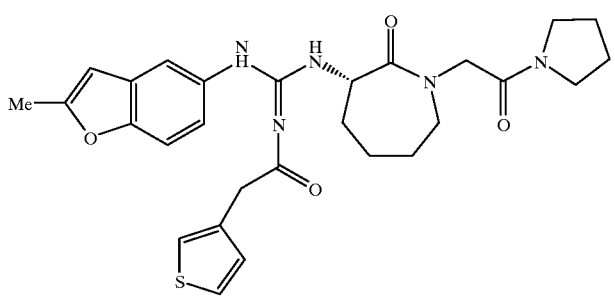 | HPLC (method A) $t_R$ = 3.0 min LRMS (ESI) m/z 536 (M + H) |
| 560 | 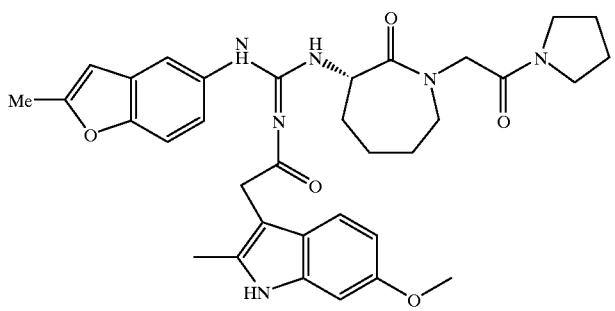 | HPLC (method A) $t_R$ = 3.0 min LRMS (ESI) m/z 613 (M + H) |
| 561 | 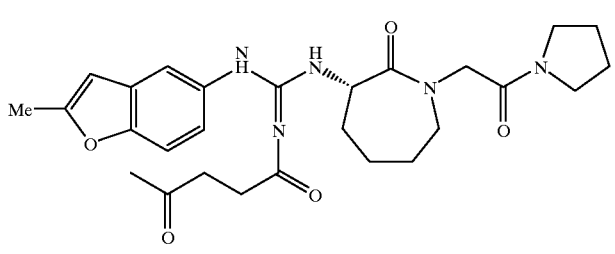 | HPLC (method A) $t_R$ = 2.8 min LRMS (ESI) m/z 510 (M + H) |
| 562 | 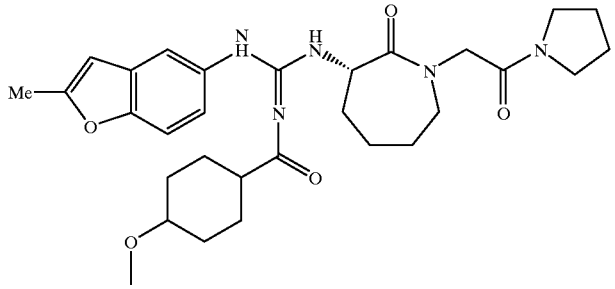 | HPLC (method A) $t_R$ = 3.0 min LRMS (ESI) m/z 552 (M + H) |

-continued

| Example | Structure | Characterization |
|---|---|---|
| 563 | 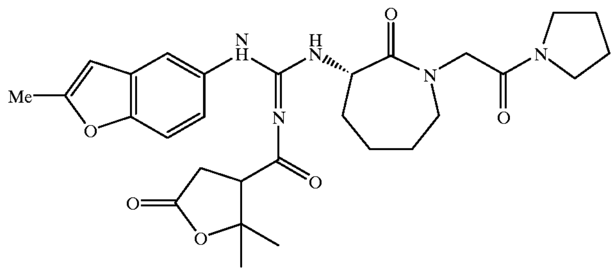 | HPLC (method A)<br>$t_R$ = 2.9 min<br>LRMS (ESI) m/z<br>552 (M + H) |
| 564 | 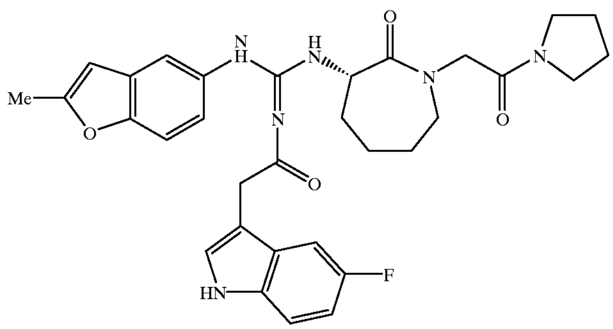 | HPLC (method D)<br>$t_R$ = 3.3 min<br>LRMS (ESI) m/z<br>587 (M + H) |
| 565 | 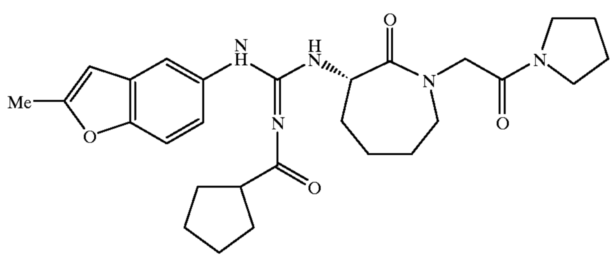 | HPLC (method A)<br>$t_R$ = 3.1 min<br>LRMS (ESI) m/z<br>508 (M + H) |
| 566 | 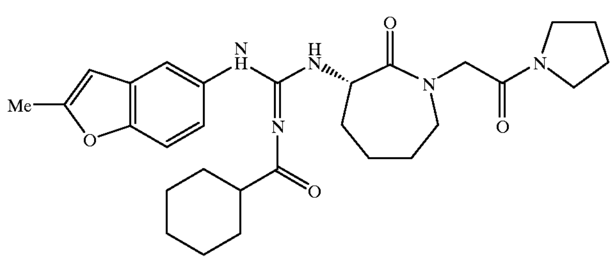 | HPLC (method A)<br>$t_R$ = 3.3 min<br>LRMS (ESI) m/z<br>522 (M + H) |
| 567 | 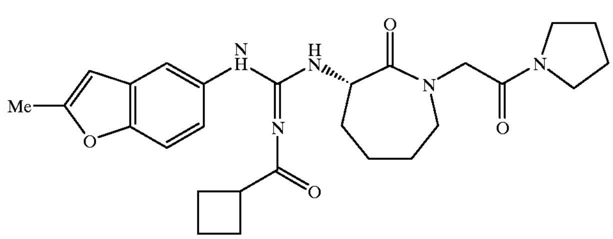 | HPLC (method A)<br>$t_R$ = 3.3 min<br>LRMS (ESI) m/z<br>494 (M + H) |

-continued

| Example | Structure | Characterization |
|---|---|---|
| 568 | 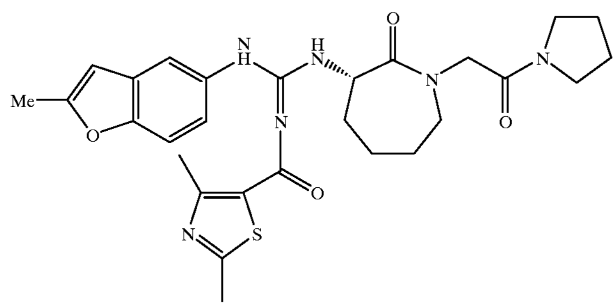 | HPLC (method A)<br>$t_R$ = 3.9 min<br>LRMS (ESI) m/z<br>551 (M + H) |
| 569 | 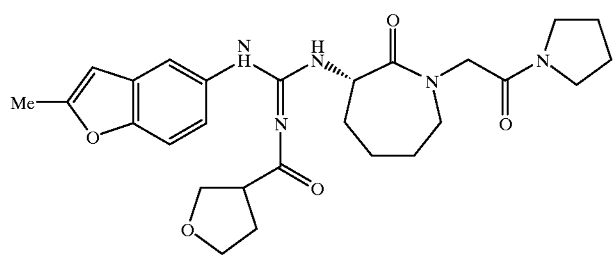 | HPLC (method A)<br>$t_R$ = 2.7 min<br>LRMS (ESI) m/z<br>510 (M + H) |
| 570 | 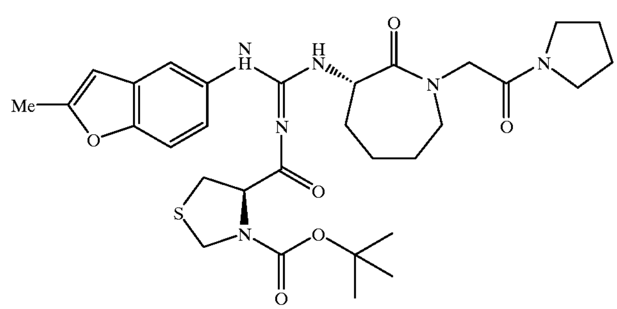 | HPLC (method A)<br>$t_R$ = 3.4 min<br>LRMS (ESI) m/z<br>627 (M + H) |
| 571 | 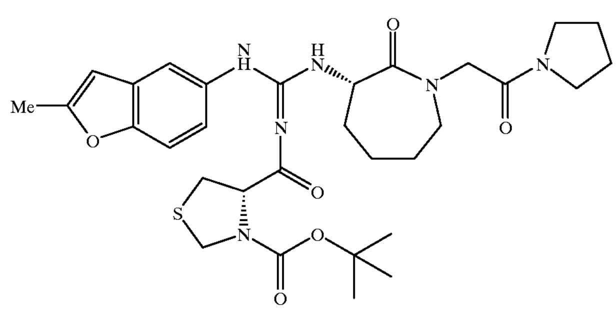 | HPLC (method A)<br>$t_R$ = 3.3 min<br>LRMS (ESI) m/z<br>627 (M + H) |
| 572 | 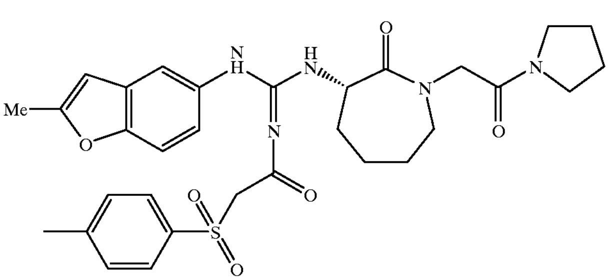 | HPLC (method A)<br>$t_R$ = 3.3 min<br>LRMS (ESI) m/z<br>608 (M + H) |

-continued

| Example | Structure | Characterization |
|---------|-----------|------------------|
| 573 | 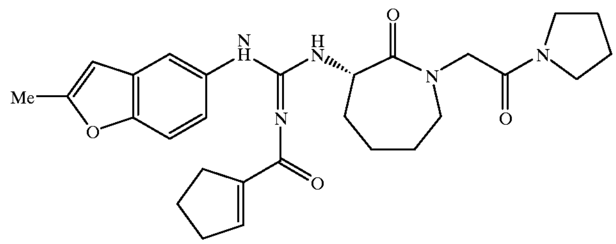 | HPLC (method A)<br>$t_R$ = 3.0 min<br>LRMS (ESI) m/z<br>506 (M + H) |
| 574 | 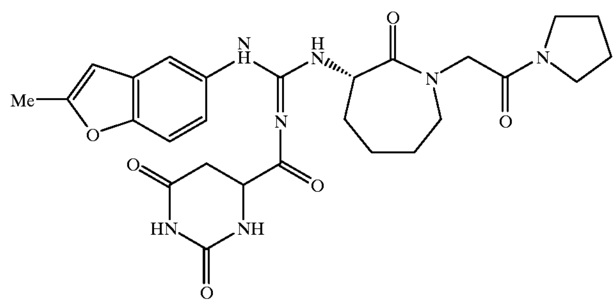 | HPLC (method A)<br>$t_R$ = 2.7 min<br>LRMS (ESI) m/z<br>552 (M + H) |
| 575 | 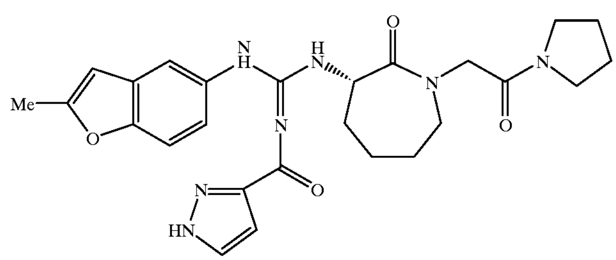 | HPLC (method A)<br>$t_R$ = 2.7 min<br>LRMS (ESI) m/z<br>506 (M + H) |

EXAMPLES 576 to 578

Using the procedures described in Examples 355 and 496, the following compounds were prepared

| Example | Structure | characterization |
|---------|-----------|------------------|
| 576 | 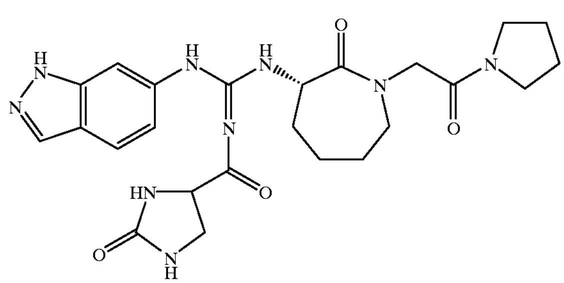 | HPLC (method A)<br>$t_R$ = 1.9 min<br>LRMS (ESI) m/z<br>510 (M + H) |

-continued

| Example | Structure | characterization |
|---|---|---|
| 577 | 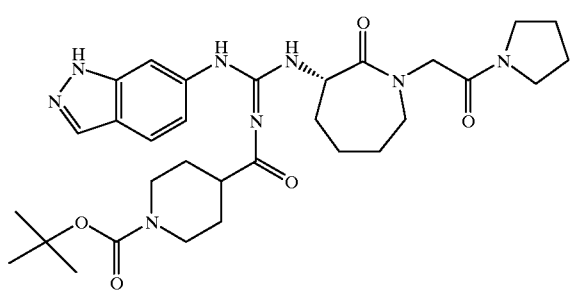 | HPLC (method A)<br>$t_R$ = 2.1 min<br>LRMS (ESI) m/z<br>538 (M + H) |
| 578 | 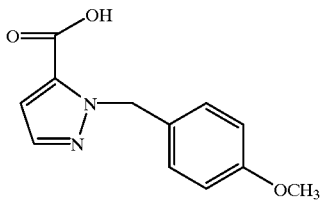 | |

EXAMPLE 579

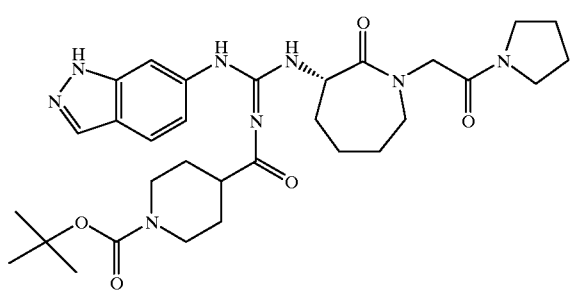

To a solution of 1,4-Piperidinedicarboxylic acid, 1-(1,1-dimethylethyl) ester (0.57 g, 2.48 mmol) in acetonitrile (7.0 mL) was added 1,1'-carbonyldiimidazole (0.37 g, 2.29 mmol). After stirring at room temperature for 1 h, Example 578 (0.76 g, 1.91 mmol) was added. The mixture was stirred at room temperature for 50 hrs and concentrated. The residue was then dissolved in tetrahydrofuran(10 mL) and 2N aqueous lithium hydroxide was added. The resulting mixture was stirred at room temperature for 1 h and then extracted with ethyl acetate. The organic layers was washed saturated sodium chloride, dried over magnesium sulfate and concentrated to provide 1.37 g of orange oil. Flash chromatography (silica, 6% methanol/ethyl acetate) provided Title compound(0.55 g, 47%): LRMS (ESI) m/z 609 (M+H); HPLC (Method D) $t_R$=3.0 min.

EXAMPLE 580

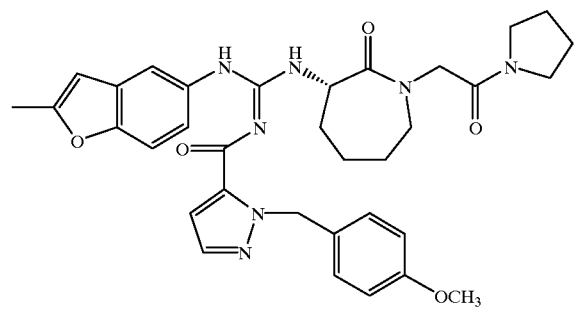

To a solution of methyl 1-[(4-methoxyphenyl)methyl]-1H-Pyrazole-5-carboxylate (586 mg, 2.38 mmol) in THF (5 mL) was added 2.5 M LiOH in water (5 mL). After stirring at room temperature for 10 hours, the volume was reduced to 4 mL in vacuo which caused the precipitation of white solids. The pH was adjusted to 4 with acetic acid (ca. 2 mL) and the mixture was extracted with ethyl acetate (3×10 mL). The combined organic extracts were dried over sodium sulfate and concentrated in vacuo to provide part A com pound (526 mg, 95%) as a white solid: LCMS (ESI, positive ion spectrum, HPLC method F), m/z 233 (M+H) $t_R$=3.0 min.

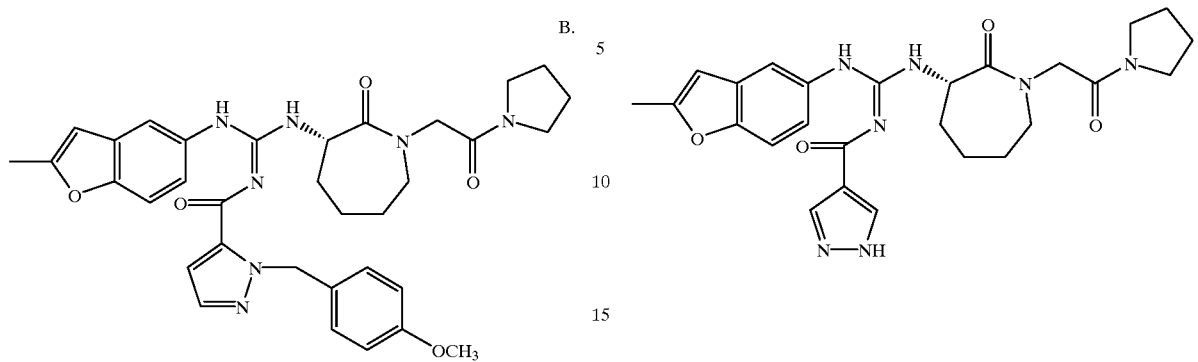

To a solution of part A compound (46 mg, 0.20 mmol) in THF (0.4 mL) was added 1,1'-carbonyldiimidazole (33 mg, 0.20 mmol). After one hour, Example 496 part A compound (82 mg, 0.20 mmol) was added and the solution was stirred for 20 hours. At that point, methanol (1 mL) was added and the solvent removed in vacuo. Flash chromatography (silica, 25 mm dia column, 3% methanol/chloroform) of the residue provided a crude product which was further purified on a 2 g C-18 cartridge eluting with 80% methanol/water. This provided Title compound (38 mg, 30%) as an off-white foam: LCMS (ESI, positive ion spectrum, HPLC method F), m/z 626 (M+H), $t_R$=3.8 min.

EXAMPLE 581

To a suspension of 4-pyrazolecarboxylic acid (224 mg, 2.0 mmol) in chloroform (10 mL) was added diisopropylethylamine (508 mg, 4.0 mmol), 4-dimethylaminopyridine (25 mg, 0.2 mmol), and Boc₂O (654 mg, 3.0 mmol) to produce a solution. After 15 hours, the reaction was quenched with saturated aqueous ammonium chloride (10 mL) and extracted with chloroform (3×10 mL). The combined chloroform extracts were dried with magnesium sulfate and concentrated in vacuo. The residue was purified by flash chromatography (silica, 25 mm dia column, 20% methanol/chloroform) to yield part A compound (333 mg, 79%) as an oil: LCMS (ESI, positive ion spectrum, HPLC method F), m/z 213 (M+H), $t_R$=2.2 min.

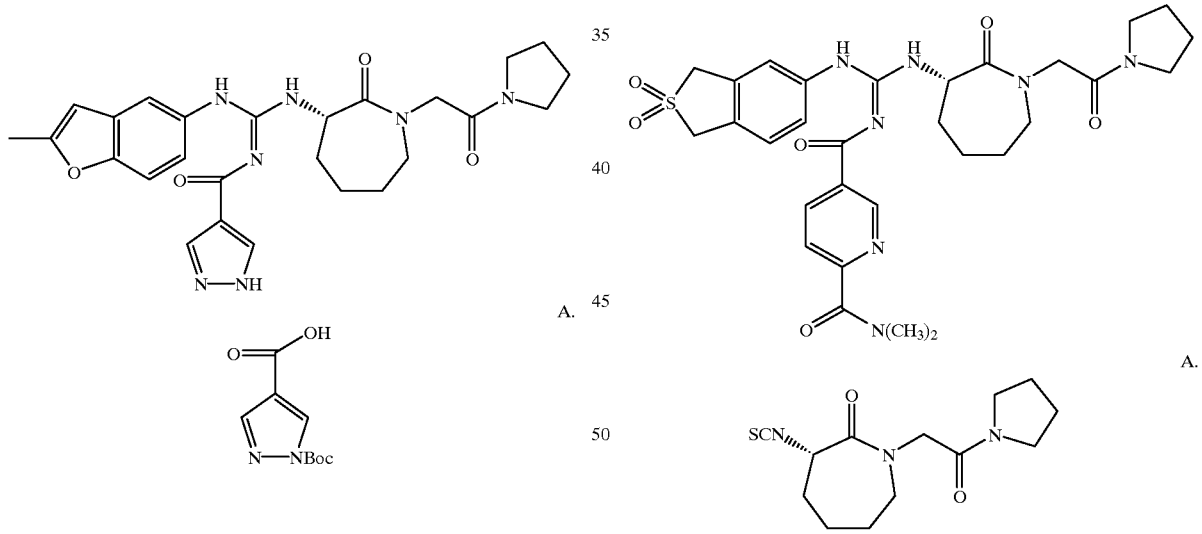

To a solution of part A compound (98 mg, 0.46 mmol) in THF (1 mL) was added 1,1'-carbonyldiimidazole (75 mg, 0.46 mmol) and the mixture stirred for one hour. At that point, Example 496 part A compound (189 mg, 0.46 mmol) was added and the reaction stirred for 18 hours. Methanol (1 mL) was then added, the solvent removed in vacuo, and the residue purified by flash chromatography (silica, 30 mm dia column, 3.5% methanol/chloroform). This gave Title compound (83 mg, 30%) as a yellow foam: LCMS (ESI, positive ion spectrum, HPLC method F), m/z 506 (M+H), $t_R$=2.3 min.

EXAMPLE 582

To a solution of (S)-1-[(3-amino-hexahydro-2-oxo-1H-azepin-1-yl)acetyl]pyrrolidine (239 mg, 1.0 mmol) in chloroform (2 mL) at room temperature was added 1,1'-carbonothioylbis-2(1H)-pyridinone (232 mg, 1.0 mmol). After 4 hours, the reaction mixture was placed directly on a silica column (30 mm dia.) and eluted with 0.5% methanol/chloroform to yield part A compound (236 mg, 84%) as a viscous oil: LCMS (ESI, positive ion spectrum, HPLC method F), m/z 282 (M+H), $t_R$=2.0 min.

B.

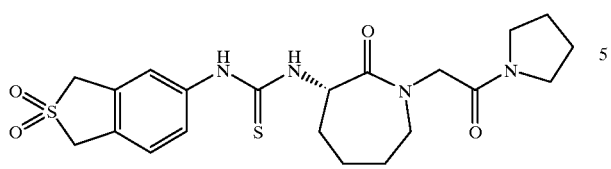

To a solution part A compound (230 mg, 0.82 mmol) in chloroform (2 mL) was added 1,3-dihydro-benzo[c]thiophen-5-amine, 2,2-dioxide (150 mg, 0.82 mmol) followed by DMF (1 mL). The slurry was heated at 50° C. for 20 hours to produce a clear solution. The solvent was removed in vacuo and the residue was chromatographed (silica, 40 mm dia column, 2% methanol/chloroform) to yield crude product. Trituration with ether (5×2 mL) provided part B compound (436 mg): LCMS (ESI, positive ion spectrum, HPLC method F), m/z 465 (M+H) $t_R$=2.2 min.

C.

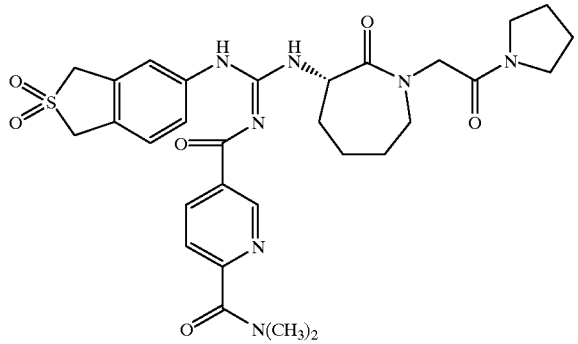

Part B compound was transformed to Title compound using the methods described in Example 496 to yield (86 mg, 16%) of an oily yellow solid: LCMS (ESI, positive ion spectrum, HPLC method F), m/z 624 (M+H), $t_R$=2.7 min.

EXAMPLE 583

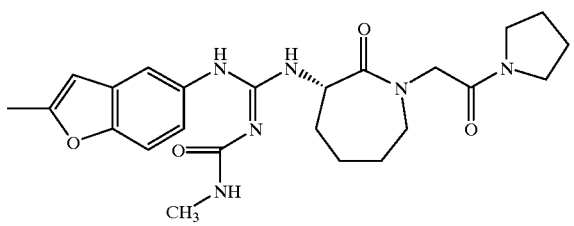

To a solution of Example 496 compound A (42 mg, 0.10 mmol) in chloroform (0.3 mL) was added methyl isocyanate (6.44 mg, 0.11 mmol). After 17 hours, methanol (0.2 mL) was added and the product was purified by flash chromatography (silica, 25 mm dia column, 10% methanol/chloroform) to yield Title compound (47 mg, 100%) as a yellow foam: LCMS (ESI, positive ion spectrum, HPLC method F), m/z 469 (M+H), $t_R$=2.9 min.

EXAMPLES 584 and 585

Using the procedures described in Example 583, the following compounds were prepared.

| Example | Structure | Characterization |
| --- | --- | --- |
| 584 | 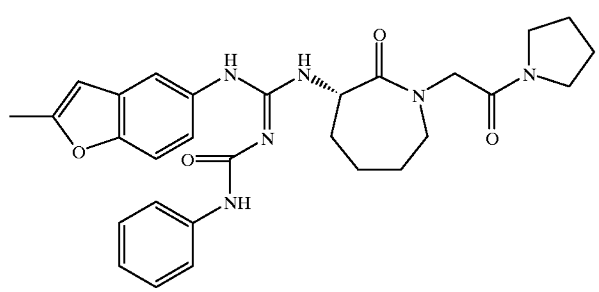 | LCMS (ESI, HPLC method F), m/z 531 (M + H), $t_R$ = 3.5 min. |

-continued

| Example | Structure | Characterization |
|---|---|---|
| 585 | 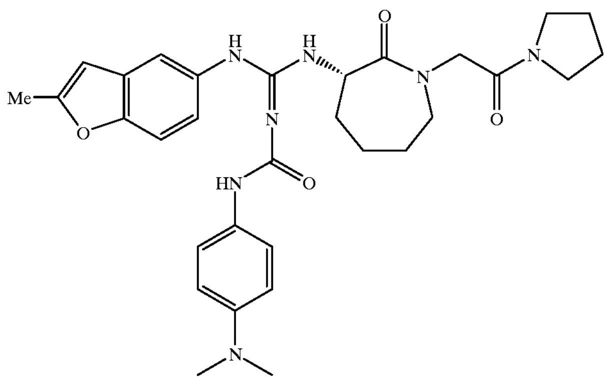 | HPLC (method A) $t_R$ = 2.7 min. LRMS (ESI) m/z 574 (M + H) |

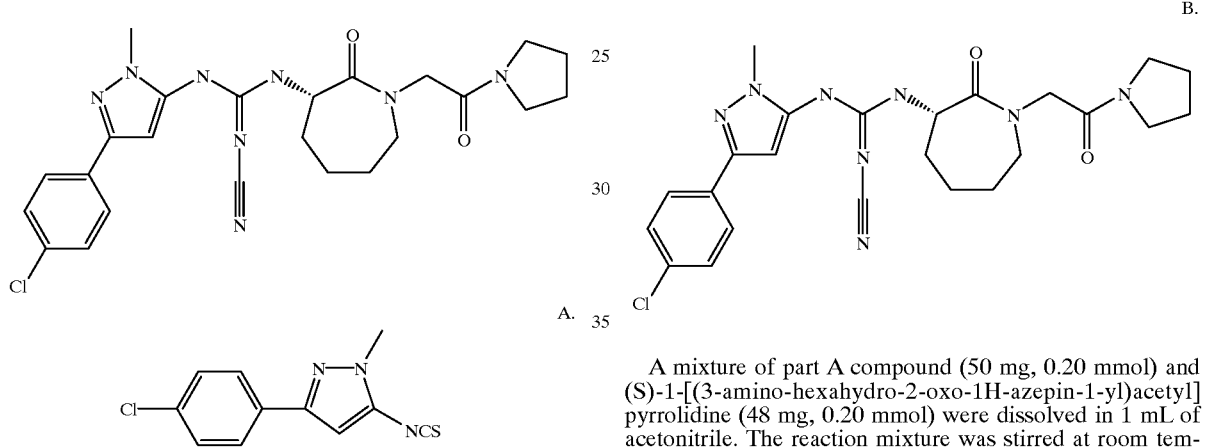

EXAMPLE 586

1-Methyl-3-(4-chlorophenyl)pyrazol-5-amine (2.1 g, 10 mmol) and thiophosgene (0.73 mL, 10 mmol) were dissolved in 45 mL of water. The reaction mixture was stirred at room temperature for 4 hours and 100 mL of ethyl acetate was added. The organic layer was separated, dried over sodium sulfate and concentrated. Chromatography (silica, chloroform) provided part A compound as a light yellow solid:(1.4 g, 57%).

A mixture of part A compound (50 mg, 0.20 mmol) and (S)-1-[(3-amino-hexahydro-2-oxo-1H-azepin-1-yl)acetyl] pyrrolidine (48 mg, 0.20 mmol) were dissolved in 1 mL of acetonitrile. The reaction mixture was stirred at room temperature for 4 hours and was then concentrated in vacuo. The residue was dissolved in 1 mL of DNF. Sodium cyanamide (13 mg, 0.20 mmol) and $HgCl_2$ (54 mg, 0.20 mmol) were added to the reaction mixture. The reaction was stirred at room temperature for 30 min. The mixture was diluted with 20 mL of ethyl acetate. The organic solution was washed with brine (2×20 mL) and concentrated. The residue was purified by preparative HPLC (C-18 reverse phase column; solvent A: 90:10 $H_2O$:MeOH+0.1% TFA, solvent B: 10:90 $H_2O$:MeOH+0.1% TFA) to give the Title compound (25 mg, 25%) as a white solid: HPLC (Method B) $t_R$=4.4 min; LCMS (ESI) m/z 497 (M+H)

EXAMPLE 587

Using the procedure described in Example 138, the following compound was prepared

| Example | structure | characterization |
|---|---|---|
| 587 | 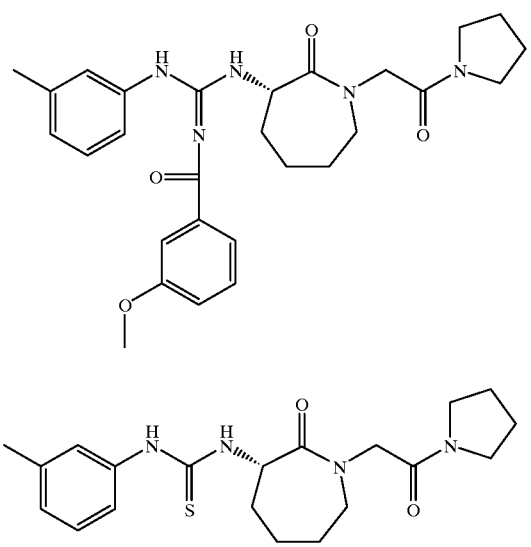 | HPLC (method D)<br>$t_R$ 3.0 min<br>LRMS (ESI) m/z<br>463 (M + H) |

EXAMPLE 588

(3-Methylphenyl)isothiocyanate (1.1 g, 7.5 mmol) and (S)-1-[(3-amino-hexahydro-2-oxo-1H-azepin-1-yl)acetyl] pyrrolidine (1.8 g, 7.5 mmol) were dissolved in 50 mL of acetonitrile. The mixture was stirred at room temperature for 3 hours and was then concentrated to give part A compound (2.9 g, 100%)

To a solution of part A compound (2.9 g, 7.5 mmol) in 7 M ammonia/methanol (68 mL, 472 mmol) was added mercuric oxide (16 g, 75 mmol). The reaction was stirred at room temperature for 30 minutes, filtered through celite and concentrated to give part B compound (2.5 g, 90%) as a yellow foam.

To a solution of 1,1'-carbonyldiimidazole (19 mg, 0.12 mmol) in 0.5 mL of acetonitrile was added 3-methoxybenzoic acid (20 mg, 0.13 mmol). The mixture was stirred at room temperature for 2 hours. A solution of part B compound (37 mg, 0.10 mmol) in 0.2 mL of acetonitrile was added to the reaction mixture. The reaction was stirred at room temperature for another 24 hours, and 0.5 mL of water was added. The mixture was loaded onto a C-18 cartridge (Varian mega bond Elut, 2 g, prewashed sequentially with 20 mL of acetonitrile and 20 mL of water.) The cartridge was eluted with 40 mL of 20% acetonitrile/water and twice with 10 mL-portions of acetonitrile. The product-containing fractions were concentrated to give the Title compound: (18 mg, 36%); HPLC (Method A) $t_R$=3.4 min; LCMS (ESI) m/z 506 (M+H)

EXAMPLES 589–633

Using the procedure described in Example 588, the following compounds were prepared

| Example | structure | characterization |
|---|---|---|
| 589 | 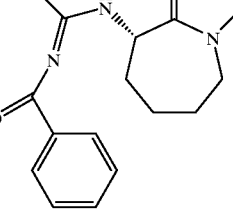 | HPLC (method D) $t_R$ 3.3 min LCMS (ESI) m/z 476 (M + H) |
| 590 | 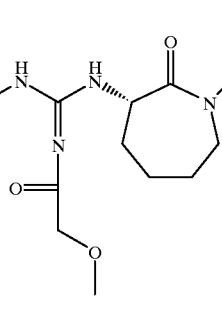 | HPLC (method A) $t_R$ 2.6 min LCMS (ESI) m/z 444 (M + H) |
| 591 | 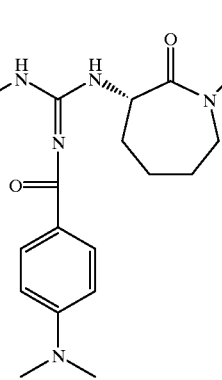 | HPLC (method A) $t_R$ 3.3 min LCMS (ESI) m/z 519 (M + H) |
| 592 | 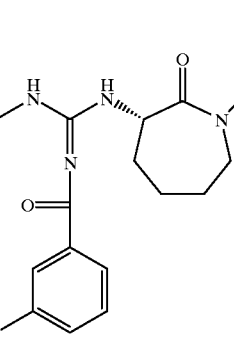 | HPLC (method A) $t_R$ 4.0 min LCMS (ESI) m/z 510 (M + H) |

-continued

| Example | structure | characterization |
|---|---|---|
| 593 | 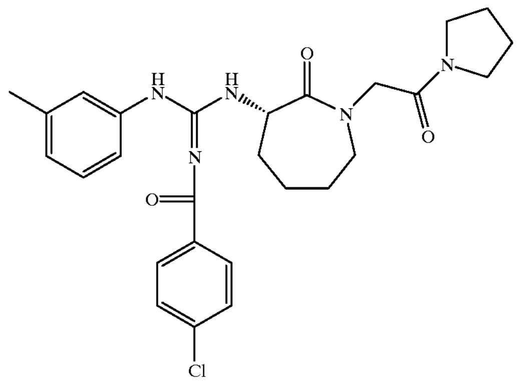 | HPLC (method A) t_R 3.8 min LCMS (ESI) m/z 510 (M + H) |
| 594 | 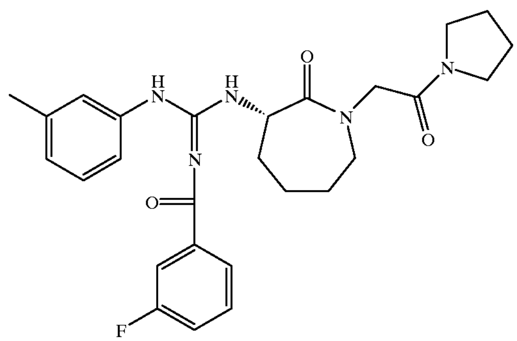 | HPLC (method A) t_R 3.7 min LCMS (ESI) m/z 494 (M + H) |
| 595 | 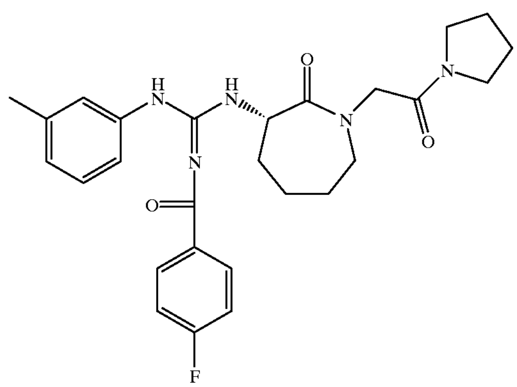 | HPLC (method A) t_R 3.9 min LCMS (ESI) m/z 494 (M + H) |
| 596 | 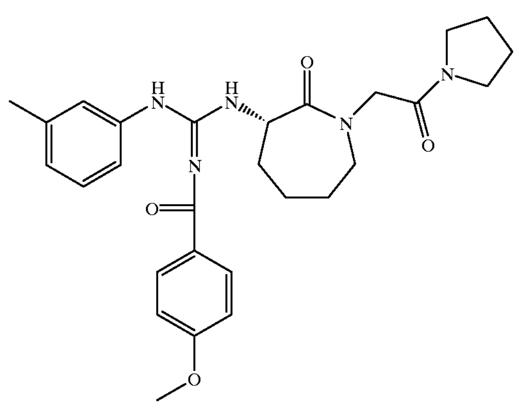 | HPLC (method A) t_R 3.3 min LCMS (ESI) m/z 506 (M + H) |

-continued

| Example | structure | characterization |
|---|---|---|
| 597 | 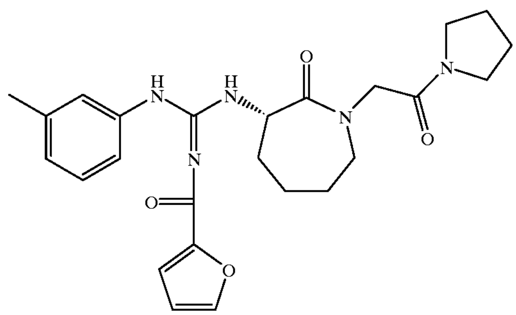 | HPLC (method A) $t_R$ 3.0 min<br>LCMS (ESI) m/z<br>466 (M + H) |
| 598 | 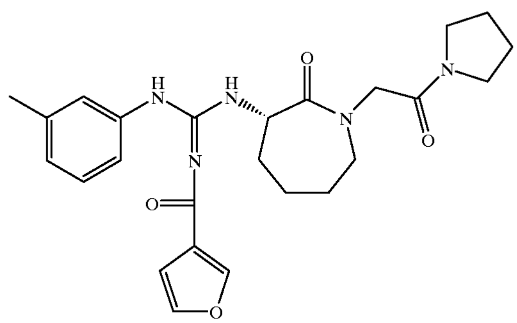 | HPLC (method A) $t_R$ 3.0 min<br>LCMS (ESI) m/z<br>466 (M + H) |
| 599 | 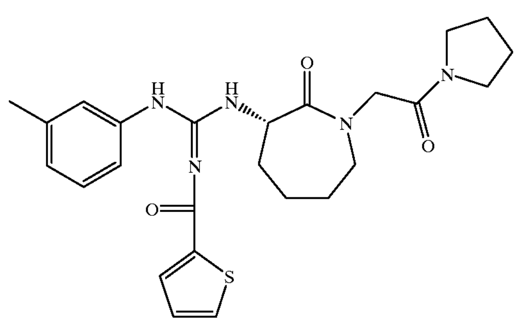 | HPLC (method A) $t_R$ 3.6 min<br>LCMS (ESI) m/z<br>482 (M + H) |
| 600 | 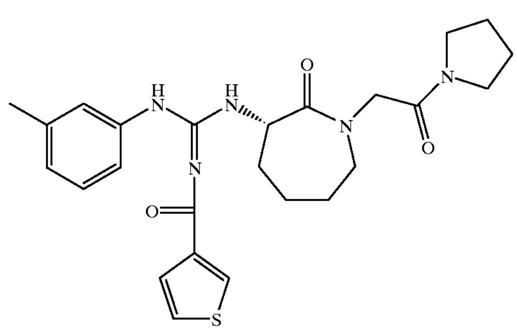 | HPLC (method A) $t_R$ 3.1 min<br>LCMS (ESI) m/z<br>482 (M + H) |

-continued

| Example | structure | characterization |
|---|---|---|
| 601 | 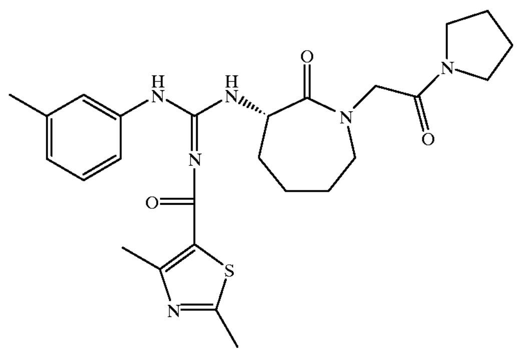 | HPLC (method D) $t_R$ 4.0 min LCMS (ESI) m/z 511 (M + H) |
| 602 | 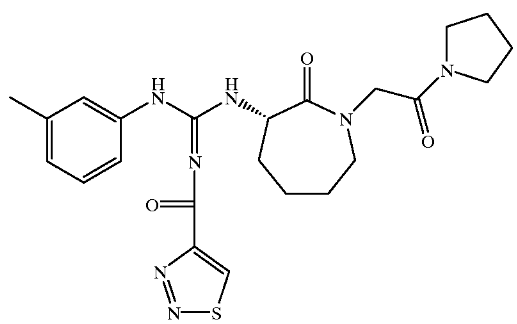 | HPLC (method D) $t_R$ 3.1 min LCMS (ESI) m/z 484 (M + H) |
| 603 | 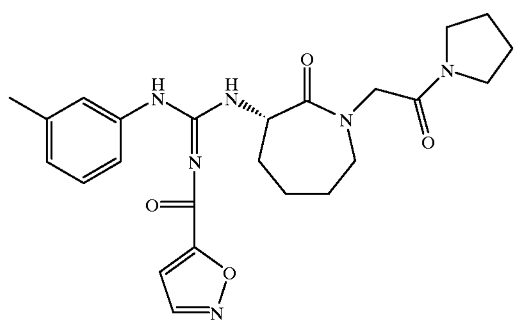 | HPLC (method D) $t_R$ 3.6 min LCMS (ESI) m/z 467 (M + H) |
| 604 | 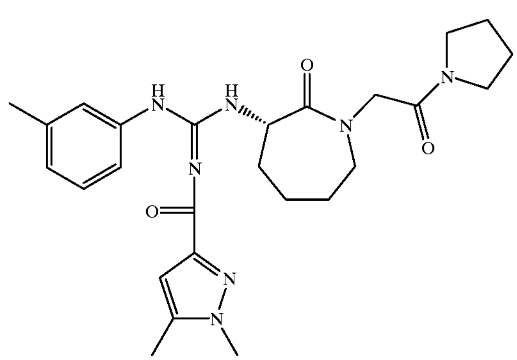 | HPLC (method D) $t_R$ 3.0 min LCMS (ESI) m/z 494 (M + H) |

-continued

| Example | structure | characterization |
|---|---|---|
| 605 | 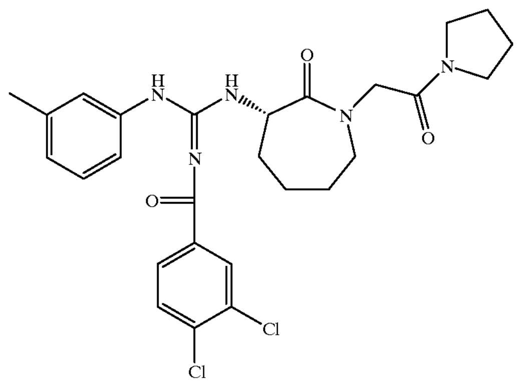 | HPLC (method D) $t_R$ 4.6 min LCMS (ESI) m/z 544 (M + H) |
| 606 | 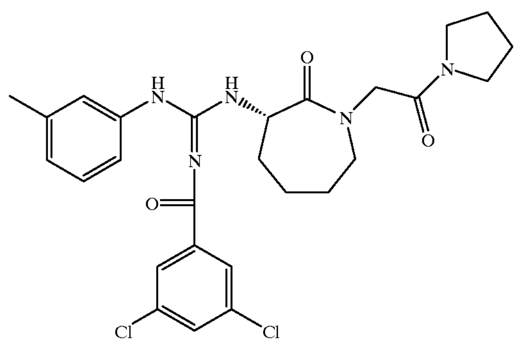 | HPLC (method D) $t_R$ 4.8 min LCMS (ESI) m/z 544 (M + H) |
| 607 | 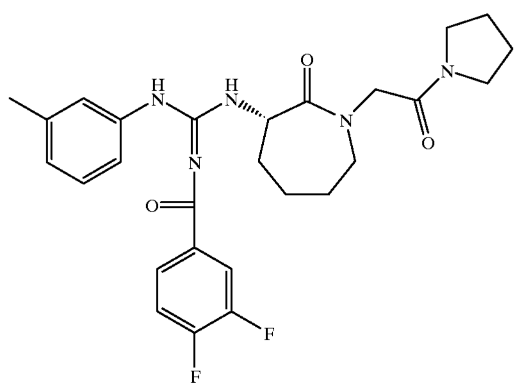 | HPLC (method D) $t_R$ 4.1 min LCMS (ESI) m/z 512 (M + H) |
| 608 | 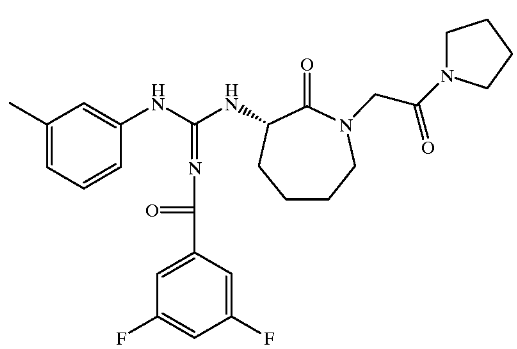 | HPLC (method D) $t_R$ 4.3 min LCMS (ESI) m/z 512 (M + H) |

-continued

| Example | structure | characterization |
|---|---|---|
| 609 | 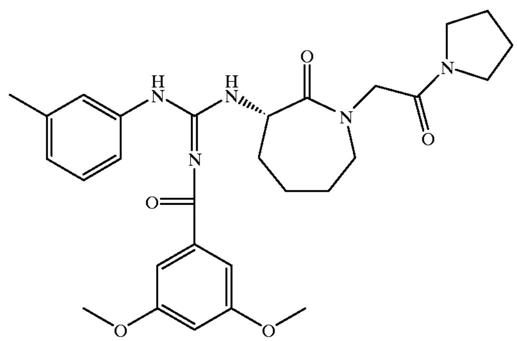 | HPLC (method D) t<sub>R</sub> 3.6 min LCMS (ESI) m/z 536 (M + H) |
| 610 | 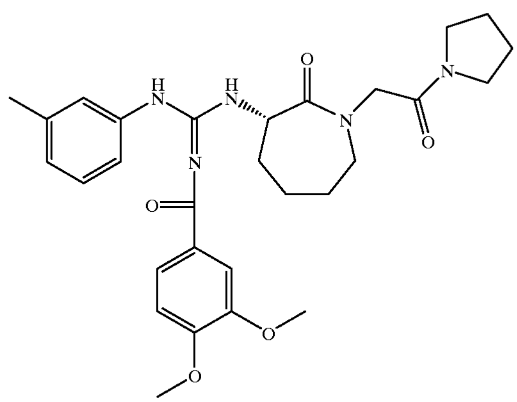 | HPLC (method D) t<sub>R</sub> 3.2 min LCMS (ESI) m/z 536 (M + H) |
| 611 | 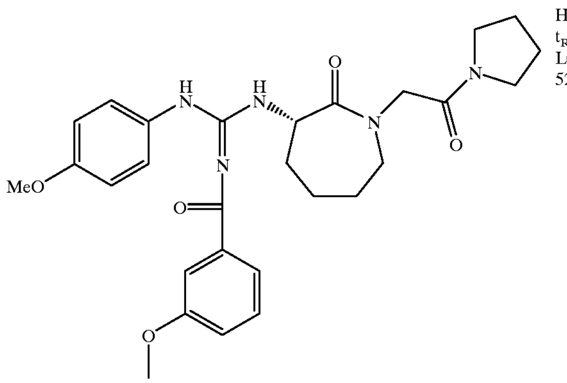 | HPLC (method A) t<sub>R</sub> 3.2 min LCMS (ESI) m/z 522 (M + H) |
| 612 | 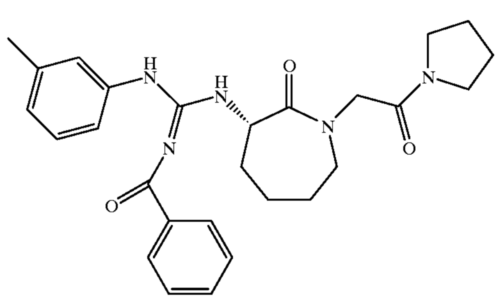 | HPLC (method D) t<sub>R</sub> 3.1 min LCMS (ESI) m/z 492 (M + H) |

-continued
| Example | structure | characterization |
|---|---|---|
| 613 | 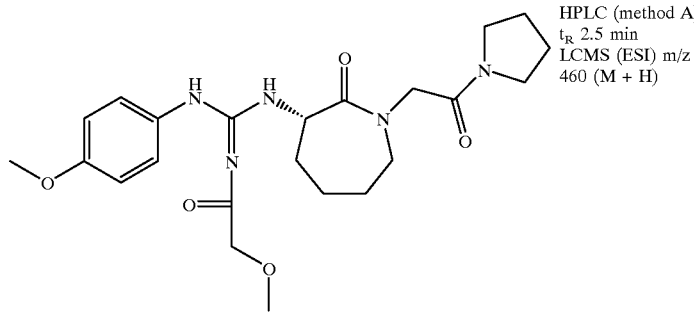 | HPLC (method A) $t_R$ 2.5 min LCMS (ESI) m/z 460 (M + H) |
| 614 | 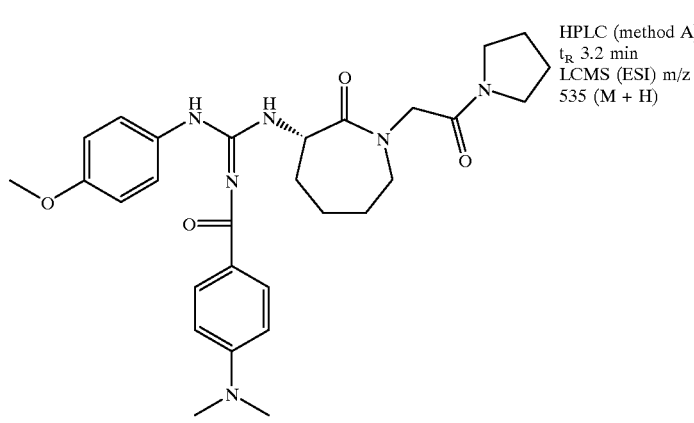 | HPLC (method A) $t_R$ 3.2 min LCMS (ESI) m/z 535 (M + H) |
| 615 | 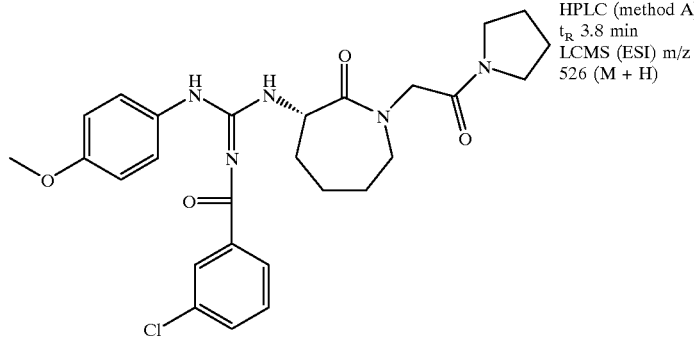 | HPLC (method A) $t_R$ 3.8 min LCMS (ESI) m/z 526 (M + H) |
| 616 | 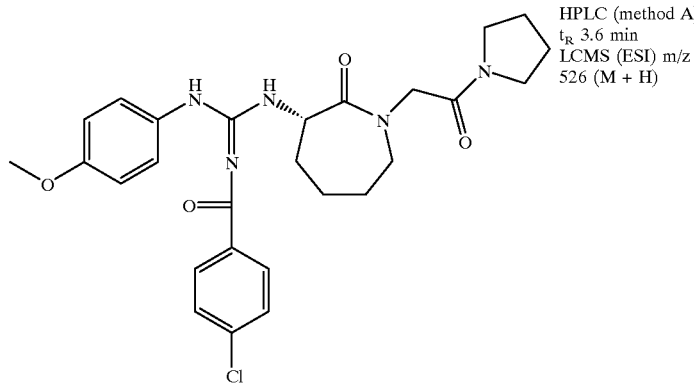 | HPLC (method A) $t_R$ 3.6 min LCMS (ESI) m/z 526 (M + H) |

-continued

| Example | structure | characterization |
|---|---|---|
| 617 | 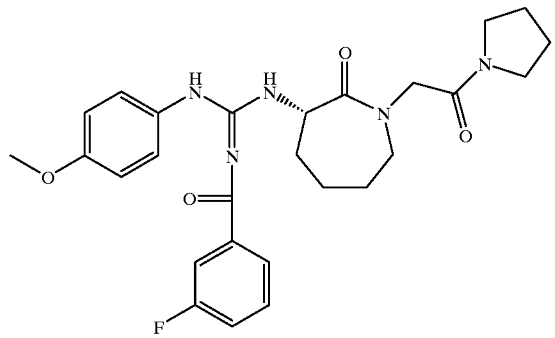 | HPLC (method A) $t_R$ 3.5 min<br>LCMS (ESI) m/z 510 (M + H) |
| 618 | 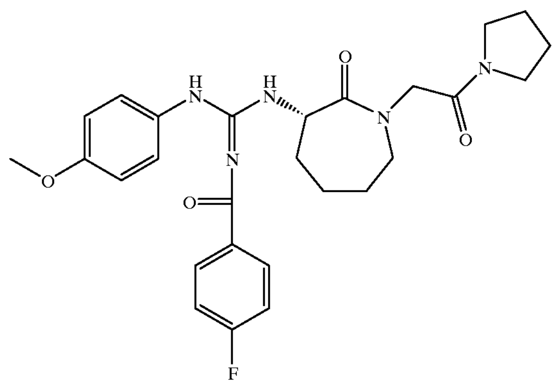 | HPLC (method A) $t_R$ 3.3 min<br>LCMS (ESI) m/z 510 (M + H) |
| 619 | 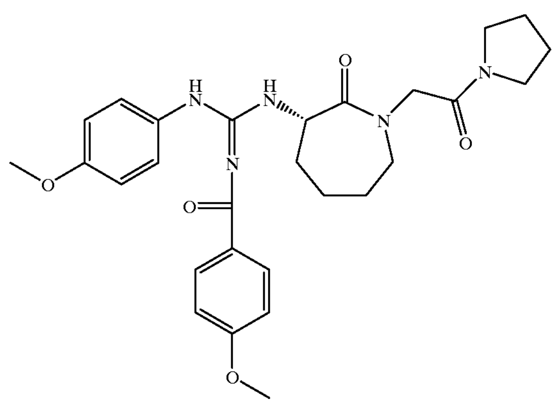 | HPLC (method A) $t_R$ 3.2 min<br>LCMS (ESI) m/z 522 (M + H) |
| 620 | 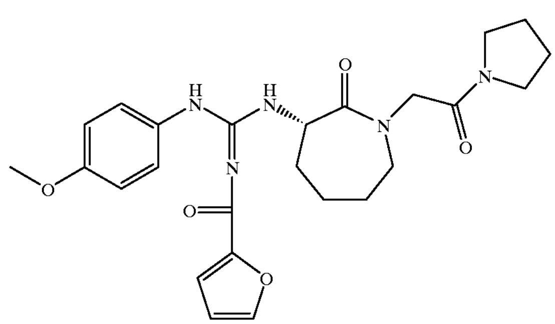 | HPLC (method A) $t_R$ 2.8 min<br>LCMS (ESI) m/z 482 (M + H) |

-continued

| Example | structure | characterization |
|---|---|---|
| 621 | 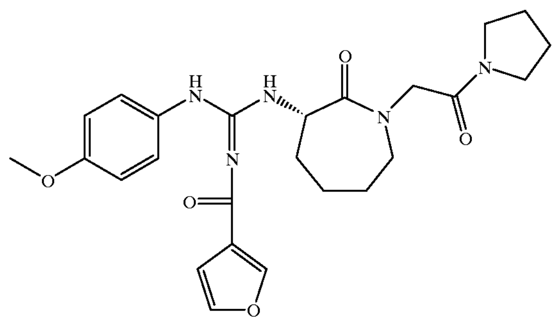 | HPLC (method A)<br>$t_R$ 2.8 min<br>LCMS (ESI) m/z<br>482 (M + H) |
| 622 | 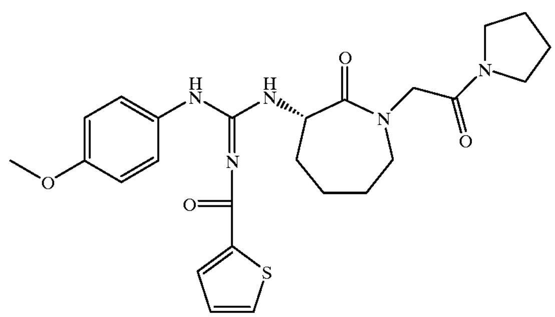 | HPLC (method A)<br>$t_R$ 3.4 min<br>LCMS (ESI) m/z<br>498 (M + H) |
| 623 | 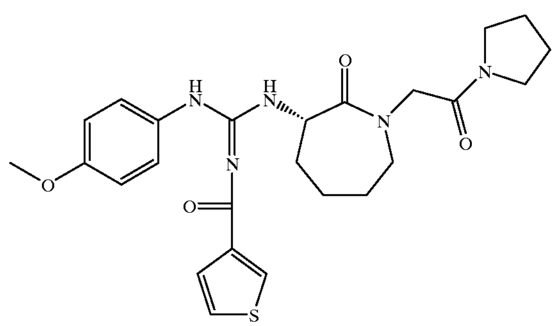 | HPLC (method A)<br>$t_R$ 2.9 min<br>LCMS (ESI) m/z<br>498 (M + H) |
| 624 | 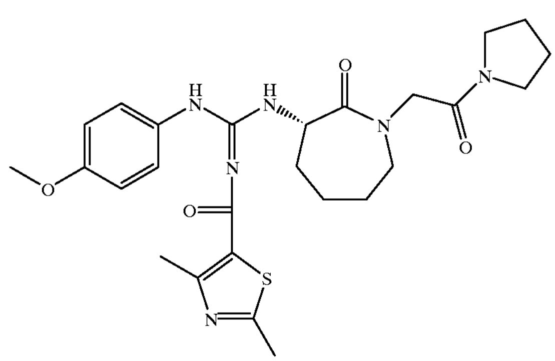 | HPLC (method D)<br>$t_R$ 3.8 min<br>LCMS (ESI) m/z<br>527 (M + H) |

-continued
| Example | structure | characterization |
|---|---|---|
| 625 | 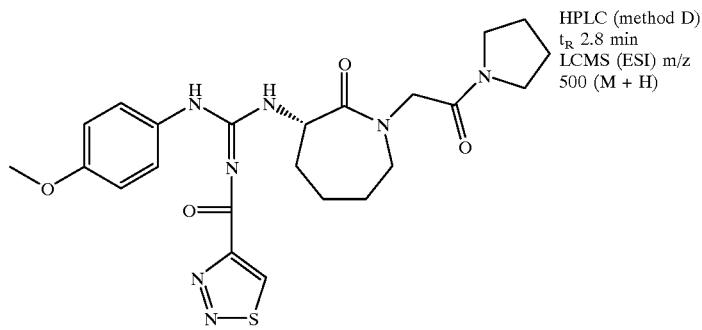 | HPLC (method D)<br>$t_R$ 2.8 min<br>LCMS (ESI) m/z<br>500 (M + H) |
| 626 | 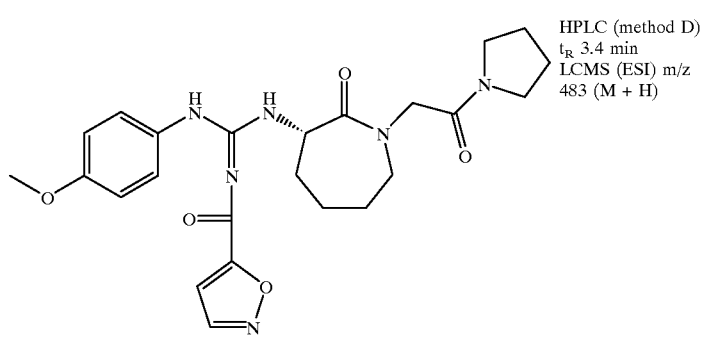 | HPLC (method D)<br>$t_R$ 3.4 min<br>LCMS (ESI) m/z<br>483 (M + H) |
| 627 | 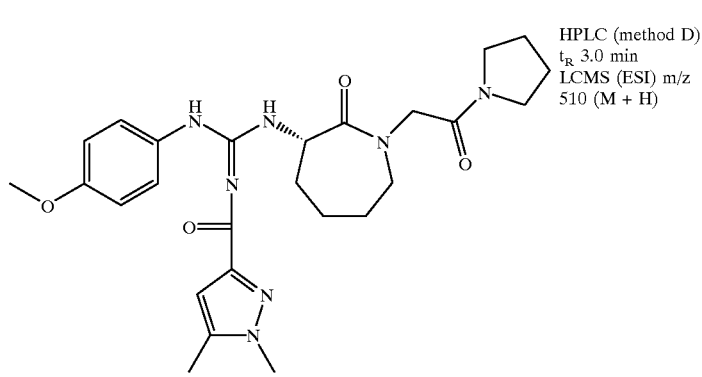 | HPLC (method D)<br>$t_R$ 3.0 min<br>LCMS (ESI) m/z<br>510 (M + H) |
| 628 | 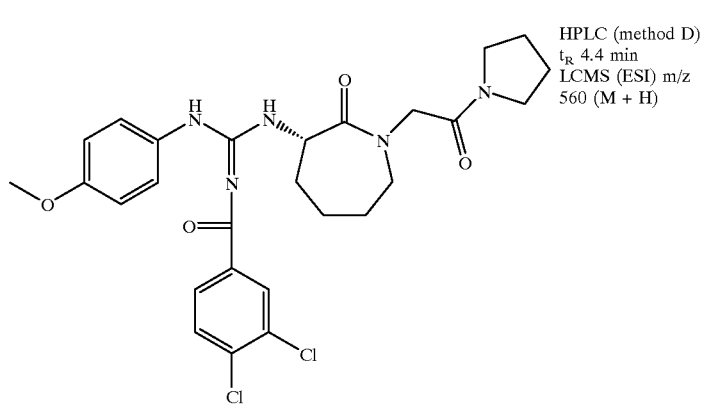 | HPLC (method D)<br>$t_R$ 4.4 min<br>LCMS (ESI) m/z<br>560 (M + H) |

-continued

| Example | structure | characterization |
|---|---|---|
| 629 | 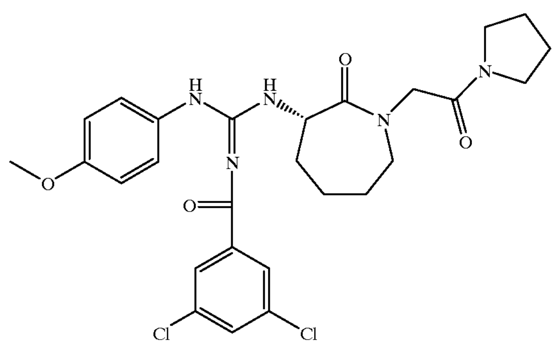 | HPLC (method D) $t_R$ 4.6 min<br>LCMS (ESI) m/z 560 (M + H) |
| 630 | 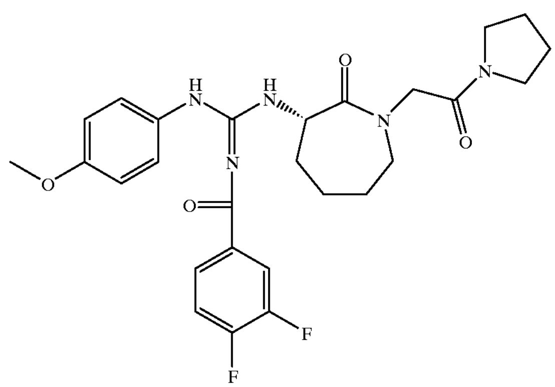 | HPLC (method A) $t_R$ 3.9 min<br>LCMS (ESI) m/z 528 (M + H) |
| 631 | 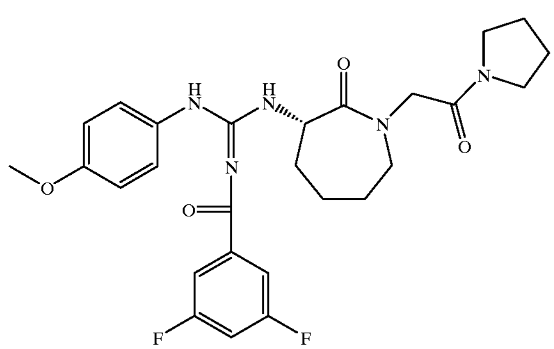 | HPLC (method D) $t_R$ 4.1 min<br>LCMS (ESI) m/z 528 (M + H) |
| 632 | 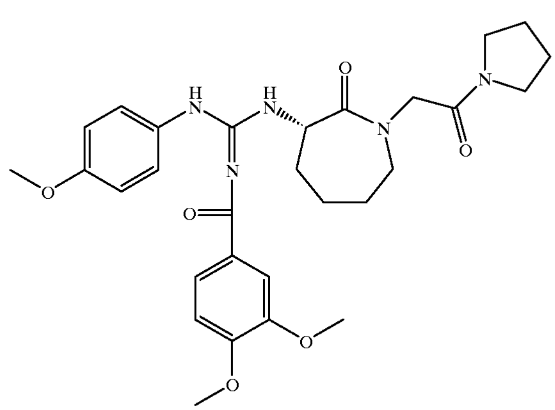 | HPLC (method D) $t_R$ 3.0 min<br>LCMS (ESI) m/z 552 (M + H) |

-continued

| Example | structure | characterization |
|---|---|---|
| 633 | 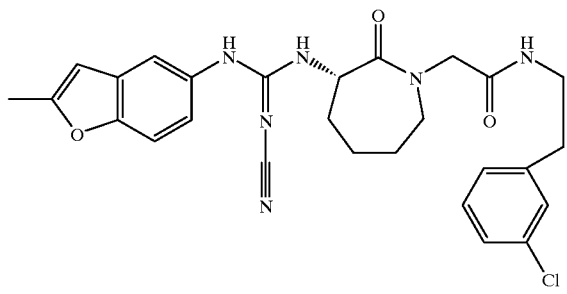 | HPLC (method A) $t_R$ 3.4 min<br>LCMS (ESI) m/z 552 (M + H) |

EXAMPLE 634

To Example 260 part C compound (50 mg, 0.13 mmol) and TFFH (45 mg, 0.17 mmol) in acetonitrile (1.0 mL) under nitrogen was added triethylamine (0.017 mL, 0.13 mol). The resulting solution was stirred for 5 min at which time 3-chlorophenylethanamine (40 mg, 0.26 mmol) was added. Stirring was continued for 2 h. The reaction was added to an SCX cartridge (3 g, prewashed 4×10 mL with acetonitrile). The cartridge was eluted with acetonitrile (10 mL) and then with 50% acetonitrile/methanol (10 mL). Evaporation of product-containing fractions afforded the Title compound (37 mg, 55%): LRMS (ESI) m/z 521 (M+H) ; HPLC (Method A) $t_R$ 4.2 min.

EXAMPLES 635 to 640

Using the procedure described in Example 634 the following compounds were prepared. Some compounds required preparative HPLC purification (YMC Pack ODSA S5, 20×100 mm, 20 mL/min, detection at 220 nm; solvent A=10% MeOH/H$_2$O+0.% TFA, B=90% MeOH/H$_2$O+0.1% TFA; 30% B to 100% B over 10 min and 100% B for 10 min.) after the SCX purification.

| Example | Structure | Characterization |
|---|---|---|
| 635 | 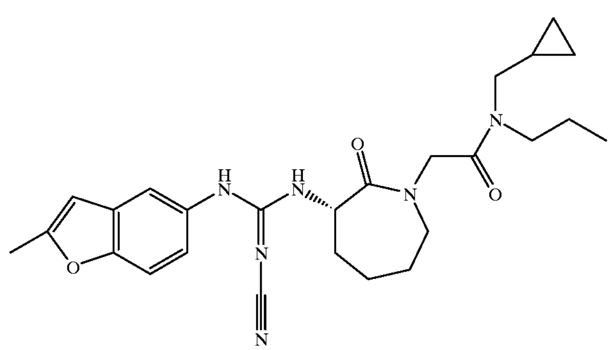 | HPLC (method A) $t_R$ 4.1 min<br>LCMS (ESI) m/z 479 (M + H) |

| Example | Structure | Characterization |
|---------|-----------|------------------|
| 636 | 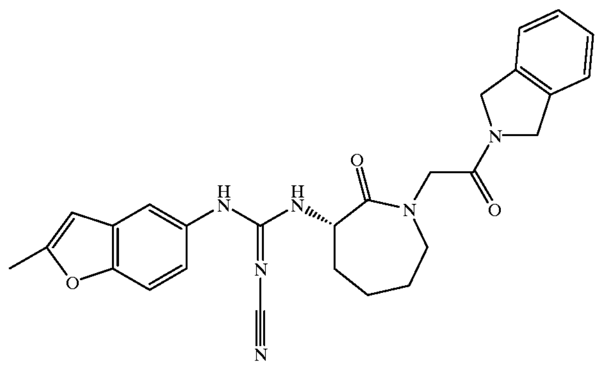 | HPLC (method A)<br>$t_R$ 4.1 min<br>LCMS (ESI) m/z<br>499 (M + H) |
| 637 | 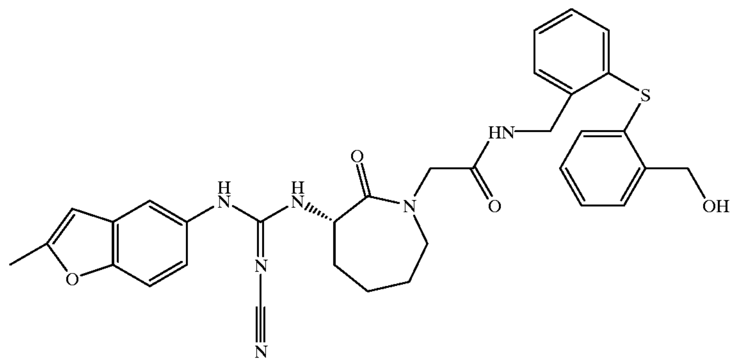 | HPLC (method A)<br>$t_R$ 4.1 min<br>LCMS (ESI) m/z<br>611 (M + H) |
| 638 | 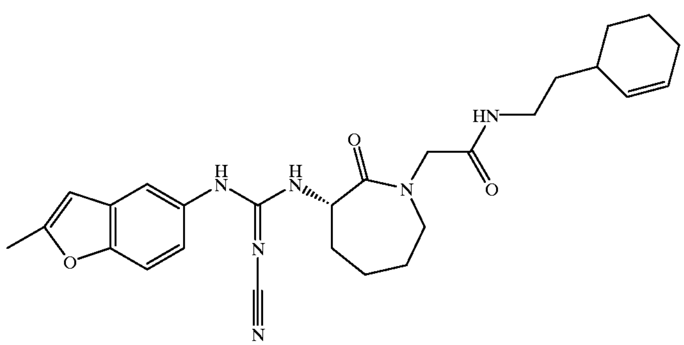 | HPLC (method A)<br>$t_R$ 4.2 min<br>LCMS (ESI) m/z<br>491 (M + H) |
| 639 | 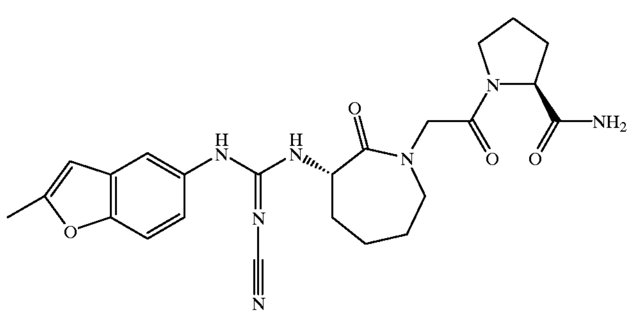 | HPLC (method A)<br>$t_R$ 3.3 min<br>LCMS (ESI) m/z<br>480 (M + H) |

| Example | Structure | Characterization |
|---|---|---|
| 640 | 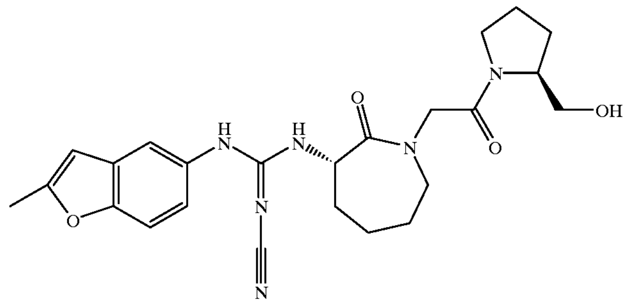 | HPLC (method A)<br>$t_R$ 3.5 min<br>LCMS (ESI) m/z<br>467 (M + H) |

EXAMPLE 641

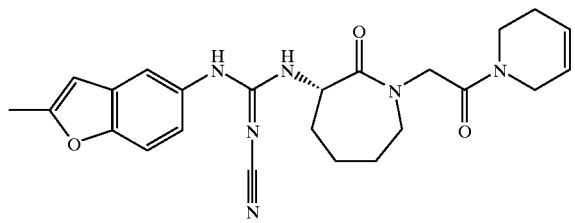

To a solution of Example 260 part C compound (50 mg, 0.13 mmol) and TFFH (45 mg, 0.17 mmol) in acetonitrile (1.0 mL) at 0° C. under nitrogen was added triethylamine (0.017 mL, 0.13 mmol). The resulting solution was stirred for 20 min at 0° C. at which time 1,2,3,6-tetrahydropyridine (21 mg, 0.26 mmol) was added. The reaction was stirred for 2 h. The reaction was added to an SCX cartridge (3 g, prewashed 4×10 mL with acetonitrile). The cartridge was eluted with acetonitrile (10 mL) and then with 50% acetonitrile/methanol (10 mL). Evaporation of product-containing fractions afforded the Title compound (17 mg, 29%): LRMS (ESI) m/z 449 (M+H) ; HPLC (Method D) $t_R$=3.6 min.

EXAMPLES 642–740

Using the procedure described in Example 641 the following compounds were prepared. Some compounds required preparative HPLC purification (YMC Pack ODSA S5, 20×100 mm, 20 mL/min, detection at 220 nm; solvent A=10% MeOH/H$_2$O+0.% TFA, B=90% MeOH/H$_2$O+0.1% TFA; 30% B to 100% B over 10 min and 100% B for 10 min.) after SCX purification

| Example | Structure | Characterization |
|---|---|---|
| 642 | 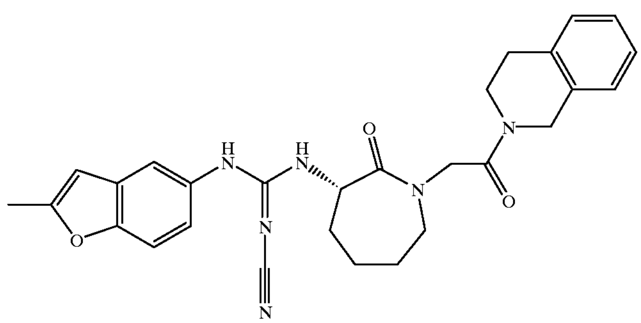 | HPLC (method D)<br>$t_R$ 3.9 min<br>LRMS (ESI)<br>m/z 499 (M+H) |
| 643 | 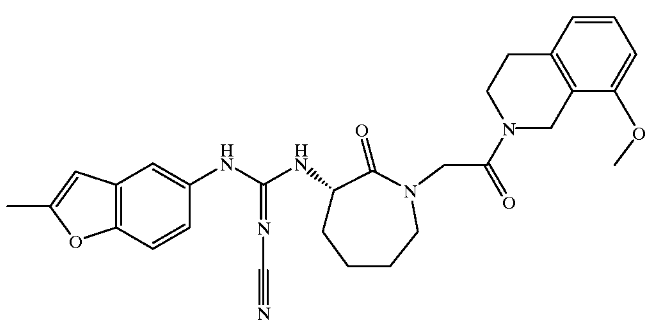 | HPLC (method D)<br>$t_R$ 3.6 min<br>LRMS (ESI)<br>m/z 517 (M+H) |

-continued
| Example | Structure | Characterization |
|---|---|---|
| 644 | 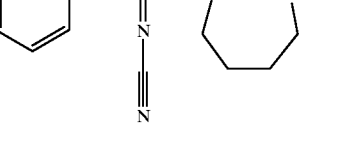 | HPLC (method D)<br>$t_R$ 4.0 min<br>LRMS (ESI)<br>m/z 521 (M+H) |
| 645 | 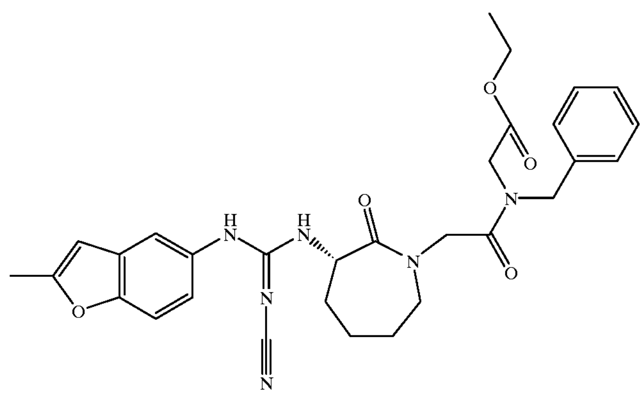 | HPLC (method D)<br>$t_R$ 4.0 min<br>LRMS (ESI)<br>m/z 559 (M+H) |
| 646 | 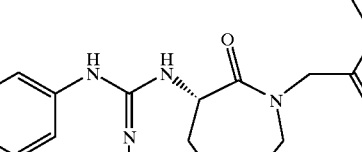 | HPLC (method D)<br>$t_R$ 3.7 min<br>LRMS (ESI)<br>m/z 583 (M+H) |
| 647 | 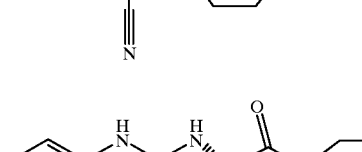 | HPLC (method D)<br>$t_R$ 4.0 min<br>LRMS (ESI)<br>m/z 580 (M+H) |
| 648 | 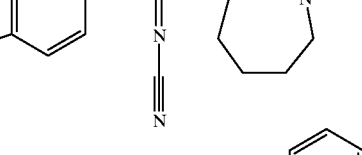 | HPLC (method A)<br>$t_R$ 3.5 min<br>LRMS (ESI)<br>m/z 467 (M+H) |

-continued

| Example | Structure | Characterization |
|---|---|---|
| 649 | 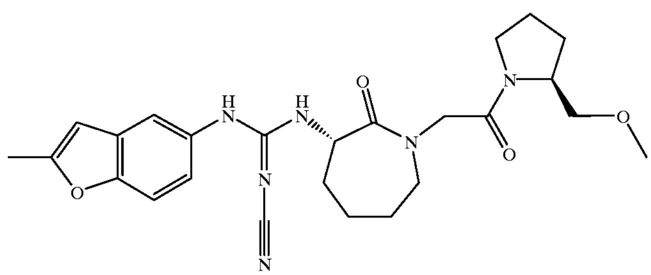 | HPLC (method A)<br>$t_R$ 3.7 min<br>LRMS (ESI)<br>m/z 481 (M+H) |
| 650 | 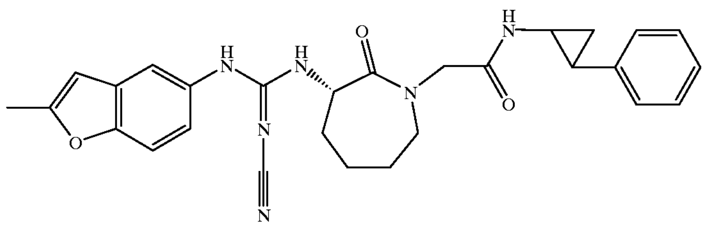 | HPLC (method A)<br>$t_R$ 4.0 min<br>LRMS (ESI)<br>m/z 499 (M+H) |
| 651 | 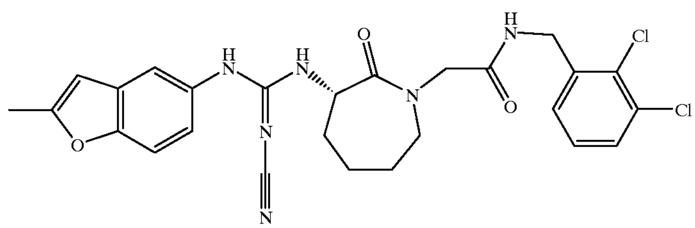 | HPLC (method A)<br>$t_R$ 4.2 min<br>LRMS (ESI)<br>m/z 541 (M+H) |
| 652 | 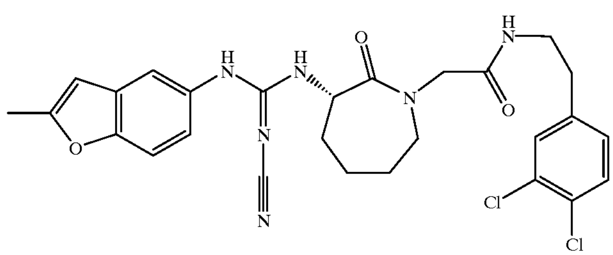 | HPLC (method A)<br>$t_R$ 4.3 min<br>LRMS (ESI)<br>m/z 555 (M+H) |
| 653 | 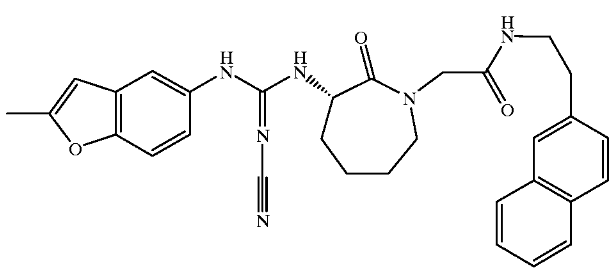 | HPLC (method A)<br>$t_R$ 4.3 min<br>LRMS (ESI)<br>m/z 537 (M+H) |
| 654 | 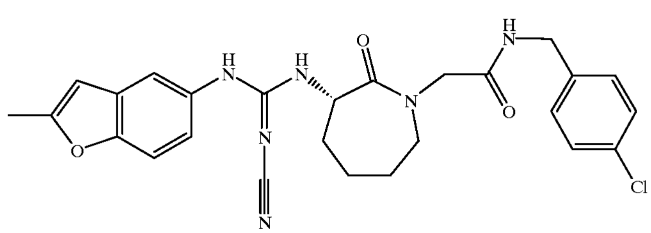 | HPLC (method A)<br>$t_R$ 4.1 min<br>LRMS (ESI)<br>m/z 507 (M+H) |

| Example | Structure | Characterization |
|---|---|---|
| 655 | 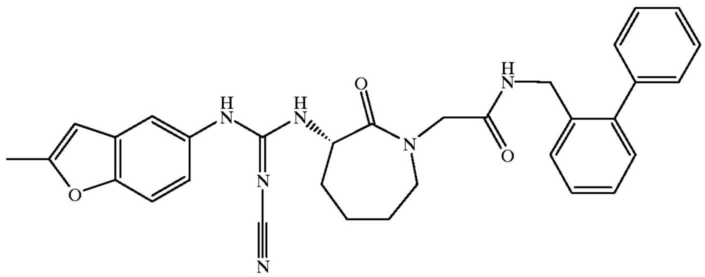 | HPLC (method A) $t_R$ 4.3 min LRMS (ESI) m/z 549 (M+H) |
| 656 | 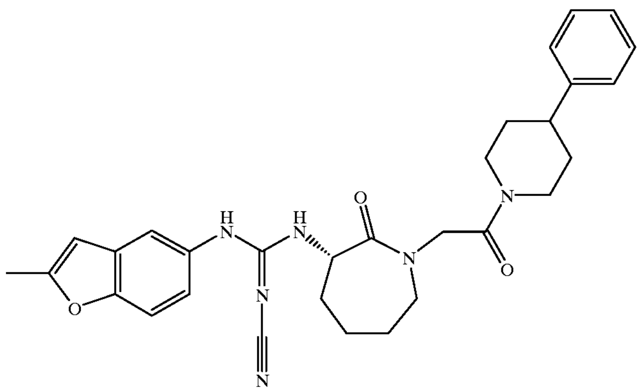 | HPLC (method A) $t_R$ 4.3 min LRMS (ESI) m/z 527 (M+H) |
| 657 | 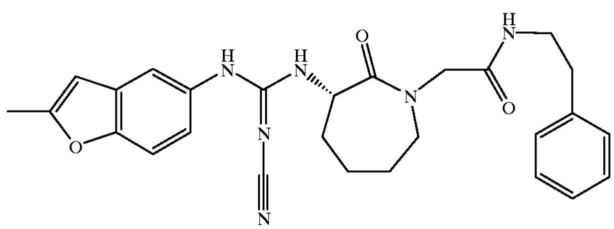 | LC MS (ESI, posion, conditions F) m/z 487 (M+H), $t_R$ 3.6 min |
| 658 | 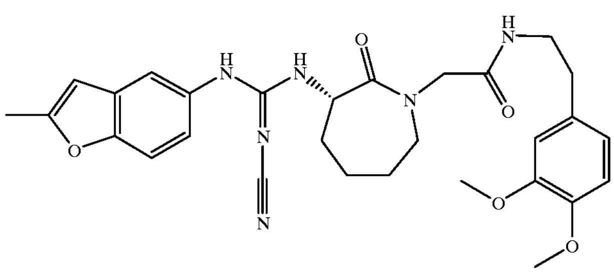 | LC MS (ESI, posion, conditions F) m/z 547 (M+H), $t_R$ 3.4 min |
| 659 | 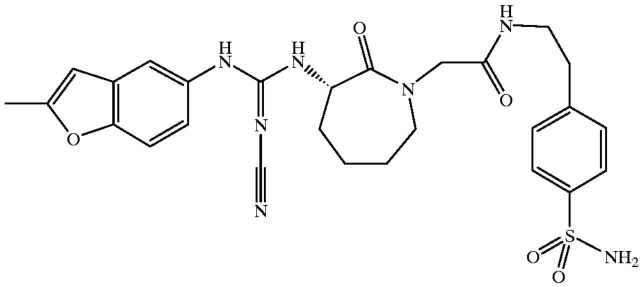 | LC MS (ESI, posion, conditions F) m/z 566 (M+H), $t_R$ 3.0 min |

| Example | Structure | Characterization |
|---|---|---|
| 660 | 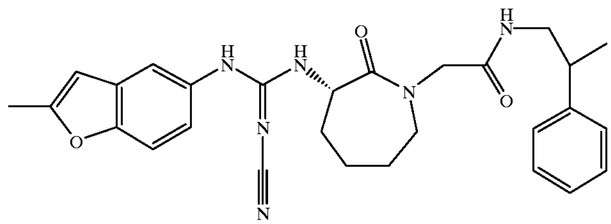 | LC MS (ESI, posion, conditions F) m/z 501 (M+H), $t_R$ 3.6 min |
| 661 | 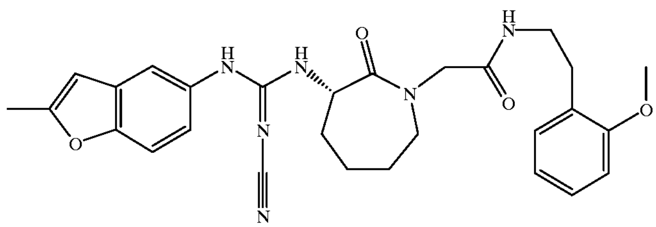 | LC MS (ESI, posion, conditions F) m/z 503 (M+H), $t_R$ 3.2 min |
| 662 | 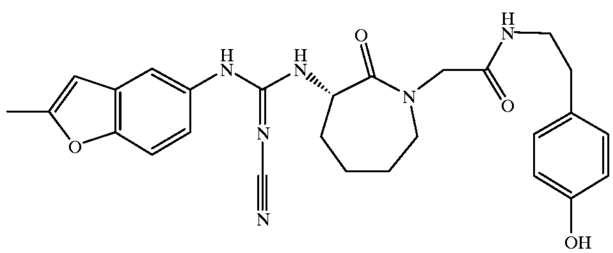 | LC MS (ESI, posion, conditions F) m/z 501 (M+H), $t_R$ 3.7 min |
| 663 | 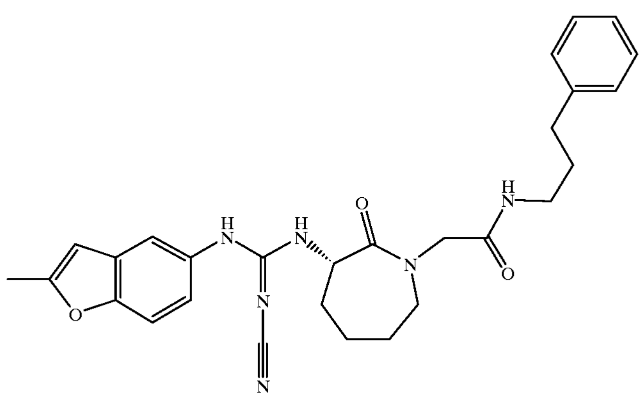 | LC MS (ESI, posion, conditions F) m/z 501 (M+H), $t_R$ 3.7 min |
| 664 | 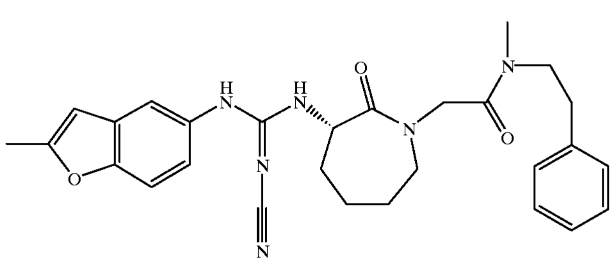 | LC MS (ESI, posion, conditions F) m/z 501 (M+H), $t_R$ 3.7 min |

-continued

| Example | Structure | Characterization |
|---|---|---|
| 665 | 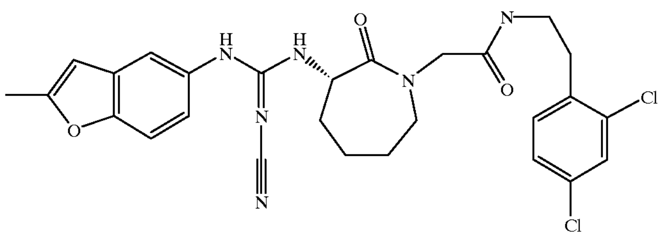 | LC MS (ESI, posion, conditions F) m/z 555 (M+H), $t_R$ 4.0 min |
| 666 | 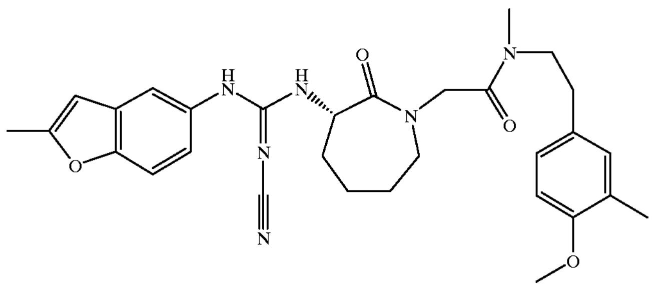 | LC MS (ESI, posion, conditions F) m/z 561 (M+H), $t_R$ 3.5 min |
| 667 | 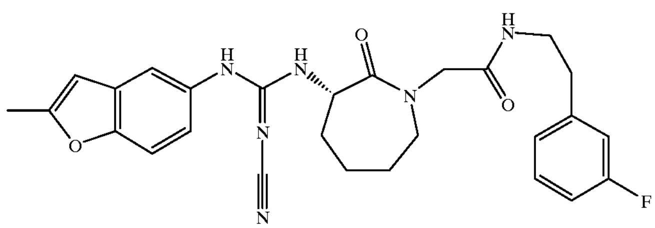 | LC MS (ESI, posion, conditions F) m/z 505 (M+H), $t_R$ 3.6 min |
| 668 | 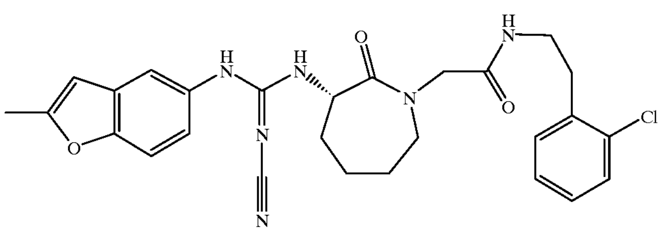 | LC MS (ESI, posion, conditions F) m/z 521 (M+H), $t_R$ 3.7 min |
| 669 | 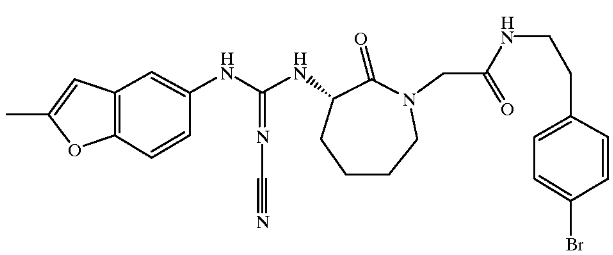 | LC MS (ESI, posion, conditions F) m/z 565 (M+H), $t_R$ 3.8 min |
| 670 | 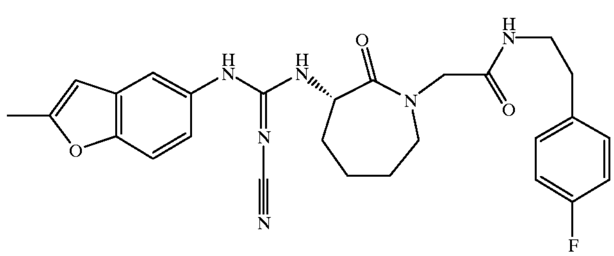 | LC MS (ESI, posion, conditions F) m/z 505 (M+H), $t_R$ 3.6 min |

| Example | Structure | Characterization |
|---------|-----------|------------------|
| 671 | 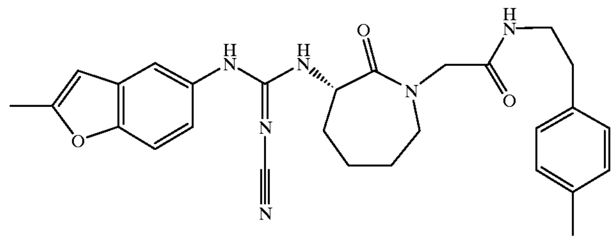 | LC MS (ESI, posion, conditions F) m/z 501 (M+H), $t_R$ 3.7 min |
| 672 | 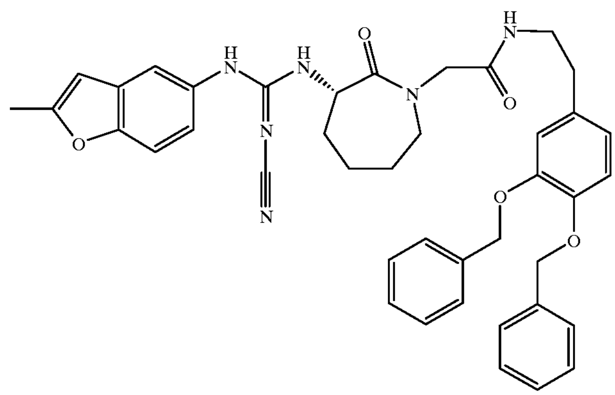 | LC MS (ESI, posion, conditions F) m/z 699 (M+H), $t_R$ 4.2 min |
| 673 | 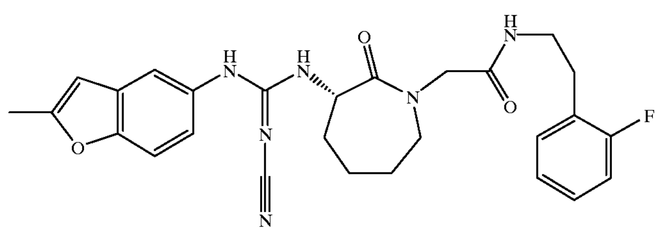 | LC MS (ESI, posion, conditions F) m/z 505 (M+H), $t_R$ 3.5 min |
| 674 | 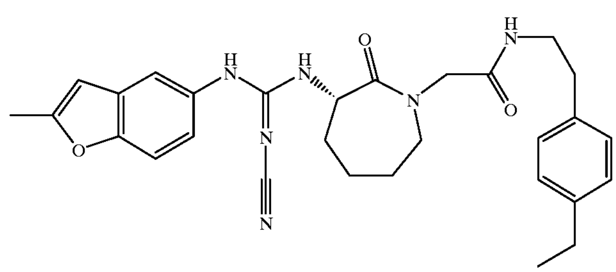 | LC MS (ESI, posion, conditions F) m/z 515 (M+H), $t_R$ 3.9 min |
| 675 | 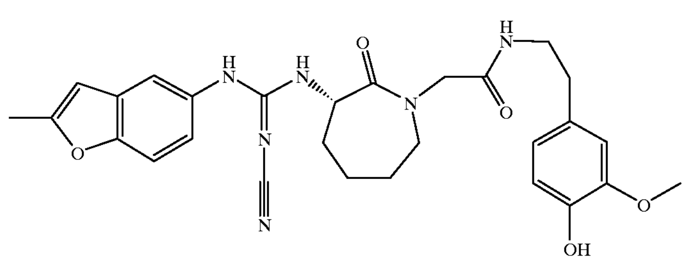 | LC MS (ESI, posion, conditions F) m/z 533 (M+H), $t_R$ 3.2 min |

-continued
| Example | Structure | Characterization |
|---|---|---|
| 676 | 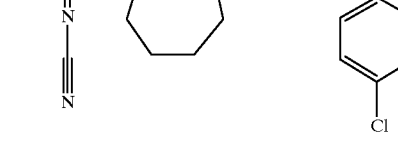 | LC MS (ESI, posion, conditions F) m/z 535 (M+H), t$_R$ 3.8 min |
| 677 | 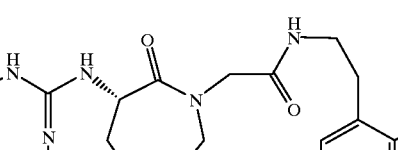 | LC MS (ESI, posion, conditions F) m/z 547 (M+H), t$_R$ 3.6 min |
| 678 | 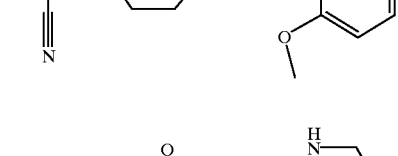 | LC MS (ESI, posion, conditions F) m/z 531 (M+H), t$_R$ 3.6 min |
| 679 | 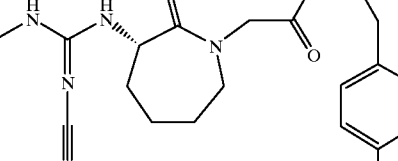 | LC MS (ESI, posion, conditions F) m/z 533 (M+H), t$_R$ 3.7 min |
| 680 | 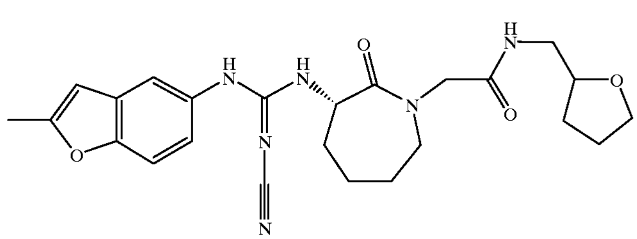 | LC MS (ESI, posion, conditions F) m/z 467 (M+H), t$_R$ 3.1 min |

-continued

| Example | Structure | Characterization |
|---|---|---|
| 681 | 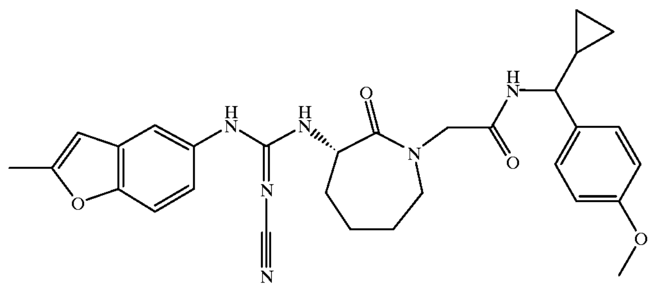 | LC MS (ESI, posion, conditions F) m/z 543 (M+H), $t_R$ 3.6 min |
| 682 | 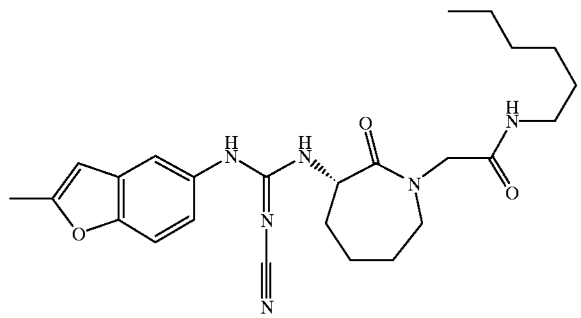 | LC MS (ESI, posion, conditions F) m/z 467 (M+H), $t_R$ 3.7 min |
| 683 | 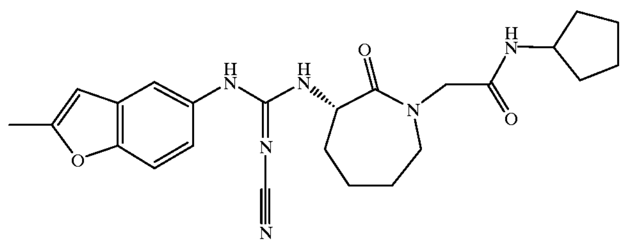 | LC MS (ESI, posion, conditions F) m/z 451 (M+H), $t_R$ 3.4 min |
| 684 | 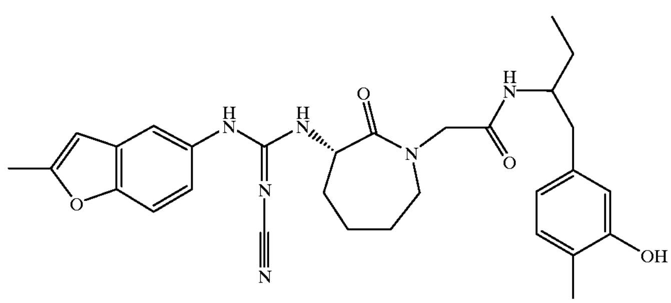 | LC MS (ESI, posion, conditions F) m/z 545 (M+H), $t_R$ 3.6 min |
| 685 | 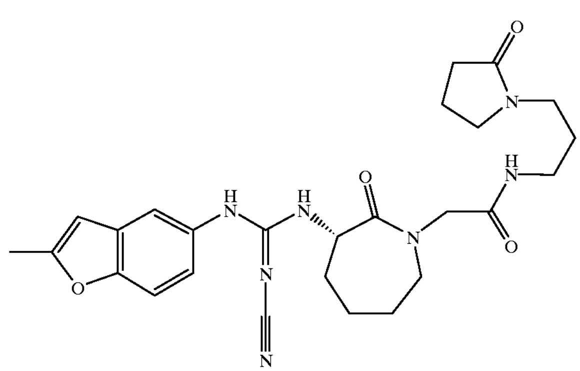 | LC MS (ESI, posion, conditions F) m/z 508 (M+H), $t_R$ 3.0 min |

-continued
| Example | Structure | Characterization |
|---|---|---|
| 686 | 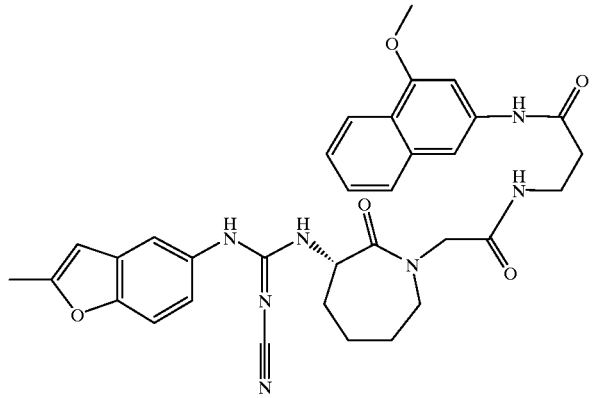 | LC MS (ESI, posion, conditions F) m/z 610 (M+H), $t_R$ 3.8 min |
| 687 | 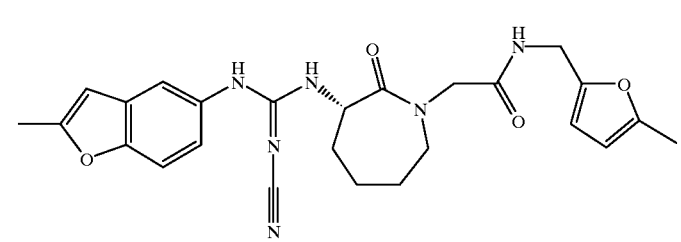 | LC MS (ESI, posion, conditions F) m/z 477 (M+H), $t_R$ 3.4 min |
| 688 | 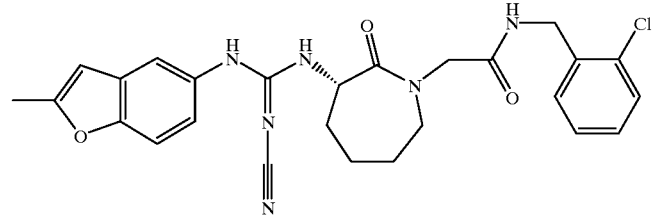 | LC MS (ESI, posion, conditions F) m/z 507 (M+H), $t_R$ 3.6 min |
| 689 | 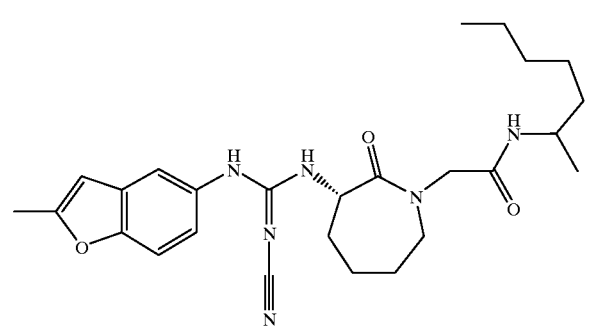 | LC MS (ESI, posion, conditions F) m/z 481 (M+H), $t_R$ 3.8 min |
| 690 | 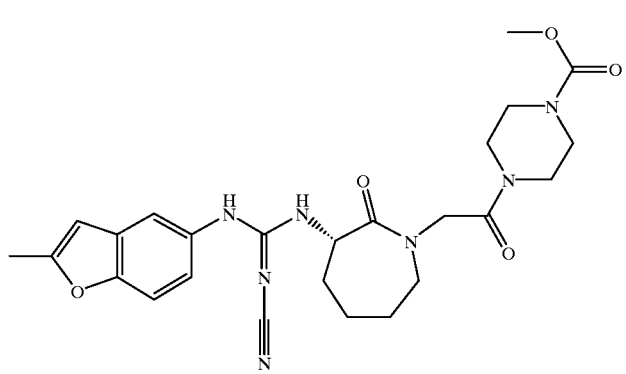 | LC MS (ESI, posion, conditions F) m/z 524 (M+H), $t_R$ 3.3 min |

-continued

| Example | Structure | Characterization |
|---------|-----------|------------------|
| 691 | 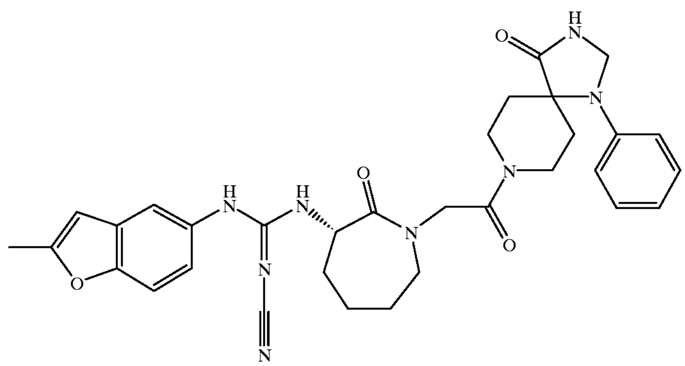 | LC MS (ESI, posion, conditions F) m/z 597 (M+H), $t_R$ 3.6 min |
| 692 | 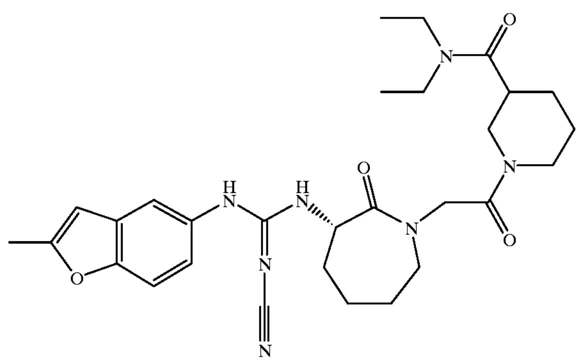 | LC MS (ESI, posion, conditions F) m/z 550 (M+H), $t_R$ 3.4 min |
| 693 | 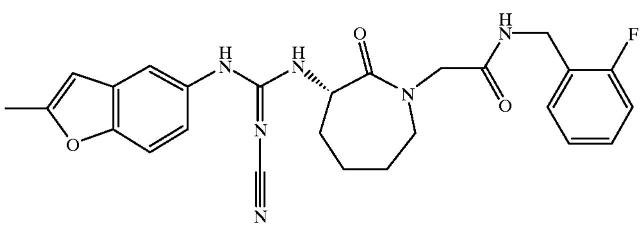 | LC MS (ESI, posion, conditions F) m/z 491 (M+H), $t_R$ 3.4 min |
| 694 | 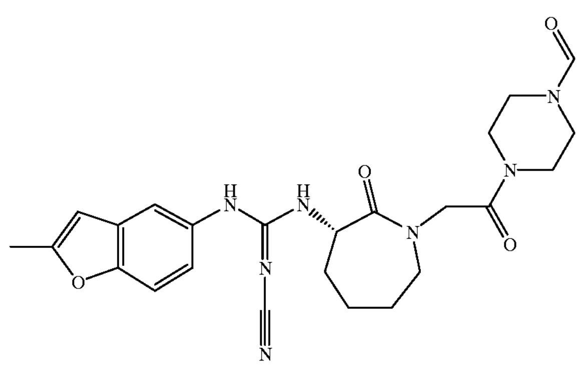 | LC MS (ESI, posion, conditions F) m/z 480 (M+H), $t_R$ 2.9 min |

-continued

| Example | Structure | Characterization |
|---|---|---|
| 695 | 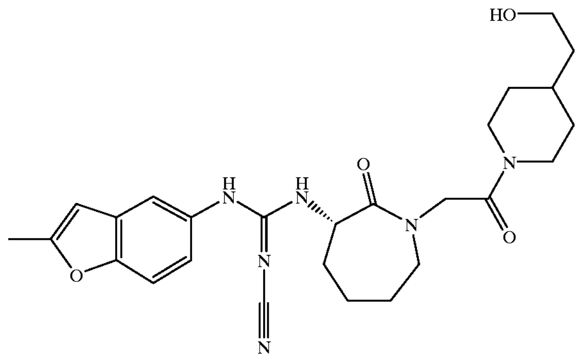 | LC MS (ESI, posion, conditions F) m/z 495 (M+H), t_R 3.2 min |
| 696 | 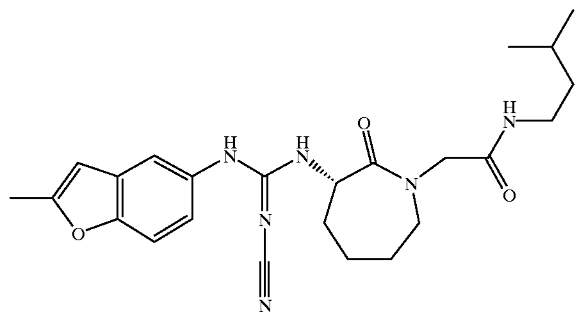 | LC MS (ESI, posion, conditions F) m/z 453 (M+H), t_R 3.5 min |
| 697 | 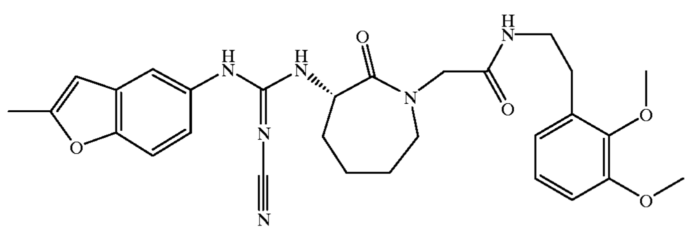 | HPLC (method A) t_R 4.0 min LRMS (ESI) m/z 547 (M+H) |
| 698 | 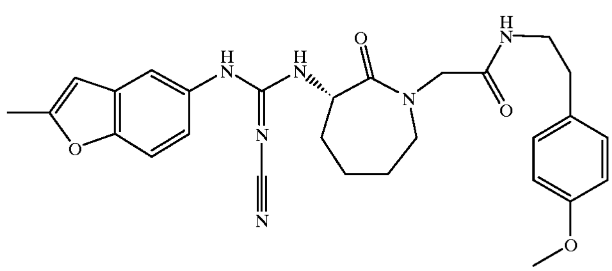 | HPLC (method A) t_R 4.0 min LRMS (ESI) m/z 517 (M+H) |
| 699 | 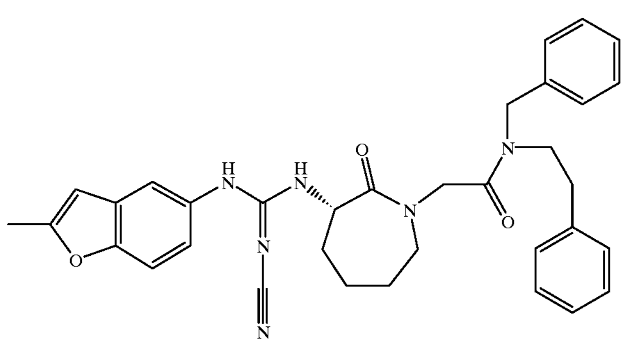 | HPLC (method A) t_R 4.5 min LRMS (ESI) m/z 577 (M+H) |

-continued

| Example | Structure | Characterization |
|---|---|---|
| 700 | 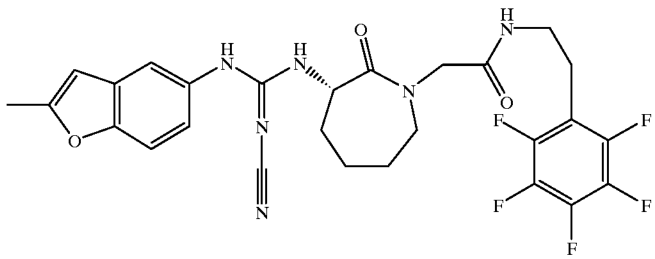 | HPLC (method D)<br>$t_R$ 3.8 min<br>LRMS (ESI)<br>m/z 577 (M+H) |
| 701 | 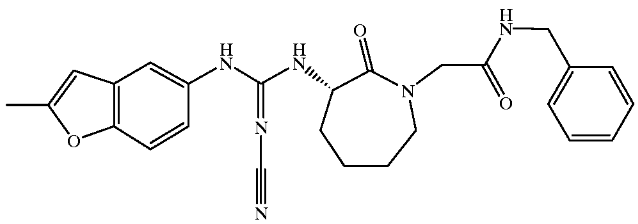 | HPLC (method D)<br>$t_R$ 3.4 min<br>LRMS (ESI)<br>m/z 473 (M+H) |
| 702 | 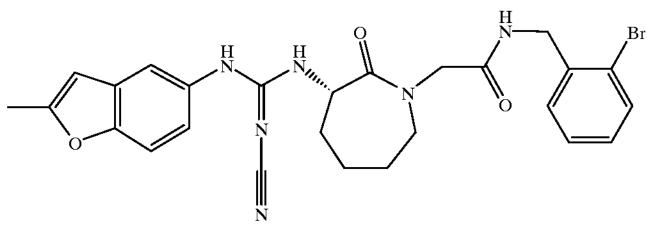 | HPLC (method D)<br>$t_R$ 3.7 min<br>LRMS (ESI)<br>m/z 551 (M+H) |
| 703 | 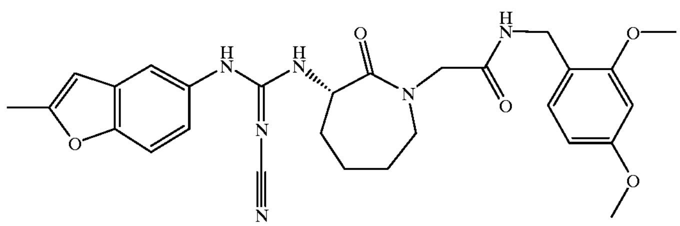 | HPLC (method D)<br>$t_R$ 3.6 min<br>LRMS (ESI)<br>m/z 533 (M+H) |
| 704 | 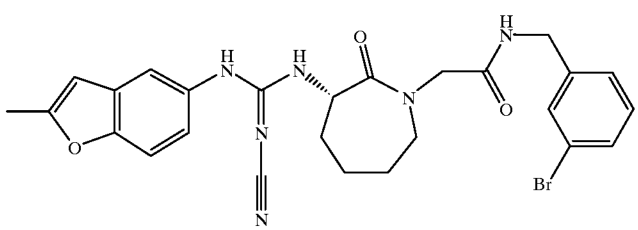 | HPLC (method D)<br>$t_R$ 3.7 min<br>LRMS (ESI)<br>m/z 551 (M+H) |
| 705 | 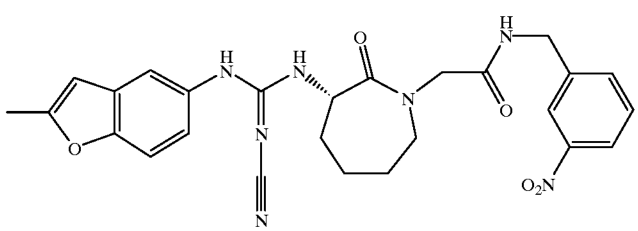 | HPLC (method D)<br>$t_R$ 3.0 min<br>LRMS (ESI)<br>m/z 518 (M+H) |

-continued

| Example | Structure | Characterization |
|---------|-----------|------------------|
| 706 | 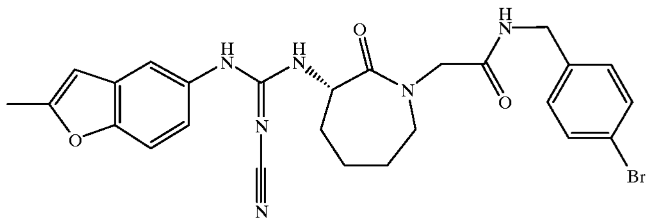 | HPLC (method D)<br>t_R 3.8 min<br>LRMS (ESI)<br>m/z 551 (M+H) |
| 707 | 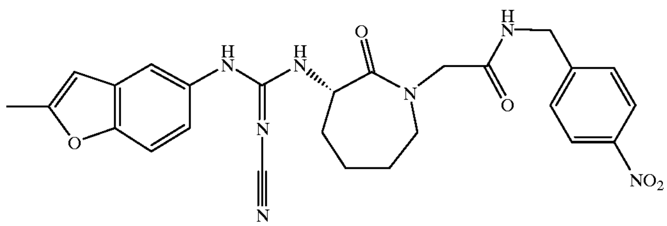 | HPLC (method D)<br>t_R 3.0 min<br>LRMS (ESI)<br>m/z 518 (M+H) |
| 708 | 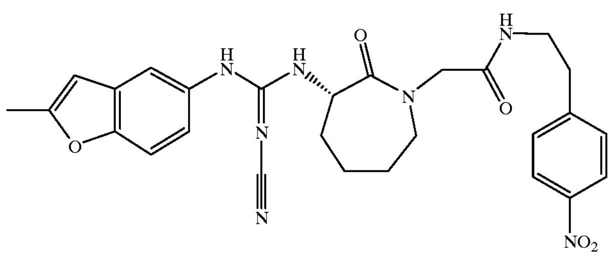 | HPLC (method D)<br>t_R 3.1 min<br>LRMS (ESI)<br>m/z 532 (M+H) |
| 709 | 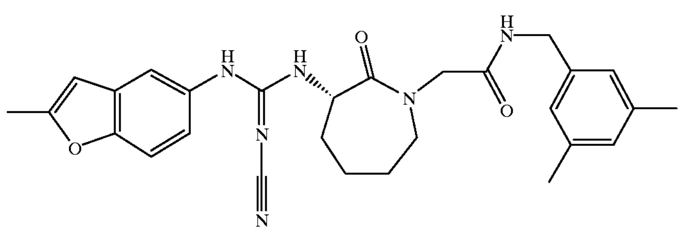 | HPLC (method D)<br>t_R 3.8 min<br>LRMS (ESI)<br>m/z 501 (M+H) |
| 710 | 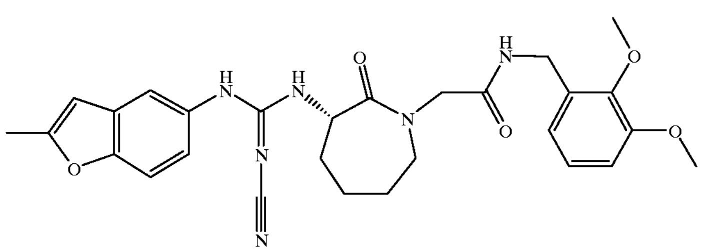 | HPLC (method D)<br>t_R 3.4 min<br>LRMS (ESI)<br>m/z 533 (M+H) |
| 711 | 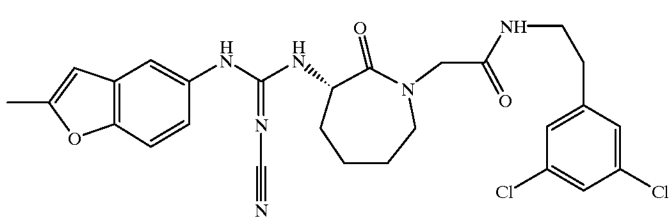 | HPLC (method D)<br>t_R 3.9 min<br>LRMS (ESI)<br>m/z 541 (M+H) |

| Example | Structure | Characterization |
|---|---|---|
| 712 | 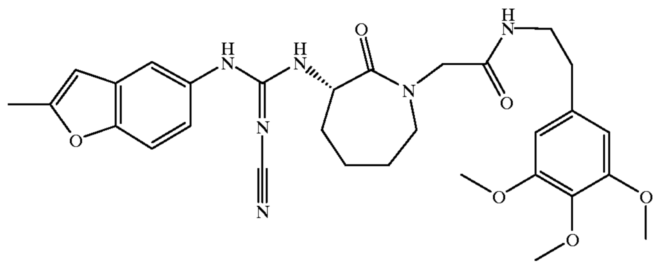 | HPLC (method D)<br>$t_R$ 3.5 min<br>LRMS (ESI)<br>m/z 591 (M+H) |
| 713 | 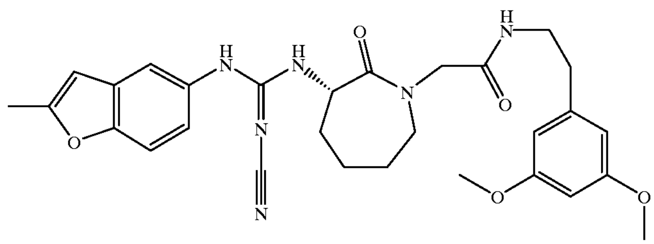 | HPLC (method D)<br>$t_R$ 3.6 min<br>LRMS (ESI)<br>m/z 547 (M+H) |
| 714 | 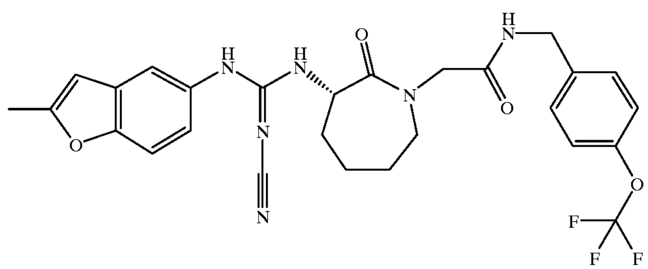 | HPLC (method D)<br>$t_R$ 3.8 min<br>LRMS (ESI)<br>m/z 557 (M+H) |
| 715 | 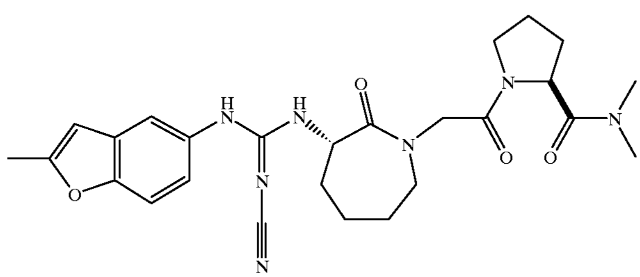 | HPLC (method D)<br>$t_R$ 3.2 min<br>LRMS (ESI)<br>m/z 508 (M+H) |
| 716 | 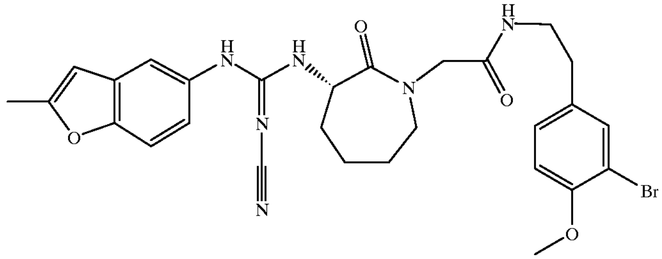 | HPLC (method D)<br>$t_R$ 3.7 min<br>LRMS (ESI)<br>m/z 595 (M+H) |

-continued

| Example | Structure | Characterization |
|---|---|---|
| 717 | 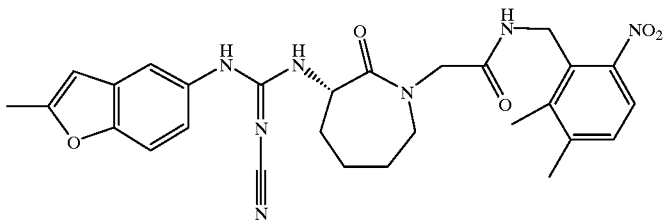 | HPLC (method D)<br>$t_R$ 3.7 min<br>LRMS (ESI)<br>m/z 546 (M+H) |
| 718 | 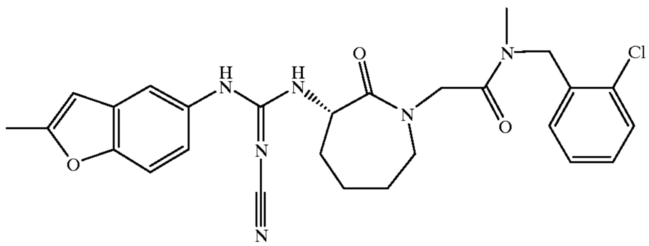 | HPLC (method D)<br>$t_R$ 3.8 min<br>LRMS (ESI)<br>m/z 521 (M+H) |
| 719 | 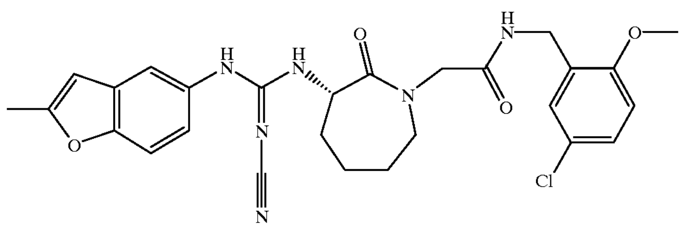 | HPLC (method D)<br>$t_R$ 3.7 min<br>LRMS (ESI)<br>m/z 537 (M+H) |
| 720 | 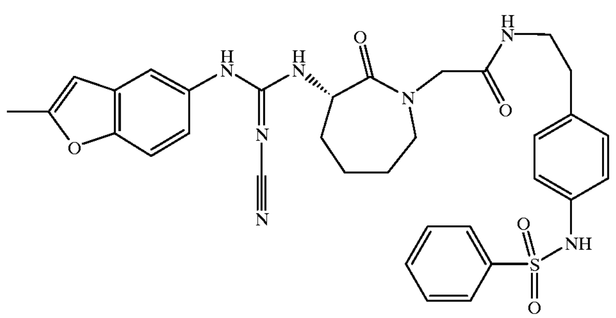 | HPLC (method D)<br>$t_R$ 3.5 min<br>LRMS (ESI)<br>m/z 642 (M+H) |
| 721 | 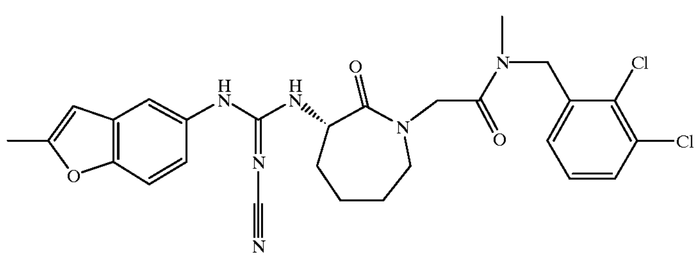 | HPLC (method D)<br>$t_R$ 4.0 min<br>LRMS (ESI)<br>m/z 555 (M+H) |
| 722 | 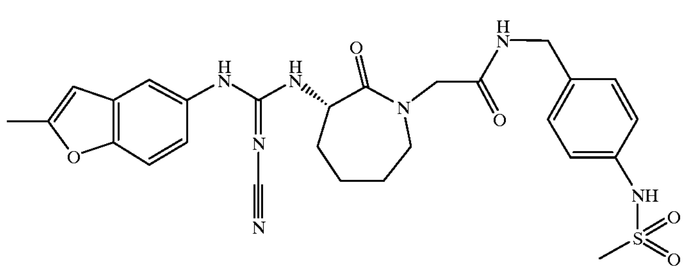 | HPLC (method D)<br>$t_R$ 3.1 min<br>LRMS (ESI)<br>m/z 566 (M+H) |

-continued

| Example | Structure | Characterization |
|---|---|---|
| 723 | 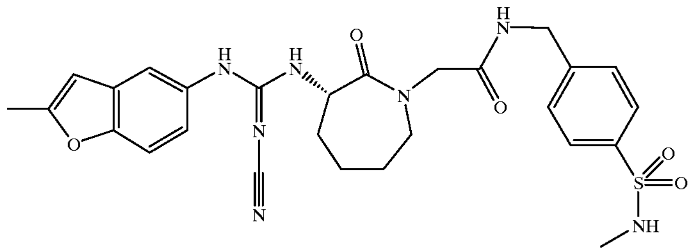 | HPLC (method D) t_R 3.1 min LRMS (ESI) m/z 566 (M+H) |
| 724 | 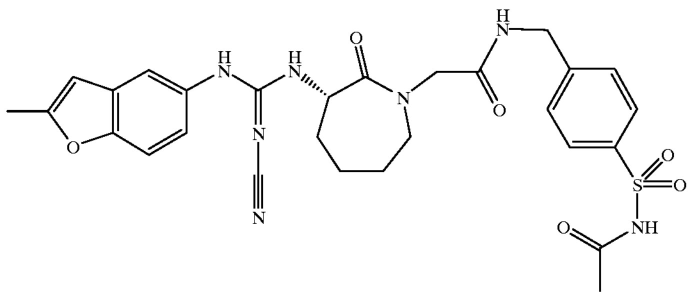 | HPLC (method D) t_R 3.1 min LRMS (ESI) m/z 594 (M+H) |
| 725 | 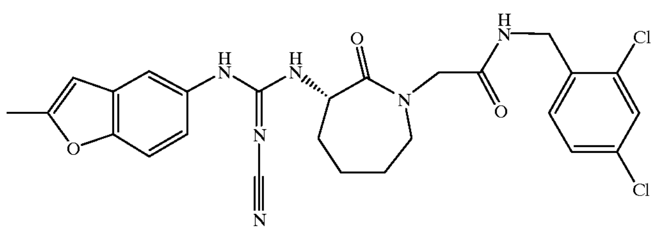 | LC MS (ESI, posion, conditions F) m/z 541 (M+H), t_R 3.8 min |
| 726 | 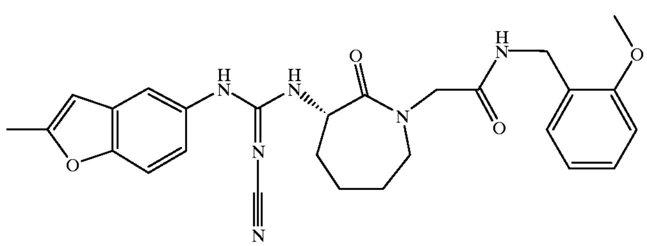 | LC MS (ESI, posion, conditions F) m/z 503 (M+H), t_R 3.5 min |
| 727 | 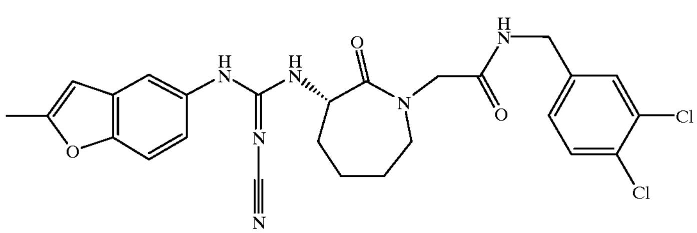 | LC MS (ESI, posion, conditions F) m/z 541 (M+H), t_R 3.8 min |
| 728 | 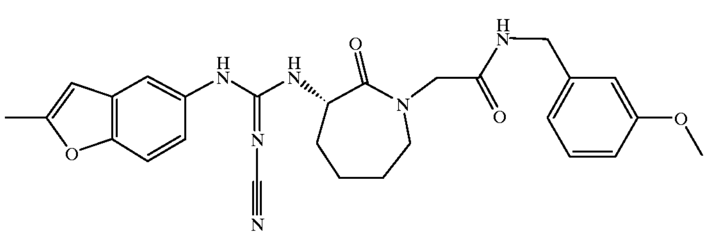 | LC MS (ESI, posion, conditions F) m/z 503 (M+H), t_R 3.4 min |

| Example | Structure | Characterization |
|---|---|---|
| 729 | 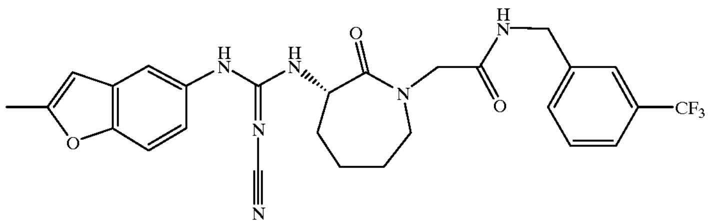 | LC MS (ESI, posion, conditions F) m/z 541 (M+H), $t_R$ 3.7 min |
| 730 | 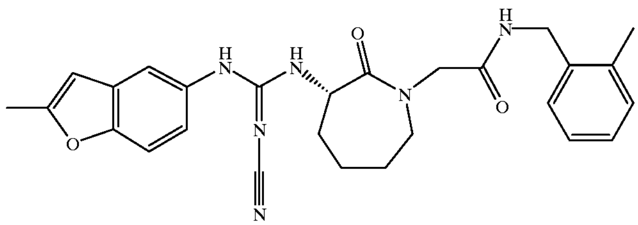 | LC MS (ESI, posion, conditions F) m/z 487 (M+H), $t_R$ 3.5 min |
| 731 | 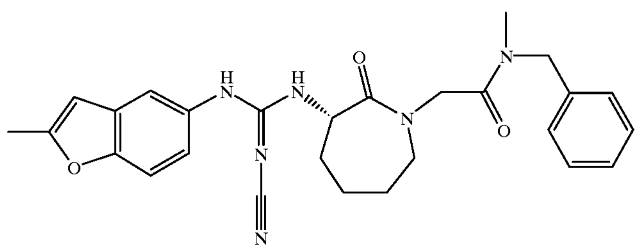 | LC MS (ESI, posion, conditions F) m/z 487 (M+H), $t_R$ 3.6 min |
| 732 | 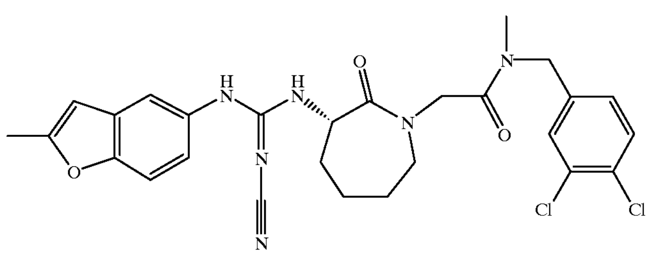 | LC MS (ESI, posion, conditions F) m/z 555 (M+H), $t_R$ 3.9 min |
| 733 | 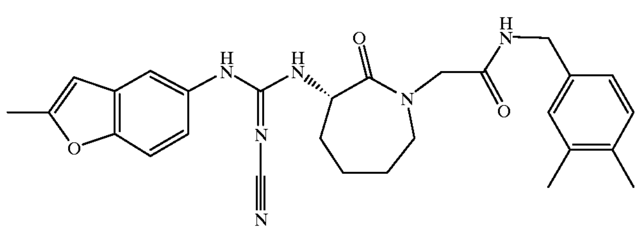 | LC MS (ESI, posion, conditions F) m/z 501 (M+H), $t_R$ 3.7 min |
| 734 | 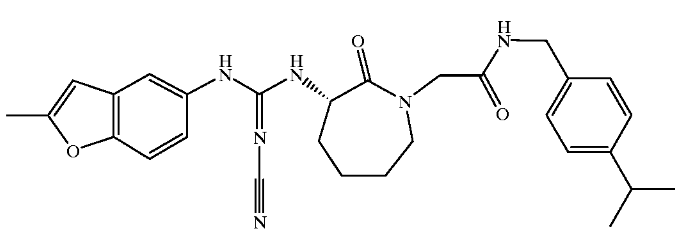 | LC MS (ESI, posion, conditions F) m/z 515 (M+H), $t_R$ 3.9 min |

| Example | Structure | Characterization |
|---|---|---|
| 735 | 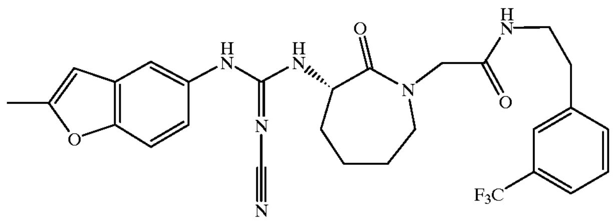 | LC MS (ESI, posion, conditions F) m/z 555 (M+H), $t_R$ 3.8 min |
| 736 | 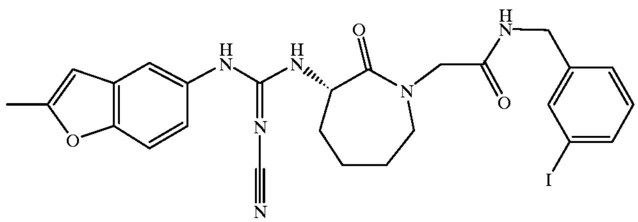 | LC MS (ESI, posion, conditions F) m/z 599 (M+H), $t_R$ 3.7 min |
| 737 | 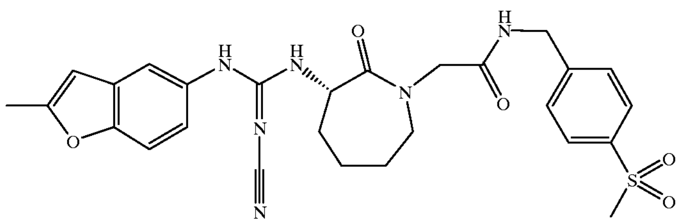 | LC MS (ESI, posion, conditions F) m/z 551 (M+H), $t_R$ 3.1 min |
| 738 | 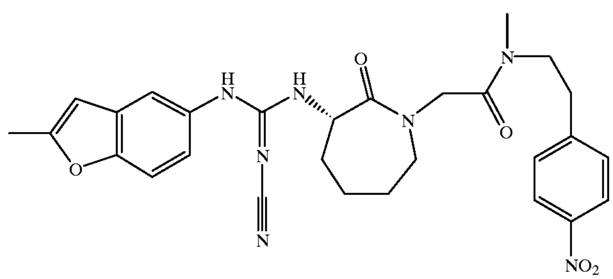 | LC MS (ESI, posion, conditions F) m/z 546 (M+H), $t_R$ 3.6 min |
| 739 | 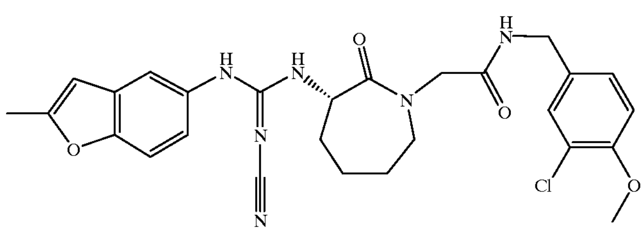 | LC MS (ESI, posion, conditions F) m/z 537 (M+H), $t_R$ 3.5 min |
| 740 | 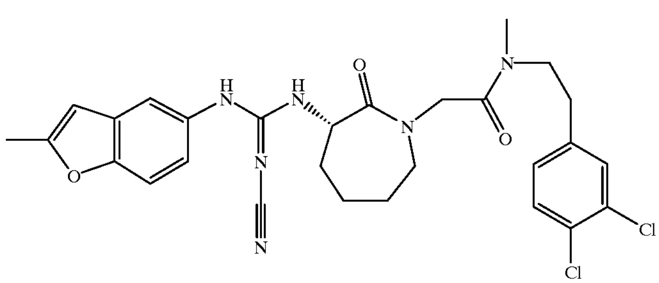 | LC MS (ESI, posion, conditions F) m/z 569 (M+H), $t_R$ 4.0 min |

EXAMPLE 741

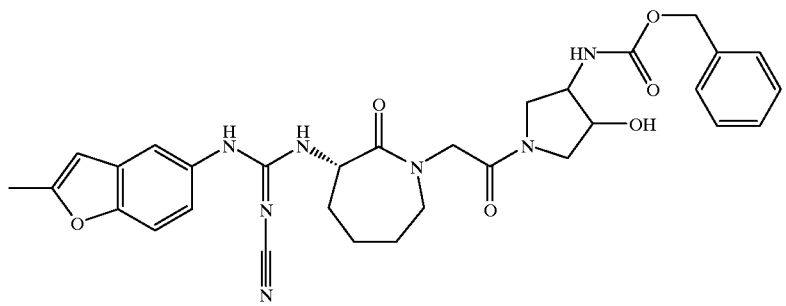

A.

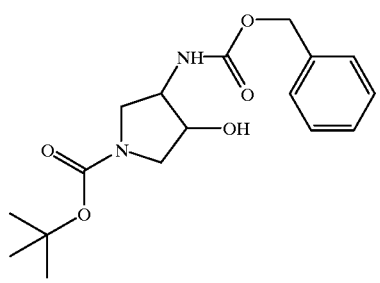

Benzylchloroformate (2.6 mL, 18 mmol) was added to a solution of t-butyl 3-amino-4-hydroxy-1-pyrrolidinecarboxylate (3.0 g, 15 mmol) and pyridine (1.4 mL, 18 mmol) in chloroform (30 mL) stirring at 0° C. After stirring at 0° C. for 1 h, the reaction was transferred to a separatory funnel with dichloromethane and water. Washing the organic layer with water (2x) and drying over $MgSO_4$, afforded 6.1 g of crude product after evaporation of the solvent. Flash chromatography (silica, 50 mm dia column, 40% ethyl acetate/hexane (2 L) and ethyl acetate (1 L)) afforded part A compound (3.45 g, 58%): $^1$H-NMR ($CDCl_3\delta$) 7.34 (m, 5 H), 5.21 (m, 1 H), 5.06 (s, 2 H), 4.21 (m, 1 H), 3.95 (m, 1 H), 3.74 (m, 1 H), 3.62 (m, 1 H), 3.23 (m, 2 H), 1.44 (s, 9 H).

Trifluoroacetic acid (1.8 mL, 24 mmol) was added to a stirring solution of part A compound (0.80 g, 2.4 mmol). After stirring at ambient temperature for 3 h, the reaction was evaporated in vacuo. The residue was co-evaporated twice with dichloromethane, and then with methanol and dichloromethane again. A methanol solution of this residue was then added to BIORAD resin (AG-W50x2, hydrogen form, 18 g, prewashed with 40 mL each of methanol, water, and 50% methanol/water). After washing the column with methanol (40 mL), the column was eluted with 2N ammonia in methanol to afford part B compound (0.46 g, 82%): LRMS (ESI) m/z 237 (M+H).

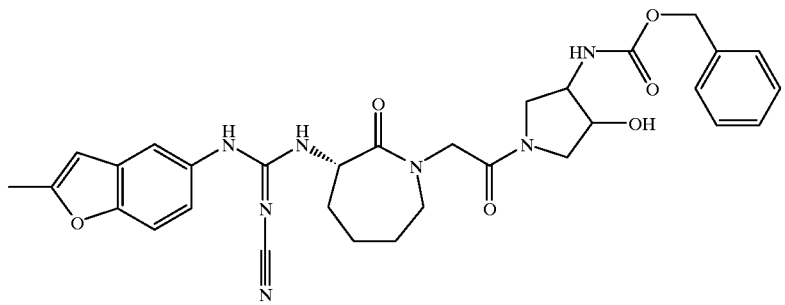

B.

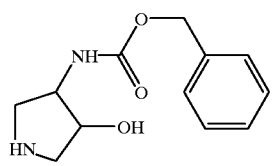

To a mixture of Example 260 part C compound (0.24 g, 0.63 mmol) and TFFH (0.22 g, 0.83 mmol) in acetonitrile (4.9 mL) at 0° C. under nitrogen was added triethylamine (0.083 mL, 0.63 mmol). The resulting solution was stirred for 20 min at 0° C. at which time part B compound (0.30 g, 1.3 mmol) was added. After stirring at ambient temperature for 3 h, the reaction was transferred to a separatory funnel with ethyl acetate and washed with 5% KHSO$_4$, saturated NaHCO$_3$, and brine and dried over MgSO$_4$ to afford 0.66 g of crude product. Flash chromatography (silica, 25 mm dia column, 3% methanol/dichloromethane) afforded the Title compound (0.16 g, 42%): LRMS (ESI) m/z 602 (M+H); HPLC (Method D) t$_R$=3.7 min.

EXAMPLE 742

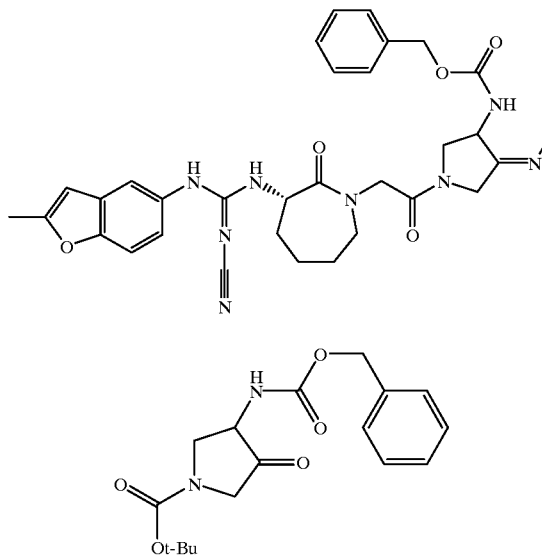

A.

Sulfur trioxide-pyridine complex (6.3 g, 40 mmol) was added to a stirring solution of Example 741 part A compound (2.7 g, 7.9 mmol) and triethylamine (13.2 mL, 95 mmol) in dimethylsulfoxide (29 mL) at 38° C. After stirring at 38° C. for 35 min, the reaction was transferred to a separatory funnel with ethyl acetate (250 mL) and washed with 5% KHSO$_4$ (3×80 mL), saturated NaHCO$_3$ (80 mL), water (80 mL) and brine (80 mL) and dried over MgSO$_4$ to afford 3.1 g of crude product after concentration. Flash chromatography (silica, 50 mm dia column, 30% ethyl acetate/hexane) afforded part A compound (1.6 g, 61%).

B.

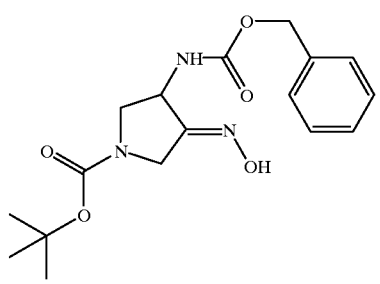

Hydroxyamine (50% in water, 1.8 g, 28 mmol) was added to a solution of part A compound (0.50 g, 1.5 mmol) in ethanol. After stirring at 40° C. for 30 min, the reaction was evaporated in vacuo and the residue transferred to a separatory funnel with ethyl acetate/1% KHSO$_4$. Extraction with ethyl acetate (2×), washing the combined organic layers with brine and drying over MgSO$_4$ afforded crude product after concentration. Flash chromatography (silica, 15 mm dia column, 25% ethyl acetate/hexane) afforded part B compound (0.52 g, 99%): LC MS (ESI, HPLC conditions A) m/z=350 (M+H), t$_R$=3.4 min.

C.

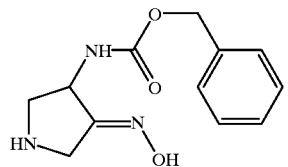

This material was prepared from part B compound using the procedure described in Example 741.

D.

The title compound was prepared from part C compound and Example 260 part C compound using the procedure described in Example 741: HPLC (Method1) t$_R$=3.9 min; LRMS (ESI) m/z 615 (M+H)

EXAMPLE 743

A.

Methoxyamine hydrochloride (0.25 g, 3.0 mmol) was added to a solution of Example 742 part A compound (0.50 g, 1.5 mmol) and sodium bicarbonate (1M in water, 3.0 mL, 3.0 mmol) in ethanol (10 mL) and tetrahydrofuran (10 mL). After stirring at 40° C. for 1 day, the reaction was evaporated in vacuo and the residue transferred to a separatory funnel with ethyl acetate/1% KHSO$_4$. Extraction with ethyl acetate (2×), washing the combined organic layers with brine and drying over MgSO$_4$ afforded crude product after concentration. Flash chromatography (silica, 15 mm dia column, 25% ethyl acetate/hexane) afforded part A compound (0.31 g, 57%): LC-MS (ESI, conditions F) m/z 364 (M+H), t$_R$=3.6 min.

B.

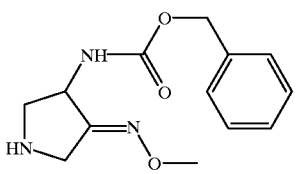

This material was prepared from part A compound using the procedure described in Example 741.

C.

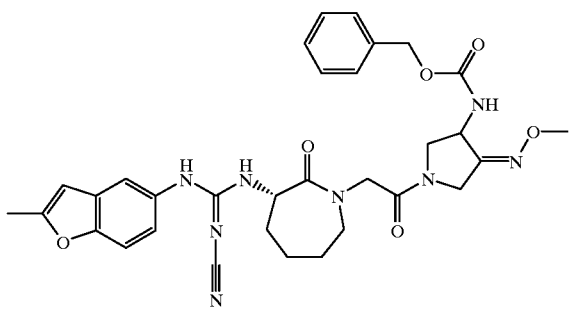

The title compound was prepared from part B compound and Example 260 part C compound using the procedure described in Example 741: HPLC (Method1) t$_R$=4.1 min; LRMS (ESI) m/z 629 (M+H)

EXAMPLE 744

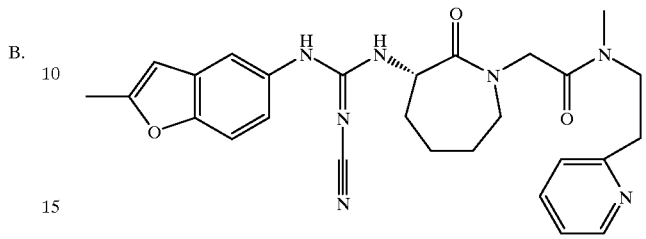

To a mixture of Example 260 part C compound (50 mg, 0.13 mmol) and TFFH (45 mg, 0.17 mmol) in acetonitrile (1.0 mL) at 0° C. under nitrogen was added triethylamine (0.017 mL, 0.13 mmol). The resulting solution was stirred for 10 min at 0° C. upon which time N-N-methyl-2-pyridineethanamine (35 mg, 0.26 mmol) was added. The reaction was stirred for 3 h. The reaction was transferred to a separatory funnel with ethyl acetate and washed with water and saturated sodium bicarbonate and dried over MgSO$_4$ to afford crude product after evaporation of the solvent. Flash chromatography (silica, 15 mm dia column, 5% methanol/dichloromethane) afforded Title compound (50 mg, 77%): LRMS (ESI) m/z 502 (M+H); HPLC (Method A) t$_R$=2.8 min.

EXAMPLES 745 to 759

Using the procedure described in Example 744 the following can be prepared.

| Example | Structure | Characterization |
| --- | --- | --- |
| 745 | 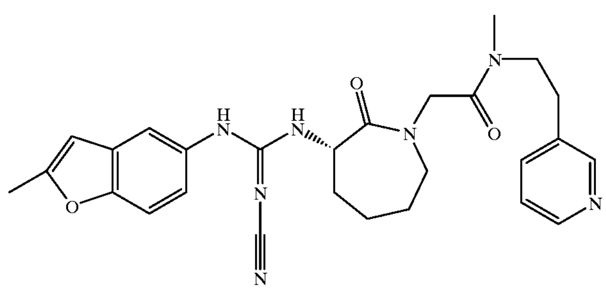 | HPLC (method A) t$_R$ 2.9 min LCMS (ESI) m/z 502 (M + H) |
| 746 | 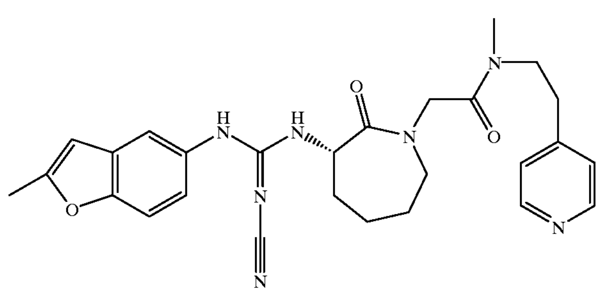 | HPLC (method A) t$_R$ 2.9 min LCMS (ESI) m/z 502 (M + H) |

-continued

| Example | Structure | Characterization |
|---|---|---|
| 747 | 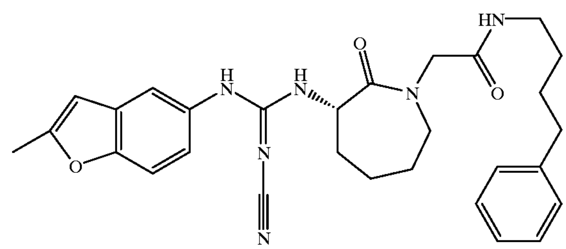 | HPLC (method A) $t_R$ 4.2 min<br>LCMS (ESI) m/z 515 (M + H) |
| 748 | 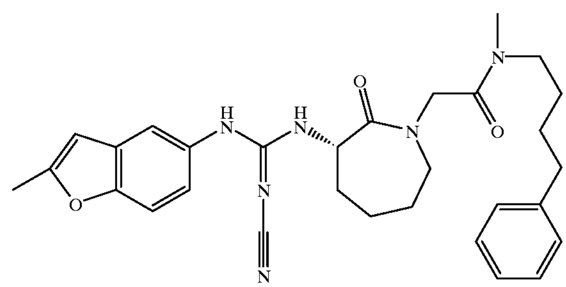 | HPLC (method A) $t_R$ 4.4 min<br>LCMS (ESI) m/z 529 (M + H) |
| 749 | 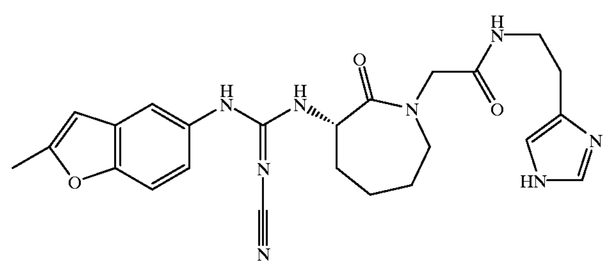 | HPLC (method A) $t_R$ 2.9 min<br>LCMS (ESI) m/z 477 (M + H) |
| 750 | 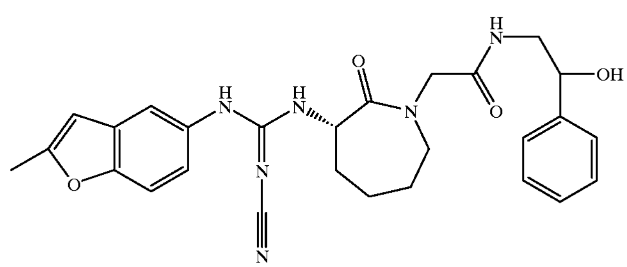 | HPLC (method A) $t_R$ 3.7 min<br>LCMS (ESI) m/z 503 (M + H) |
| 751 | 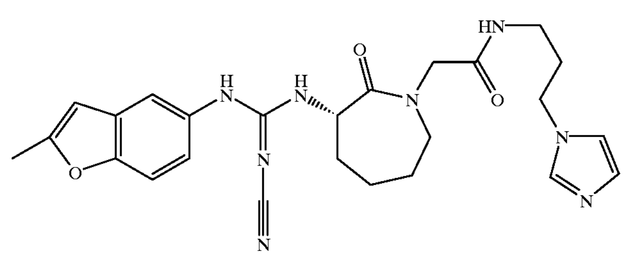 | HPLC (method A) $t_R$ 2.8 min<br>LCMS (ESI) m/z 491 (M + H) |

| Example | Structure | Characterization |
|---|---|---|
| 752 | 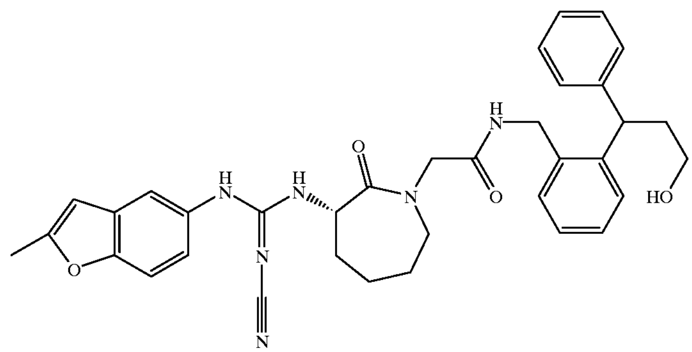 | HPLC (method A)<br>$t_R$ 4.2 min<br>LCMS (ESI) m/z<br>607 (M + H) |
| 753 | 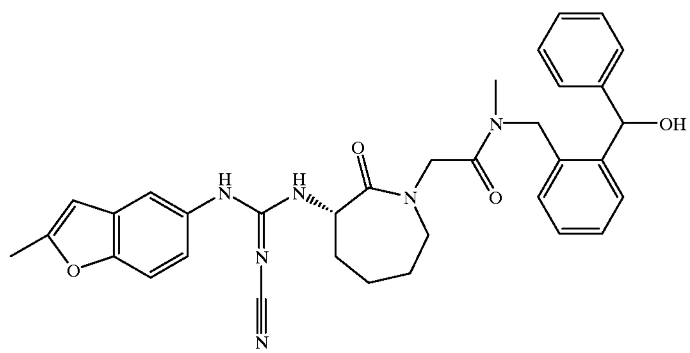 | HPLC (method A)<br>$t_R$ 4.2 min<br>LCMS (ESI) m/z<br>611 (M + H) |
| 754 | 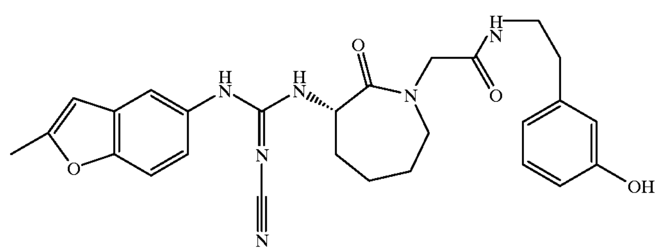 | HPLC (method A)<br>$t_R$ 3.6 min<br>LCMS (ESI) m/z<br>503 (M + H) |
| 755 | 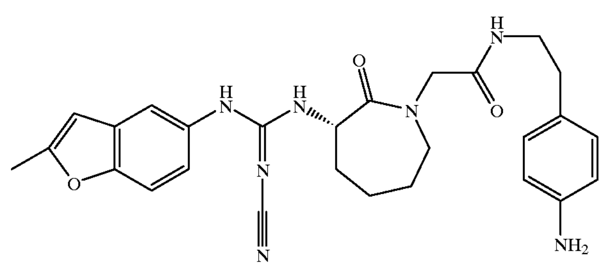 | HPLC (method A)<br>$t_R$ 3.0 min<br>LCMS (ESI) m/z<br>502 (M + H) |
| 756 | 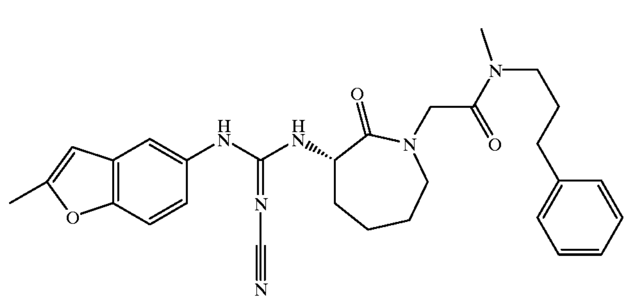 | HPLC (method A)<br>$t_R$ 4.2 min<br>LCMS (ESI) m/z<br>515 (M + H) |

| Example | Structure | Characterization |
|---|---|---|
| 757 | 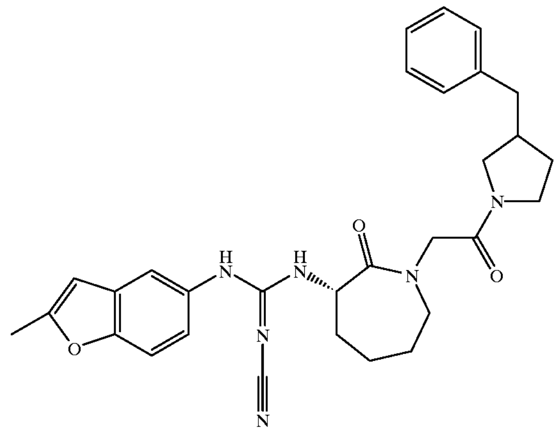 | HPLC (method A) $t_R$ 4.2 min LCMS (ESI) m/z 527 (M + H) |
| 758 | 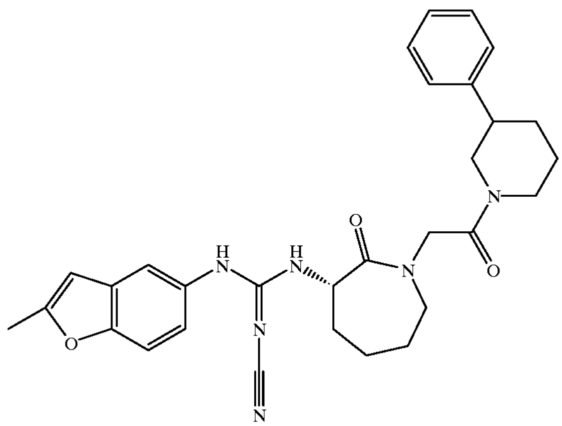 | HPLC (method A) $t_R$ 4.3 min LCMS (ESI) m/z 527 (M + H) |

EXAMPLE 760

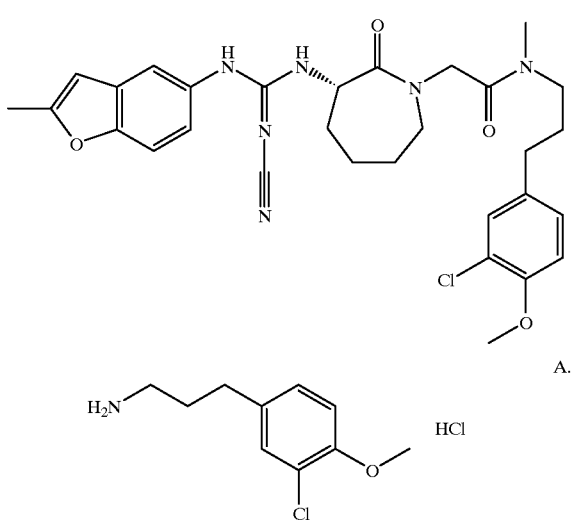

Sulfuryl chloride (1.4 mL, 17.5 mmol) was added to a solution of 4-methoxy-benzenepropanamine (2.0 g, 12 mmol) in acetic acid (16 mL) which was maintained at <25° C. with an ice bath when necessary. After stirring at room temperature for 15 min, the reaction was poured into ether (80 mL). After 1 h at 4° C. the solid which formed was collected by filtration to afford part A compound (1.4 g, 49%): LRMS (ESI) m/z 200 (M+H); HPLC (Method A) $t_R$=2.1 min.

Sodium bicarbonate (1N in water, 10 mL, 10 mmol) was slowly added to a mixture of part A compound (1.1 g, 4.8 mmol) in tetrahydrofuran (14 mL). Ethyl chloroformate (0.56 g, 0.50 mL, 5.2 mmol) was then added over 5 min. After stirring at ambient temperature for 30 min, the reaction mixture was transferred to a separatory funnel with dichloromethane. Extraction with dichloromethane (60 mL) and drying over $MgSO_4$ afforded an intermediate after concentration in vacuo: 1.6 g; HPLC (method A) $t_R$=3.8 min). To a solution of this material in tetrahydrofuran (7 mL) was added lithium aluminum hydride (1M in tetrahydrofuran, 5.2 mL, 5.2 mmol) and the mixture was heated to reflux. After refluxing for 2 h, the reaction was cooled and quenched by slowly adding water. After evaporation in vacuo, the residue was transferred to a separatory funnel with dichloromethane/water. Extraction with dichloromethane (2×) and drying over MgSO₄ afforded part B compound (0.92 g, 89%) after concentration in vacuo: HPLC (method A) t$_R$=2.1 min.

C.

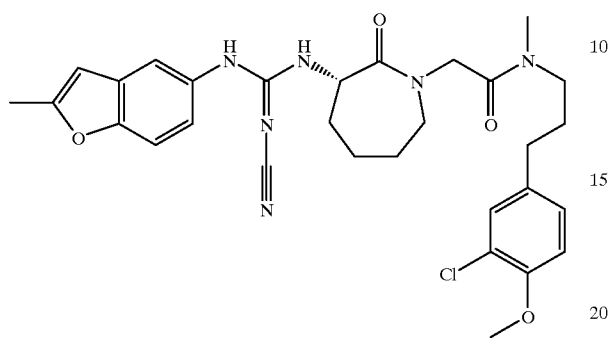

To a solution of Example 260 part C compound (52 mg, 0.13 mmol) in dichloromethane (1.0 mL) was added WSC (42 mg, 0.22 mmol) and 1-hydroxybenzotriazole (HOBT, 18 mg, 0.14 mmol). After stirring at ambient temperature for 30 min, part B compound (30 mg, 0.14 mmol) was added. After stirring at ambient temperature for 5 h, the reaction was transferred to a separatory funnel with dichloromethane/water. Extraction with dichloromethane (2×), and drying over MgSO₄ afforded crude product after evaporation of the solvent. Flash chromatography (silica, 15 mm dia column, 2% methanol/dichloromethane) afforded Title compound (48 mg, 64%): LRMS (ESI) m/z 579 (M+H); HPLC (Method A) t$_R$=4.2 min.

EXAMPLES 761 to 768

Using the procedure described in Example 760 the following can be prepared.

| Example | Structure | Characterization |
|---------|-----------|------------------|
| 761 | 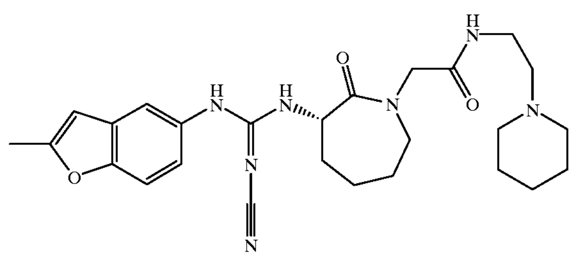 | HPLC (method A) t$_R$ = 2.9 min LRMS (ESI) m/z 494 (M + H) |
| 762 | 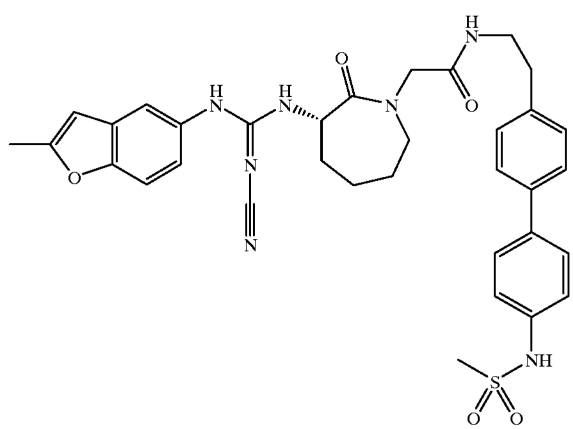 | HPLC (method A) t$_R$ = 3.9 min LRMS (ESI) m/z 656 (M + H) |
| 763 | 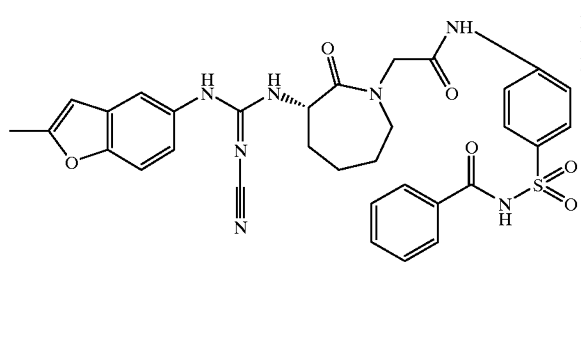 | HPLC (method A) t$_R$ = 3.7 min LRMS (ESI) m/z 656 (M + H) |

-continued

| Example | Structure | Characterization |
|---|---|---|
| 764 | 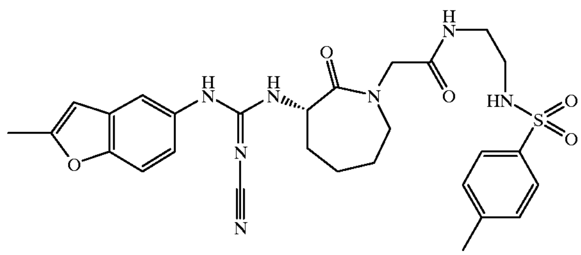 | HPLC (method A)<br>$t_R$ = 3.8 min<br>LRMS (ESI) m/z<br>580 (M + H) |
| 765 | 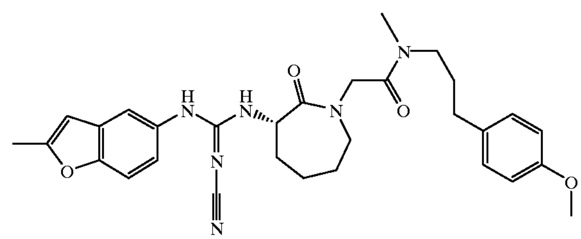 | HLC (method A)<br>$t_R$ = 4.1 min<br>LRMS (ESI) m/z<br>545 (M + H) |
| 766 | 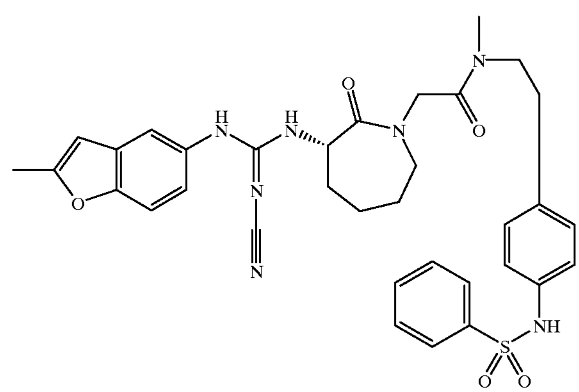 | HPLC (method A)<br>$t_R$ = 3.9 min<br>LRMS (ESI) m/z<br>656 (M + H) |
| 767 | 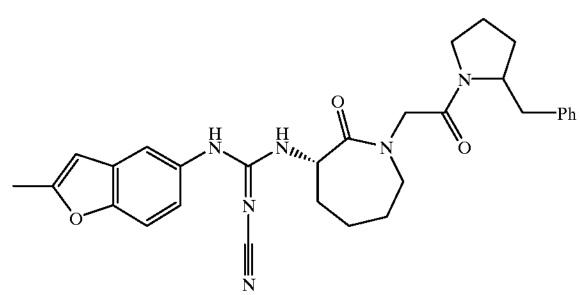 | HPLC (method A)<br>$t_R$ = 4.2 min<br>LRMS (ESI) m/z<br>527 (M + H) |
| 768 | 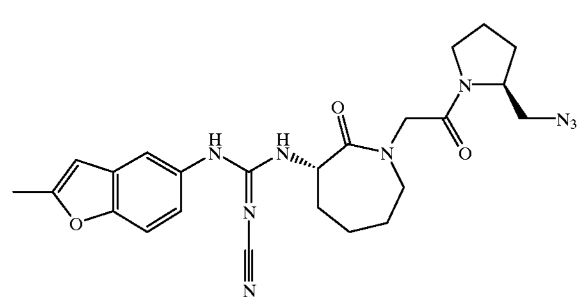 | HPLC (method A)<br>$t_R$ = 3.9 min<br>LRMS (ESI) m/z<br>492 (M + H) |

-continued

| Example | Structure | Characterization |
|---|---|---|
| 769 | 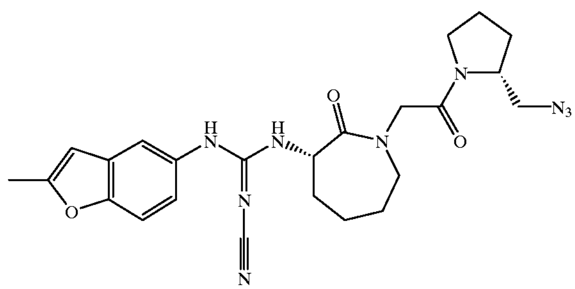 | HPLC (method A) $t_r$ = 4.2 min<br>LRMS (ESI) m/z 492 (M + H) |

EXAMPLE 770

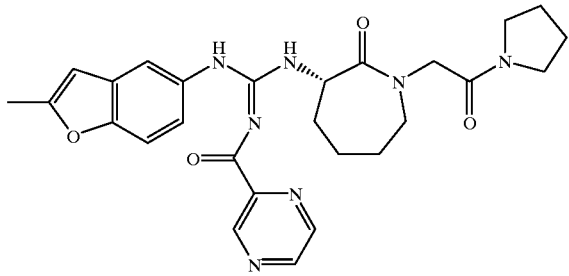

To a solution of pyrazinecarboxylic acid, (36 mg, 0.29 mmol) in DMF (0.48 mL) was added 1,1'-carbonyldiimidazole (48 mg, 0.29 mmol). After stirring at ambient temperature for 15 min, the Example 496 part A compound (100 mg, 0.24 mmol) was added. After stirring at ambient temperature for 2 h, the reaction was diluted with ethyl acetate and transferred to a separatory funnel. The mixture was washed with water (3×) and dried over $MgSO_4$ which afforded crude product after evaporation of the solvent. Flash chromatography (silica gel, 15 mm dia column, 3% $MeOH/CH_2Cl_2$) afforded the Title compound (97 mg, 48%): LC-MS (ESI, conditions F) m/z 518 (M+H), $t_R$=3.1 min.

EXAMPLES 771 and 772

Using the procedure described in Example 770 the following can be prepared.

| Example | Structure | Characterization |
|---|---|---|
| 771 | 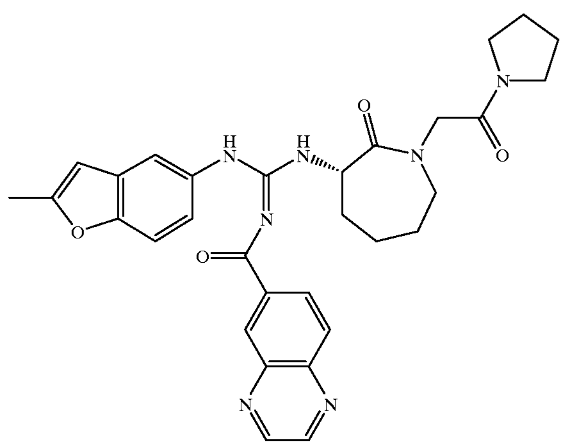 | HPLC (method A) $t_R$ = 4.0 min<br>LRMS (ESI) m/z 568 (M + H) |

| Example | Structure | Characterization |
|---|---|---|
| 772 | 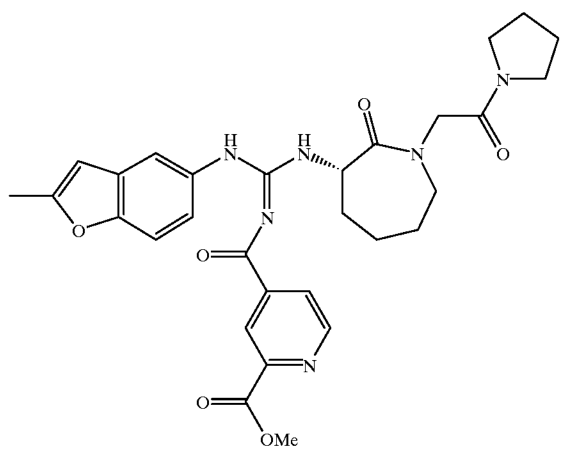 | LRMS (ESI) m/z 575 (M + H) |

EXAMPLE 773

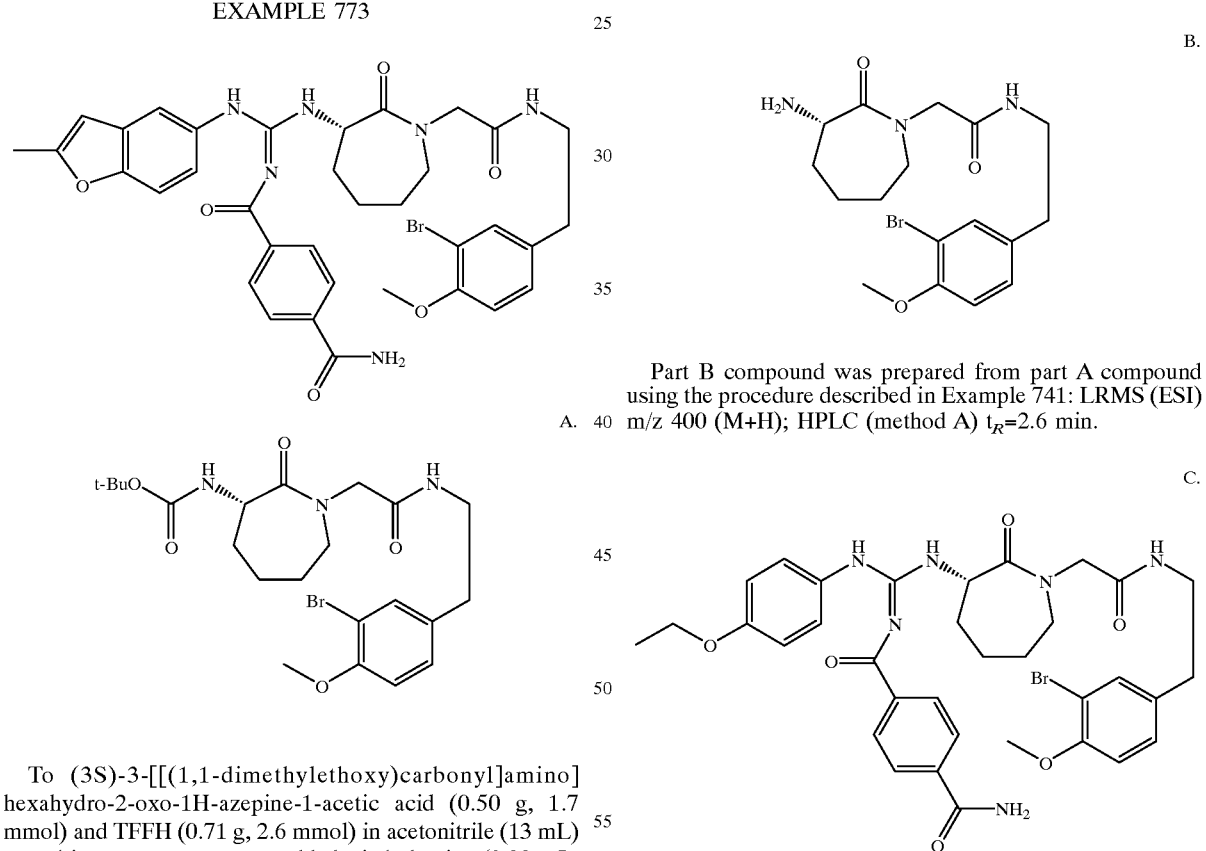

A.

To (3S)-3-[[(1,1-dimethylethoxy)carbonyl]amino]hexahydro-2-oxo-1H-azepine-1-acetic acid (0.50 g, 1.7 mmol) and TFFH (0.71 g, 2.6 mmol) in acetonitrile (13 mL) at ambient temperature was added triethylamine (0.29 mL, 2.0 mmol). The resulting solution was stirred for 20 min at which time 3-bromo-4-methoxybenzeneethanamine (0.80 g, 3.5 mmol) was added. After stirring at ambient temperature for 2 h, the reaction was transferred to a separatory funnel with dichloromethane/0.2 N sodium hydroxide. Extraction with dichloromethane (2×20 mL) and drying over $MgSO_4$ afforded 1.9 g of crude product. Flash chromatography (silica, 25 mm dia column, 5% methanol/dichloromethane) afforded part A compound (0.78 g, 89%): LC MS (ESI, conditions F) m/z 500 (M+H), $t_R$=4.0 min.

B.

Part B compound was prepared from part A compound using the procedure described in Example 741: LRMS (ESI) m/z 400 (M+H); HPLC (method A) $t_R$=2.6 min.

C.

Sodium hydride (13 mg, 0.53 mmol) was added to a suspension of 1,4-benzenedicarboxamide (60 mg, 0.37 mmol) in DMF (1.8 mL). To this mixture was added 2-methyl-5-isothiocyanatobenzofuran (68 mg, 0.36 mmol) and the reaction was stirred at 60° C. for 30 min. The heating bath was removed and part B compound (0.14 g, 0.35 mmol) and mercuric chloride (98 mg, 0.36 mmol) were added. After stirring at ambient temperature for 2 h, the reaction was diluted with ethyl acetate and filtered through Celite. Evaporation of the filtrate afforded crude product. Flash chromatography (silica, 15 mm dia column, 2% methanol/dichloromethane) afforded the Title compound (60 mg, 23%): LRMS (ESI) m/z 717 (M+H); HPLC (Method A) $t_R$=3.9 min.

EXAMPLES 774 to 792

The following compounds were prepared using the dures described in Example 773.

| Example | Structure | Characterization |
|---|---|---|
| 774 | 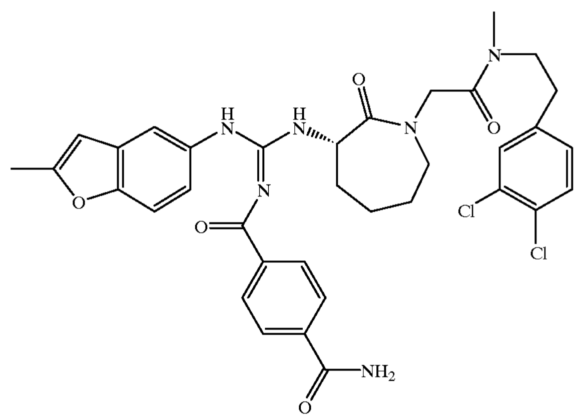 | HPLC (method A) $t_R$ = 4.2 min LRMS (ESI) m/z 691 (M + H) |
| 775 | 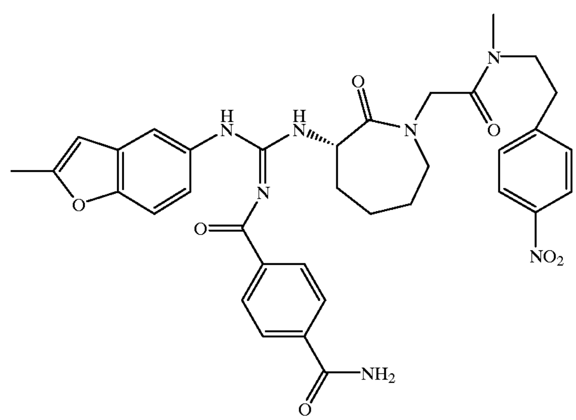 | HPLC (method A) $t_R$ = 3.9 min LRMS (ESI) m/z 668 (M + H) |
| 776 | 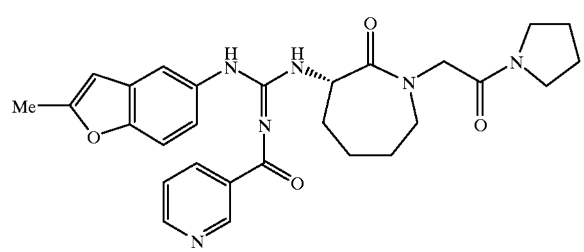 | HPLC (method A) $t_R$ = 4.1 min. LRMS (ESI) m/z 517 (M + 1) |
| 777 | 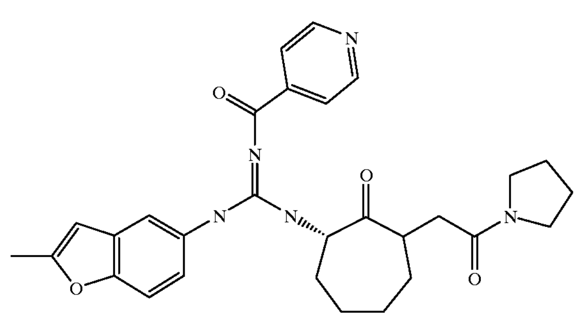 | HPLC (method A) $t_R$ = 3.6 min LRMS (ESI) m/z 517 (M + H) |

-continued

| Example | Structure | Characterization |
|---------|-----------|------------------|
| 778 | 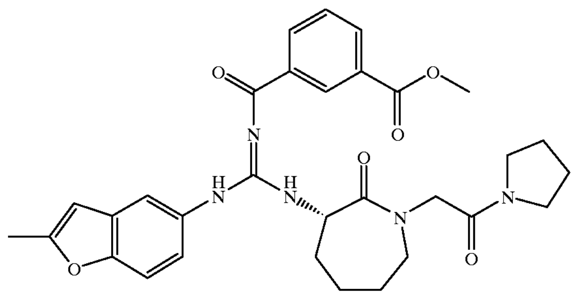 | HPLC (method A)<br>$t_R$ = 4.1 min<br>LRMS (ESI) m/z<br>574 (M + H) |
| 779 | 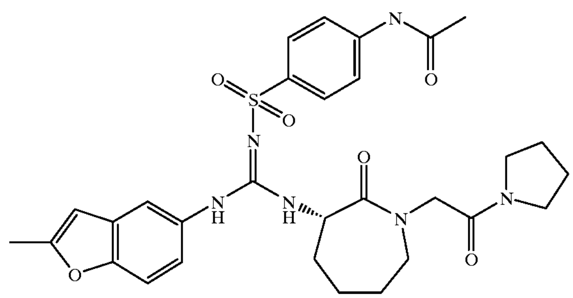 | HPLC (method A)<br>$t_R$ = 3.7 min<br>LRMS (ESI) m/z<br>609 (M + H) |
| 780 | 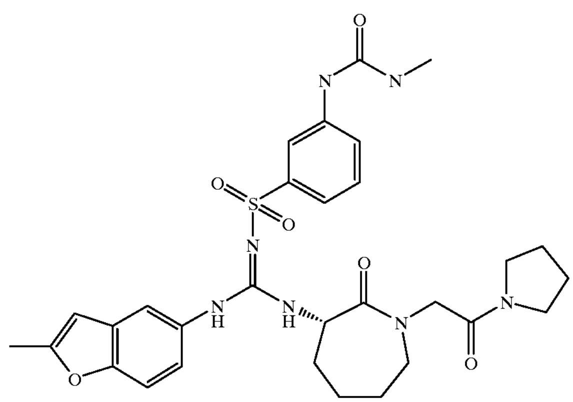 | HPLC (method A)<br>$t_R$ = 3.7 min<br>LRMS (ESI) m/z<br>624 (M + H) |
| 781 | 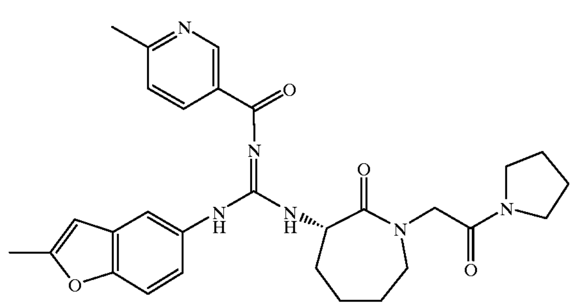 | HPLC (method A)<br>$t_R$ = 3.5 min<br>LRMS (ESI) m/z<br>531 (M + H) |

-continued

| Example | Structure | Characterization |
|---------|-----------|------------------|
| 782 | 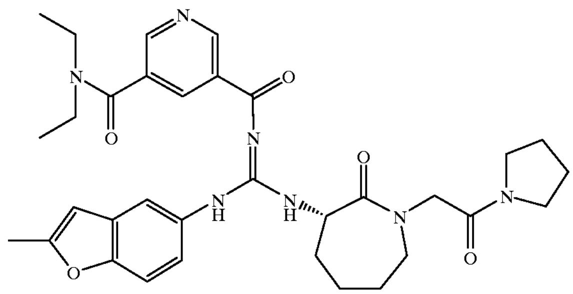 | HPLC (method A)<br>$t_R$ = 4.1 min<br>LRMS (ESI) m/z<br>616 (M + H) |
| 783 | 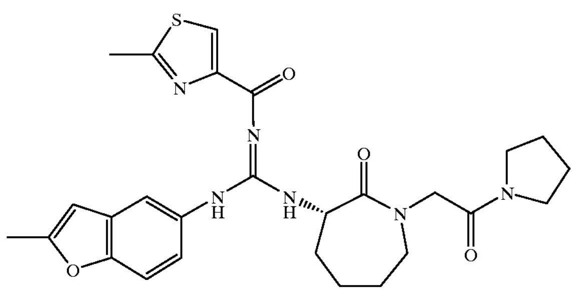 | HPLC (method A)<br>$t_R$ = 3.3 min<br>LRMS (ESI) m/z<br>537 (M + H) |
| 784 | 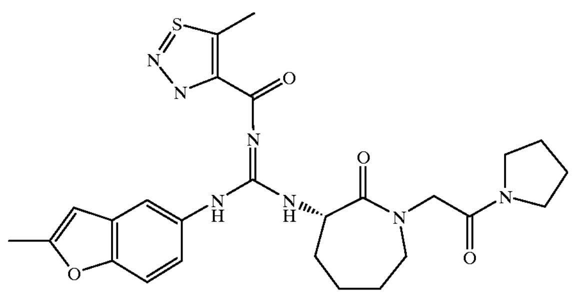 | HPLC (method A)<br>$t_R$ = 4.5 min<br>LRMS (ESI) m/z<br>538 (M + H) |
| 785 | 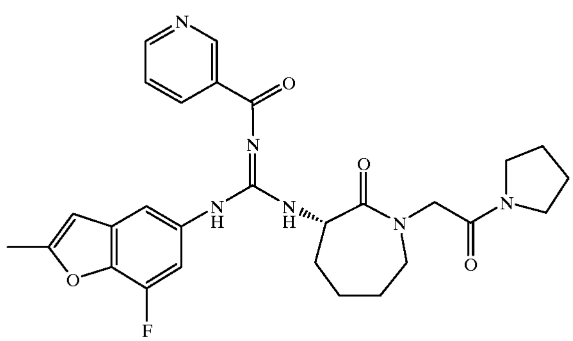 | HPLC (method A)<br>$t_R$ = 3.7 min<br>LRMS (ESI) m/z<br>535 (M + H) |

-continued

| Example | Structure | Characterization |
|---------|-----------|------------------|
| 786 | 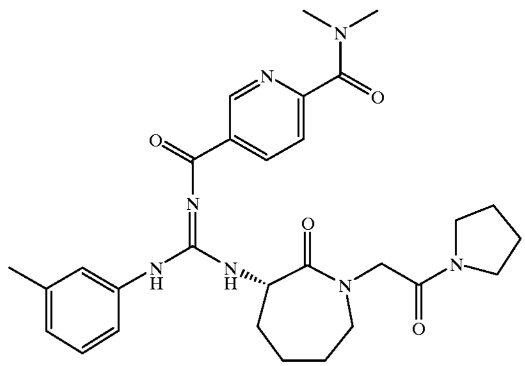 | HPLC (method A) $t_R$ = 3.9 min LRMS (ESI) m/z 548 (M + H) |
| 787 | 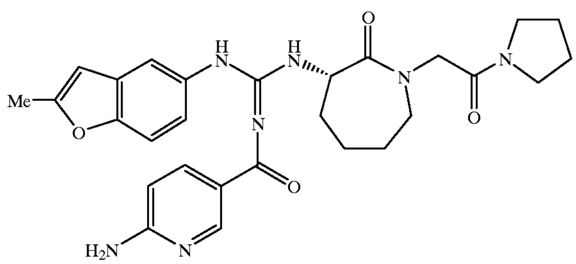 | HPLC (method A) $t_R$ = 3.4 min. LRMS (ESI) m/z 532 (M + 1) |
| 788 | 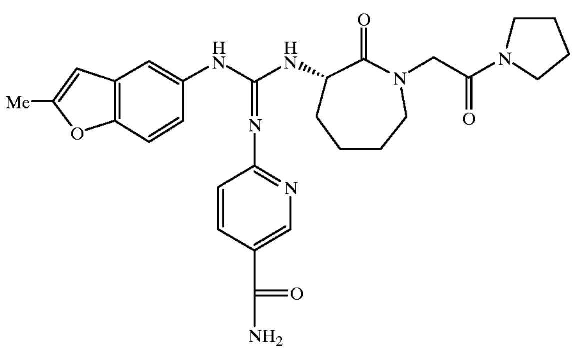 | HPLC (method A) $t_R$ = 3.0 min. LRMS (ESI) m/z 532 (M + 1) |
| 789 | 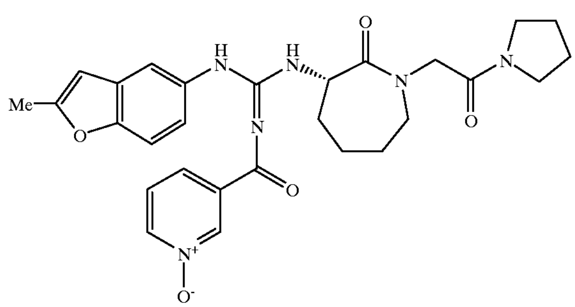 | HPLC (method A) $t_R$ = 4.0 min LRMS (ESI) m/z 533 (M + 1) |

-continued
| Example | Structure | Characterization |
|---|---|---|
| 790 | 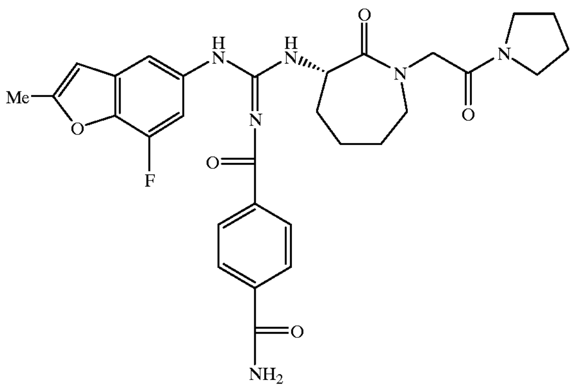 | HPLC (method A) $t_R$ = 3.6 min LRMS (ESI) m/z 577 (M + H) |
| 791 | 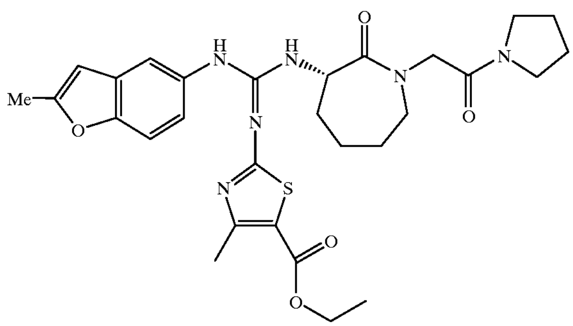 | HPLC (method A) $t_R$ = 3.8 min. LRMS (ESI) m/z 581 (M + 1) |
| 792 | 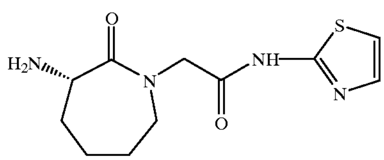 | |
EXAMPLE 793
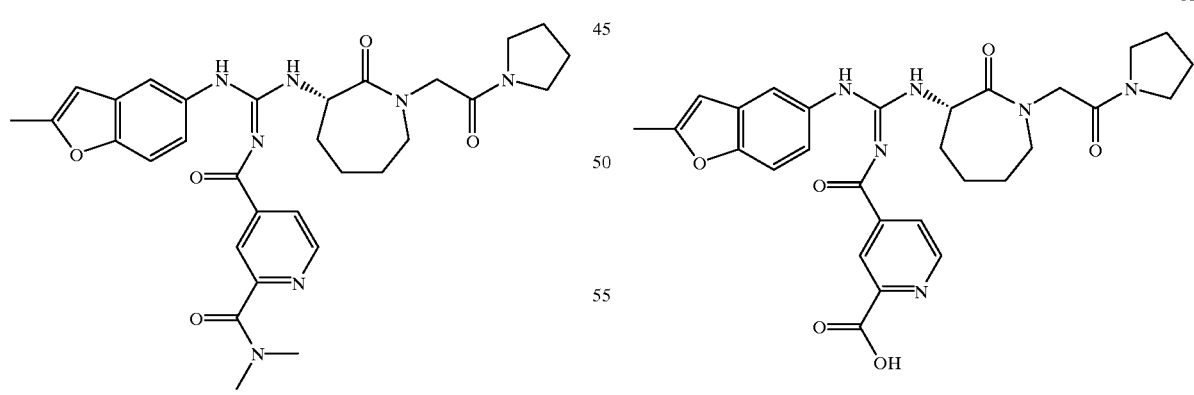
-continued
A.

Lithium hydroxide (1N in water, 0.5 mL, 0.5 mmol) was added to a solution of Example 771 compound (59 mg, 0.1 mmol) in tetrahydrofuran (1 mL). After stirring at ambient temperature for 4 h, the reaction was transferred to a separatory funnel with ethyl acetate/water. The aqueous layer was acidified to pH 5, and extracted with ethyl acetate (3×). The combined organic layers were dried over $MgSO_4$ and evaporated to afford part A compound (39 mg, 69%); HPLC (method A) $t_R$=4.0 min.

B.

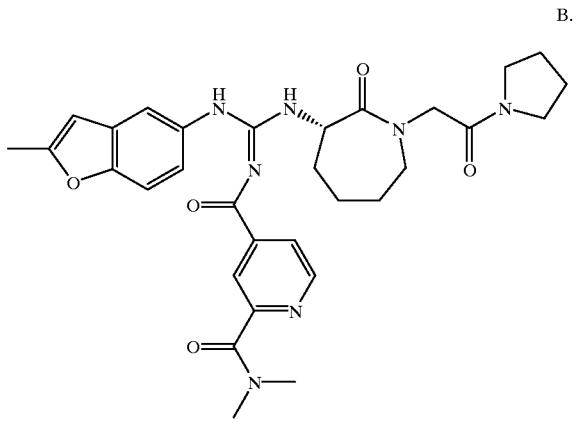

To part A compound (39 mg, 0.07 mmol) and TFFH (29 mg, 0.11 mmol) in acetonitrile (0.53 mL) at ambient temperature under nitrogen was added triethylamine (0.011 mL, 0.08 mmol). The resulting solution was stirred for 10 min at which time dimethylamine (2N in tetrahydrofuran, 0.04 mL, 0.08 mmol) was added. After stirring at ambient temperature for 4 h, the reaction was transferred to a separatory funnel with ethyl acetate and washed with 5% $KHSO_4$, saturated $NaHCO_3$, and brine and dried over $MgSO_4$. Concentration in vacuo and flash chromatography of the residue(silica, 15 mm dia column, 4% methanol/dichloromethane) afforded the Title compound (0.16 g, 42%): LRMS (ESI) m/z 588 (M+H); HPLC (Method A) $t_R$=3.9 min.

EXAMPLES 794 to 808

Using the methodology described in 793, the following compounds were prepared.

| Example | structure | characterization |
|---|---|---|
| 794 | 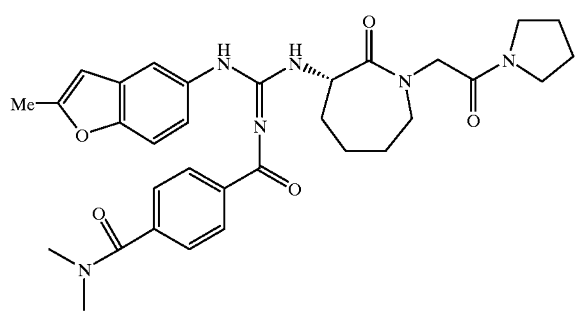 | HPLC (method A) $t_R$ = 3.4 min. LRMS (ESI) m/z 587 (M + 1) |
| 795 | 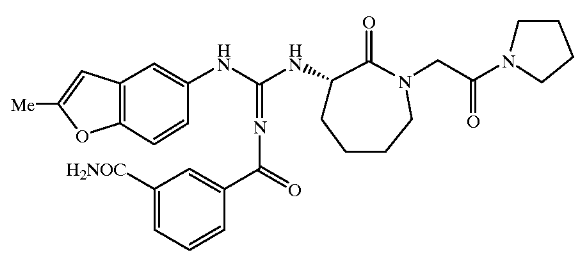 | HPLC (method A) $t_R$ = 3.6 min LRMS (ESI) m/z 587 (M + H) |

-continued

| Example | structure | characterization |
|---|---|---|
| 796 | 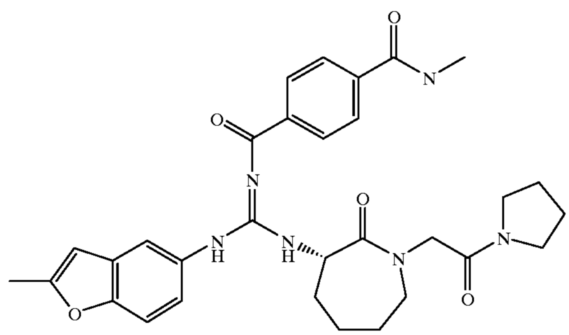 | HPLC (method A)<br>$t_R$ = 3.4 min<br>LRMS (ESI) m/z<br>573 (M + H) |
| 797 | 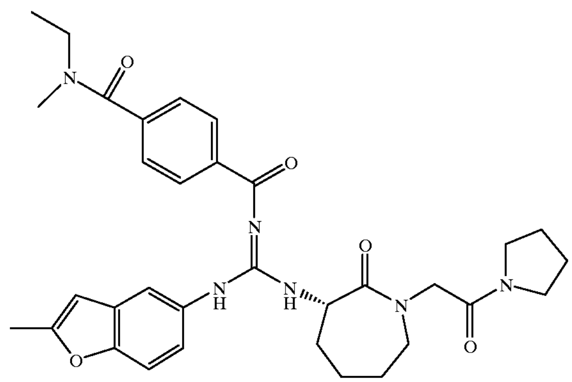 | HPLC (method A)<br>$t_R$ = 3.6 min<br>LRMS (ESI) m/z<br>601 (M + H) |
| 798 | 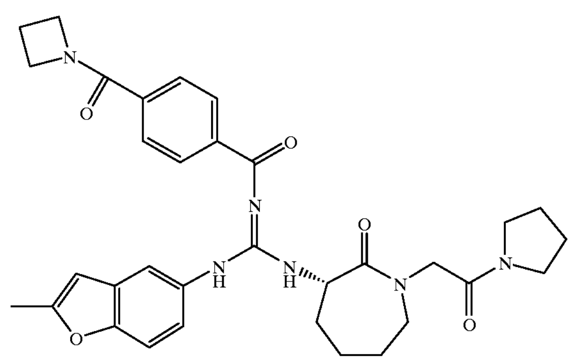 | HPLC (method A)<br>$t_R$ = 3.6 min<br>LRMS (ESI) m/z<br>599 (M + H) |
| 799 | 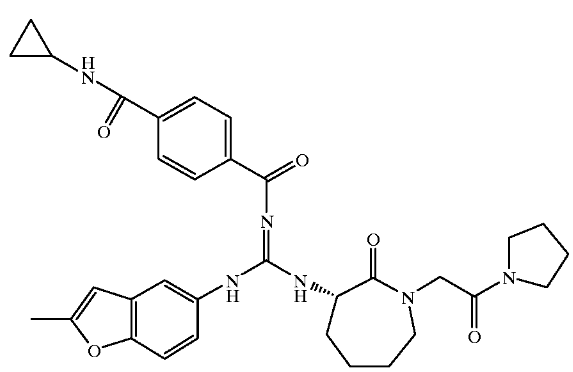 | HPLC (method A)<br>$t_R$ = 3.6 min<br>LRMS (ESI) m/z<br>599 (M + H) |

-continued

| Example | structure | characterization |
|---|---|---|
| 800 | 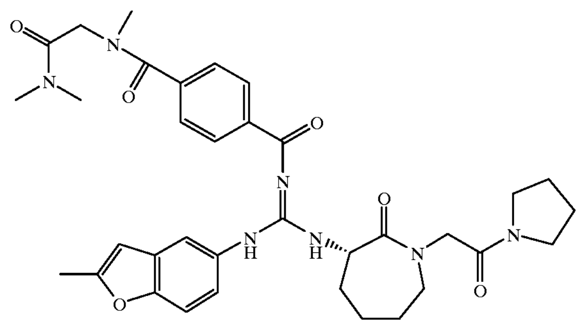 | HPLC (method A)<br>$t_R$ = 3.4 min<br>LRMS (ESI) m/z<br>658 (M + H) |
| 801 | 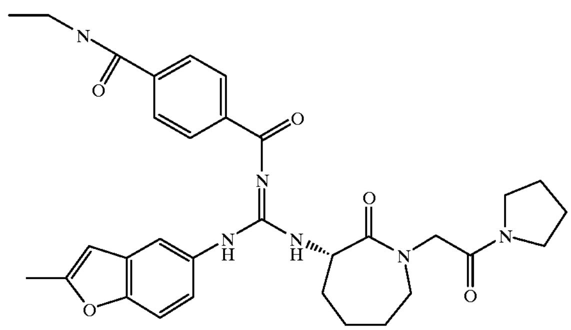 | HPLC (method A)<br>$t_R$ = 3.6 min<br>LRMS (ESI m/z<br>587 (M + H) |
| 802 | 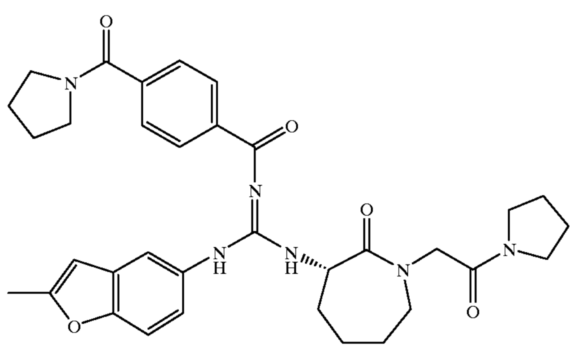 | HPLC (method A)<br>$t_R$ = 3.6 min<br>LRMS (ESI) m/z<br>613 (M + H) |
| 803 | 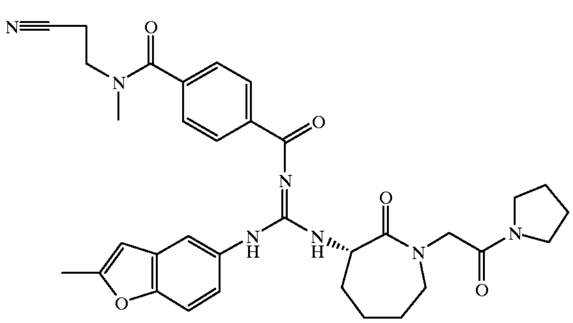 | HPLC (method A)<br>$t_R$ = 3.4 min<br>LRMS (ESI) m/z<br>626 (M + H) |

-continued

| Example | structure | characterization |
|---|---|---|
| 804 | 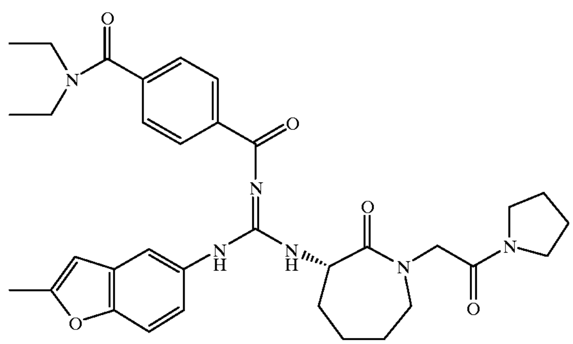 | HPLC (method A)<br>$t_R$ = 3.8 min<br>LRMS (ESI) m/z<br>615 (M + H) |
| 805 | 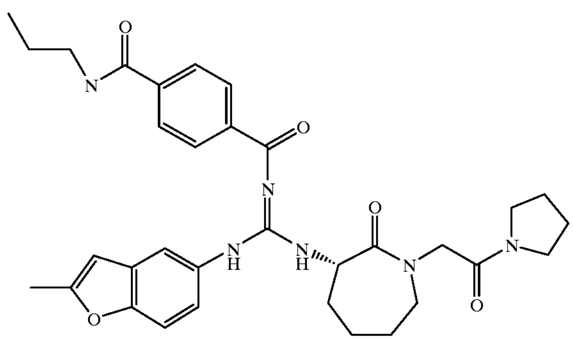 | HPLC (method A)<br>$t_R$ = 3.8 min<br>LRMS (ESI) m/z<br>601 (M + H) |
| 806 | 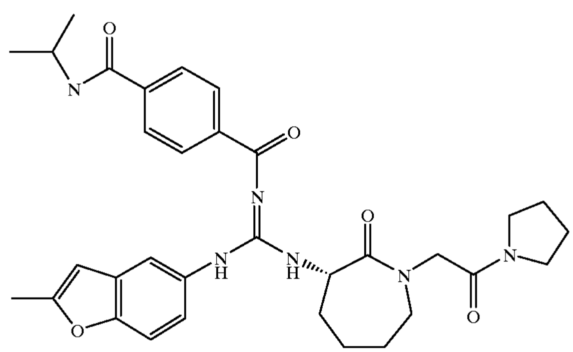 | HPLC (method A)<br>$t_R$ = 3.7 min<br>LRMS (ESI) m/z<br>601 (M + H) |
| 807 | 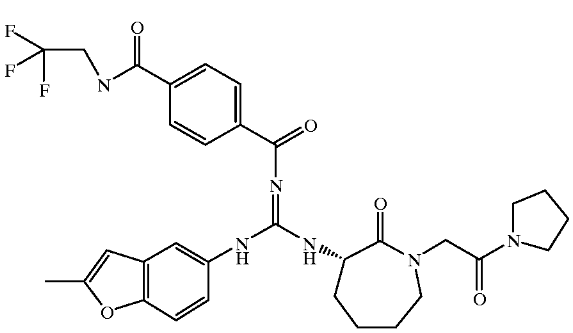 | HPLC (method A)<br>$t_R$ = 3.9 min<br>LRMS (ESI) m/z<br>641 (M + H) |

-continued

| Example | structure | characterization |
|---|---|---|
| 808 | 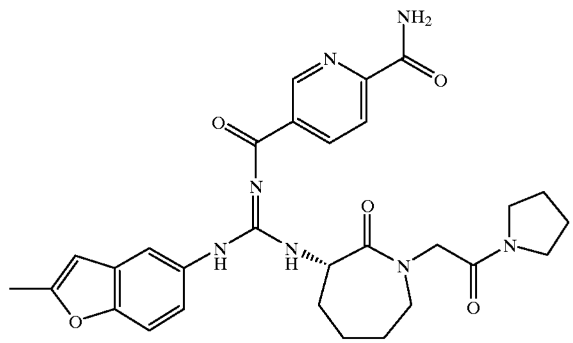 | HPLC (method A)<br>$t_R$ = 4.0 min<br>LRMS (ESI) m/z<br>560 (M + H) |

EXAMPLE 809

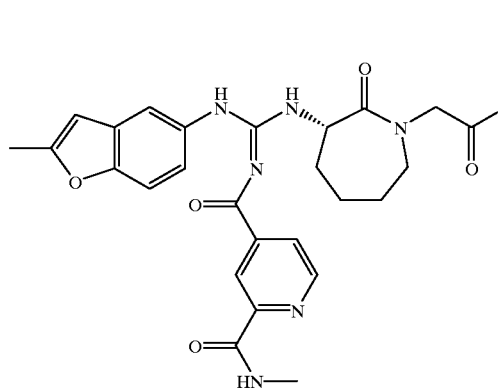

EXAMPLE 810

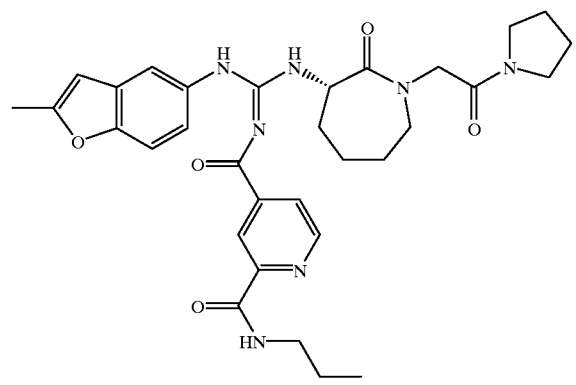

To a solution of Example 793 part A compound (0.15 g, 0.27 mmol) in DMF (0.44 mL). was added 1,1'-carbonyldiimidazole (44 mg, 0.27 mmol). After stirring at ambient temperature for 15 min, methylamine (2 N in tetrahydrofuran, 0.27 mL, 0.54 mmol) was added. After stirring at ambient temperature for 3 h, the reaction mixture was transferred to a separatory funnel with ethyl acetate/water. Extraction with ethyl acetate, washing with water (2×), and drying over MgSO$_4$, afforded crude product after concentration in vacuo. Flash chromatography (silica, 15 mm dia column, 3% methanol/dichloromethane) afforded the Title compound (100 mg, 67%): LRMS (ESI) m/z 574 (M+H); HPLC (Method A) $t_R$=4.2 min.

To a solution of Example 793 part A compound (0.15 g, 0.27 mmol) in dichloromethane (1.5 mL) was added WSC (84 mg, 0.27 mmol) and 1-hydroxybenzotriazole (HOBT, 37 mg, 0.27 mmol). After stirring at ambient temperature for 30 min, propylamine (16 mg, 0.022 mL, 0.27 mmol) was added. After stirring at ambient temperature for 3.5 h, the reaction was transferred to a separatory funnel with dichloromethane/water. Extraction with dichloromethane (2×), and drying over Na$_2$SO$_4$ afforded crude product after evaporation of the solvent. Flash chromatography (silica, 15 mm dia column, 1.5% methanol/dichloromethane) afforded the Title compound (0.14 g, 88%): LRMS (ESI) m/z 602 (M+H); HPLC (Method A) $t_R$=4.5 min.

EXAMPLES 811 to 826

Using the procedure described in Example 810 the following compounds were prepared.

| Example | structure | characterization |
|---------|-----------|------------------|
| 811 | 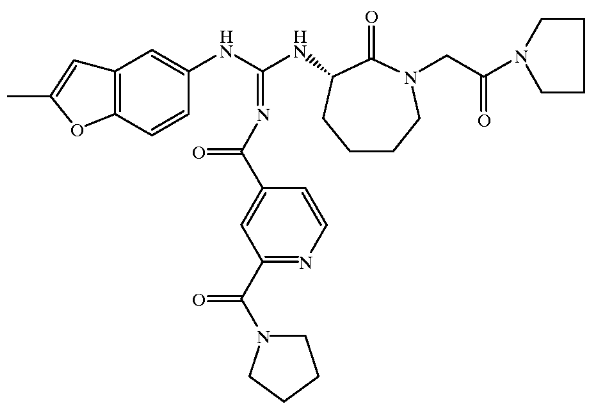 | HPLC (method A) $t_R$ = 4.2 min LRMS (ESI) m/z 614 (M + H) |
| 812 | 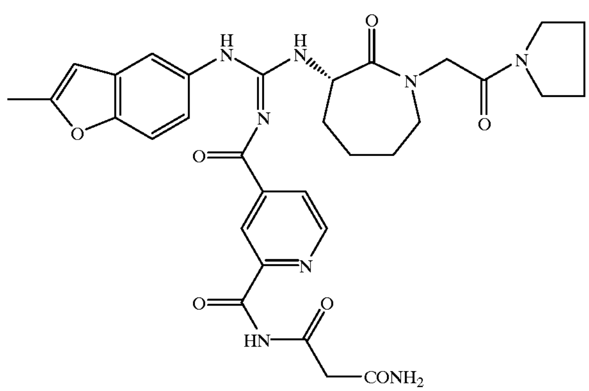 | HPLC (method A) $t_R$ = 3.8 min LRMS (ESI) m/z 617 (M + H) |
| 813 | 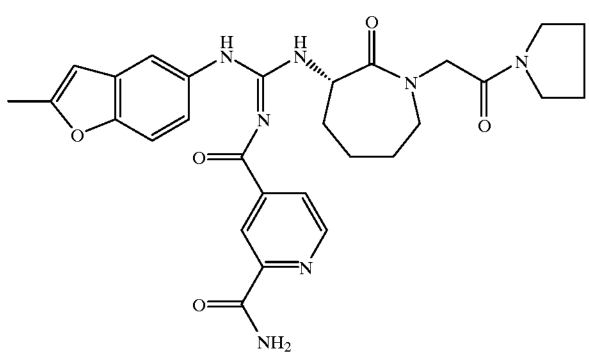 | HPLC (method A) $t_R$ = 4.0 min LRMS (ESI) m/z 560 (M + H) |
| 814 | 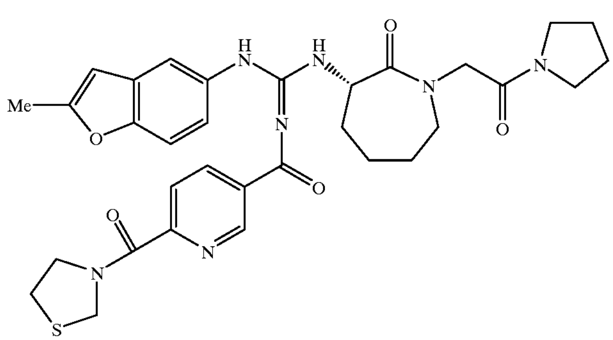 | HPLC (method A) $t_R$ = 4.2 min. LRMS (ESI) m/z 632 (M + H) |

-continued

| Example | structure | characterization |
|---|---|---|
| 815 | 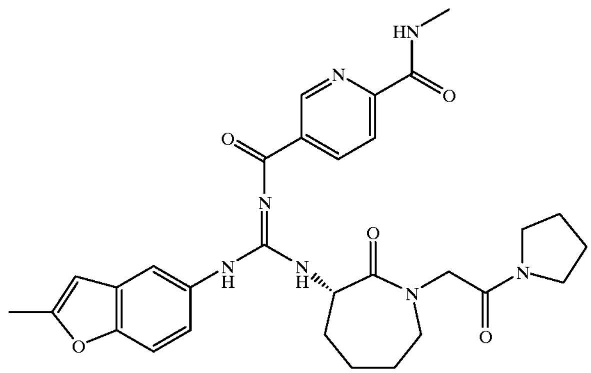 | HPLC (method A)<br>$t_R$ = 4.0 min<br>LRMS (ESI) m/z<br>574 (M + H) |
| 816 | 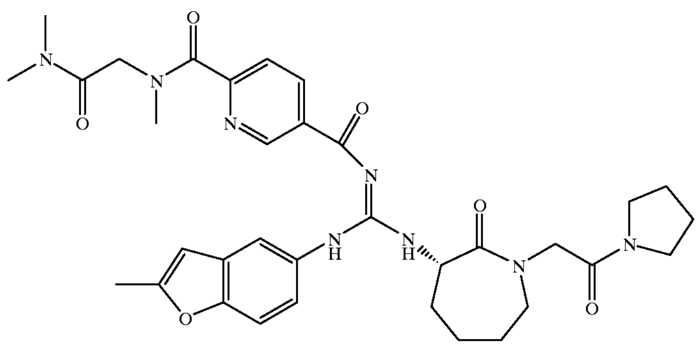 | HPLC (method A)<br>$t_R$ = 3.7 min<br>LRMS (ESI) m/z<br>659 (M + H) |
| 817 | 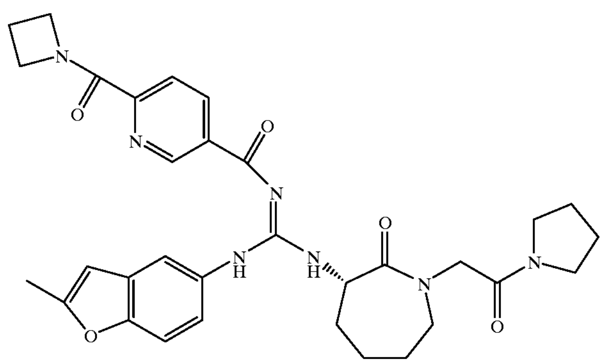 | HPLC (method A)<br>$t_R$ = 4.2 min<br>LRMS (ESI) m/z<br>600 (M + H) |
| 818 | 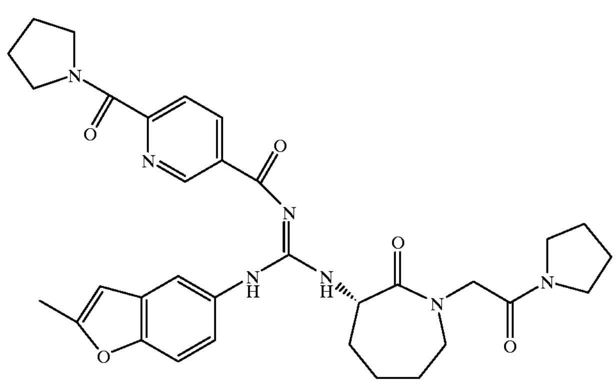 | HPLC (method A)<br>$t_R$ = 4.1 min<br>LRMS (ESI) m/z<br>614 (M + H) |

| Example | structure | characterization |
|---|---|---|
| 819 | 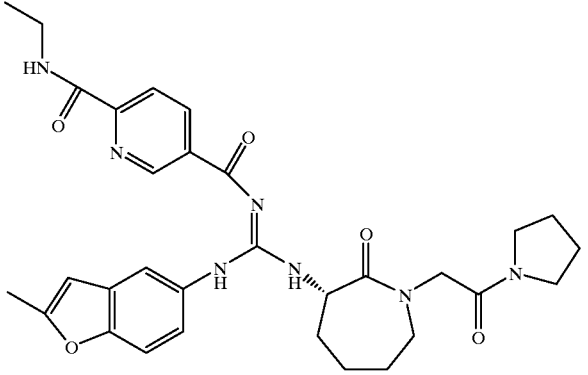 | HPLC (method A)<br>$t_R$ = 4.4 min<br>LRMS (ESI) m/z<br>588 (M + H) |
| 820 | 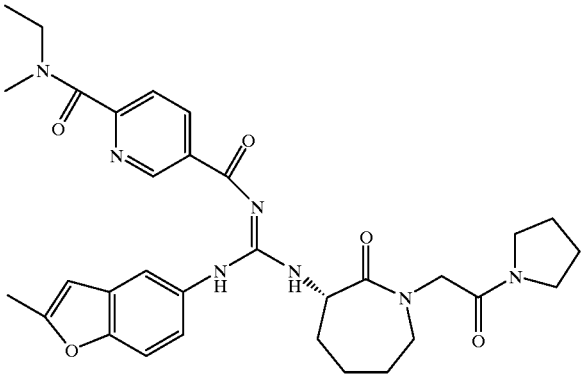 | HPLC (method A)<br>$t_R$ = 4.3 min<br>LRMS (ESI) m/z<br>602 (M + H) |
| 821 | 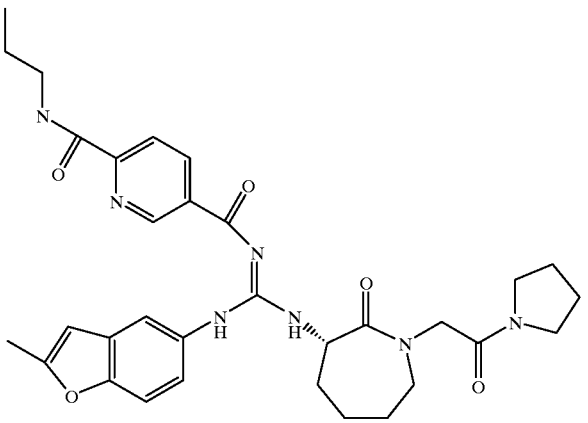 | HPLC (method A)<br>$t_R$ = 4.6 min<br>LRMS (ESI) m/z<br>602 (M + H) |

| Example | structure | characterization |
|---|---|---|
| 822 | 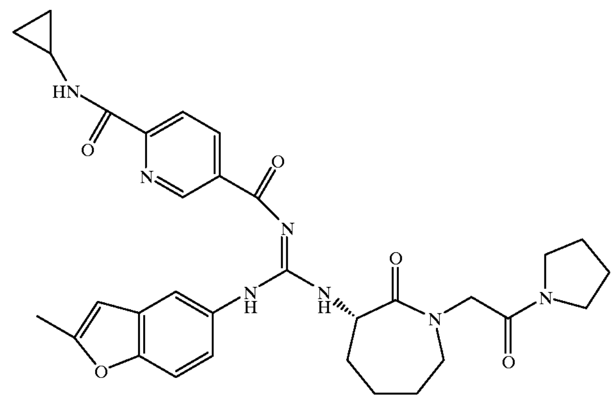 | HPLC (method A)<br>$t_R$ = 4.2 min<br>LRMS (ESI) m/z<br>600 (M + H) |
| 823 | 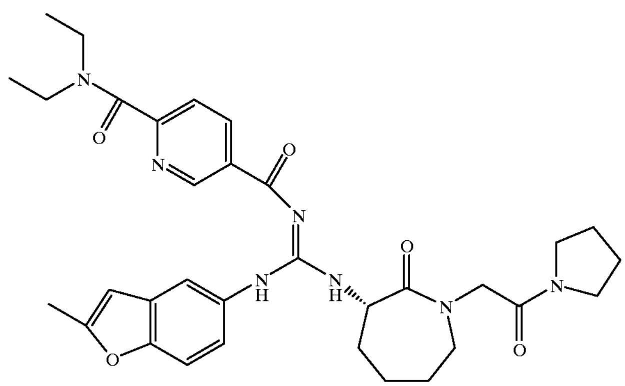 | HPLC (method A)<br>$t_R$ = 4.1 min<br>LRMS (ESI) m/z<br>616 (M + H) |
| 824 | 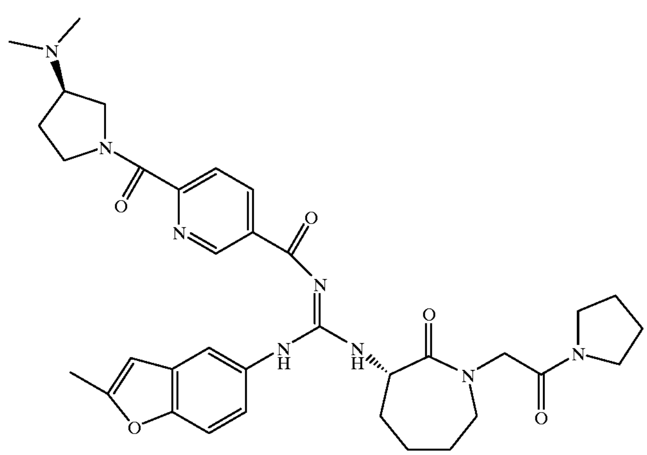 | HPLC (method A)<br>$t_R$ = 3.4 min<br>LRMS (ESI) m/z<br>657 (M + H) |

| Example | structure | characterization |
|---|---|---|
| 825 | 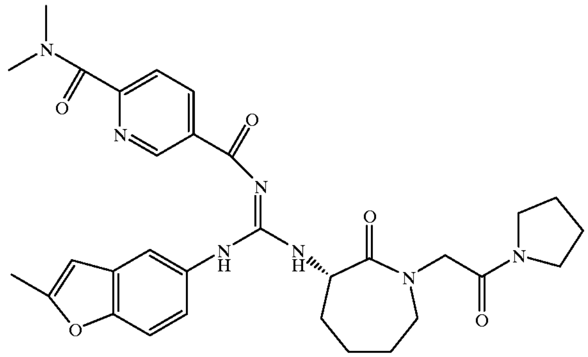 | HPLC (method A)<br>$t_R$ = 3.7 min<br>LRMS (ESI) m/z<br>589 (M + H) |
| 826 | 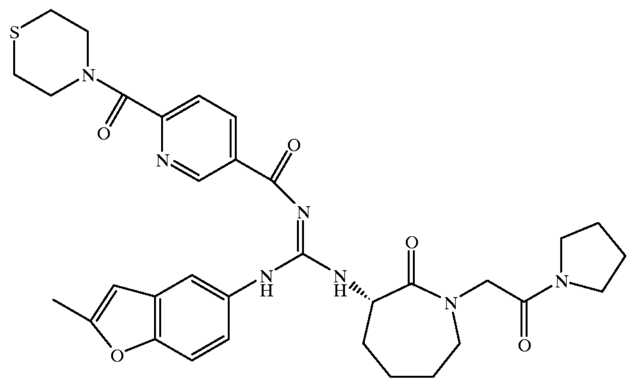 | HPLC (method A)<br>$t_R$ = 4.4 min<br>LRMS (ESI) m/z<br>646 (M + H) |

EXAMPLE 827

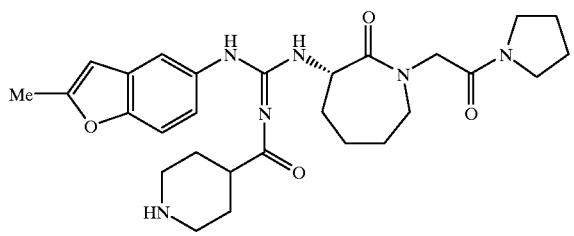

To a solution of Example 553 compound (3.60 g, 5.78 mmol) in dichloromethane (15 ml) was added trifluoroacetic acid (5 ml, 64.9 mmol). After stirring at room temperature for 2.5 h, the reaction mixture was diluted with dichloromethane, neutralized with saturated sodium bicarbonate and extracted with dichloromethane. The organic layers were washed with saturated sodium chloride, dried over magnesium sulfate and concentrated in vacuo to provide 2.93 g (97%) of Title compound as a yellow solid: LRMS (ESI) m/z 523 (M+H); HPLC (Method A) $t_R$=2.1 min.

EXAMPLES 828 to 830

Using the procedure described in Example 827, the following compounds were prepared. Sodium hydroxide was used for the neutralization in place of sodium bicarbonate.

| Example | Structure | characterization |
|---|---|---|
| 828 | 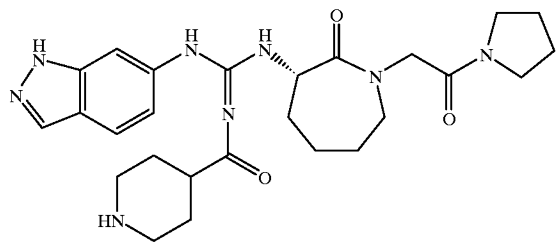 | HPLC (method A)<br>$t_R$ = 1.65 min<br>LRMS (ESI) m/z<br>509 (M + H) |
| 829 | 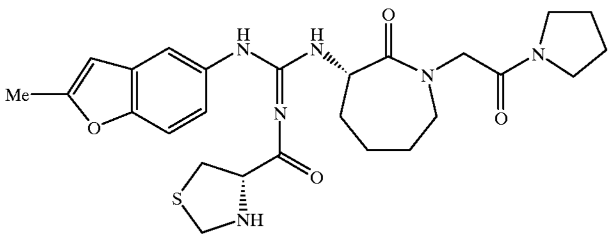 | HPLC (method A)<br>$t_R$ = 2.9 min<br>LRMS (ESI) m/z<br>527 (M + H) |
| 830 | 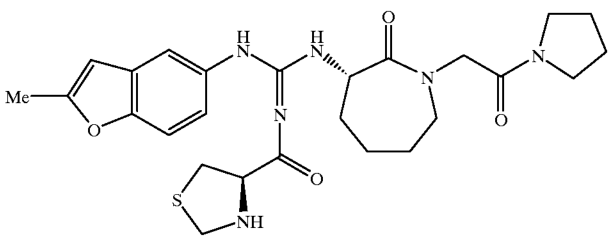 | HPLC (method A)<br>$t_R$ = 2.9 min<br>LRMS (ESI) m/z<br>527 (M + H) |

EXAMPLE 831

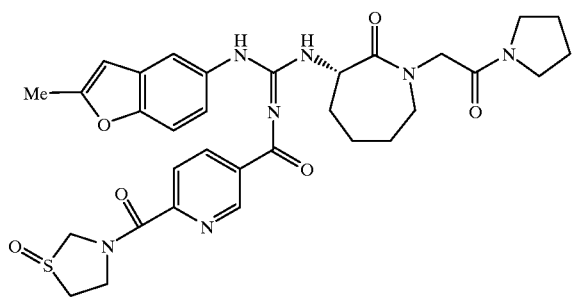

m-Chloroperbenzoic acid (85%, 11 mg, 0.05 mmol) was added to a solution of Example 814 compound (32 mg, 0.05 mmol) in methylene chloride (1.0 mL) at 0° C. The resulting solution was allowed to warm to room temperature and stirred at that temperature for 2 h. The reaction was diluted with methylene chloride, washed with saturated aqueous NaHCO$_3$, saturated aqueous NaCl, dried (MgSO$_4$) and concentrated. The residue was purified by flash chromatography (silica, 0% to 5% methanol in methylene chloride) to give Title compound (16 mg, 48%) as a white solid: HPLC (method A) $t_R$=4.1 min; LRMS (ESI) m/z 648 (M+1).

EXAMPLES 832 and 833

Using the method described in Example Example 831, the following compounds were prepared.

| Example | structure | characterization |
|---|---|---|
| 832 | 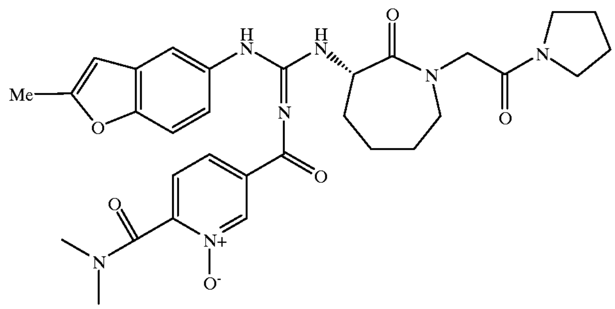 | HPLC (method A)<br>$t_R$ = 4.1 min.<br>LRMS (ESI) m/z<br>604 (M + H) |
| 833 | 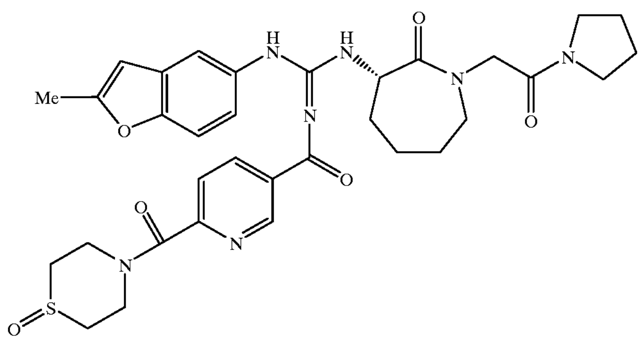 | HPLC (method A)<br>$t_R$ = 3.8 min.<br>LRMS (ESI) m/z<br>662 (M + H) |

EXAMPLE 834

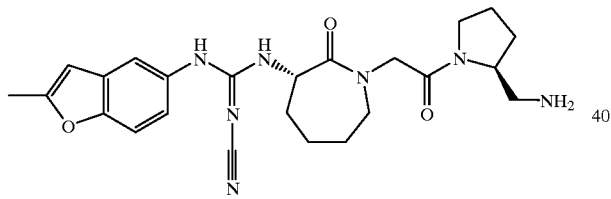

A mixture of Example 767 compound (0.63 g, 1.3 mmol) and 10% palladium on carbon in ethanol (12 mL) was stirred under a balloon of hydrogen at ambient temperature for 7.5 h. The mixture was filtered through Celite and the pad was rinsed with methanol. The filtrate was evaporated in vacuo to afford the Title compound (0.61 g, 100%): LRMS (ESI) m/z 466 (M+H); HPLC (Method A) $t_R$=3.0 min.

EXAMPLE 835

Using the procedure described in Example 834 the following compound was prepared.

| Example | structure | characterization |
|---|---|---|
| 835 | 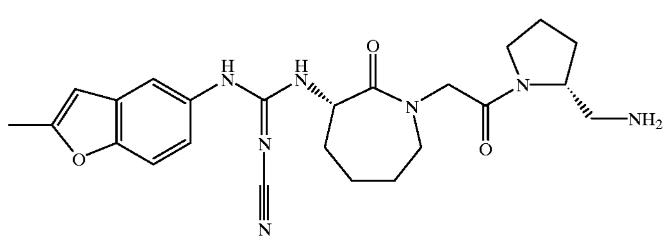 | HPLC (method A)<br>$t_R$ = 3.3 min<br>LRMS (ESI) m/z<br>466 (M + H) |

EXAMPLE 836

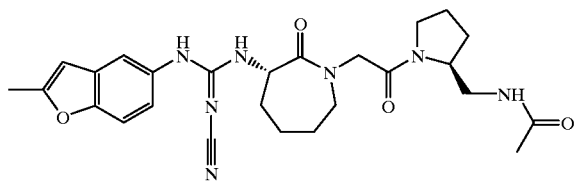

N-Acetylimidazole (25 mg, 0.22 mmol) was added to a solution of Example 834 compound (93 mg, 0.20 mmol) in DMF (0.5 mL). After stirring at ambient temperature for 4 h, the reaction was transferred to a separatory funnel with dichloromethane/water. Extraction with dichloromethane (2×) and drying over $MgSO_4$ afforded crude product after concentration in vacuo. Flash chromatography (silica, 15 mm dia column, 5% methanol/dichloromethane) afforded the Title compound (70 mg, 69%): LRMS (ESI) m/z 508 (M+H); HPLC (Method A) $t_R$=3.7 min.

EXAMPLES 837 and 838

Using the procedure described in Example 836 the following compounds were prepared.

| Example | structure | characterization |
|---|---|---|
| 837 | 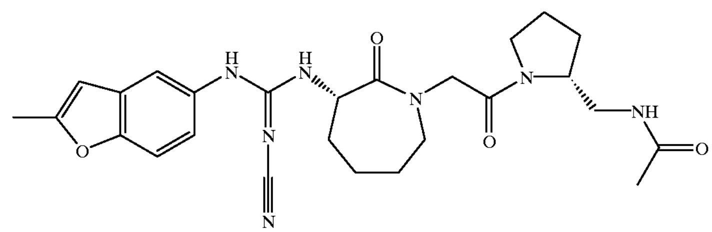 | HPLC (method A) $t_R$ = 3.4 min LRMS (ESI) m/z 508 (M + H) |
| 838 | 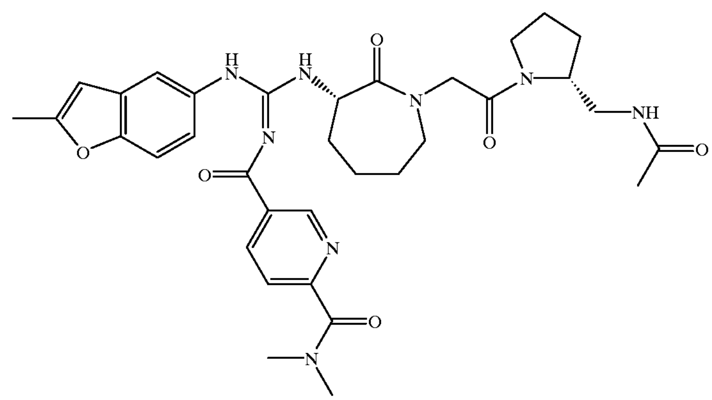 | HPLC (method D) $t_R$ = 3.6 min LRMS (ESI) m/z 659 (M + H) |

EXAMPLE 839

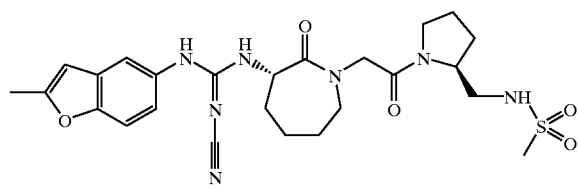

Methanesulfonyl chloride (25 mg, 0.017 mL, 0.22 mmol) was added to a solution of Example 843 compound (93 mg, 0.20 mmol) and triethylamine (30 mg, 0.042 mL, 0.30 mmol) in dichloromethane (0.5 mL) stirring at 0° C. After stirring at ambient temperature for 3.5 h, the reaction was transferred to a separatory funnel with dichloromethane/water. Extraction with dichloromethane (2×) and drying over $MgSO_4$ afforded crude product after concentration in vacuo. Flash chromatography (silica, 15 mm dia column, 4% methanol/dichloromethane) afforded the Title compound (65 mg, 60%): LRMS (ESI) m/z 544 (M+H); HPLC (Method A) $t_R$=3.6 min.

EXAMPLES 840–847

Using the procedure described in Example 839 the following compounds were prepared. In some cases methanol/ethyl acetate was used for chromatography.

| Example | structure | characterization |
|---|---|---|
| 840 | 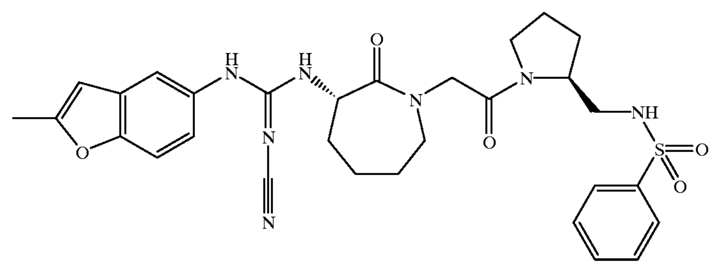 | HPLC (method A) $t_R$ = 4.1 min LRMS (ESI) m/z 606 (M + H) |
| 841 | 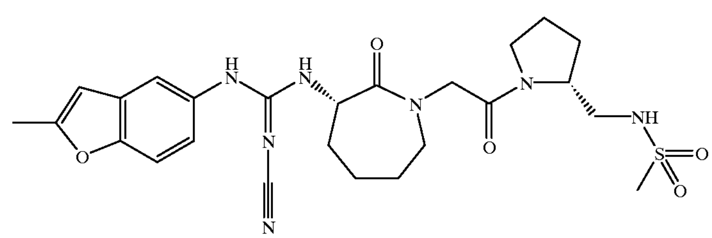 | HPLC (method A) $t_R$ = 3.5 min LRMS (ESI) m/z 544 (M + H) |
| 842 | 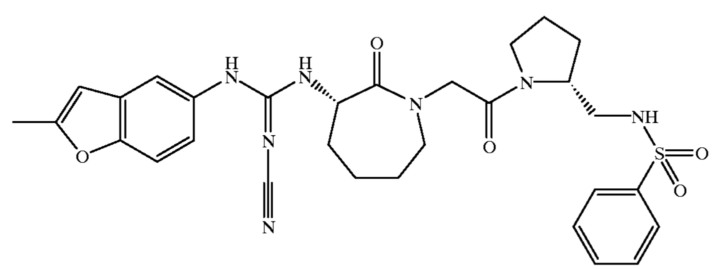 | HPLC (method A) $t_R$ = 3.8 min LRMS (ESI) m/z 606 (M + H) |

-continued

| Example | structure | characterization |
|---|---|---|
| 843 | 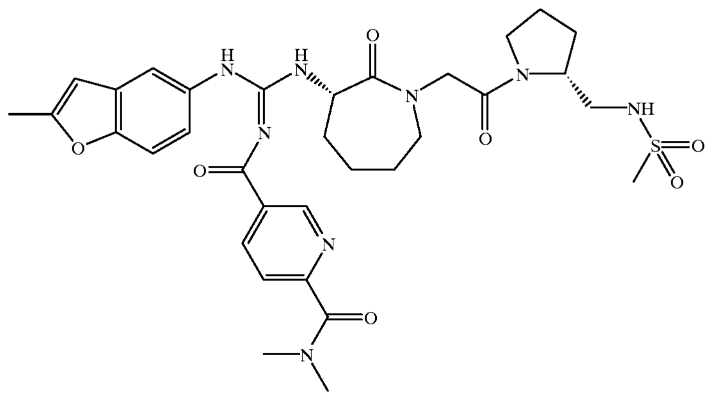 | HPLC (method D)<br>$t_R$ = 3.6 min<br>LRMS (ESI) m/z<br>695 (M + H) |
| 844 | 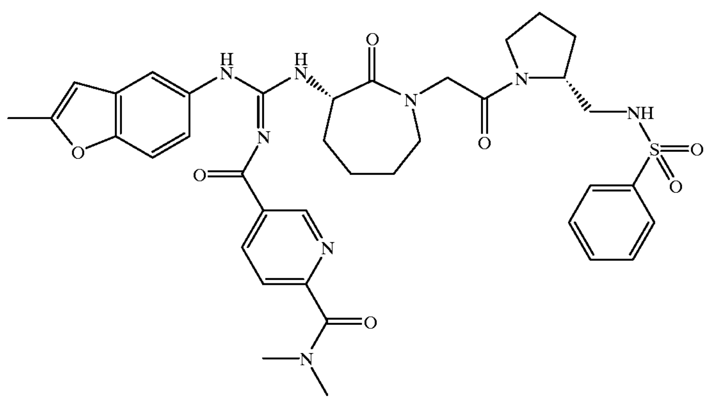 | HPLC (method D)<br>$t_R$ = 4.0 min<br>LRMS (ESI) m/z<br>757 (M + H) |
| 845 | 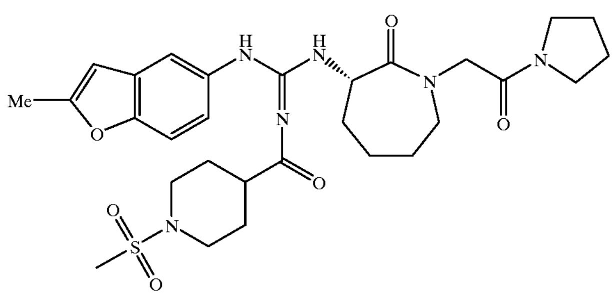 | HPLC (method A)<br>$t_R$ = 2.7 min<br>LRMS (ESI) m/z<br>601 (M + H) |
| 846 | 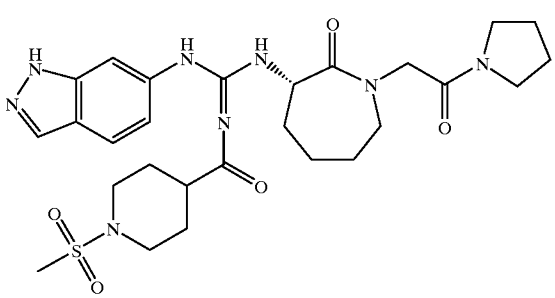 | HPLC (method A)<br>$t_R$ = 2.3 min<br>LRMS (ESI) m/z<br>587 (M + H) |

| Example | structure | characterization |
|---|---|---|
| 847 | 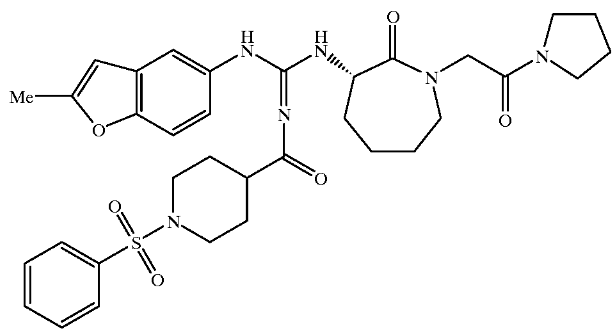 | HPLC (method A)<br>$t_R$ = 3.1 min<br>LRMS (ESI) m/z<br>663 (M + H) |

EXAMPLE 848

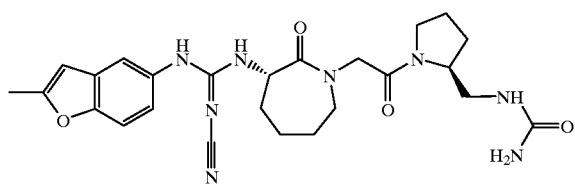

Trimethylsilylisocyanate (29 mg, 0.034 mL, 0.21 mmol) was added to a solution of Example 834 compound (93 mg, 0.20 mmol) in dichloromethane (0.5 mL). After stirring at ambient temperature for 3.5 h, the reaction was transferred to a separatory funnel with dichloromethane/water. Extraction with dichloromethane (2×) and drying over $MgSO_4$ afforded crude product after concentration in vacuo. Flash chromatography (silica, 15 mm dia column, 7% methanol/dichloromethane) afforded the Title compound (55 mg, 54%): LRMS (ESI) m/z 509 (M+H); HPLC (Method A) $t_R$=3.6 min.

EXAMPLES 849 to 852

Using the procedure described in Example 848 the following can be prepared.

| Example | structure | characterization |
|---|---|---|
| 849 | 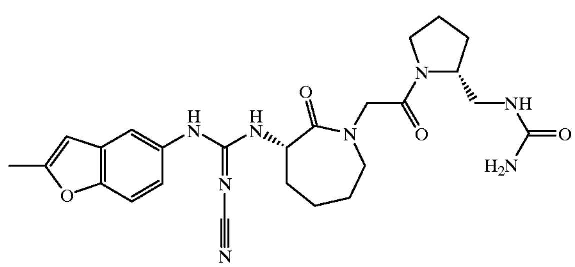 | HPLC (method A)<br>$t_R$ = 3.4 min<br>LRMS (ESI) m/z<br>509 (M + H) |
| 850 | 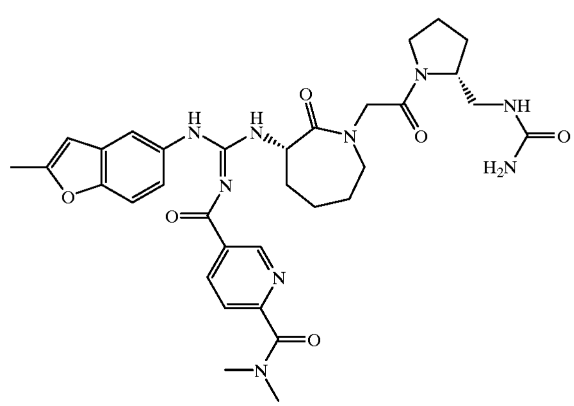 | HPLC (method D)<br>$t_R$ = 3.5 min<br>LRMS (ESI) m/z<br>660 (M + H) |

| Example | structure | characterization |
|---|---|---|
| 851 | 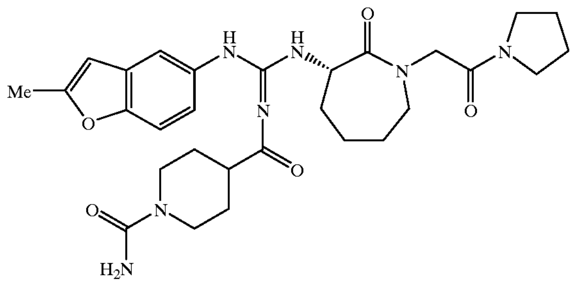 | HPLC (method A) $t_R$ = 2.5 min LRMS (ESI) m/z 566 (M + H) |
| 852 | 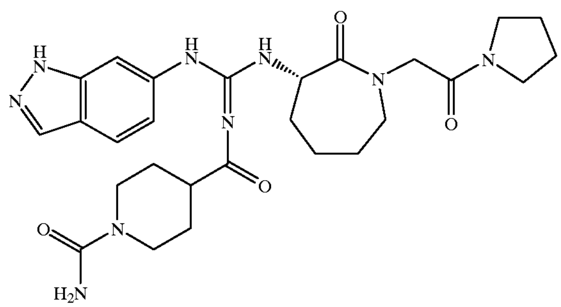 | HPLC (method A) $t_R$ = 2.1 min LRMS (ESI) m/z 552 (M + H) |

EXAMPLE 853

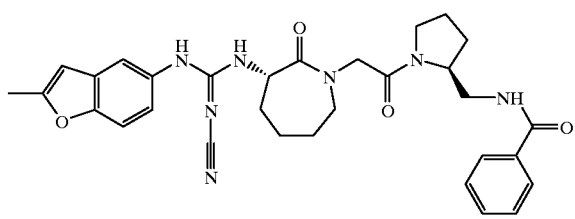

To a solution of benzoic acid (20 mg, 0.16 mmol) in dichloromethane (1.0 mL) was added WSC (51 mg, 0.26 mmol) and 1-hydroxybenzotriazole (HOBT, 22 mg, 0.16 mmol). After stirring at ambient temperature for 30 min, Example 843 compound (0.81 g, 0.17 mmol) was added. After stirring at ambient temperature for 4 h, the reaction was transferred to a separatory funnel with dichloromethane/water. Extraction with dichloromethane (2×), and drying over MgSO$_4$ afforded crude product after evaporation of the solvent. Flash chromatography (silica, 15 mm dia column, 2% methanol/dichloromethane) afforded the Title compound (56 mg, 61%): LRMS (ESI) m/z 570 (M+H); HPLC (Method A) $t_R$=4.1 min.

EXAMPLES 854 to 858

Using the procedure described in Example 853 the following compounds were prepared.

| Example | structure | characterization |
|---|---|---|
| 854 | 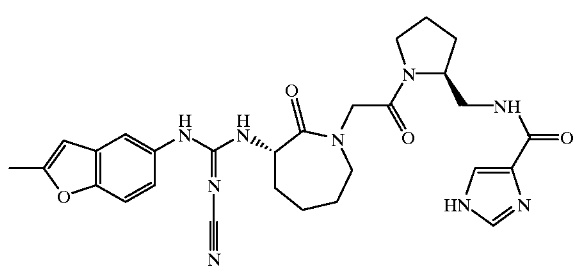 | HPLC (method A) $t_R$ = 3.2 min LRMS (ESI) m/z 560 (M + H) |

-continued

| Example | structure | characterization |
|---------|-----------|------------------|
| 855 | 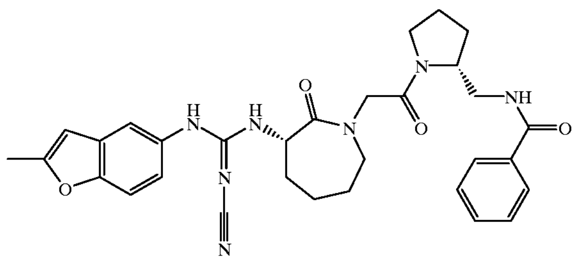 | HPLC (method A) $t_R$ = 3.9 min LRMS (ESI) m/z 570 (M + H) |
| 856 | 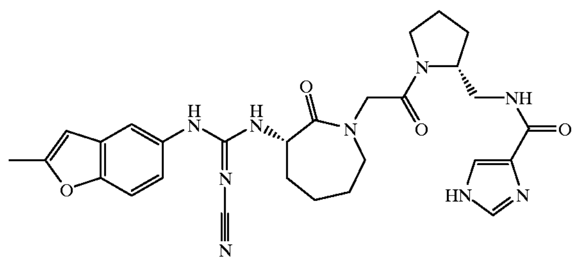 | HPLC (method A) $t_R$ = 3.9 min LRMS (ESI) m/z 570 (M + H) |
| 857 | 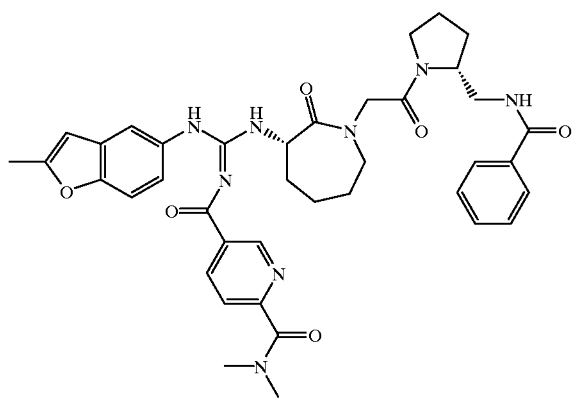 | HPLC (method D) $t_R$ = 4.0 min LRMS (ESI) m/z 721 (M + H) |
| 858 | 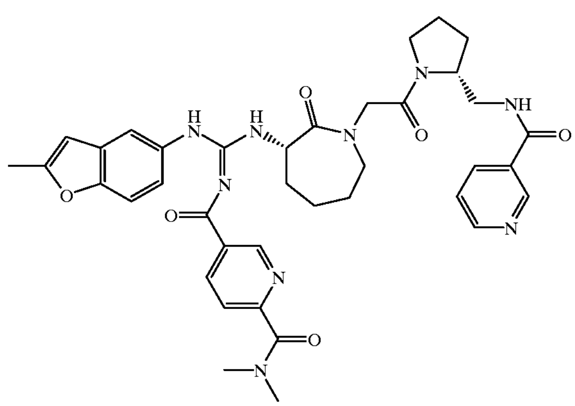 | HPLC (method D) $t_R$ = 3.6 min LRMS (ESI) m/z 722 (M + H) |

EXAMPLE 859

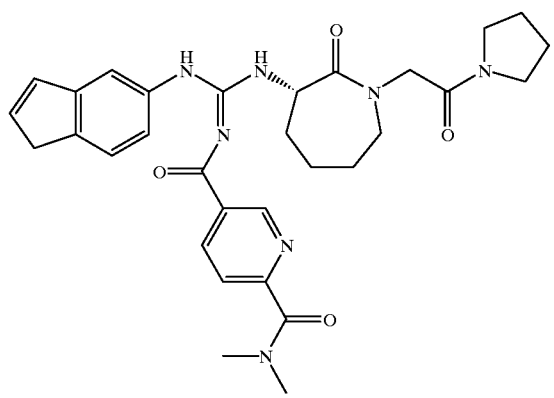

A.

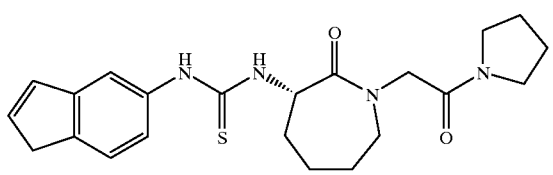

Part A compound was prepared from 1H-indene-5-amine using the procedures described in Example 335 parts A and B: LCMS (ESI, conditions F) m/z 413 (M+H), $t_R$=2.9 min.

B.

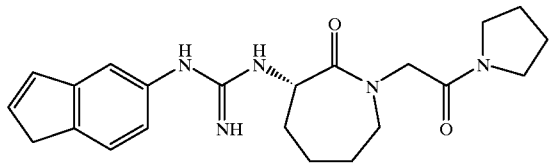

Part B compound was prepared from part A compound using the procedure described in Example 496 part A: LC-MS (ESI, conditions) m/z 396 (M+H), $t_R$=2.3 min.

C.

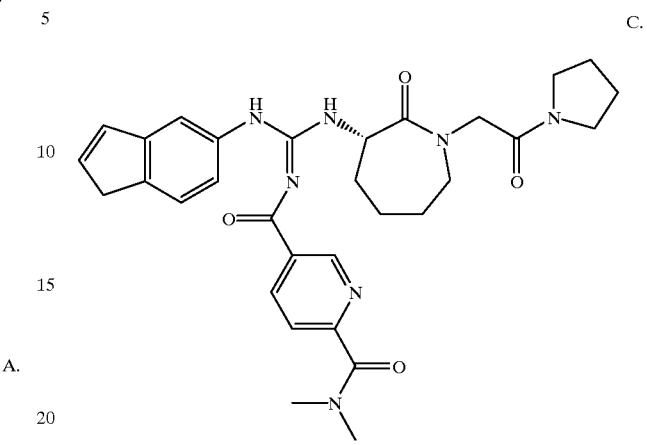

Title compound was prepared from part B compound and 6-[(dimethylamino)carbonyl]-3-pyridinecarboxylic acid using the procedure as described in Example 769. The crude reaction product was purified by preparative HPLC (YMC Pack ODSA S5, 30×250 mm, 25 mL/min; solvent A=10% MeOH/H$_2$O+0.% TFA, B=90% MeOH/H$_2$O+0.1% TFA; 30% B to 100% B over 20 min and 100% B for 20 min.) The product-containing fractions were evaporated after adding saturated sodium bicarbonate (1 mL). The residue was transferred to a separatory funnel with water/ dichloromethane. Extraction with dichloromethane (2×) and drying over MgSO$_4$ afforded Title compound: LRMS (ESI) m/z 572 (M+H); HPLC (Method A) $t_R$=4.4 min.

EXAMPLES 860 to 862

Using the procedure described in Example 859 the following compounds were prepared.

| Example | structure | characterization |
|---|---|---|
| 860 | 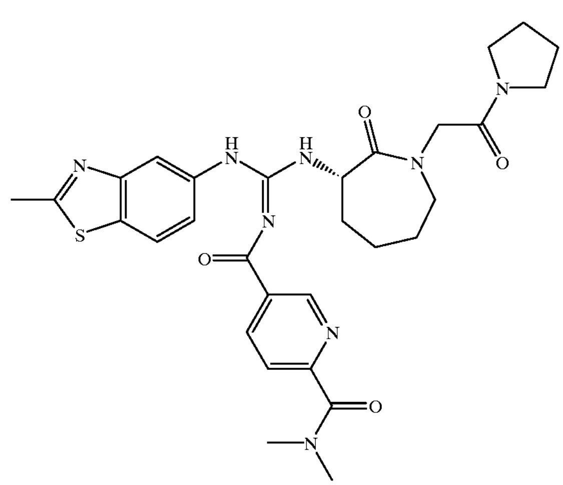 | HPLC (method A) $t_R$ = 4.2 min LRMS (ESI) m/z 605 (M + H) |

-continued

| Example | structure | characterization |
|---|---|---|
| 861 | 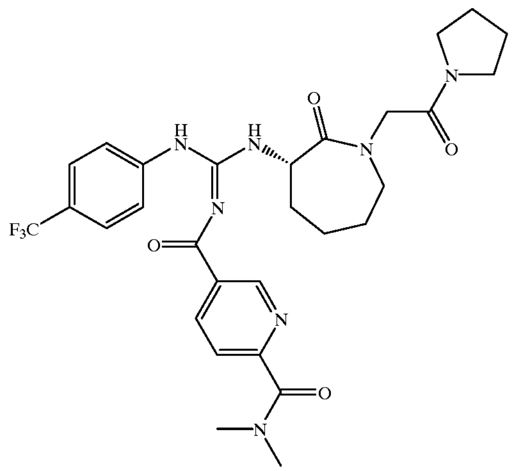 | HPLC (method A)<br>$t_R$ = 4.7 min<br>LRMS (ESI) m/z<br>602 (M + H) |
| 862 | 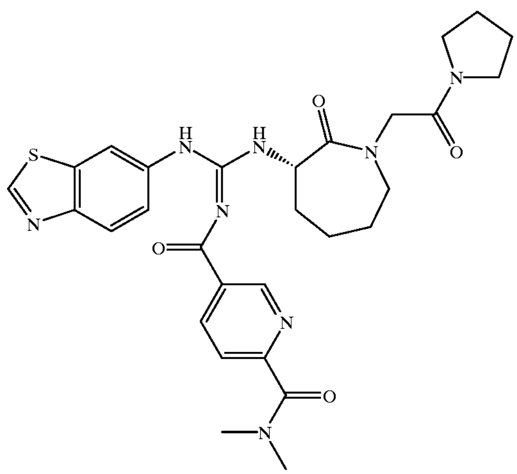 | HPLC (method A)<br>$t_R$ = 3.1 min<br>LRMS (ESI) m/z<br>591 (M + H) |

EXAMPLE 863

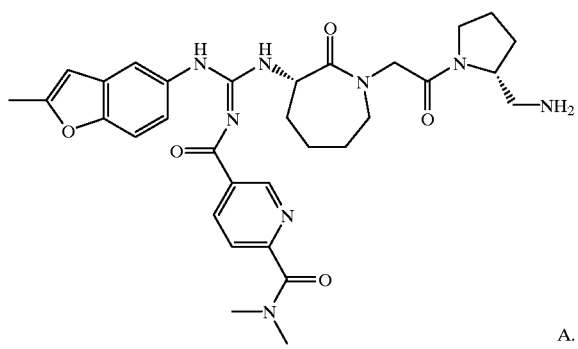

To a solution of (3S)-3-[[(1,1-dimethylethoxy)carbonyl]amino]hexahydro-2-oxo-1H-Azepine-1-acetic acid (1.0 g, 3.6 mmol) in dichloromethane (28.0 mL) was added WSC (1.1 g, 5.9 mmol) and 1-hydroxybenzotriazole (HOBT, 0.50 g, 3.7 mmol). After stirring at ambient temperature for 30 min, (2S)-2-(azidomethyl)pyrrolidine (0.49 g, 3.9 mmol) was added. After stirring at ambient temperature for 3.5 h, the reaction was transferred to a separatory funnel with dichloromethane/water. Extraction with dichloromethane (2×), and drying over MgSO$_4$ afforded crude product after evaporation of the solvent. Flash chromatography (silica, 25 mm dia column, 3% methanol/dichloromethane) afforded part A compound (1.4 g, 92%): HPLC (Method A) $t_R$=3.7 min.

A.

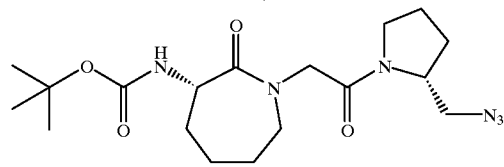

B.

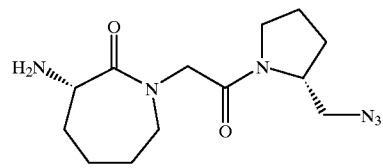

Part B compound was prepared from part A compound using procedures described in Example 741: HPLC (Method A) $t_R$=1.4 min.

C.

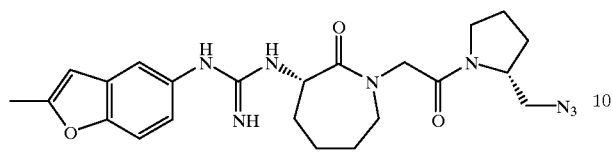

Part C compound was prepared from part B compound and 2-methyl-5-isothiocyanatobenzofuran using the procedures described in Example 335 part B and Example 496 part A: HPLC (Method A) $t_R$=3.2 min.

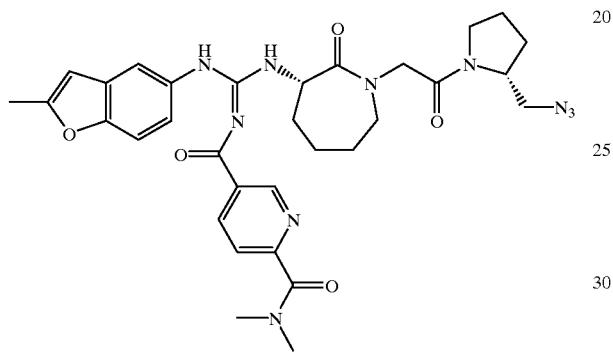

Part D compound was prepared from part C compound using the procedure described in Example 496 part C: HPLC (Method D) $t_R$=4.0 min.

E

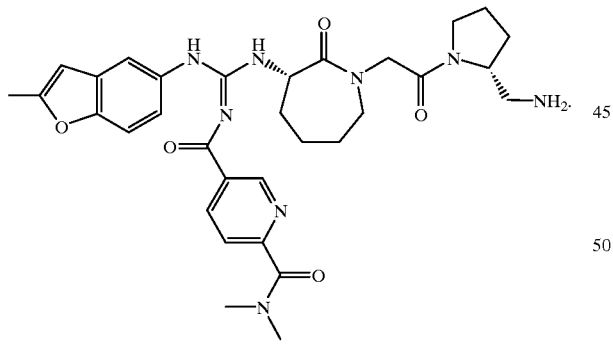

Title compound was prepared from part D compound using the procedure described in Example 834: LC-MS (ESI, conditions F) m/z 617 (M+H), $t_R$=3.3 min.

In the formulas shown above, the bond such as

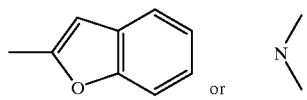

represents a methyl group, i.e.

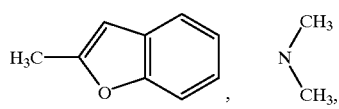

the bond such as

represents an ethyl group, i.e. $NH—C_2H_5$, etc.

What is claimed is:

1. A compound having the formula

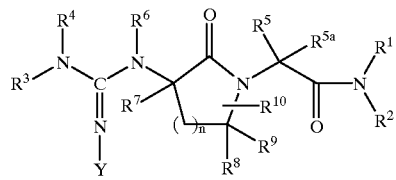

or a pharmaceutically acceptable salt thereof, or all stereoisomers thereof, wherein n is 3;

Y is selected from hydrogen, alkyl, substituted alkyl, alkenyl, substituted alkenyl, alkynyl, substituted alkynyl, aryl, cycloalkyl, heteroaryl, cycloheteroalkyl, cyano, nitro, hydroxy, amino, $—OR_a$, $—SR_a$,

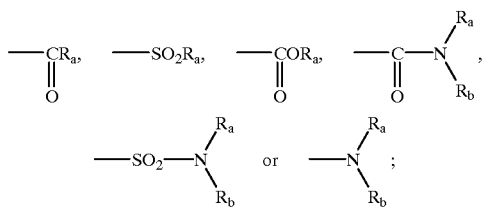

$R^1$, $R^2$, $R^4$, $R^6$, $R^8$, and $R^9$ are the same or different and are independently selected from hydrogen, alkyl, substituted alkyl, alkenyl, substituted alkenyl, alkynyl, substituted alkynyl, aryl, heteroaryl, cycloheteroalkyl, cycloalkyl, alkylcarbonyl, arylcarbonyl, cycloalkylcarbonyl, substituted alkylcarbonyl, cycloheteroalkylcarbonyl and heteroarylcarbonyl;

$R^3$ is hydrogen, alkyl, substituted alkyl, alkenyl, substituted alkenyl, alkynyl, substituted alkynyl, aryl, heteroaryl, cycloalkyl, cycloheteroalkyl, cyano, nitro, hydroxy, $—OR_a$, $—SR_a$,

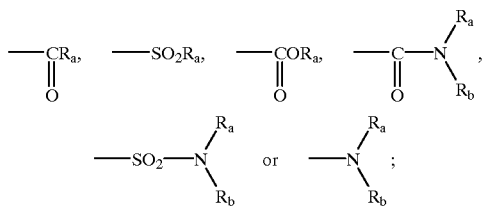

$R^5$, $R^{5a}$, and $R^7$ are the same or different and are independently selected from hydrogen, halogen, alkyl, substituted alkyl, alkenyl, substituted alkenyl, alkynyl, substituted alkynyl, heteroaryl, cycloalkyl, aryl, cycloheteroalkyl,

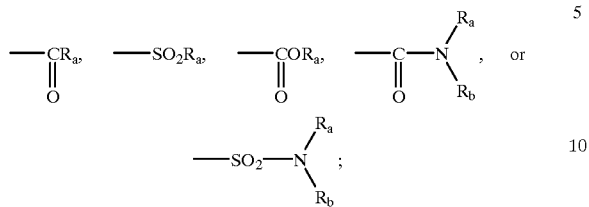

$R^{10}$ is selected from hydrogen, halogen, alkyl, substituted alkyl, alkenyl, substituted alkenyl, alkynyl, substituted alkynyl, aryl, heteroaryl, cycloalkyl, alkylcarbonyl, arylcarbonyl, cycloheteroalkyl, cycloalkylcarbonyl, substituted alkyl-carbonyl, cycloheteroalkylcarbonyl, heteroarylcarbonyl,

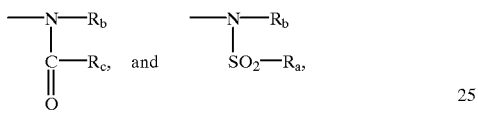

or when $R^9$ is hydrogen and $R^8$ and $R^{10}$ are on adjacent carbons they join to complete a cycloalkyl or phenyl ring;

$R_a$ and $R_b$ are the same or different and are independently selected from hydrogen, alkyl, substituted alkyl, alkenyl, substituted alkenyl, alkynyl, substituted alkynyl, aryl, heteroaryl, cycloheteroalkyl, cycloalkyl, alkylcarbonyl, arylcarbonyl, cycloalkylcarbonyl, substituted alkylcarbonyl, cycloheteroalkylcarbonyl, heteroarylcarbonyl, aminocarbonyl, alkylaminocarbonyl and dialkylaminocarbonyl;

$R_c$ is hydrogen, halogen, alkyl, substituted alkyl, alkenyl, substituted alkenyl, aryl, heteroaryl, cycloalkyl, cycloheteroaryl,

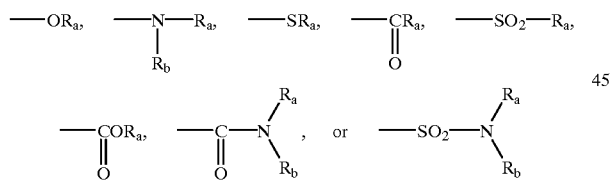

and wherein $R^1$ and $R^2$, and/or $R_a$ and $R_b$ can be taken together with the nitrogen to which they are attached to form a cycloheteroalkyl ring or a heteroaryl ring; and $R^5$ and $R^{5a}$ can be taken together to the carbon to which they are attached to form a cycloalkyl ring, a heteroaryl ring or a cycloheteroalkyl ring; and where one or more of $R^3$, $R^4$ or $R^6$ are H, then double bond isomers which may be formed.

2. A compound of claim 1 wherein:

$R^1$ and $R^2$ are the same or different and are selected from alkyl, substituted alkyl, alkenyl, substituted alkenyl, cycloalkyl, and cycloheteroalkyl or $R^1$ and $R^2$ taken together with the nitrogen to which they are attached form a cycloheteroalkyl ring;

$R^3$ is hydrogen, alkyl, substituted alkyl, alkenyl, substituted alkenyl, aryl, heteroaryl or cycloheteroalkyl;

Y is cyano, nitro, aryl, heteroaryl, cycloheteroalkyl,

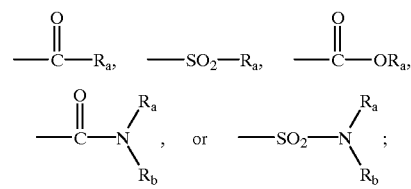

$R_a$ and $R_b$ are the same or different and are hydrogen, alkyl, substituted alkyl, alkenyl, substituted alkenyl, aryl, heteroaryl or cycloheteroalkyl;

$R^4$, $R^5$, $R^{5a}$, $R^6$, $R^7$, $R^8$, $R^9$ and $R^{10}$ are each hydrogen; and the configuration at the chiral center is S— (as judged where $R^7$ is hydrogen).

3. A compound of claim 2 wherein:

$R^1$ and $R^2$ taken together with nitrogen to which they are attached complete a pyrrolidyl, substituted pyrrolidyl, or pyrrolidyl having a fused cycloalkyl ring;

$R^3$ is aryl;

Y is cyano, heteroaryl,

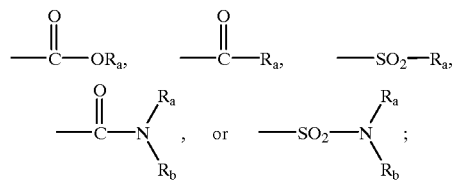

$R_a$ and $R_b$ are the same or different and are hydrogen, alkyl, aminocarbonyl, heteroaryl, aryl, or cycloheteroalkyl;

$R^4$, $R^5$, $R^{5a}$, $R^6$, $R^7$, $R^8$, $R^9$ and $R^{10}$ are each hydrogen; and the configuration at the chiral center is S— (as judged where $R^7$ is hydrogen).

4. A compound of claim 3 wherein:

$R^3$ is a substituted benzofuranyl ring.

5. A compound of claim 4 wherein:

$R^3$ is

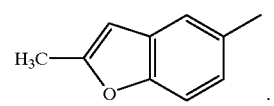

6. A compound of claim 3 wherein:

$R^1$ and $R^2$ taken together with the nitrogen to which they are attached are

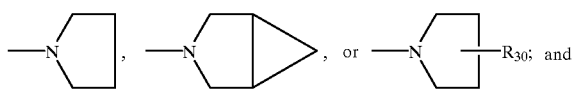

$R_{30}$ is $H_3C-C(O)-N(CH3)-$

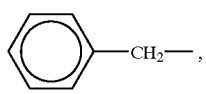

$H_2N-CH_2-$, $H_3C-C(O)-NH-CH_2-$, and $H_2N-C(O)-NH-CH_2-$.

7. A compound of claim 6 wherein:

$R^1$ and $R^2$ taken together with the nitrogen to which they are attached are

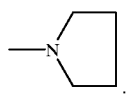

8. A compound of claim 3 wherein:
Y is cyano.

9. A compound of claim 3 wherein:
Y is a heteroaryl ring selected from

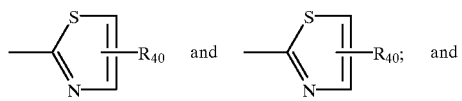

$R_{40}$ is hydrogen or $H_3C-NH-C(O)-$.

10. A compound of claim 3 wherein:

Y is $-C(O)-O-$(lower alkyl), $-C(O)-R_a$, $-C(O)-N-$(lower alkyl)$_2$, or $-C(O)-NH-C(O)-NH_2$; and $R_a$ is heteroaryl, aryl or cycloheteroaryl.

11. A compound of claim 10 wherein:
$R_a$ is

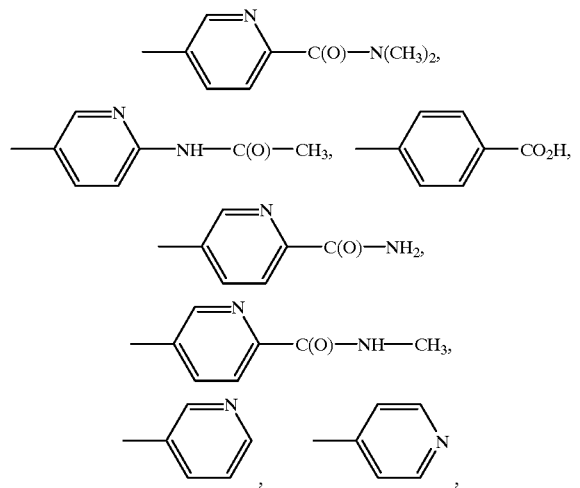

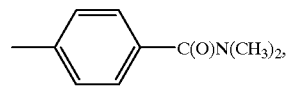

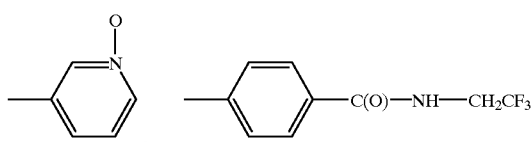

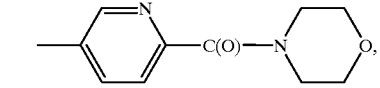

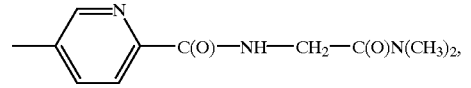

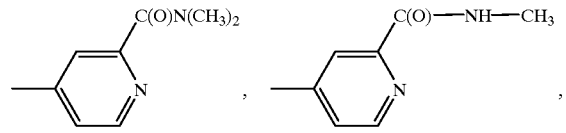

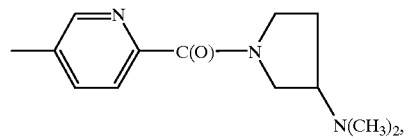

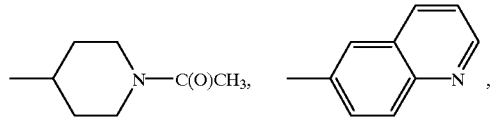

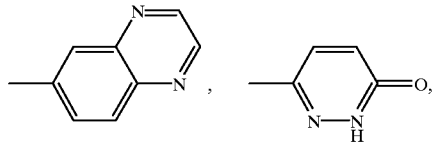

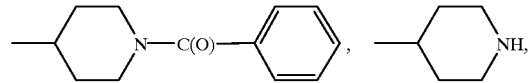

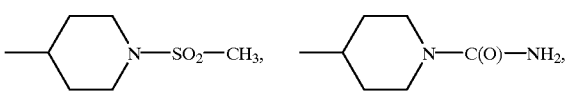

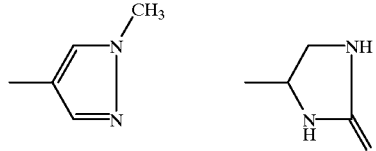

, or

12. A compound of claim 11 wherein: $R_a$ is

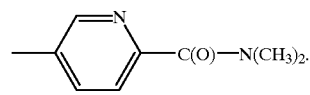

13. A compound of claim 3 wherein:
Y is $SO_2NH_2$ or $SO_2-CH_3$.

14. A compound of claim 1 of the formula:
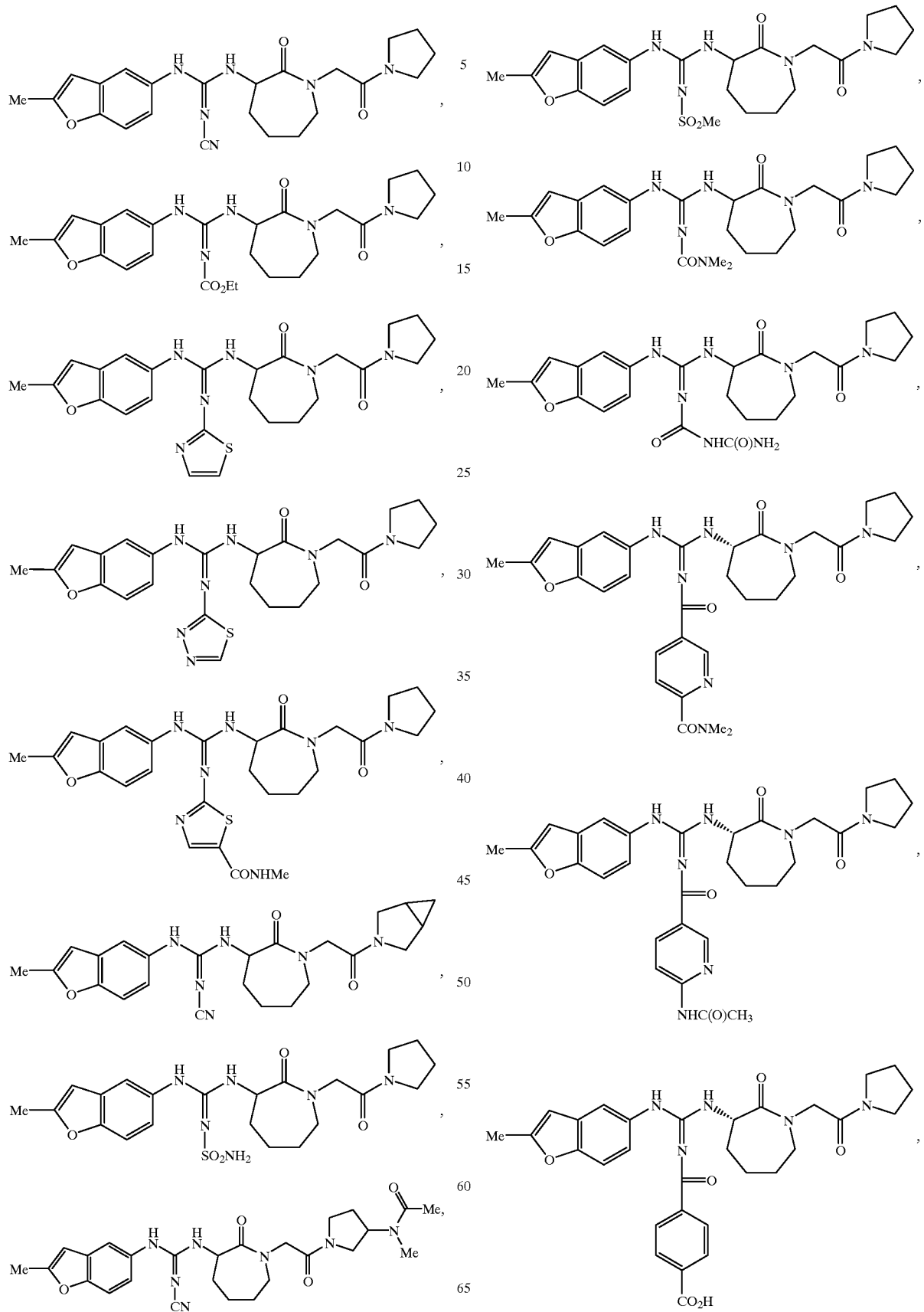

425
-continued
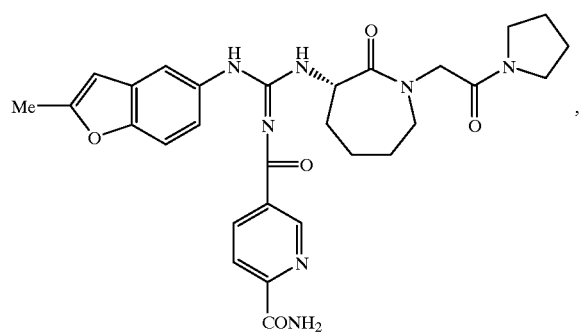
,
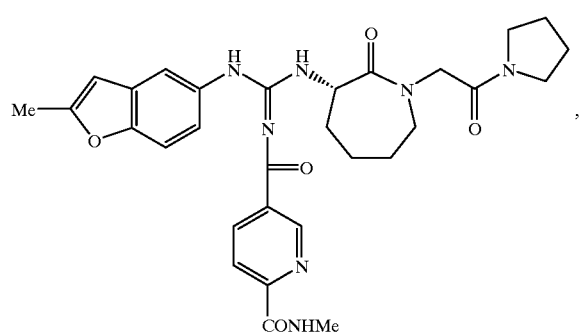
,
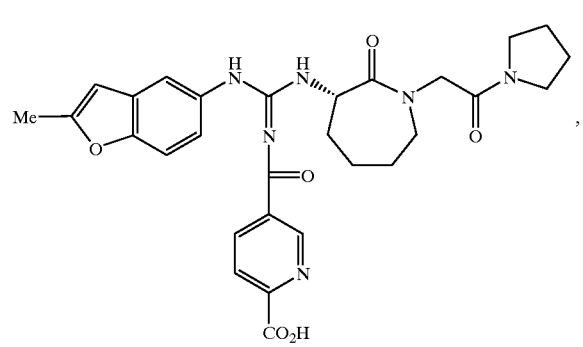
,
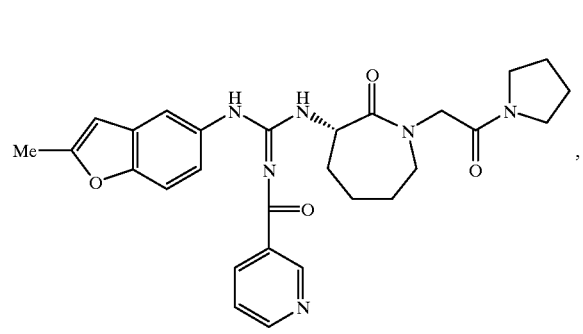
,
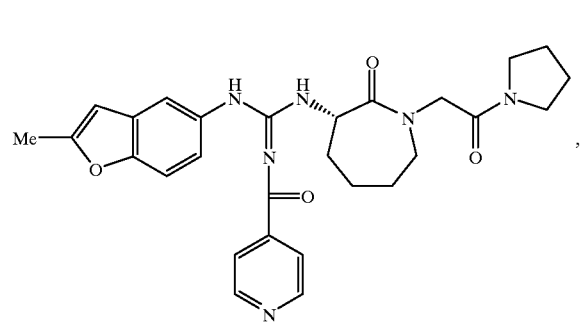
,
426
-continued
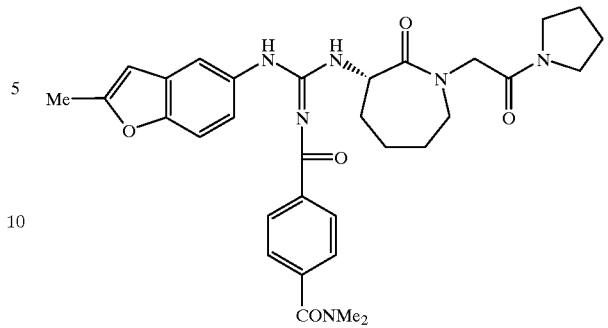
,
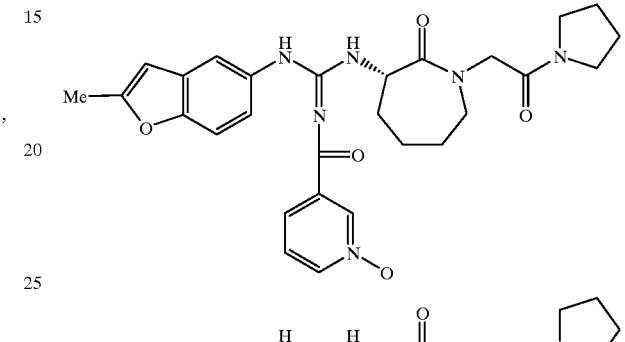
,
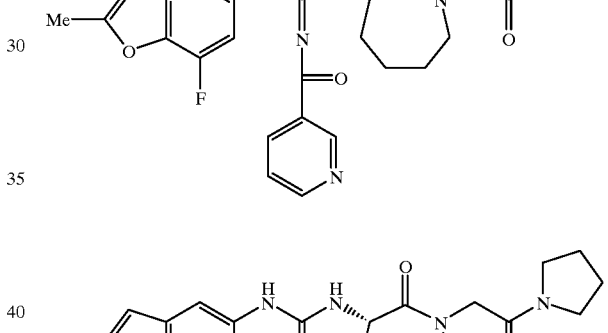
,
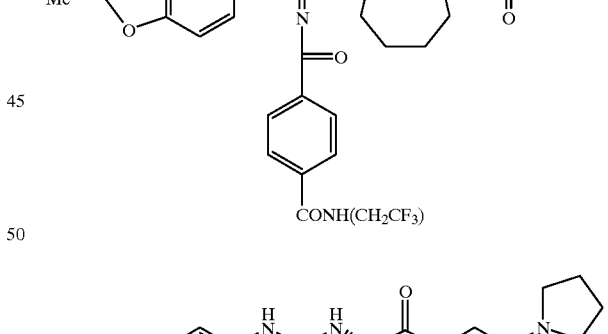
,
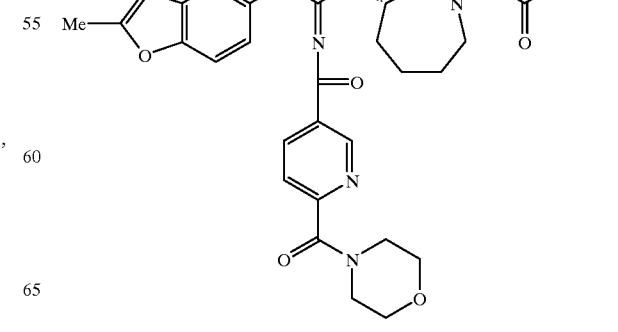
, 427
-continued
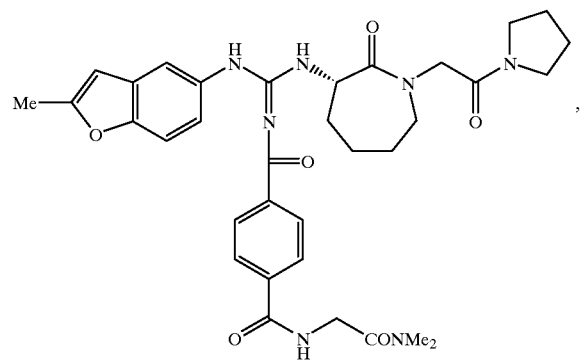,
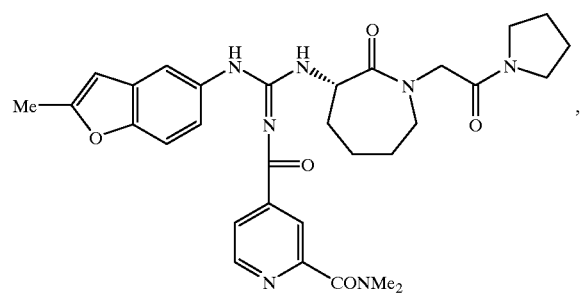,
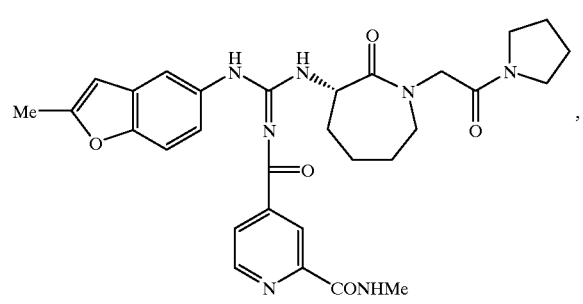,
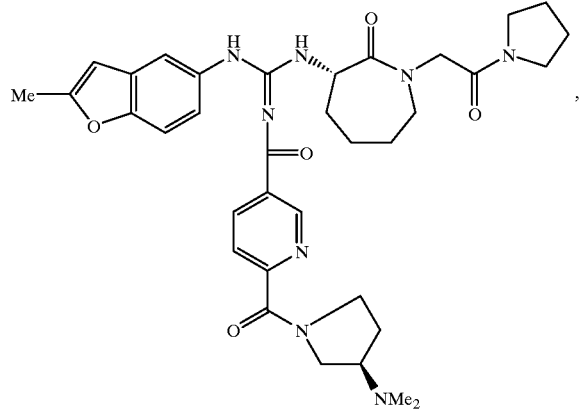,
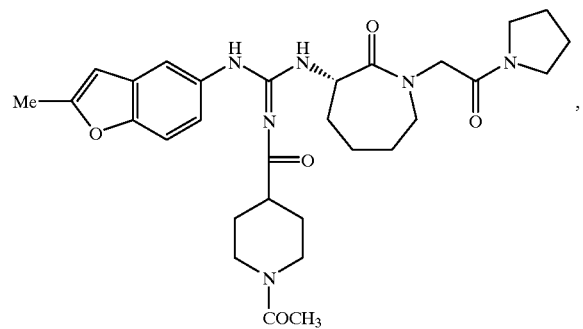,
428
-continued
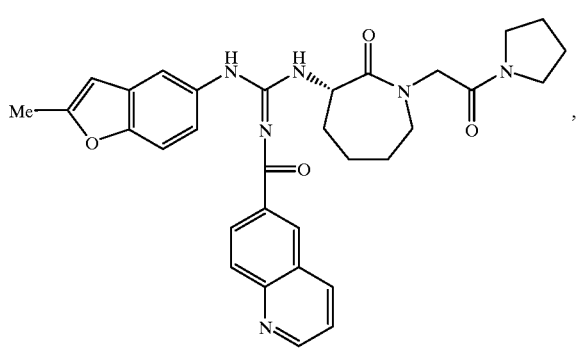,
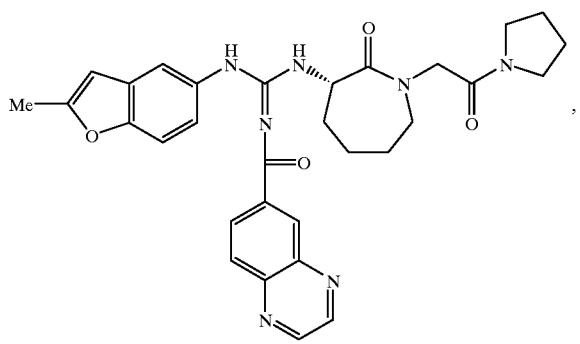,
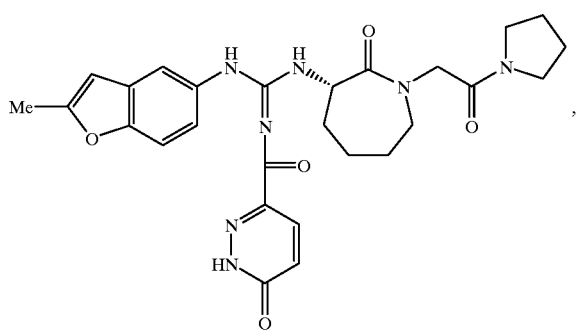,
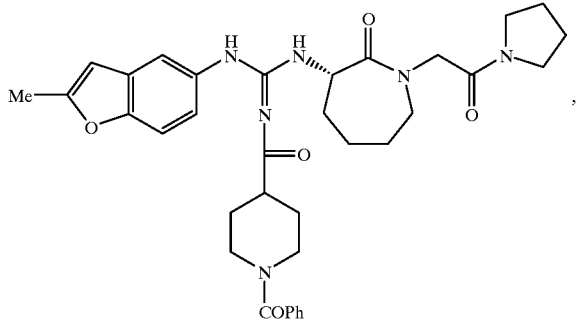,
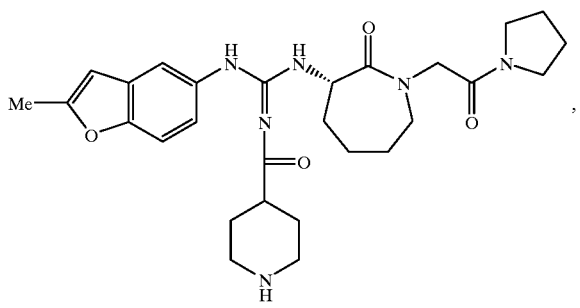, 15. The compound of claim 1 of the formula 16. A pharmaceutical composition comprising a compound as defined in claim 1 and a pharmaceutically acceptable carrier therefor.

17. A method for treating cardiovascular diseases associated with thromboses, which comprises administering to a mammalian species in need of treatment a therapeutically effective amount of a compound as defined in claim 1.

18. A method for treating thromboses, coronary artery disease or cerebrovascular disease, which comprises administering to a mammalian species in need of treatment a therapeutically effective amount of a compound as defined in claim 1.

* * * * *